United States Patent
Boloor et al.

(10) Patent No.: US 12,172,998 B2
(45) Date of Patent: Dec. 24, 2024

(54) HISTONE DEMETHYLASE INHIBITORS

(71) Applicant: CELGENE QUANTICEL RESEARCH, INC., San Diego, CA (US)

(72) Inventors: Amogh Boloor, San Diego, CA (US); Toufike Kanouni, Rancho Santa Fe, CA (US); Jeffrey Alan Stafford, San Diego, CA (US); James Marvin Veal, Apex, NC (US); Michael Brennan Wallace, San Diego, CA (US)

(73) Assignee: CELGENE QUANTICEL RESEARCH, INC., San Diego, CA (US)

( * ) Notice: Subject to any disclaimer, the term of this patent is extended or adjusted under 35 U.S.C. 154(b) by 0 days.

(21) Appl. No.: 17/980,291

(22) Filed: Nov. 3, 2022

(65) Prior Publication Data

US 2023/0117519 A1    Apr. 20, 2023

Related U.S. Application Data

(60) Continuation of application No. 17/026,763, filed on Sep. 21, 2020, now Pat. No. 11,535,616, which is a continuation of application No. 16/790,878, filed on Feb. 14, 2020, now Pat. No. 10,815,234, which is a continuation of application No. 16/137,219, filed on Sep. 20, 2018, now Pat. No. 10,611,763, which is a continuation of application No. 15/588,561, filed on May 5, 2017, now Pat. No. 10,112,940, which is a division of application No. 14/855,950, filed on Sep. 16, 2015, now Pat. No. 9,643,965.

(60) Provisional application No. 62/051,691, filed on Sep. 17, 2014.

(51) Int. Cl.
  *C07D 471/04* (2006.01)
  *C07D 487/04* (2006.01)

(52) U.S. Cl.
  CPC ......... *C07D 471/04* (2013.01); *C07D 487/04* (2013.01)

(58) Field of Classification Search
  CPC .................................................. C07D 471/04
  See application file for complete search history.

(56) References Cited

U.S. PATENT DOCUMENTS

| | | | |
|---|---|---|---|
| 9,643,965 B2 | 5/2017 | Boloor et al. | |
| 10,030,017 B2 | 7/2018 | Boloor et al. | |
| 10,112,940 B2 | 10/2018 | Boloor et al. | |
| 10,202,381 B2 | 2/2019 | Boloor et al. | |
| 10,208,039 B2 | 2/2019 | Boloor et al. | |
| 10,611,763 B2 | 4/2020 | Boloor et al. | |
| 10,815,234 B2 | 10/2020 | Boloor et al. | |
| 11,535,616 B2 * | 12/2022 | Boloor ................. | C07D 487/04 |
| 2004/0242604 A1 | 12/2004 | Bhattacharya et al. | |
| 2007/0190634 A1 | 8/2007 | Bebbington et al. | |
| 2007/0254901 A1 | 11/2007 | Bilodeau et al. | |
| 2008/0045561 A1 | 2/2008 | Nemecek et al. | |
| 2014/0213591 A1 | 7/2014 | Chen et al. | |
| 2014/0371195 A1 | 12/2014 | Labelle et al. | |
| 2015/0376169 A1 | 12/2015 | Boloor et al. | |
| 2016/0039808 A1 | 2/2016 | Kanouni et al. | |
| 2016/0083379 A1 | 3/2016 | Boloor et al. | |
| 2016/0194323 A1 | 7/2016 | Boloor et al. | |
| 2017/0240546 A1 | 8/2017 | Boloor et al. | |
| 2018/0162857 A1 | 6/2018 | Boloor et al. | |
| 2018/0297999 A1 | 10/2018 | Boloor et al. | |
| 2019/0023704 A1 | 1/2019 | Boloor et al. | |
| 2020/0199122 A1 | 6/2020 | Boloor et al. | |

FOREIGN PATENT DOCUMENTS

| | | |
|---|---|---|
| EP | 3 193 601 A1 | 7/2017 |
| EP | 3 430 008 A1 | 1/2019 |
| EP | 3 453 710 A1 | 3/2019 |
| JP | 2007-501854 A1 | 2/2007 |
| JP | 2008-510823 A | 4/2008 |
| JP | 2017-529346 A | 10/2017 |
| JP | 2019-508452 A | 3/2019 |
| JP | 5552608 B2 | 7/2019 |
| WO | 2003/033472 A1 | 4/2003 |
| WO | 2008033747 A2 | 3/2008 |
| WO | 2009036055 A1 | 3/2009 |
| WO | 2014/053491 A1 | 4/2014 |
| WO | 2014/100818 A1 | 6/2014 |
| WO | 2014100463 A1 | 6/2014 |
| WO | 2014144850 A1 | 9/2014 |
| WO | 2014151106 A1 | 9/2014 |
| WO | 2014164708 A1 | 10/2014 |

(Continued)

OTHER PUBLICATIONS

"Extended European search Report received in EP Patent Application No. 15842582.7, mailed on Feb. 7, 2018", 6 pages.
"Extended European Search Report received in European Patent Application No. 15842574.4, mailed on Jun. 6, 2018", 5 pages.
"International Preliminary Report on Patentability received for PCT Application No. PCT/US17/22546, mailed on Sep. 27, 2018", 6 pages.
"Partial Supplementary European Search Report received for European Patent Application No. 17767452.0, mailed on Jul. 8, 2019", 10 pages.
Database Genbank, "*Homo sapiens* Jumonji Domain Containing 2C, mRNA, Complete cds", GenBank Accession No. BC143571.1, Jan. 8, 2009, 3 pages.

(Continued)

*Primary Examiner* — Paul V Ward
(74) *Attorney, Agent, or Firm* — William M. Evans

(57) ABSTRACT

The present invention relates generally to compositions and methods for treating cancer and neoplastic disease. Provided herein are substituted pyrido[3,4-d]pyrimidin-4-one derivative compounds and pharmaceutical compositions comprising said compounds. The subject compounds and compositions are useful for inhibition of histone demethylase. Furthermore, the subject compounds and compositions are useful for the treatment of cancer, such as prostate cancer, breast cancer, bladder cancer, lung cancer and/or melanoma and the like.

13 Claims, No Drawings

(56) References Cited

FOREIGN PATENT DOCUMENTS

| WO | 2015/200709 A | 12/2015 |
|---|---|---|
| WO | 2015/200709 A1 | 12/2015 |
| WO | 2016/044429 A1 | 3/2016 |
| WO | 2017/161012 A1 | 9/2017 |

OTHER PUBLICATIONS

Fuhrhop, et al., "Organic Synthesis: Concepts, Methods, Starting Materials", 2nd Edition, John Wiley & Sons ISBN, 1994.
Gilchrist, "Heterocyclic Chemistry", 2nd Edition, John Wiley & Sons, 1992.
Hoffman, "Organic Chemistry, An Intermediate Text", Oxford University Press, 1996.
House, "Modern Synthetic Reactions", 2nd Edition, 1972.
Larock, "Comprehensive Organic Transformations: A Guide to Functional Group Preparations", 2nd Edition, Wiley-VCH, 1999.
March, "Advanced Organic Chemistry: Reactions, Mechanisms and Structure", 4th Edition, Wiley-Interscience, 1992.
Otera, "Modem Carbonyl Chemistry", Wiley-VCH, 2000.
Patai, "Patai's 1992 Guide to the Chemistry of Functional Groups", Interscience, 1992.
Remington, "Remington: The Science and Practice of Pharmacy", 21st Edition, 2005.
Sandler, et al., "Organic Functional Group Preparations", 2nd Edition, Academic Press, 1983.
Solomons, "Organic Chemistry", 7th Edition, John Wiley & Sons, 2000.
Stowell, "Intermediate Organic Chemistry", 2nd Edition, Wiley-Interscience, 1993.
Extended European Search Report received for European Patent Application No. 17767452.0, mailed on Oct. 24, 2019, 10 pages.
Berge et al., Pharmaceutical Salts. Journal of Pharmaceutical Sciences 66(1):1-19 (Jan. 1977).
Bundgard et al., Design of Prodrugs, pp. 7-9, 21-24 (1985).
Higuchi et al., "Pro-drugs as Novel Delivery Systems," A.C.S. Symposium Series, 1975, vol. 14.
International Preliminary Report on Patentability mailed, Mar. 30, 2017, in related International Iapplication No. PCT/US2015/050432, filed Sep. 16, 2015.
International Preliminary Report on Patentability mailed, Sep. 24, 2015, in related International Application No. PCT/US2014/024998, filed Mar. 12, 2014.
International Search Report and Written Opinion mailed, Jul. 10, 2014, in related International Application No. PCT/US2014/024998, filed Mar. 12, 2014.
International Search Report and Written Opinion mailed, Dec. 14, 2015, in related International Patent Application No. PCT/US2015/050432, filed Sep. 16, 2015.
International Search Report and Written Opinion mailed, Jul. 19, 2017, in related International Application No. PCT/US2017/022546, filed Mar. 15, 2017.
Klose et al., "JmjC-domain-containing proteins and histone demethylation." Nature Reviews Genetics 7:715-727 Sep. 2006).
Lachner et al., An epigenetic road map for histone lysine methylation. Journal of Cell Science 116:2117-2124 Jun. 1, 2003).
Lin et al., Loss of the retinoblastoma binding protein 2 (RBP2) histone demethylase suppresses tumorigenesis in mice lacking RB1 or Men 1.PNAS108(33):13379-13386 (2011).
Margueron et al. The key to development: interpreting the histone code? Current Opinion in Genetics & Development 15:163-176 (2005).
McMahon et al., "VEGF Receptor Signaling in Tumor Angiogenesis," The Oncologist 2000; 5(suppl. 1 ):3-10 at NWW.TheOncologist.com.
Pinedo et al., "Translational Research: The Role of VEGF in Tumor Angiogenesis," The Oncologist 2000; 5(Suppl. 1):1-2 at www.TheOncologist.com.
Search Report and Written Opinion mailed, Nov. 28, 2017, in related Singapore Patent Application No. 11201702147T, filed Sep. 16, 2015.
Stahl et al., Handbook of Pharmaceutical Salts. Verlag Helvetica Chimica Acta, Zurich, 2002.
Notice of Allowance received for Japanese Patent Application No. 2017-514615, mailed on Jun. 5, 2019, 3 pages.
Office Action received for Japanese Patent Application No. 2018-548321, mailed on Feb. 22, 2021, 7 pages ( 4 pages of English Translation and 3 pages of Official Copy).

\* cited by examiner

HISTONE DEMETHYLASE INHIBITORS

CROSS REFERENCE

This application is a continuation of U.S. patent application Ser. No. 17/026,763, filed Sep. 21, 2020, which is a continuation of U.S. patent application Ser. No. 16/790,878, filed Feb. 14, 2020 (U.S. Pat. No. 10,815,234), which is a continuation of U.S. patent application Ser. No. 16/137,219, filed Sep. 20, 2018 (U.S. Pat. No. 10,611,763), which is a continuation of U.S. patent application Ser. No. 15/588,561, filed May 5, 2017 (U.S. Pat. No. 10,112,940), which is a divisional of U.S. patent application Ser. No. 14/855,950, filed Sep. 16, 2015 (U.S. Pat. No. 9,643,965), which claims the benefit of U.S. Provisional Application No. 62/051,691 filed Sep. 17, 2014, the contents of which are hereby incorporated by reference in their entireties for all purposes.

BACKGROUND

A need exists in the art for an effective treatment of cancer and neoplastic disease.

BRIEF SUMMARY OF THE INVENTION

Provided herein are substituted pyrido[3,4-d]pyrimidin-4-one derivative compounds and pharmaceutical compositions comprising said compounds. The subject compounds and compositions are useful for inhibition histone demethylase. Furthermore, the subject compounds and compositions are useful for the treatment of cancer, such as prostate cancer, breast cancer, bladder cancer, lung cancer and/or melanoma and the like. The substituted pyrido[3,4-d]pyrimidin-4-one derivative compounds described herein are based upon a substituted pyrido[3,4-d]pyrimidin-4-one ring system bearing a hydroxy group at the 4-position, and an oxygen-based substituent at the 2-position.

One embodiment provides a compound of Formula (I), or pharmaceutically acceptable salt thereof,

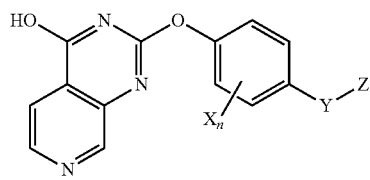

Formula (I)

wherein,

X is halogen and n is 0 or 1;

Y is —O—, —S—, —SO$_2$—, —CF$_2$—, —(CH$_2$)—N(H)—, —(CH$_2$)—N(H)—(C=O)—, —(CH$_2$)—N(C$_1$-C$_3$alkyl) —(C=O)—; and Z is aryl, carbocyclyl, or heterocyclyl.

One embodiment provides a compound of Formula (II), or pharmaceutically acceptable salt thereof,

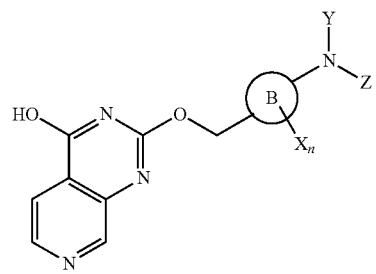

Formula (II)

wherein,

X is halogen and n is 0 or 1;

ring B is chosen from:

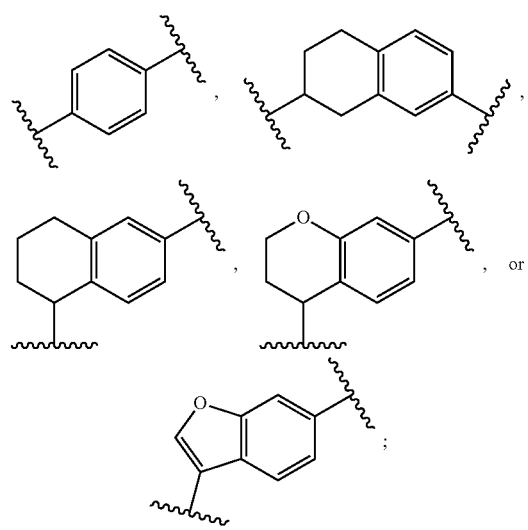

Y is C$_1$-C$_3$ alkyl; and

Z is aryl or heteroaryl.

One embodiment provides a compound of Formula (III), or pharmaceutically acceptable salt thereof,

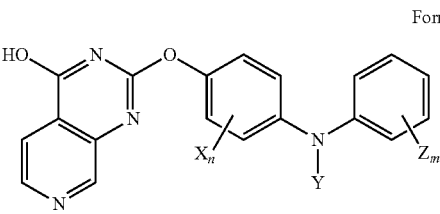

Formula (III)

wherein,

X is halogen and n is 0 or 1;

Y is hydrogen or C$_1$-C$_3$ alkyl;

Z is halogen, —OH, —NH$_2$, —CN, alkyl, alkoxy, alkylamino, carbocyclyl, aryl, heterocyclyl, heteroaryl, aralkyl, heterocyclylalkyl, or carbocyclylalkyl; and m is 0, 1, or 2.

One embodiment provides a compound of Formula (IV), or pharmaceutically acceptable salt thereof,

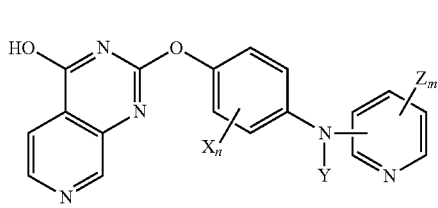

Formula (IV)

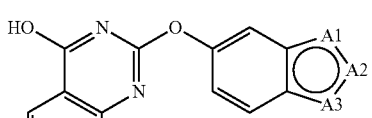

Formula (VII)

wherein,

X is halogen and n is 0 or 1;

Y is hydrogen or $C_1$-$C_3$ alkyl;

Z is halogen, —OH, —$NH_2$, —CN, alkyl, alkoxy, alkylamino, carbocyclyl, aryl, heterocyclyl, heteroaryl, aralkyl, heterocyclylalkyl, or carbocyclylalkyl; and m is 0, 1, or 2.

One embodiment provides a compound of Formula (V), or pharmaceutically acceptable salt thereof, wherein, A1, A2, and A3 are chosen from C—H, N or N—R, provided that at least one of A1, A2, or A3 is C—H, and at least one of A1, A2, or A3 is N—R; and R is aryl, aralkyl, or carbocyclylalkyl.

Another embodiment provides the compound of Formula (VII), or pharmaceutically acceptable salt thereof, having a structure selected from Formula (VIIa)-(VIId) as described below:

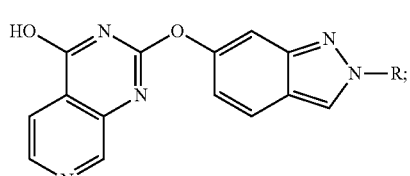

Formula (VIIa)

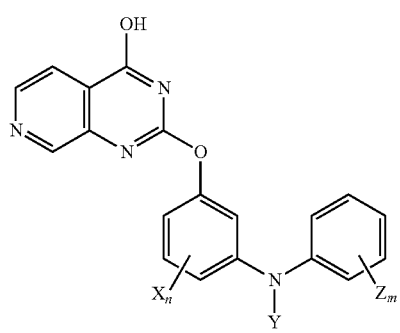

Formula (V)

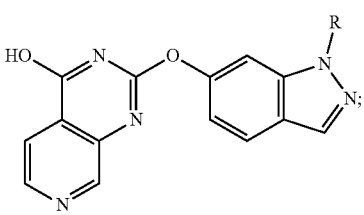

Formula (VIIb)

wherein,

X is halogen and n is 0 or 1;

Y is hydrogen or $C_1$-$C_3$ alkyl;

Z is halogen, —OH, —$NH_2$, —CN, alkyl, alkoxy, alkylamino, carbocyclyl, aryl, heterocyclyl, heteroaryl, aralkyl, heterocyclylalkyl, or carbocyclylalkyl; and m is 0, 1, or 2.

One embodiment provides a compound of Formula (VI), or pharmaceutically acceptable salt thereof,

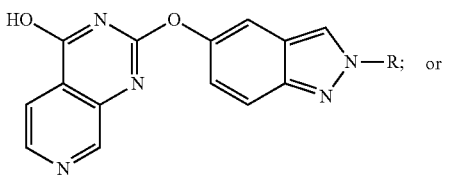

Formula (VIc)  or

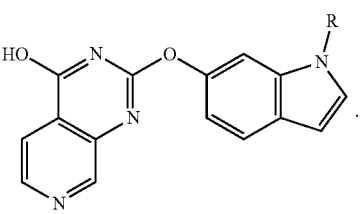

Formula (VIId)

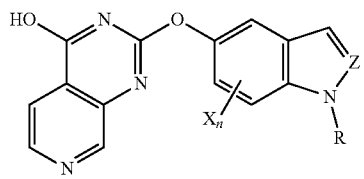

Formula (VI)

One embodiment provides a compound of Formula (VIII), or pharmaceutically acceptable salt thereof,

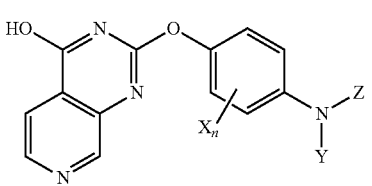

Formula (VIII)

wherein,

X is halogen and n is 0 or 1;

Z is N or C—H;

R is alkyl, aryl, aralkyl, or carbocyclylalkyl.

One embodiment provides a compound of Formula (VII), or pharmaceutically acceptable salt thereof, wherein,
X is halogen and n is 0 or 1;
Y is $C_1$-$C_3$ alkyl; and
Z is aralkyl.

One embodiment provides a compound of Formula (IX), or pharmaceutically acceptable salt thereof, Formula (IX)

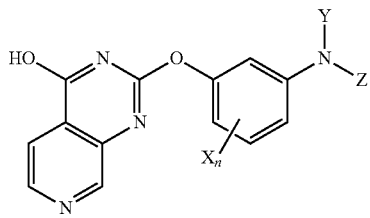

wherein,
X is halogen and n is 0 or 1;
Y is $C_1$-$C_3$ alkyl; and
Z is aralkyl.

One embodiment provides a compound of Formula (X), or pharmaceutically acceptable salt thereof, Formula (X)

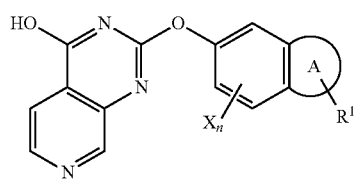

wherein,
X is halogen and n is 0 or 1;
ring A, represented by

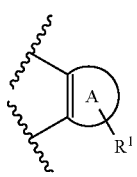

is chosen from:

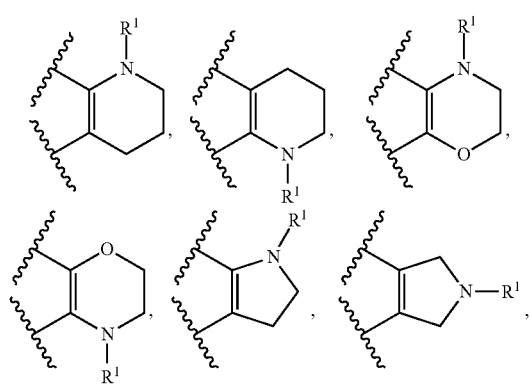

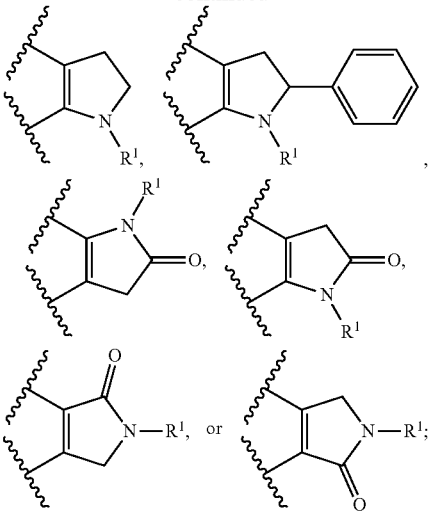

and
$R^1$ is alkyl, aryl, aralkyl, carbocyclyl, carbocyclylalkyl, —(C=O)aryl, or —(SO$_2$)aryl.

One embodiment provides a pharmaceutical composition comprising a compound of Formula (I)-(X), or pharmaceutically acceptable salt thereof, and at least one pharmaceutically acceptable excipient.

One embodiment provides a method for inhibiting a histone demethylase enzyme comprising contacting the histone demethylase enzyme with a compound of Formula (I)-(X).

One embodiment provides a method for treating cancer in subject in need thereof comprising administering to the subject a composition comprising a compound of Formula (I)-(X), or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—$^c$—C(O)N(R$^a$)$_2$, —R$^b$—N(R$^a$)C(O)OR$^a$, —R$^b$—N(R$^a$) C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond.

Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1] heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O) R$^a$, —R$^b$—C(O)OR$^a$, —R$^b$—C(O)N(R$^a$)$_2$, —R$^b$—O— R$^c$—C(O)N(R$^a$)$_2$, —R$^b$—N(R$^a$)C(O)OR$^a$, —R$^b$—N(R$^a$) C(O)R$^a$, —R$^b$—N(R$^a$)S(O)$_t$R$^a$ (where t is 1 or 2), —R$^b$— S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Carbocyclylalkyl" refers to a radical of the formula —R$^c$-carbocyclyl where R$^c$ is an alkylene chain as defined above. The alkylene chain and the carbocyclyl radical is optionally substituted as defined above.

"Carbocyclylalkoxy" refers to a radical bonded through an oxygen atom of the formula —O—R$^c$-carbocyclyl where R$^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula $-R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula $-O-R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) TC-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein may contain one or more asymmetric centers and may thus give rise to enantiomers, diastereomers, and other stereoisomeric forms that may be defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans). Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

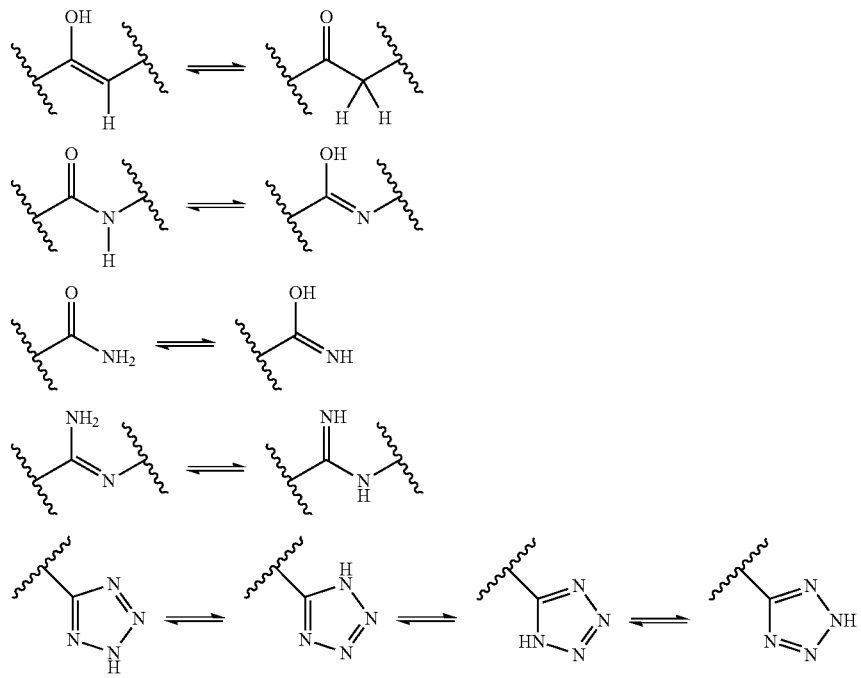

-continued

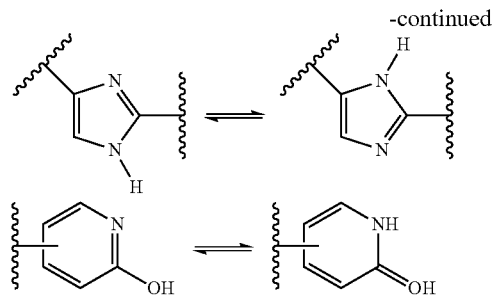

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted pyrido[3,4-d]pyrimidin-4-one derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Substituted Pyrido[3,4-d]pyrimidin-4-one Derivative Compounds

Substituted pyrido[3,4-d]pyrimidin-4-one derivative compounds are described herein that inhibit a histone demethylase enzyme. These compounds, and compositions comprising these compounds, are useful for the treatment of cancer and neoplastic disease. The compounds described herein are useful for treating prostate cancer, breast cancer, bladder cancer, lung cancer and/or melanoma and the like.

One embodiment provides a compound of Formula (I), or pharmaceutically acceptable salt thereof,

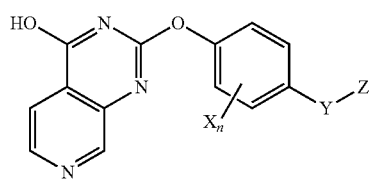

Formula (I)

wherein,
X is halogen and n is 0 or 1;
Y is —O—, —S—, —SO$_2$—, —CF$_2$—, —(CH$_2$)—N(H)—, —(CH$_2$)—N(H)—(C=O)—, —(CH$_2$)—N(C$_1$-C$_3$ alkyl)-(C=O)—; and
Z is aryl, carbocyclyl, or heterocyclyl.

Another embodiment provides the compound of Formula (I), or pharmaceutically acceptable salt thereof, wherein n is 0. Another embodiment provides the compound of Formula (I), or pharmaceutically acceptable salt thereof, wherein n is 1 and X is fluoro.

Another embodiment provides the compound of Formula (I), or pharmaceutically acceptable salt thereof, wherein Y is —O—. Another embodiment provides the compound of Formula (I), or pharmaceutically acceptable salt thereof, wherein Y is —S—. Another embodiment provides the compound of Formula (I), or pharmaceutically acceptable salt thereof, wherein Y is —SO$_2$. Another embodiment provides the compound of Formula (I), or pharmaceutically acceptable salt thereof, wherein Y is —CF$_2$—. Another embodiment provides the compound of Formula (I), or pharmaceutically acceptable salt thereof, wherein Y is —(CH$_2$)N(H)(C=O)—. Another embodiment provides the compound of Formula (I), or pharmaceutically acceptable salt thereof, wherein Y is —(CH$_2$)—N(C$_1$-C$_3$ alkyl)-.

Another embodiment provides the compound of Formula (I), or pharmaceutically acceptable salt thereof, wherein Z is aryl. Another embodiment provides the compound of Formula (I), or pharmaceutically acceptable salt thereof, wherein Z is phenyl optionally substituted with halogen, alkyl, alkoxy, or carbocyclyl. Another embodiment provides the compound of Formula (I), or pharmaceutically acceptable salt thereof, wherein Z is carbocyclyl. Another embodiment provides the compound of Formula (I), or pharmaceutically acceptable salt thereof, wherein Z is 1,2,3,4-tetrahydronaphthalenyl.

Another embodiment provides the compound of Formula (I), or pharmaceutically acceptable salt thereof, wherein Z is heterocyclyl. Another embodiment provides the compound of Formula (I), or pharmaceutically acceptable salt thereof, wherein Z is chromanyl.

One embodiment provides a compound of Formula (II), or pharmaceutically acceptable salt thereof,

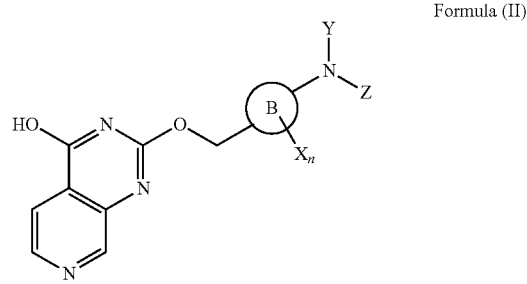

Formula (II)

wherein,
X is halogen and n is 0 or 1;
ring B is chosen from:

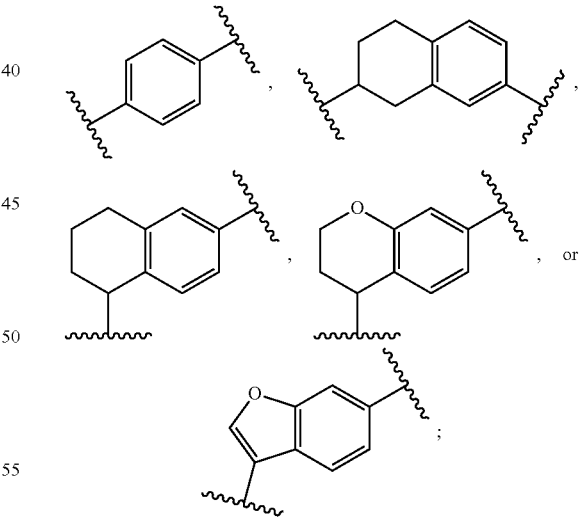

Y is C$_1$-C$_3$alkyl; and
Z is aryl or heteroaryl.

Another embodiment provides the compound of Formula (II), or pharmaceutically acceptable salt thereof, wherein n is 0. Another embodiment provides the compound of Formula (II), or pharmaceutically acceptable salt thereof, wherein n is 1 and X is fluoro.

Another embodiment provides the compound of Formula (II), or pharmaceutically acceptable salt thereof, wherein Y is $C_1$ alkyl. Another embodiment provides the compound of Formula (II), or pharmaceutically acceptable salt thereof, wherein Y is $C_2$ alkyl.

Another embodiment provides the compound of Formula (II), or pharmaceutically acceptable salt thereof, wherein ring B is

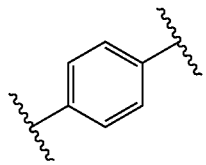

Another embodiment provides the compound of Formula (II), or pharmaceutically acceptable salt thereof, wherein ring B is

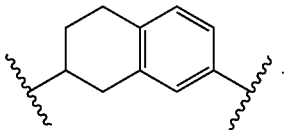 [SMILES: *c1ccc2c(c1)CC(*)CC2]

Another embodiment provides the compound of Formula (II), or pharmaceutically acceptable salt thereof, wherein ring B is

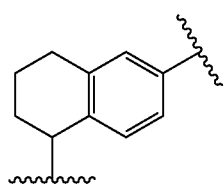

Another embodiment provides the compound of Formula (II), or pharmaceutically acceptable salt thereof, wherein ring B is

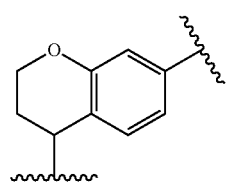

Another embodiment provides the compound of Formula (II), or pharmaceutically acceptable salt thereof, wherein ring B is

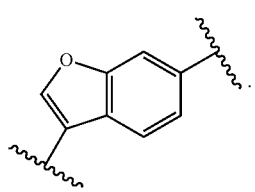 [SMILES: *c1ccc2c(*)coc2c1]

Another embodiment provides the compound of Formula (II), or pharmaceutically acceptable salt thereof, wherein Z is aryl. Another embodiment provides the compound of Formula (II), or pharmaceutically acceptable salt thereof, wherein Z is phenyl optionally substituted with alkyl, —(C═O)N($R^a$)$_2$, heteroaryl, or heterocyclyl; wherein each $R^a$ is independently hydrogen or $C_1$-$C_3$ alkyl. Another embodiment provides the compound of Formula (II), or pharmaceutically acceptable salt thereof, wherein Z is heteroaryl.

Another embodiment provides the compound of Formula (II), or pharmaceutically acceptable salt thereof, wherein Z is

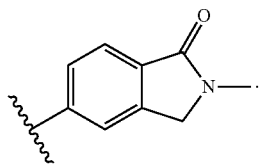 [SMILES: *c1ccc2c(c1)CN(C)C2=O]

One embodiment provides a compound of Formula (III), or pharmaceutically acceptable salt thereof, Formula (III)

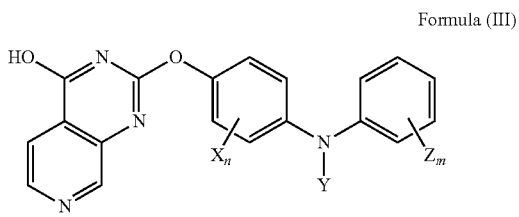

wherein,
X is halogen and n is 0 or 1;
Y is hydrogen, $C_1$-$C_3$ alkyl, cycloalkyl, or heterocyclyl;
Z is halogen, —OH, —NH$_2$, —CN, alkyl, alkoxy, alkylamino, dialkylamino, —SO$_2$-alkyl, carbocyclyl, aryl, heterocyclyl, heteroaryl, aralkyl, heterocyclylalkyl, heterocyclyl-(aminoalkyl)-, or carbocyclylalkyl; and m is 0, 1, or 2.

One embodiment provides a compound of Formula (III) having the structure of Formula (IIIa), or pharmaceutically acceptable salt thereof, Formula (IIIa)

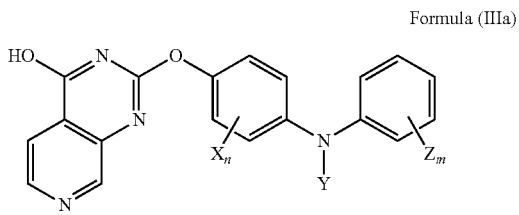

wherein,
X is halogen and n is 0 or 1;
Y is hydrogen or $C_1$-$C_3$ alkyl;
Z is halogen, —OH, —NH$_2$, —CN, alkyl, alkoxy, alkylamino, carbocyclyl, aryl, heterocyclyl, heteroaryl, aralkyl, heterocyclylalkyl, or carbocyclylalkyl; and m is 0, 1, or 2.

Another embodiment provides the compound of Formula (III), or pharmaceutically acceptable salt thereof, wherein n is 0. Another embodiment provides the compound of Formula (III), or pharmaceutically acceptable salt thereof, wherein n is 1. Another embodiment provides the compound of Formula (III), or pharmaceutically acceptable salt thereof, wherein X is fluoro.

Another embodiment provides the compound of Formula (III), or pharmaceutically acceptable salt thereof, wherein Y is hydrogen. Another embodiment provides the compound of Formula (III), or pharmaceutically acceptable salt thereof, wherein Y is $C_1$alkyl. Another embodiment provides the compound of Formula (III), or pharmaceutically acceptable salt thereof, wherein Y is $C_2$alkyl.

Another embodiment provides the compound of Formula (III), or pharmaceutically acceptable salt thereof, wherein m is 0. Another embodiment provides the compound of Formula (III), or pharmaceutically acceptable salt thereof, wherein m is 1. Another embodiment provides the compound of Formula (III), or pharmaceutically acceptable salt thereof, wherein m is 2.

Another embodiment provides the compound of Formula (III), or pharmaceutically acceptable salt thereof, wherein Z is halogen, —CN, alkyl, alkoxy, carbocyclyl, or heterocyclyl.

Another embodiment provides the compound of Formula (III), or pharmaceutically acceptable salt thereof, wherein Z is fluoro, chloro, methyl, methoxy, or morpholinyl.

One embodiment provides a compound of Formula (IV), or pharmaceutically acceptable salt thereof,

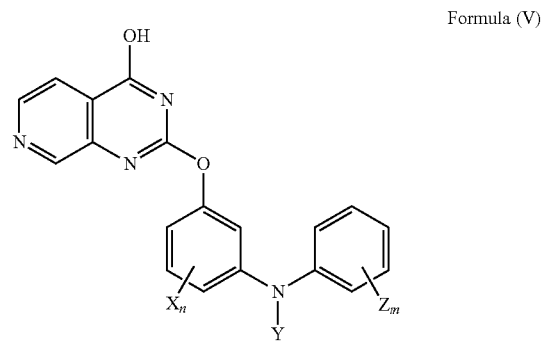

Formula (IV)

wherein,

X is halogen and n is 0 or 1;

Y is hydrogen or $C_1$-$C_3$ alkyl;

Z is halogen, —OH, —NH$_2$, —CN, alkyl, alkoxy, alkylamino, carbocyclyl, aryl, heterocyclyl, heteroaryl, aralkyl, heterocyclylalkyl, or carbocyclylalkyl; and m is 0, 1, or 2.

Another embodiment provides the compound of Formula (IV), or pharmaceutically acceptable salt thereof, wherein n is 0. Another embodiment provides the compound of Formula (IV), or pharmaceutically acceptable salt thereof, wherein n is 1. Another embodiment provides the compound of Formula (IV), or pharmaceutically acceptable salt thereof, wherein X is fluoro.

Another embodiment provides the compound of Formula (IV), or pharmaceutically acceptable salt thereof, wherein Y is hydrogen. Another embodiment provides the compound of Formula (IV), or pharmaceutically acceptable salt thereof, wherein Y is $C_1$ alkyl. Another embodiment provides the compound of Formula (IV), or pharmaceutically acceptable salt thereof, wherein Y is $C_2$ alkyl.

Another embodiment provides the compound of Formula (IV), or pharmaceutically acceptable salt thereof, wherein m is 0. Another embodiment provides the compound of Formula (IV), or pharmaceutically acceptable salt thereof, wherein m is 1. Another embodiment provides the compound of Formula (IV), or pharmaceutically acceptable salt thereof, wherein m is 2.

Another embodiment provides the compound of Formula (IV), or pharmaceutically acceptable salt thereof, wherein Z is halogen, —CN, alkyl, alkoxy, carbocyclyl, or heterocyclyl.

Another embodiment provides the compound of Formula (IV), or pharmaceutically acceptable salt thereof, wherein Z is fluoro, chloro, methyl, methoxy, or morpholinyl.

One embodiment provides a compound of Formula (V), or pharmaceutically acceptable salt thereof,

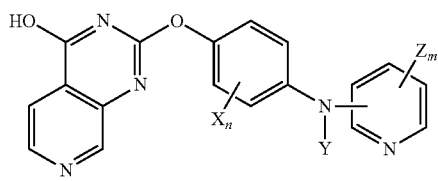

Formula (V)

wherein,

X is halogen and n is 0 or 1;

Y is hydrogen or $C_1$-$C_3$ alkyl;

Z is halogen, —OH, —NH$_2$, —CN, alkyl, alkoxy, alkylamino, carbocyclyl, aryl, heterocyclyl, heteroaryl, aralkyl, heterocyclylalkyl, or carbocyclylalkyl; and m is 0, 1, or 2.

Another embodiment provides the compound of Formula (V), or pharmaceutically acceptable salt thereof, wherein n is 0. Another embodiment provides the compound of Formula (V), or pharmaceutically acceptable salt thereof, wherein n is 1. Another embodiment provides the compound of Formula (V), or pharmaceutically acceptable salt thereof, wherein X is fluoro.

Another embodiment provides the compound of Formula (V), or pharmaceutically acceptable salt thereof, wherein Y is hydrogen. Another embodiment provides the compound of Formula (V), or pharmaceutically acceptable salt thereof, wherein Y is $C_1$alkyl. Another embodiment provides the compound of Formula (V), or pharmaceutically acceptable salt thereof, wherein Y is $C_2$alkyl.

Another embodiment provides the compound of Formula (V), or pharmaceutically acceptable salt thereof, wherein m is 0. Another embodiment provides the compound of Formula (V), or pharmaceutically acceptable salt thereof, wherein m is 1. Another embodiment provides the compound of Formula (V), or pharmaceutically acceptable salt thereof, wherein m is 2.

Another embodiment provides the compound of Formula (V), or pharmaceutically acceptable salt thereof, wherein Z is halogen, —CN, alkyl, alkoxy, carbocyclyl, or heterocyclyl.

Another embodiment provides the compound of Formula (V), or pharmaceutically acceptable salt thereof, wherein Z is fluoro, chloro, methyl, methoxy, or morpholinyl.

One embodiment provides a compound of Formula (VI), or pharmaceutically acceptable salt thereof,

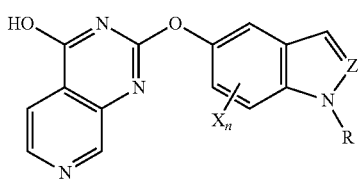

Formula (VI)

wherein,
X is halogen and n is 0 or 1;
Z is N or C—H;
R is alkyl, aryl, aralkyl, cycloalkyl, heterocyclyl, or carbocyclylalkyl.

One embodiment provides a compound of Formula (VI) having the structure of Formula (VIa), or pharmaceutically acceptable salt thereof,

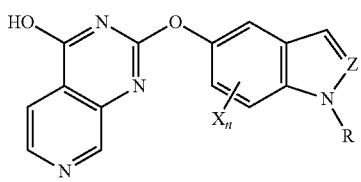

Formula (VIa)

wherein,
X is halogen and n is 0 or 1;
Z is N or C—H;
R is alkyl, aryl, aralkyl, or carbocyclylalkyl.

Another embodiment provides the compound of Formula (VI), or pharmaceutically acceptable salt thereof, wherein n is 0. Another embodiment provides the compound of Formula (VI), or pharmaceutically acceptable salt thereof, wherein n is 1 and X is fluoro.

Another embodiment provides the compound of Formula (VI), or pharmaceutically acceptable salt thereof, wherein Z is N. Another embodiment provides the compound of Formula (VI), or pharmaceutically acceptable salt thereof, wherein Z is C—H.

Another embodiment provides the compound of Formula (VI), or pharmaceutically acceptable salt thereof, wherein R is aralkyl. Another embodiment provides the compound of Formula (VI), or pharmaceutically acceptable salt thereof, wherein the aralkyl is benzyl.

Another embodiment provides the compound of Formula (VI), or pharmaceutically acceptable salt thereof, wherein R is alkyl. Another embodiment provides the compound of Formula (VI), or pharmaceutically acceptable salt thereof, wherein the alkyl is methyl.

One embodiment provides a compound of Formula (VII), or pharmaceutically acceptable salt thereof,

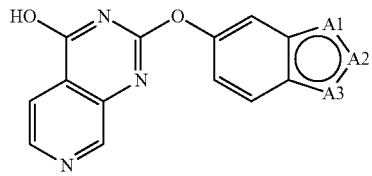

Formula (VII)

wherein,
A1, A2, and A3 are chosen from C—H, N or N—R, provided that at least one of A1, A2, or A3 is C—H, and at least one of A1, A2, or A3 is N—R; and
R is aryl, aralkyl, or carbocyclylalkyl.

Another embodiment provides the compound of Formula (VII), or pharmaceutically acceptable salt thereof, having a structure selected from Formula (VIIa)-(VIId) as described below:

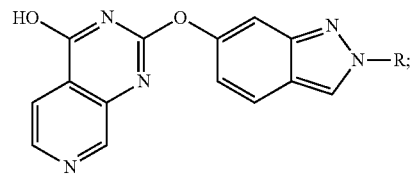

Formula (VIIa)

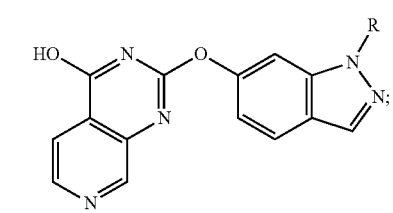

Formula (VIIb)

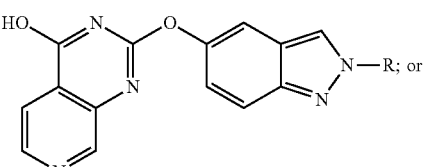

Formula (VIIc)

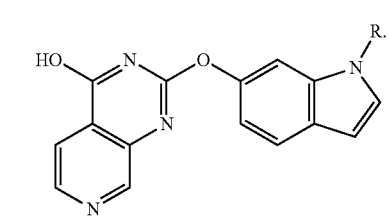

Formula (VIId)

Another embodiment provides the compound of Formula (VII), or pharmaceutically acceptable salt thereof, wherein R is aralkyl. Another embodiment provides the compound of Formula (VII), or pharmaceutically acceptable salt thereof, wherein the aralkyl is benzyl.

One embodiment provides a compound of Formula (VIII), or pharmaceutically acceptable salt thereof,

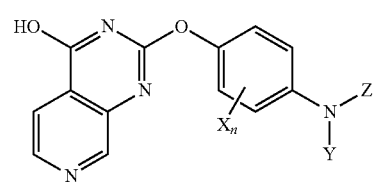

Formula (VIII)

wherein,
X is halogen and n is 0 or 1;
Y is $C_1$-$C_3$alkyl; and
Z is aralkyl.

Another embodiment provides the compound of Formula (VIII), or pharmaceutically acceptable salt thereof, wherein n is 0. Another embodiment provides the compound of Formula (VIII), or pharmaceutically acceptable salt thereof, wherein n is 1 and X is fluoro.

Another embodiment provides the compound of Formula (VIII), or pharmaceutically acceptable salt thereof, wherein Y is $C_1$ alkyl. Another embodiment provides the compound of Formula (VIII), or pharmaceutically acceptable salt thereof, wherein Y is $C_2$ alkyl.

Another embodiment provides the compound of Formula (VIII), or pharmaceutically acceptable salt thereof, wherein Z is benzyl.

One embodiment provides a compound of Formula (IX), or pharmaceutically acceptable salt thereof,

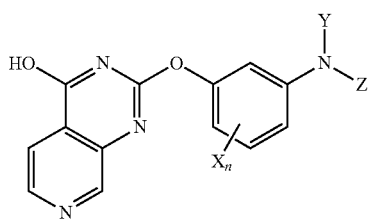

Formula (IX)

wherein,
X is halogen and n is 0 or 1;
Y is $C_1$-$C_3$alkyl; and
Z is aralkyl.

Another embodiment provides the compound of Formula (IX), or pharmaceutically acceptable salt thereof, wherein n is 0. Another embodiment provides the compound of Formula (IX), or pharmaceutically acceptable salt thereof, wherein n is 1 and X is fluoro.

Another embodiment provides the compound of Formula (IX), or pharmaceutically acceptable salt thereof, wherein Y is $C_1$ alkyl. Another embodiment provides the compound of Formula (IX), or pharmaceutically acceptable salt thereof, wherein Y is $C_2$ alkyl.

Another embodiment provides the compound of Formula (IX), or pharmaceutically acceptable salt thereof, wherein Z is benzyl.

One embodiment provides a compound of Formula (X), or pharmaceutically acceptable salt thereof,

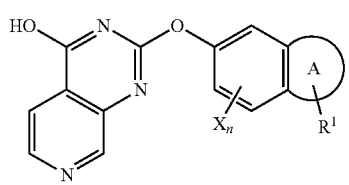

Formula (X)

wherein,
X is halogen and n is 0 or 1;
ring A, represented by

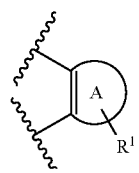

is chosen from:

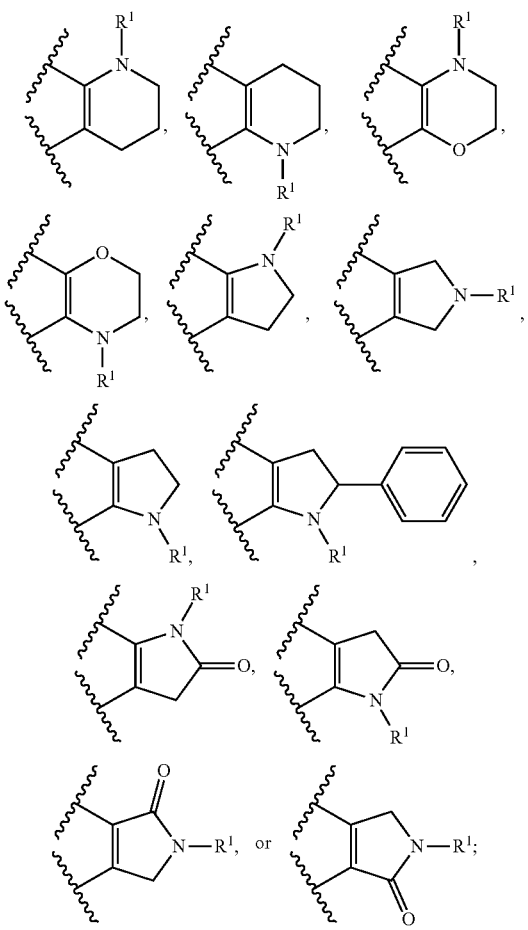

and $R^1$ is alkyl, aryl, aralkyl, carbocyclyl, carbocyclylalkyl, —(C=O)aryl, or —(SO$_2$)aryl.

Another embodiment provides the compound of Formula (X), or pharmaceutically acceptable salt thereof, wherein n is 0. Another embodiment provides the compound of Formula (X), or pharmaceutically acceptable salt thereof, wherein n is 1 and X is fluoro.

Another embodiment provides the compound of Formula (X), or pharmaceutically acceptable salt thereof, wherein ring A is

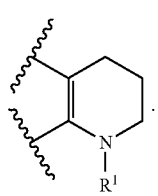

Another embodiment provides the compound of Formula (X), or pharmaceutically acceptable salt thereof, wherein ring A is

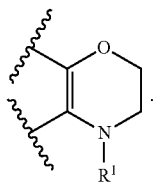

Another embodiment provides the compound of Formula (X), or pharmaceutically acceptable salt thereof, wherein ring A is

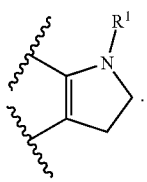

Another embodiment provides the compound of Formula (X), or pharmaceutically acceptable salt thereof, wherein ring A is

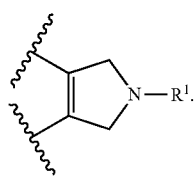

Another embodiment provides the compound of Formula (X), or pharmaceutically acceptable salt thereof, wherein ring A is

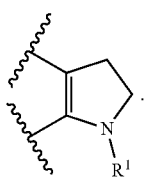

Another embodiment provides the compound of Formula (X), or pharmaceutically acceptable salt thereof, wherein $R^1$ is alkyl. Another embodiment provides the compound of Formula (X), or pharmaceutically acceptable salt thereof, wherein $R^1$ is aryl. Another embodiment provides the compound of Formula (X), or pharmaceutically acceptable salt thereof, wherein the aryl is phenyl optionally substituted with halogen. Another embodiment provides the compound of Formula (X), or pharmaceutically acceptable salt thereof, wherein $R^1$ is aralkyl. Another embodiment provides the compound of Formula (X), or pharmaceutically acceptable salt thereof, wherein the aralkyl is benzyl optionally substituted with halogen. Another embodiment provides the compound of Formula (X), or pharmaceutically acceptable salt thereof, wherein $R^1$ is carbocyclyl. Another embodiment provides the compound of Formula (X), or pharmaceutically acceptable salt thereof, wherein $R^1$ is carbocyclylalkyl.

One embodiment provides a compound of Formula (XI), or pharmaceutically acceptable salt thereof,

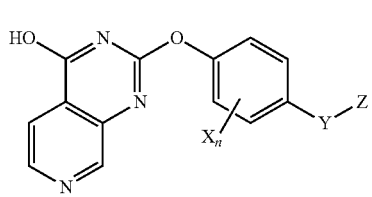

wherein,
X is halogen and n is 0 or 1;
Y is a heterocyclylene-; and
Z is aryl, carbocyclyl, or heterocyclyl.

Another embodiment provides the compound of Formula (XI), or pharmaceutically acceptable salt thereof, wherein Z is aryl. Another embodiment provides the compound of Formula (XI), or pharmaceutically acceptable salt thereof, wherein Y is chosen from

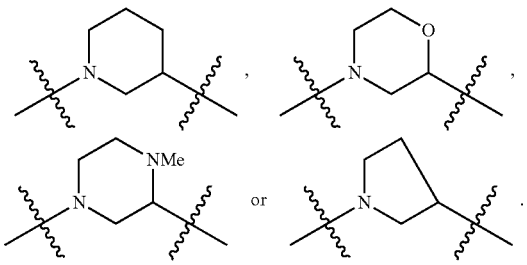

One embodiment provides a compound, or pharmaceutically acceptable salt thereof, chosen from:
2-[4-(methyl-pyridin-2-yl-amino)-phenoxy]-pyrido[3,4-d]pyrimidin-4-ol;
2-(1-methyl-1H-indol-5-yloxy)-pyrido[3,4-d]pyrimidin-4-ol;
2-(1-phenethyl-1H-indol-5-yloxy)-pyrido[3,4-d]pyrimidin-4-ol;
2-(1-benzyl-1H-indol-5-yloxy)-pyrido[3,4-d]pyrimidin-4-ol;
2-[4-(methyl-phenyl-amino)-phenoxy]-pyrido[3,4-d]pyrimidin-4-ol;
2-[4-(benzyl-methyl-amino)-phenoxy]-pyrido[3,4-d]pyrimidin-4-ol;
2-[3-(methyl-phenyl-amino)-phenoxy]-pyrido[3,4-d]pyrimidin-4-ol;
2-(1-benzyl-1H-indol-6-yloxy)-pyrido[3,4-d]pyrimidin-4-ol;
2-[3-(benzyl-methyl-amino)-phenoxy]-pyrido[3,4-d]pyrimidin-4-ol;
2-[3-fluoro-4-(methyl-phenyl-amino)-phenoxy]-pyrido[3,4-d]pyrimidin-4-ol;
2-(1-benzyl-1H-indazol-6-yloxy)-pyrido[3,4-d]pyrimidin-4-ol;
2-(2-benzyl-2H-indazol-6-yloxy)-pyrido[3,4-d]pyrimidin-4-ol;
2-{4-[methyl(2-phenylethyl)amino]phenoxy}pyridino[3,4-d]pyrimidin-4-ol;
2-[2-benzyl-2H-indazol-5-yloxy]pyridino[3,4-d]pyrimidin-4-ol;
2-(1-benzyl-1H-indazol-5-yloxy)pyridino[3,4-d]pyrimidin-4-ol;
2-{4-[(4-methoxy-phenyl)-methyl-amino]-phenoxy}-pyrido[3,4-d]pyrimidin-4-ol;

2-{4-[(3-methoxy-phenyl)-methyl-amino]-phenoxy}-pyrido[3,4-d]pyrimidin-4-ol;
2-{4-[methyl-(4-morpholin-4-yl-phenyl)-amino]-phenoxy}-pyrido[3,4-d]pyrimidin-4-ol;
2-{4-[methyl-(3-morpholin-4-yl-phenyl)-amino]-phenoxy}-pyrido[3,4-d]pyrimidin-4-ol;
2-[4-(methyl-p-tolyl-amino)-phenoxy]-pyrido[3,4-d]pyrimidin-4-ol; and
2-[4-(methyl-m-tolyl-amino)-phenoxy]-pyrido[3,4-d]pyrimidin-4-ol.

An additional embodiment provides a compound, or pharmaceutically acceptable salt thereof, chosen from:
2-(4-{methyl-[3-(4-methyl-piperazin-1-yl)-phenyl]-amino}-phenoxy)-pyrido[3,4-d]pyrimidin-4-ol;
2-(4-{[4-(4-amino-piperidin-1-yl)-phenyl]-methyl-amino}-phenoxy)-pyrido[3,4-d]pyrimidin-4-ol;
N-[4-(4-hydroxy-pyrido[3,4-d]pyrimidin-2-yloxy)-phenyl]-N-methyl-2-phenyl-acetamide;
2-[4-(3-phenyl-piperidin-1-yl)-phenoxy]-pyrido[3,4-d]pyrimidin-4-ol;
2-[4-(2-phenyl-morpholin-4-yl)-phenoxy]-pyrido[3,4-d]pyrimidin-4-ol;
2-{4-[methyl-(5-morpholin-4-yl-pyridin-3-yl)-amino]-phenoxy}-pyrido[3,4-d]pyrimidin-4-ol;
2-{4-[methyl-(1,2,3,4-tetrahydro-naphthalen-1-ylmethyl)-amino]-phenoxy}-pyrido[3,4-d]pyrimidin-4-ol;
2-(4-{[4-(2-methoxy-1-methyl-ethyl)-phenyl]-methyl-amino}-phenoxy)-pyrido[3,4-d]pyrimidin-4-ol;
3-(4-{[4-(4-hydroxy-pyrido[3,4-d]pyrimidin-2-yloxy)-phenyl]-methyl-amino}-phenyl)-butyronitrile;
2-(1-cyclopentyl-1H-indol-5-yloxy)-pyrido[3,4-d]pyrimidin-4-ol;
2-(1-phenyl-2,3-dihydro-1H-indol-5-yloxy)-pyrido[3,4-d]pyrimidin-4-ol;
2-(1-phenyl-1,2,3,4-tetrahydro-quinolin-6-yloxy)-pyrido[3,4-d]pyrimidin-4-ol;
2-{4-[(5-isopropyl-pyridin-2-yl)-methyl-amino]-phenoxy}-pyrido[3,4-d]pyrimidin-4-ol;
2-{4-[(4-isopropyl-3-morpholin-4-yl-phenyl)-methyl-amino]-phenoxy}-pyrido[3,4-d]pyrimidin-4-ol;
2-(4-{[4-(1-methoxy-ethyl)-phenyl]-methyl-amino}-phenoxy)-pyrido[3,4-d]pyrimidin-4-ol;
2-(4-{[4-(2-amino-1-methyl-ethyl)-phenyl]-methyl-amino}-phenoxy)-pyrido[3,4-d]pyrimidin-4-ol;
2-{4-[(4-{2-[(2-methoxy-ethyl)-methyl-amino]-1-methyl-ethyl}-phenyl)-methyl-amino]-phenoxy}-pyrido[3,4-d]pyrimidin-4-ol;
2-(4-{[4-(1-cyclopropyl-ethyl)-phenyl]-methyl-amino}-phenoxy)-pyrido[3,4-d]pyrimidin-4-ol;
3-{[4-(4-hydroxy-pyrido[3,4-d]pyrimidin-2-yloxy)-phenyl]-methyl-amino}-benzonitrile;
2-(4-{methyl-[3-(4-methyl-piperazin-1-ylmethyl)-phenyl]-amino}-phenoxy)-pyrido[3,4-d]pyrimidin-4-ol;
2-{4-[(4-cyclopropyl-phenyl)-methyl-amino]-phenoxy}-pyrido[3,4-d]pyrimidin-4-ol;
2-[4-[methyl-(5-methylpyridin-2-yl)amino]phenoxy]pyrido[3,4-d]pyrimidin-4-ol;
2-[4-[4-(dimethylamino)-N-methylanilino]phenoxy]pyrido[3,4-d]pyrimidin-4-ol;
4-[3-[4-(4-hydroxypyrido[3,4-d]pyrimidin-2-yl)oxy-N-methylanilino]phenyl]-1-methylpiperazin-2-one;
2-[4-[N-methyl-4-(4-methylpiperazin-1-yl)anilino]phenoxy]pyrido[3,4-d]pyrimidin-4-ol;
2-[4-[3-(dimethylamino)-N-methylanilino]phenoxy]pyrido[3,4-d]pyrimidin-4-ol;
2-[4-(N-methyl-3-pyrrolidin-1-ylanilino)phenoxy]pyrido[3,4-d]pyrimidin-4-ol;
2-[4-(N-methyl-4-pyrrolidin-1-ylanilino)phenoxy]pyrido[3,4-d]pyrimidin-4-ol;
2-[4-[3-(4-aminopiperidin-1-yl)-N-methylanilino]phenoxy]pyrido[3,4-d]pyrimidin-4-ol;
2-[4-[methyl-[(1S)-1-phenylethyl]amino]phenoxy]pyrido[3,4-d]pyrimidin-4-ol;
2-[4-[methyl-[(1R)-1-phenylethyl]amino]phenoxy]pyrido[3,4-d]pyrimidin-4-ol;
2-[4-(3-fluoro-N,4-dimethylanilino)phenoxy]pyrido[3,4-d]pyrimidin-4-ol;
2-[4-(3-phenylpyrrolidin-1-yl)phenoxy]pyrido[3,4-d]pyrimidin-4-ol;
2-[4-(N,4-dimethyl-3-morpholin-4-ylanilino)phenoxy]pyrido[3,4-d]pyrimidin-4-ol;
2-[4-(N-methyl-3-methylsulfonylanilino)phenoxy]pyrido[3,4-d]pyrimidin-4-ol;
2-[4-(N-methyl-4-methylsulfonylanilino)phenoxy]pyrido[3,4-d]pyrimidin-4-ol;
2-[4-[3-(3-aminopiperidin-1-yl)-N-methylanilino]phenoxy]pyrido[3,4-d]pyrimidin-4-ol;
2-[4-(4-ethyl-N-methyl-3-morpholin-4-ylanilino)phenoxy]pyrido[3,4-d]pyrimidin-4-ol;
2-[4-[4-ethyl-N-methyl-3-(4-methylpiperazin-1-yl)anilino]phenoxy]pyrido[3,4-d]pyrimidin-4-ol;
2-[4-[methyl-(2-morpholin-4-ylpyridin-4-yl)amino]phenoxy]pyrido[3,4-d]pyrimidin-4-ol;
2-[4-[2,3-dihydro-1H-inden-1-ylmethyl(methyl)amino]phenoxy]pyrido[3,4-d]pyrimidin-4-ol;
2-[4-[N-methyl-4-(2-methylpropyl)anilino]phenoxy]pyrido[3,4-d]pyrimidin-4-ol;
2-[4-[4-(2-hydroxypropan-2-yl)-N-methylanilino]phenoxy]pyrido[3,4-d]pyrimidin-4-ol;
2-[4-[3-[2-(dimethylamino)ethoxy]-4-ethyl-N-methylanilino]phenoxy]pyrido[3,4-d]pyrimidin-4-ol;
2-[4-[4-ethyl-3-(2-methoxyethoxy)-N-methylanilino]phenoxy]pyrido[3,4-d]pyrimidin-4-ol;
2-[4-[4-(1-methoxy-2-methylpropan-2-yl)-N-methylanilino]phenoxy]pyrido[3,4-d]pyrimidin-4-ol;
2-[4-[4-(1-hydroxy-2-methylpropan-2-yl)-N-methylanilino]phenoxy]pyrido[3,4-d]pyrimidin-4-ol;
2-[4-(N-methyl-4-propylanilino)phenoxy]pyrido[3,4-d]pyrimidin-4-ol;
2-[4-[N-methyl-4-[1-(methylamino)propan-2-yl]anilino]phenoxy]pyrido[3,4-d]pyrimidin-4-ol;
2-[4-[4-(4-aminobutan-2-yl)-N-methylanilino]phenoxy]pyrido[3,4-d]pyrimidin-4-ol;
2-[4-[N-methyl-4-[4-(methylamino)butan-2-yl]anilino]phenoxy]pyrido[3,4-d]pyrimidin-4-ol;
2-[4-[N-methyl-4-(2,2,2-trifluoroethoxy)anilino]phenoxy]pyrido[3,4-d]pyrimidin-4-ol;
2-[4-[N-methyl-4-(2-methylpropoxy)anilino]phenoxy]pyrido[3,4-d]pyrimidin-4-ol;
2-[4-[4-(2,2-dimethylpropoxy)-N-methylanilino]phenoxy]pyrido[3,4-d]pyrimidin-4-ol;
2-[4-[4-(cyclopropylmethyl)-N-methylanilino]phenoxy]pyrido[3,4-d]pyrimidin-4-ol;
2-[4-[4-[(2S)-butan-2-yl]-N-methylanilino]phenoxy]pyrido[3,4-d]pyrimidin-4-ol;
2-[4-[4-[(2R)-butan-2-yl]-N-methylanilino]phenoxy]pyrido[3,4-d]pyrimidin-4-ol;
2-[4-[N-methyl-3-(4-methylpiperazin-1-yl)anilino]phenoxy]pyrido[3,4-d]pyrimidin-4-ol;
2-[4-(N-ethylanilino)phenoxy]pyrido[3,4-d]pyrimidin-4-ol;
4-[4-(4-hydroxypyrido[3,4-d]pyrimidin-2-yl)oxy-N-methylanilino]benzonitrile;
2-[4-[methyl-(2-methylindazol-5-yl)amino]phenoxy]pyrido[3,4-d]pyrimidin-4-ol;

2-[4-(N,3,4-trimethylanilino)phenoxy]pyrido[3,4-d]pyrimidin-4-ol;
2-[4-(4-ethyl-N-methylanilino)phenoxy]pyrido[3,4-d]pyrimidin-4-ol;
2-[4-(N-methyl-4-propan-2-ylanilino)phenoxy]pyrido[3,4-d]pyrimidin-4-ol;
2-[4-[N-methyl-3-(trifluoromethyl)anilino]phenoxy]pyrido[3,4-d]pyrimidin-4-ol;
2-[4-[N-methyl-4-(trifluoromethyl)anilino]phenoxy]pyrido[3,4-d]pyrimidin-4-ol;
2-[4-[N-methyl-3-(4-methyl-1,4-diazepan-1-yl)anilino]phenoxy]pyrido[3,4-d]pyrimidin-4-ol;
2-[4-[N-methyl-3-[methyl-(1-methylpiperidin-4-yl)amino]anilino]phenoxy]pyrido[3,4-d]pyrimidin-4-ol;
2-[4-[N,3-dimethyl-5-(4-methylpiperazin-1-yl)anilino]phenoxy]pyrido[3,4-d]pyrimidin-4-ol;
2-[1-(oxan-4-yl)indol-5-yl]oxypyrido[3,4-d]pyrimidin-4-ol;
2-[4-(4-tert-butyl-N-methylanilino)phenoxy]pyrido[3,4-d]pyrimidin-4-ol;
2-[4-(N-methyl-3-propan-2-ylanilino)phenoxy]pyrido[3,4-d]pyrimidin-4-ol;
2-[4-(4-chloro-N-methylanilino)phenoxy]pyrido[3,4-d]pyrimidin-4-ol;
2-[4-(3-chloro-N-methylanilino)phenoxy]pyrido[3,4-d]pyrimidin-4-ol;
2-[4-(3-fluoro-N-methylanilino)phenoxy]pyrido[3,4-d]pyrimidin-4-ol;
2-[4-[(5-ethylpyridin-2-yl)-methylamino]phenoxy]pyrido[3,4-d]pyrimidin-4-ol;
2-[4-[4-(3,6-dihydro-2H-pyran-4-yl)-N-methylanilino]phenoxy]pyrido[3,4-d]pyrimidin-4-ol;
2-[4-[N-methyl-4-(oxan-4-yl)anilino]phenoxy]pyrido[3,4-d]pyrimidin-4-ol;
2-[4-[4-[1-(2-methoxyethylamino)propan-2-yl]-N-methylanilino]phenoxy]pyrido[3,4-d]pyrimidin-4-ol;
2-[4-[4-(cyclopropylmethoxy)-N-methylanilino]phenoxy]pyrido[3,4-d]pyrimidin-4-ol;
2-[4-[N-(2-methoxyethyl)-4-propan-2-ylanilino]phenoxy]pyrido[3,4-d]pyrimidin-4-ol;
2-(1-phenylindol-5-yl)oxypyrido[3,4-d]pyrimidin-4-ol;
2-(1-piperidin-4-ylindol-5-yl)oxypyrido[3,4-d]pyrimidin-4-ol;
2-[4-[N,4-dimethyl-3-(4-methylpiperazin-1-yl)anilino]phenoxy]pyrido[3,4-d]pyrimidin-4-ol;
2-[4-[N-methyl-4-(2,2,2-trifluoroethyl)anilino]phenoxy]pyrido[3,4-d]pyrimidin-4-ol;
2-[4-[N-methyl-4-[1-(trifluoromethyl)cyclopropyl]anilino]phenoxy]pyrido[3,4-d]pyrimidin-4-ol;
2-[4-[N-methyl-4-(1,1,1-trifluoropropan-2-yl)anilino]phenoxy]pyrido[3,4-d]pyrimidin-4-ol;
2-[4-[methyl-(6-propan-2-ylpyridin-3-yl)amino]phenoxy]pyrido[3,4-d]pyrimidin-4-ol;
2-[4-[N-methyl-4-(trifluoromethoxy)anilino]phenoxy]pyrido[3,4-d]pyrimidin-4-ol;
2-[4-(N-methyl-4-propan-2-yloxyanilino)phenoxy]pyrido[3,4-d]pyrimidin-4-ol;
2-[4-[N-(oxolan-3-yl)-4-propan-2-ylanilino]phenoxy]pyrido[3,4-d]pyrimidin-4-ol;
2-[4-(N-cyclobutyl-4-propan-2-ylanilino)phenoxy]pyrido[3,4-d]pyrimidin-4-ol;
2-{4-[(4-isopropyl-phenyl)-(2,2,2-trifluoro-ethyl)-amino]-phenoxy}-pyrido[3,4-d]pyrimidin-4-ol;
2-(4-{[4-(3-dimethylamino-1-methyl-propyl)-phenyl]-methyl-amino}-phenoxy)-pyrido[3,4-d]pyrimidin-4-ol;
(3,3-dimethyl-2,3-dihydro-benzofuran-6-yl)-methyl-[4-(4-methyl-pyrido; [3,4-d]pyrimidin-2-yloxy)-phenyl]-amine;
2-(4-(ethyl(4-isopropylphenyl)amino)phenoxy)pyrido[3,4-d]pyrimidin-4-ol; and
2-(4-((4-isopropylphenyl)(tetrahydro-2H-pyran-4-yl)amino)phenoxy)pyrido[3,4-d]pyrimidin-4-ol.

In some embodiments, the compound disclosed herein has a structure provided in Table 1.

TABLE 1

| Ex | Structure | Name |
| --- | --- | --- |
| 1 | 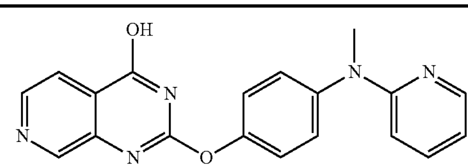 | 2-[4-(methyl-pyridin-2-yl-amino)-phenoxy]-pyrido[3,4-d]pyrimidin-4-ol |
| 2 | 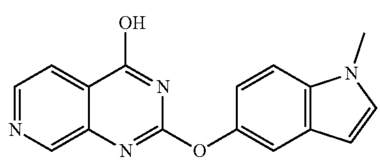 [SMILES: Cn1ccc2cc(Oc3nc(O)c4ccncc4n3)ccc21] | 2-(1-methyl-1H-indol-5-yloxy)-pyrido[3,4-d]pyrimidin-4-ol |
| 3 | 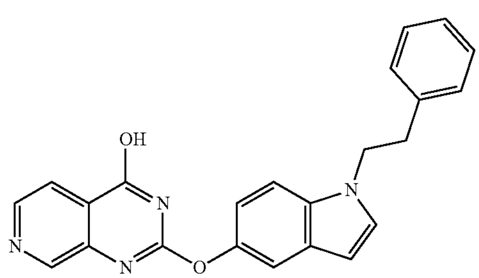 [SMILES: Oc1nc(Oc2ccc3c(ccn3CCc3ccccc3)c2)nc2cnccc12] | 2-(1-phenethyl-1H-indol-5-yloxy)-pyrido[3,4-d]pyrimidin-4-ol |

TABLE 1-continued

| Ex | Structure | Name |
|---|---|---|
| 4 | 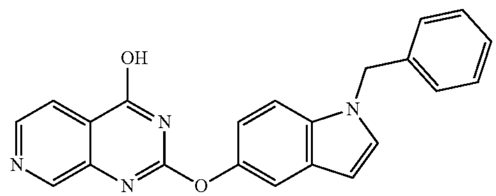 [SMILES: Oc1nc(Oc2ccc3c(ccn3Cc3ccccc3)c2)nc2cnccc12] | 2-(1-benzyl-1H-indol-5-yloxy)-pyrido[3,4-d]pyrimidin-4-ol |
| 5 | 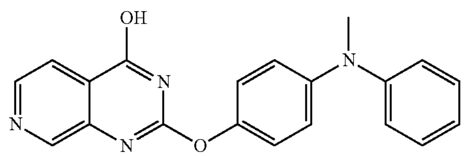 [SMILES: CN(c1ccccc1)c1ccc(Oc2nc(O)c3ccncc3n2)cc1] | 2-[4-(methyl-phenyl-amino)-phenoxy]-pyrido[3,4-d]pyrimidin-4-ol |
| 6 | 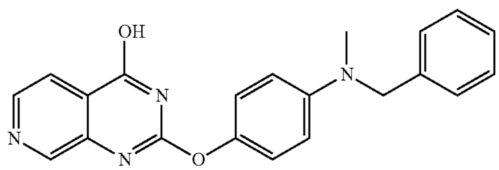 [SMILES: CN(Cc1ccccc1)c1ccc(Oc2nc(O)c3ccncc3n2)cc1] | 2-[4-(benzyl-methyl-amino)-phenoxy]-pyrido[3,4-d]pyrimidin-4-ol |
| 7 | 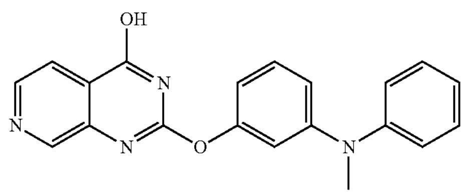 [SMILES: CN(c1ccccc1)c1cccc(Oc2nc(O)c3ccncc3n2)c1] | 2-[3-(methyl-phenyl-amino)-phenoxy]-pyrido[3,4-d]pyrimidin-4-ol |
| 8 | 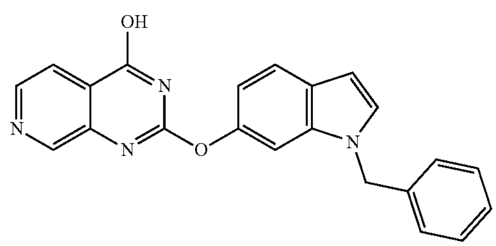 [SMILES: Oc1nc(Oc2ccc3ccn(Cc4ccccc4)c3c2)nc2cnccc12] | 2-(1-benzyl-1H-indol-6-yloxy)-pyrido[3,4-d]pyrimidin-4-ol |
| 9 | 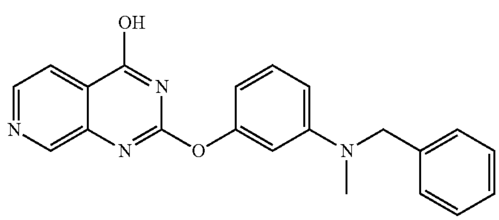 [SMILES: CN(Cc1ccccc1)c1cccc(Oc2nc(O)c3ccncc3n2)c1] | 2-[3-(benzyl-methyl-amino)-phenoxy]-pyrido[3,4-d]pyrimidin-4-ol |
| 10 | 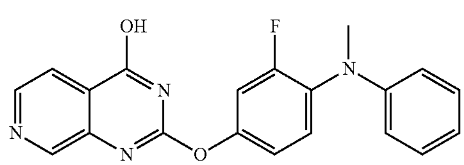 [SMILES: CN(c1ccccc1)c1ccc(Oc2nc(O)c3ccncc3n2)cc1F] | 2-[3-fluoro-4-(methyl-phenyl-amino)-phenoxy]-pyrido[3,4-d]pyrimidin-4-ol |
| 11 | 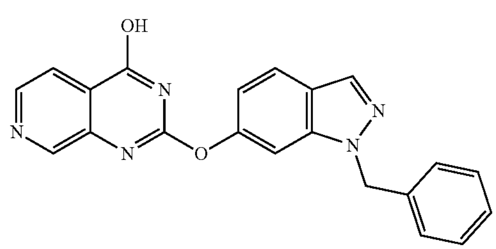 [SMILES: Oc1nc(Oc2ccc3cnn(Cc4ccccc4)c3c2)nc2cnccc12] | 2-(1-benzyl-1H-indazol-6-yloxy)-pyrido[3,4-d]pyrimidin-4-ol |

TABLE 1-continued

| Ex | Structure | Name |
|---|---|---|
| 12 | 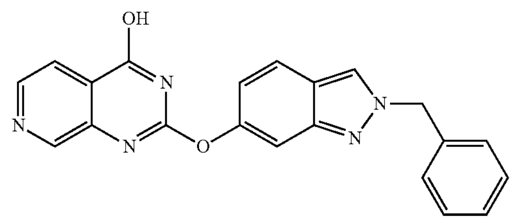 [SMILES: Oc1nc(Oc2ccc3cn(Cc4ccccc4)nc3c2)nc2cnccc12] | 2-(2-benzyl-2H-indazol-6-yloxy)-pyrido[3,4-d]pyrimidin-4-ol |
| 13 | 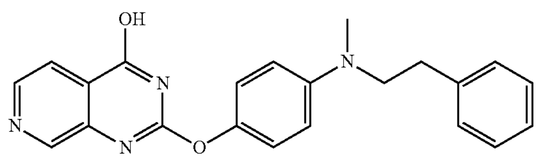 [SMILES: CN(CCc1ccccc1)c1ccc(Oc2nc(O)c3ccncc3n2)cc1] | 2-{4-[methyl(2-phenylethyl)amino]phenoxy}pyridino[3,4-d]pyrimidin-4-ol |
| 14 | 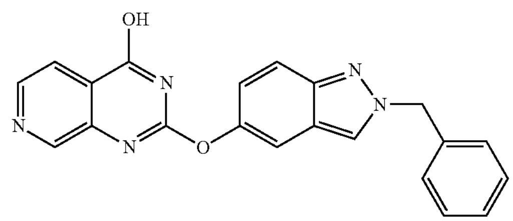 [SMILES: Oc1nc(Oc2ccc3nn(Cc4ccccc4)cc3c2)nc2cnccc12] | 2-[2-benzyl-2H-indazol-5-yloxy]pyridino[3,4-d]pyrimidin-4-ol |
| 15 | 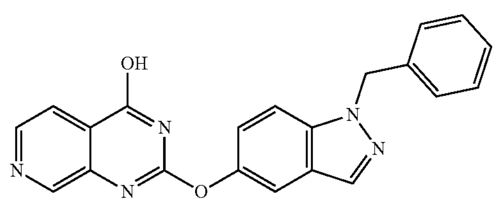 [SMILES: Oc1nc(Oc2ccc3c(cnn3Cc3ccccc3)c2)nc2cnccc12] | 2-(1-benzyl-1H-indazol-5-yloxy)-pyridino[3,4-d]pyrimidin-4-ol |
| 16 | 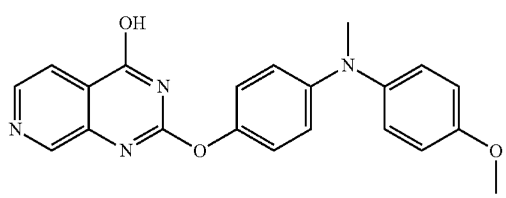 [SMILES: COc1ccc(N(C)c2ccc(Oc3nc(O)c4ccncc4n3)cc2)cc1] | 2-{4-[(4-methoxy-phenyl)-methyl-amino]-phenoxy}-pyrido[3,4-d]pyrimidin-4-ol |
| 17 | 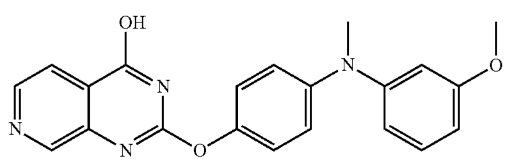 [SMILES: COc1cccc(N(C)c2ccc(Oc3nc(O)c4ccncc4n3)cc2)c1] | 2-{4-[(3-methoxy-phenyl)-methyl-amino]-phenoxy}-pyrido[3,4-d]pyrimidin-4-ol |
| 18 | 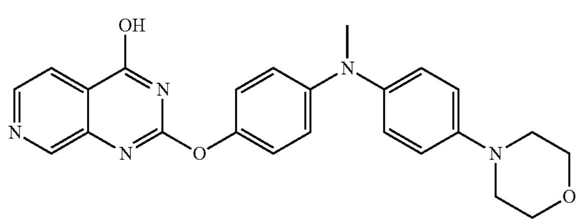 [SMILES: CN(c1ccc(Oc2nc(O)c3ccncc3n2)cc1)c1ccc(N2CCOCC2)cc1] | 2-{4-[methyl-(4-morpholin-4-yl-phenyl)-amino]-phenoxy}-pyrido[3,4-d]pyrimidin-4-ol |
| 19 | 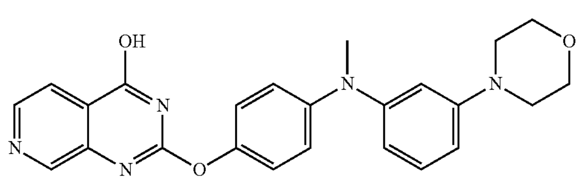 [SMILES: CN(c1ccc(Oc2nc(O)c3ccncc3n2)cc1)c1cccc(N2CCOCC2)c1] | 2-{4-[methyl-(3-morpholin-4-yl-phenyl)-amino]-phenoxy}-pyrido[3,4-d]pyrimidin-4-ol |

TABLE 1-continued

| Ex | Structure | Name |
|---|---|---|
| 20 | 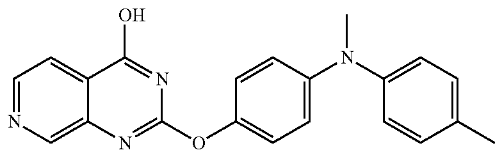 [SMILES: Cc1ccc(N(C)c2ccc(Oc3nc(O)c4ccncc4n3)cc2)cc1] | 2-[4-(methyl-p-tolyl-amino)-phenoxy]-pyrido[3,4-d]pyrimidin-4-ol |
| 21 | 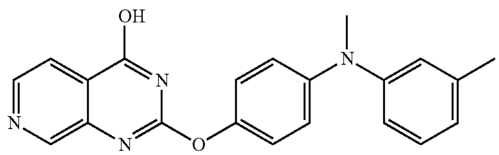 [SMILES: Cc1cccc(N(C)c2ccc(Oc3nc(O)c4ccncc4n3)cc2)c1] | 2-[4-(methyl-m-tolyl-amino)-phenoxy]-pyrido[3,4-d]pyrimidin-4-ol |
| 22 | 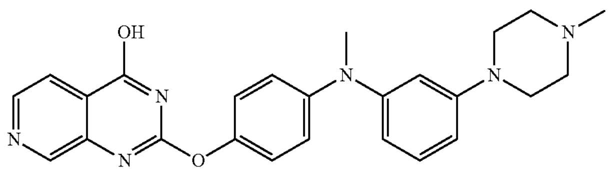 [SMILES: CN1CCN(c2cccc(N(C)c3ccc(Oc4nc(O)c5ccncc5n4)cc3)c2)CC1] | 2-(4-{methyl-[3-(4-methyl-piperazin-1-yl)-phenyl]-amino}-phenoxy)-pyrido[3,4-d]pyrimidin-4-ol |
| 23 | 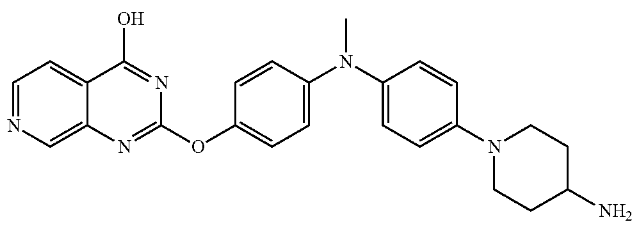 [SMILES: CN(c1ccc(Oc2nc(O)c3ccncc3n2)cc1)c1ccc(N2CCC(N)CC2)cc1] | 2-(4-{[4-(4-amino-piperidin-1-yl)-phenyl]-methyl-amino}-phenoxy)-pyrido[3,4-d]pyrimidin-4-ol |
| 24 | 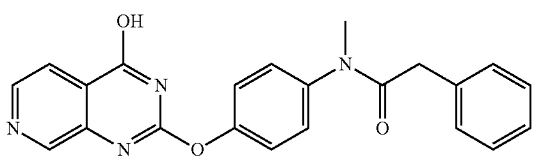 [SMILES: CN(C(=O)Cc1ccccc1)c1ccc(Oc2nc(O)c3ccncc3n2)cc1] | N-[4-(4-hydroxy-pyrido[3,4-d]pyrimidin-2-yloxy)-phenyl]-N-methyl-2-phenyl-acetamide |
| 25 | 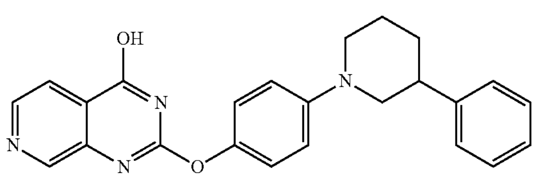 [SMILES: Oc1nc(Oc2ccc(N3CCCC(c4ccccc4)C3)cc2)nc2cnccc12] | 2-[4-(3-phenyl-piperidin-1-yl)-phenoxy]-pyrido[3,4-d]pyrimidin-4-ol |
| 26 | 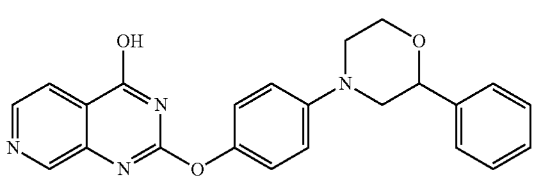 | 2-[4-(2-phenyl-morpholin-4-yl)-phenoxy]-pyrido[3,4-d]pyrimidin-4-ol |
| 27 | 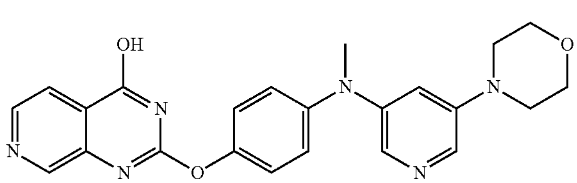 [SMILES: CN(c1ccc(Oc2nc(O)c3ccncc3n2)cc1)c1cncc(N2CCOCC2)c1] | 2-{4-[methyl-(5-morpholin-4-yl-pyridin-3-yl)-amino]-phenoxy}-pyrido[3,4-d]pyrimidin-4-ol |

TABLE 1-continued

| Ex | Structure | Name |
|---|---|---|
| 28 | 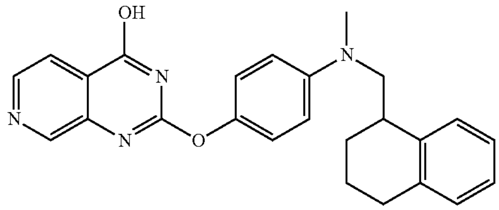 [SMILES: CN(CC1CCCc2ccccc21)c1ccc(Oc2nc(O)c3ccncc3n2)cc1] | 2-{4-[methyl-(1,2,3,4-tetrahydro-naphthalen-1-ylmethyl)-amino]-phenoxy}-pyrido[3,4-d]pyrimidin-4-ol |
| 29 | 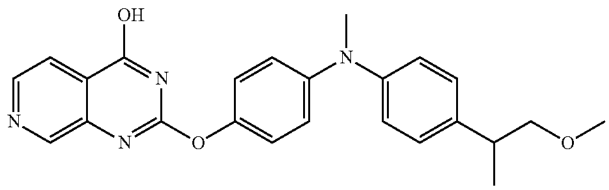 [SMILES: COCC(C)c1ccc(N(C)c2ccc(Oc3nc(O)c4ccncc4n3)cc2)cc1] | 2-(4-{[4-(2-methoxy-1-methyl-ethyl)-phenyl]-methyl-amino}-phenoxy)-pyrido[3,4-d]pyrimidin-4-ol |
| 30 | 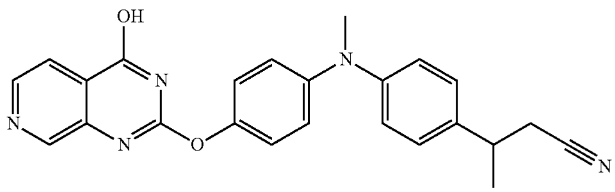 [SMILES: CC(CC#N)c1ccc(N(C)c2ccc(Oc3nc(O)c4ccncc4n3)cc2)cc1] | 3-(4-{[4-(4-hydroxy-pyrido[3,4-d]pyrimidin-2-yloxy)-phenyl]-methyl-amino}-phenyl)-butyronitrile |
| 31 | 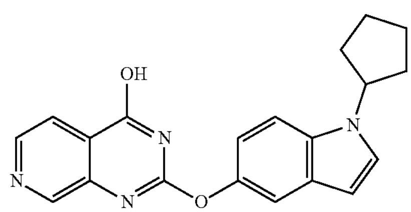 [SMILES: Oc1nc(Oc2ccc3c(ccn3C3CCCC3)c2)nc2cnccc12] | 2-(1-cyclopentyl-1H-indol-5-yloxy)-pyrido[3,4-d]pyrimidin-4-ol |
| 32 | 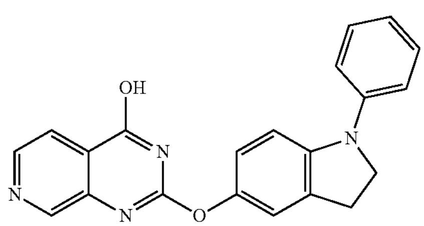 [SMILES: Oc1nc(Oc2ccc3c(c2)CCN3c2ccccc2)nc2cnccc12] | 2-(1-phenyl-2,3-dihydro-1H-indol-5-yloxy)-pyrido[3,4-d]pyrimidin-4-ol |
| 33 | 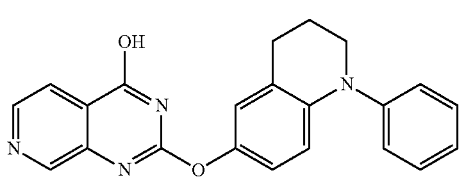 [SMILES: Oc1nc(Oc2ccc3c(c2)CCCN3c2ccccc2)nc2cnccc12] | 2-(1-phenyl-1,2,3,4-tetrahydro-quinolin-6-yloxy)-pyrido[3,4-d]pyrimidin-4-ol |

TABLE 1-continued

| Ex | Structure | Name |
|---|---|---|
| 34 | 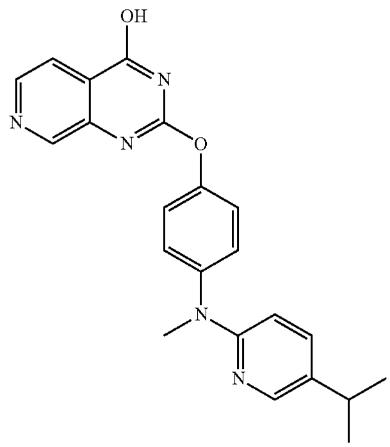 [SMILES: CC(C)c1ccc(N(C)c2ccc(Oc3nc(O)c4ccncc4n3)cc2)nc1] | 2-{4-[(5-isopropyl-pyridin-2-yl)-methyl-amino]-phenoxy}-pyrido[3,4-d]pyrimidin-4-ol |
| 35 | 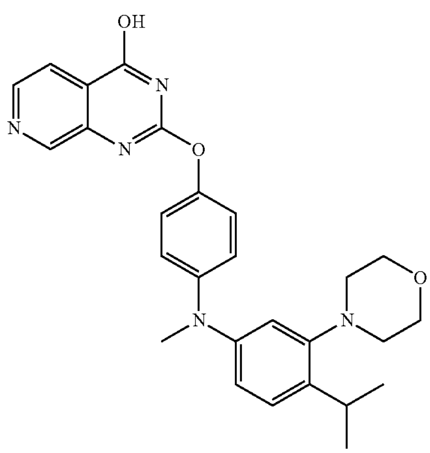 [SMILES: CC(C)c1ccc(N(C)c2ccc(Oc3nc(O)c4ccncc4n3)cc2)cc1N1CCOCC1] | 2-{4-[(4-isopropyl-3-morpholin-4-yl-phenyl)-methyl-amino]-phenoxy}-pyrido[3,4-d]pyrimidin-4-ol |
| 36 | 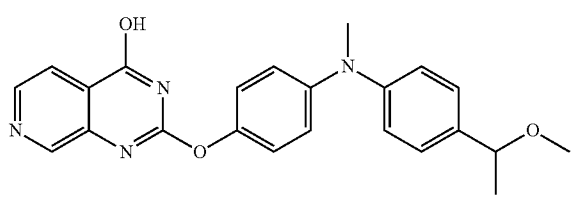 [SMILES: COC(C)c1ccc(N(C)c2ccc(Oc3nc(O)c4ccncc4n3)cc2)cc1] | 2-(4-{[4-(1-methoxy-ethyl)-phenyl]-methyl-amino}-phenoxy)-pyrido[3,4-d]pyrimidin-4-ol |
| 37 | 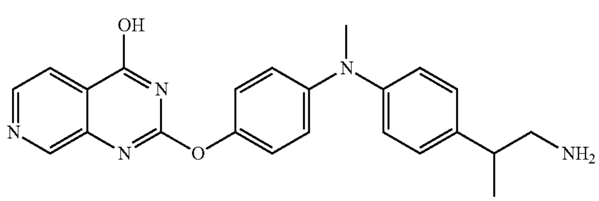 [SMILES: CC(CN)c1ccc(N(C)c2ccc(Oc3nc(O)c4ccncc4n3)cc2)cc1] | 2-(4-{[4-(2-amino-1-methyl-ethyl)-phenyl]-methyl-amino}-phenoxy)-pyrido[3,4-d]pyrimidin-4-ol |
| 38 | 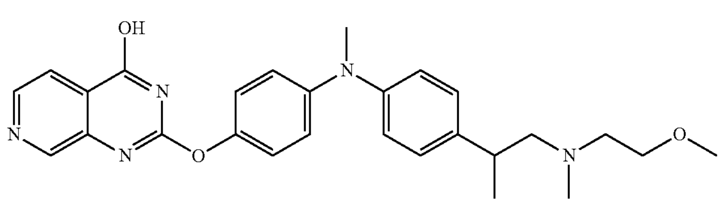 [SMILES: COCCN(C)CC(C)c1ccc(N(C)c2ccc(Oc3nc(O)c4ccncc4n3)cc2)cc1] | 2-{4-[(4-{2-[(2-methoxy-ethyl)-methyl-amino]-1-methyl-ethyl}-phenyl)-methyl-amino]-phenoxy}-pyrido[3,4-d]pyrimidin-4-ol |

TABLE 1-continued

| Ex | Structure | Name |
|---|---|---|
| 39 | 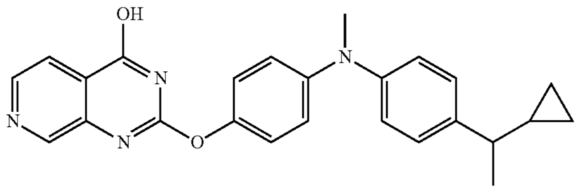 [SMILES: CC(c1ccc(N(C)c2ccc(Oc3nc(O)c4ccncc4n3)cc2)cc1)C1CC1] | 2-(4-{[4-(1-cyclopropyl-ethyl)-phenyl]-methyl-amino}-phenoxy)-pyrido[3,4-d]pyrimidin-4-ol |
| 40 | 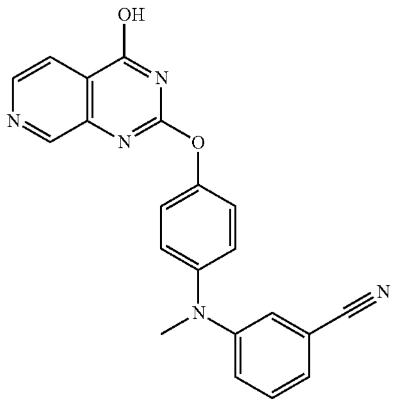 [SMILES: CN(c1ccc(Oc2nc(O)c3ccncc3n2)cc1)c1cccc(C#N)c1] | 3-{[4-(4-hydroxy-pyrido[3,4-d]pyrimidin-2-yloxy)-phenyl]-methyl-amino}-benzonitrile |
| 41 | 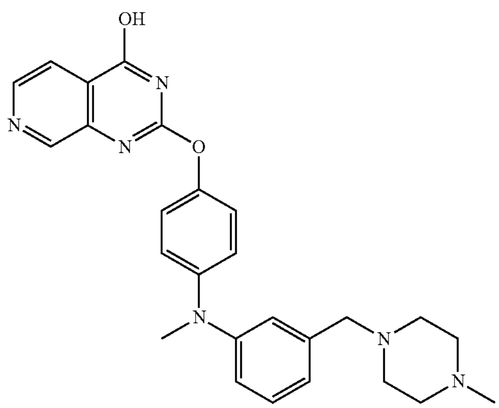 [SMILES: CN1CCN(Cc2cccc(N(C)c3ccc(Oc4nc(O)c5ccncc5n4)cc3)c2)CC1] | 2-(4-{methyl-[3-(4-methyl-piperazin-1-ylmethyl)-phenyl]-amino}-phenoxy)-pyrido[3,4-d]pyrimidin-4-ol |
| 42 | 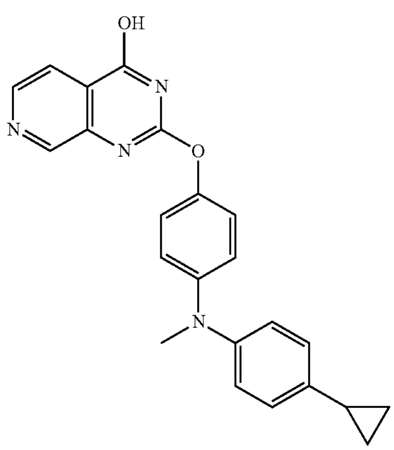 [SMILES: CN(c1ccc(Oc2nc(O)c3ccncc3n2)cc1)c1ccc(C2CC2)cc1] | 2-{4-[(4-cyclopropyl-phenyl)-methyl-amino]-phenoxy}-pyrido[3,4-d]pyrimidin-4-ol |
| 43 | 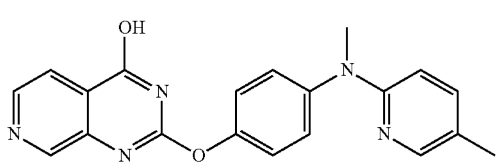 [SMILES: Cc1ccc(N(C)c2ccc(Oc3nc(O)c4ccncc4n3)cc2)nc1] | 2-[4-[methyl-(5-methylpyridin-2-yl)amino]phenoxy]pyrido[3,4-d]pyrimidin-4-ol |

TABLE 1-continued

| Ex | Structure | Name |
|---|---|---|
| 44 | 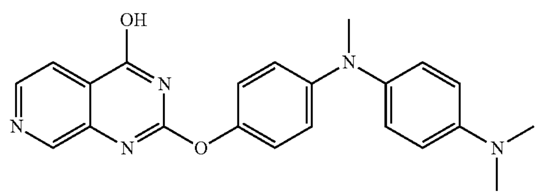 [SMILES: CN(C)c1ccc(N(C)c2ccc(Oc3nc(O)c4ccncc4n3)cc2)cc1] | 2-[4-[4-(dimethylamino)-N-methylanilino]phenoxy]pyrido[3,4-d]pyrimidin-4-ol |
| 45 | 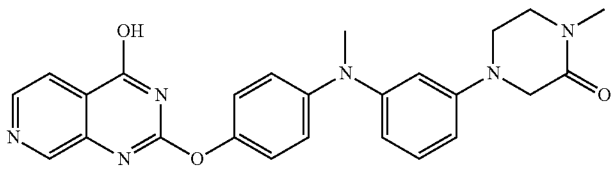 [SMILES: CN1CCN(c2cccc(N(C)c3ccc(Oc4nc(O)c5ccncc5n4)cc3)c2)CC1=O] | 4-[3-[4-(4-hydroxypyrido[3,4-d]pyrimidin-2-yl)oxy-N-methylanilino]phenyl]-1-methylpiperazin-2-one |
| 46 | 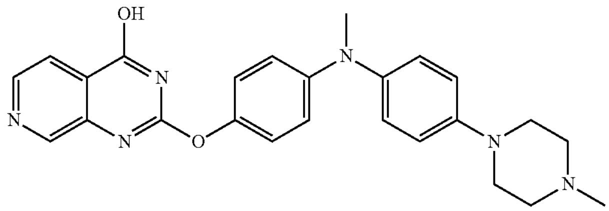 [SMILES: CN1CCN(c2ccc(N(C)c3ccc(Oc4nc(O)c5ccncc5n4)cc3)cc2)CC1] | 2-[4-[N-methyl-4-(4-methylpiperazin-1-yl)anilino]phenoxy]pyrido[3,4-d]pyrimidin-4-ol |
| 47 | 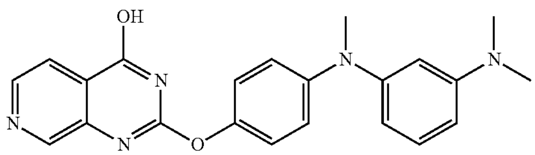 [SMILES: CN(C)c1cccc(N(C)c2ccc(Oc3nc(O)c4ccncc4n3)cc2)c1] | 2-[4-[3-(dimethylamino)-N-methylanilino]phenoxy]pyrido[3,4-d]pyrimidin-4-ol |
| 48 | 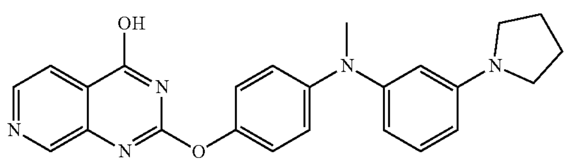 [SMILES: CN(c1ccc(Oc2nc(O)c3ccncc3n2)cc1)c1cccc(N2CCCC2)c1] | 2-[4-(N-methyl-3-pyrrolidin-1-ylanilino)phenoxy]pyrido[3,4-d]pyrimidin-4-ol |
| 49 | 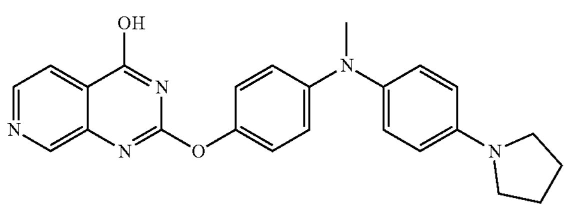 [SMILES: CN(c1ccc(Oc2nc(O)c3ccncc3n2)cc1)c1ccc(N2CCCC2)cc1] | 2-[4-(N-methyl-4-pyrrolidin-1-ylanilino)phenoxy]pyrido[3,4-d]pyrimidin-4-ol |
| 50 | 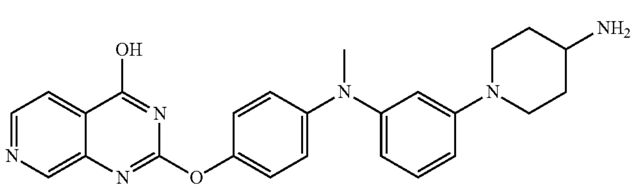 [SMILES: CN(c1ccc(Oc2nc(O)c3ccncc3n2)cc1)c1cccc(N2CCC(N)CC2)c1] | 2-[4-[3-(4-aminopiperidin-1-yl)-N-methylanilino]phenoxy]pyrido[3,4-d]pyrimidin-4-ol |
| 51 | 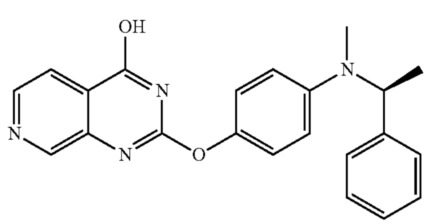 [SMILES: C[C@@H](c1ccccc1)N(C)c1ccc(Oc2nc(O)c3ccncc3n2)cc1] | 2-[4-[methyl-[(1S)-1-phenylethyl]amino]phenoxy]pyrido[3,4-d]pyrimidin-4-ol |

TABLE 1-continued

| Ex | Structure | Name |
| --- | --- | --- |
| 52 | 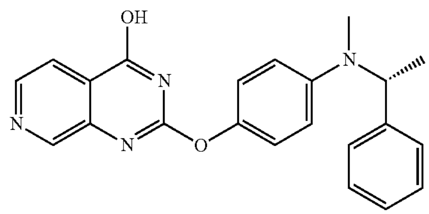 [SMILES: C[C@H](c1ccccc1)N(C)c1ccc(Oc2nc(O)c3ccncc3n2)cc1] | 2-[4-[methyl-[(1R)-1-phenylethyl]amino]phenoxy]pyrido[3,4-d]pyrimidin-4-ol |
| 53 | 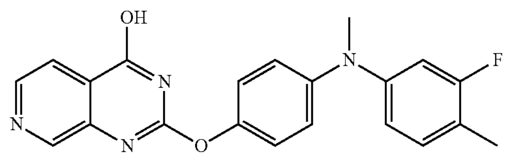 [SMILES: Cc1ccc(N(C)c2ccc(Oc3nc(O)c4ccncc4n3)cc2)cc1F] | 2-[4-(3-fluoro-N,4-dimethylanilino)phenoxy]pyrido[3,4-d]pyrimidin-4-ol |
| 54 | 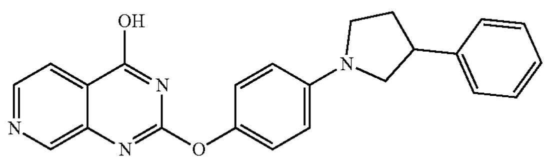 [SMILES: Oc1nc(Oc2ccc(N3CCC(c4ccccc4)C3)cc2)nc2cnccc12] | 2-[4-(3-phenylpyrrolidin-1-yl)phenoxy]pyrido[3,4-d]pyrimidin-4-ol |
| 55 | 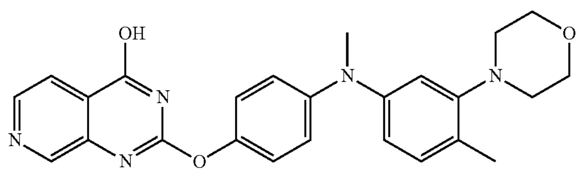 [SMILES: Cc1ccc(N(C)c2ccc(Oc3nc(O)c4ccncc4n3)cc2)cc1N1CCOCC1] | 2-[4-(N,4-dimethyl-3-morpholin-4-ylanilino)phenoxy]pyrido[3,4-d]pyrimidin-4-ol |
| 56 | 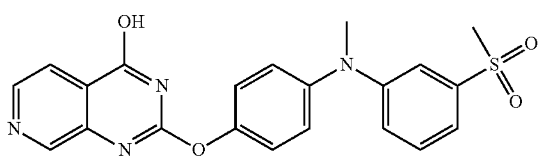 [SMILES: CN(c1ccc(Oc2nc(O)c3ccncc3n2)cc1)c1cccc(S(C)(=O)=O)c1] | 2-[4-(N-methyl-3-methylsulfonylanilino)phenoxy]pyrido[3,4-d]pyrimidin-4-ol |
| 57 | 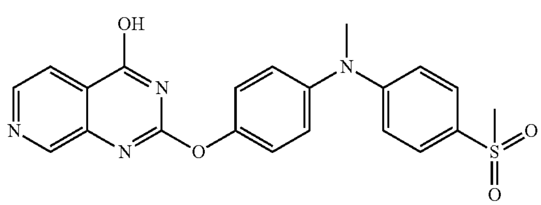 [SMILES: CN(c1ccc(Oc2nc(O)c3ccncc3n2)cc1)c1ccc(S(C)(=O)=O)cc1] | 2-[4-(N-methyl-4-methylsulfonylanilino)phenoxy]pyrido[3,4-d]pyrimidin-4-ol |
| 58 | 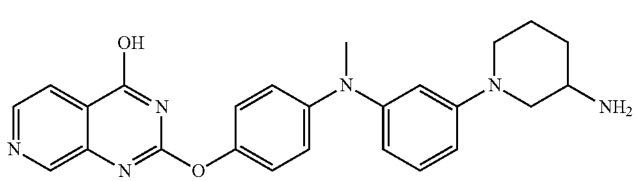 [SMILES: CN(c1ccc(Oc2nc(O)c3ccncc3n2)cc1)c1cccc(N2CCCC(N)C2)c1] | 2-[4-[3-(3-aminopiperidin-1-yl)-N-methylanilino]phenoxy]pyrido[3,4-d]pyrimidin-4-ol |
| 59 | 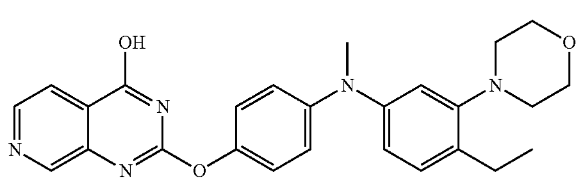 [SMILES: CCc1ccc(N(C)c2ccc(Oc3nc(O)c4ccncc4n3)cc2)cc1N1CCOCC1] | 2-[4-(4-ethyl-N-methyl-3-morpholin-4-ylanilino)phenoxy]pyrido[3,4-d]pyrimidin-4-ol |

TABLE 1-continued

| Ex | Structure | Name |
|---|---|---|
| 60 | 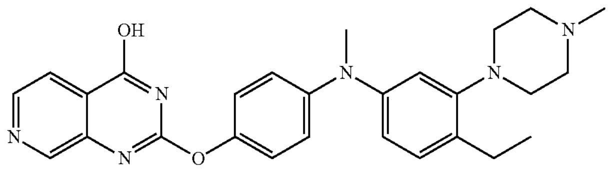 [SMILES: CCc1ccc(N(C)c2ccc(Oc3nc(O)c4ccncc4n3)cc2)cc1N1CCN(C)CC1] | 2-[4-[4-ethyl-N-methyl-3-(4-methylpiperazin-1-yl)anilino]phenoxy]pyrido[3,4-d]pyrimidin-4-ol |
| 61 | 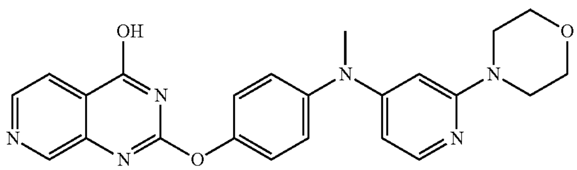 [SMILES: CN(c1ccc(Oc2nc(O)c3ccncc3n2)cc1)c1ccnc(N2CCOCC2)c1] | 2-[4-[methyl-(2-morpholin-4-ylpyridin-4-yl)amino]phenoxy]pyrido[3,4-d]pyrimidin-4-ol |
| 62 | 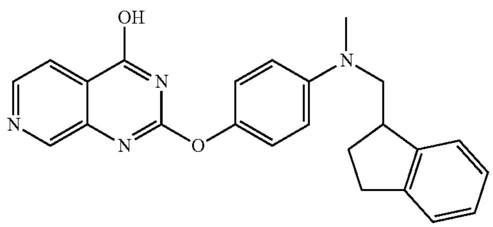 [SMILES: CN(CC1CCc2ccccc21)c1ccc(Oc2nc(O)c3ccncc3n2)cc1] | 2-[4-[2,3-dihydro-1H-inden-1-ylmethyl(methyl)amino]phenoxy]pyrido[3,4-d]pyrimidin-4-ol |
| 63 | 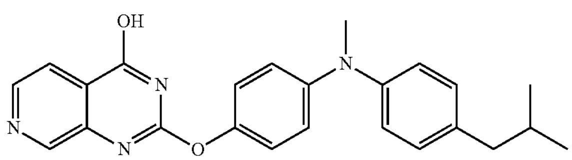 [SMILES: CC(C)Cc1ccc(N(C)c2ccc(Oc3nc(O)c4ccncc4n3)cc2)cc1] | 2-[4-[N-methyl-4-(2-methylpropyl)anilino]phenoxy]pyrido[3,4-d]pyrimidin-4-ol |
| 64 | 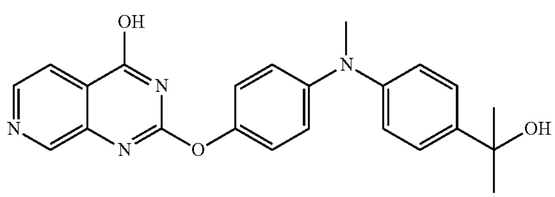 [SMILES: CN(c1ccc(Oc2nc(O)c3ccncc3n2)cc1)c1ccc(C(C)(C)O)cc1] | 2-[4-[4-(2-hydroxypropan-2-yl)-N-methylanilino]phenoxy]pyrido[3,4-d]pyrimidin-4-ol |
| 65 | 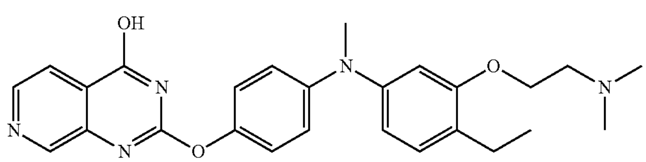 [SMILES: CCc1ccc(N(C)c2ccc(Oc3nc(O)c4ccncc4n3)cc2)cc1OCCN(C)C] | 2-[4-[3-[2-(dimethylamino)ethoxy]-4-ethyl-N-methylanilino]phenoxy]pyrido[3,4-d]pyrimidin-4-ol |
| 66 | 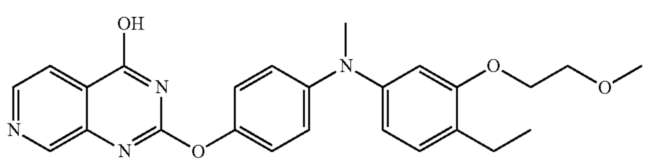 [SMILES: CCc1ccc(N(C)c2ccc(Oc3nc(O)c4ccncc4n3)cc2)cc1OCCOC] | 2-[4-[4-ethyl-3-(2-methoxyethoxy)-N-methylanilino]phenoxy]pyrido[3,4-d]pyrimidin-4-ol |
| 67 | 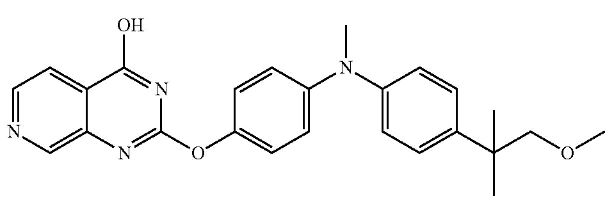 [SMILES: COCC(C)(C)c1ccc(N(C)c2ccc(Oc3nc(O)c4ccncc4n3)cc2)cc1] | 2-[4-[4-(1-methoxy-2-methylpropan-2-yl)-N-methylanilino]phenoxy]pyrido[3,4-d]pyrimidin-4-ol |

TABLE 1-continued

| Ex | Structure | Name |
|---|---|---|
| 68 | 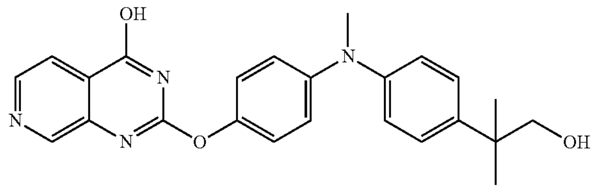 [SMILES: CN(c1ccc(Oc2nc(O)c3ccncc3n2)cc1)c1ccc(C(C)(C)CO)cc1] | 2-[4-[4-(1-hydroxy-2-methylpropan-2-yl)-N-methylanilino]phenoxy]pyrido[3,4-d]pyrimidin-4-ol |
| 69 | 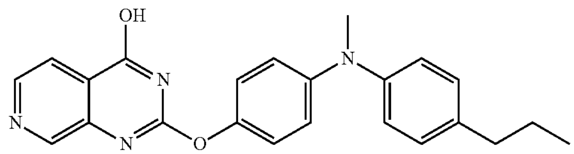 [SMILES: CCCc1ccc(N(C)c2ccc(Oc3nc(O)c4ccncc4n3)cc2)cc1] | 2-[4-(N-methyl-4-propylanilino)phenoxy]pyrido[3,4-d]pyrimidin-4-ol |
| 70 | 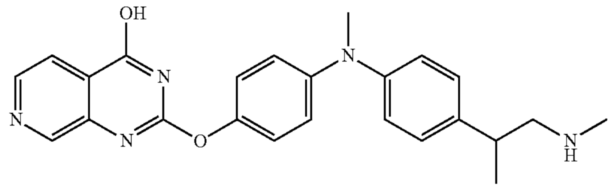 | 2-[4-[N-methyl-4-[1-(methylamino)propan-2-yl]anilino]phenoxy]pyrido[3,4-d]pyrimidin-4-ol |
| 71 | 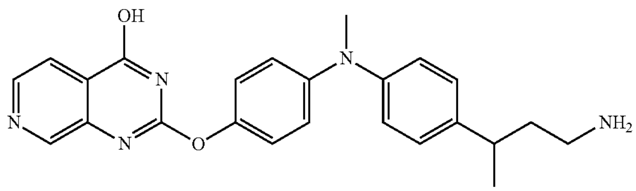 [SMILES: CC(CCN)c1ccc(N(C)c2ccc(Oc3nc(O)c4ccncc4n3)cc2)cc1] | 2-[4-[4-(4-aminobutan-2-yl)-N-methylanilino]phenoxy]pyrido[3,4-d]pyrimidin-4-ol |
| 72 | 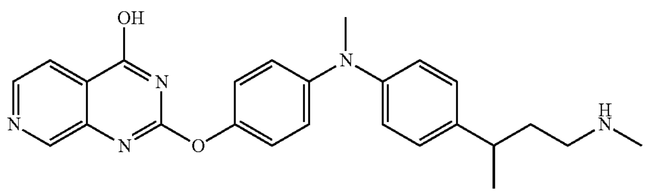 [SMILES: CNCCC(C)c1ccc(N(C)c2ccc(Oc3nc(O)c4ccncc4n3)cc2)cc1] | 2-[4-[N-methyl-4-[4-(methylamino)butan-2-yl]anilino]phenoxy]pyrido[3,4-d]pyrimidin-4-ol |
| 73 | 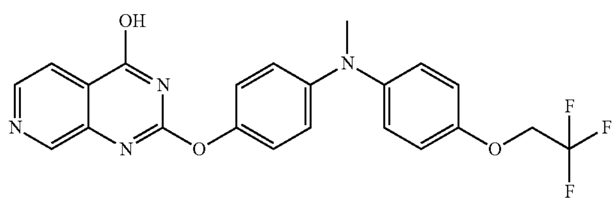 [SMILES: CN(c1ccc(OCC(F)(F)F)cc1)c1ccc(Oc2nc(O)c3ccncc3n2)cc1] | 2-[4-[N-methyl-4-(2,2,2-trifluoroethoxy)anilino]phenoxy]pyrido[3,4-d]pyrimidin-4-ol |
| 74 | 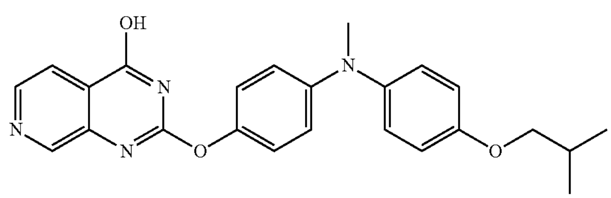 [SMILES: CC(C)COc1ccc(N(C)c2ccc(Oc3nc(O)c4ccncc4n3)cc2)cc1] | 2-[4-[N-methyl-4-(2-methylpropoxy)anilino]phenoxy]pyrido[3,4-d]pyrimidin-4-ol |
| 75 | 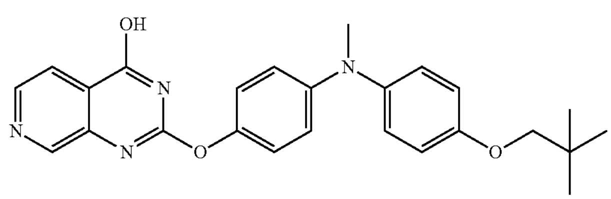 [SMILES: CN(c1ccc(OCC(C)(C)C)cc1)c1ccc(Oc2nc(O)c3ccncc3n2)cc1] | 2-[4-[4-(2,2-dimethylpropoxy)-N-methylanilino]phenoxy]pyrido[3,4-d]pyrimidin-4-ol |

TABLE 1-continued

| Ex | Structure | Name |
|---|---|---|
| 76 | 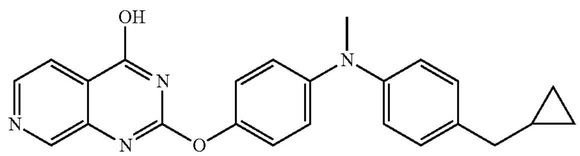 [SMILES: CN(c1ccc(CC2CC2)cc1)c1ccc(Oc2nc(O)c3ccncc3n2)cc1] | 2-[4-[4-(cyclopropylmethyl)-N-methylanilino]phenoxy]pyrido[3,4-d]pyrimidin-4-ol |
| 77 | 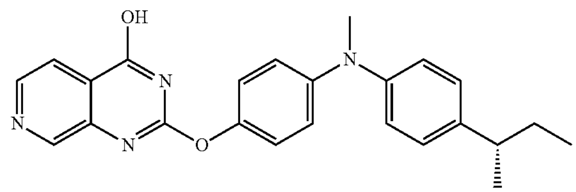 | 2-[4-[4-[(2S)-butan-2-yl]-N-methylanilino]phenoxy]pyrido[3,4-d]pyrimidin-4-ol |
| 78 | 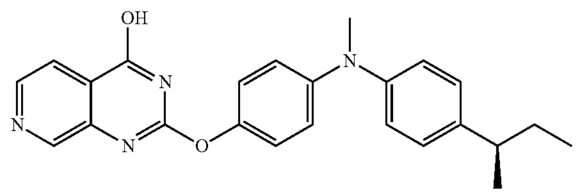 | 2-[4-[4-[(2R)-butan-2-yl]-N-methylanilino]phenoxy]pyrido[3,4-d]pyrimidin-4-ol |
| 79 | 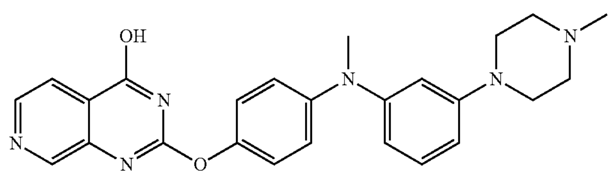 [SMILES: CN1CCN(c2cccc(N(C)c3ccc(Oc4nc(O)c5ccncc5n4)cc3)c2)CC1] | 2-[4-[N-methyl-3-(4-methylpiperazin-1-yl)anilino]phenoxy]pyrido[3,4-d]pyrimidin-4-ol |
| 80 | 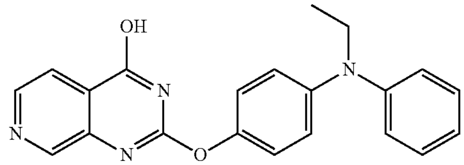 [SMILES: CCN(c1ccccc1)c1ccc(Oc2nc(O)c3ccncc3n2)cc1] | 2-[4-(N-ethylanilino)phenoxy]pyrido[3,4-d]pyrimidin-4-ol |
| 81 | 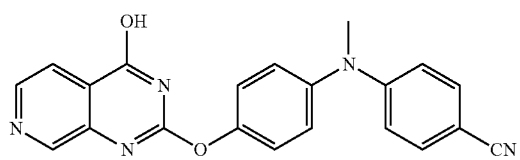 [SMILES: CN(c1ccc(C#N)cc1)c1ccc(Oc2nc(O)c3ccncc3n2)cc1] | 4-[4-(4-hydroxypyrido[3,4-d]pyrimidin-2-yl)oxy-N-methylanilino]benzonitrile |
| 82 | 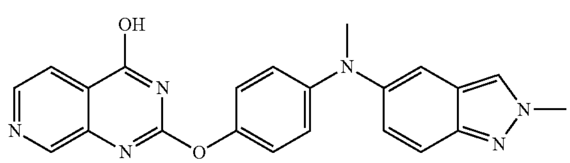 [SMILES: CN(c1ccc(Oc2nc(O)c3ccncc3n2)cc1)c1ccc2nn(C)cc2c1] | 2-[4-[methyl-(2-methylindazol-5-yl)amino]phenoxy]pyrido[3,4-d]pyrimidin-4-ol |
| 83 | 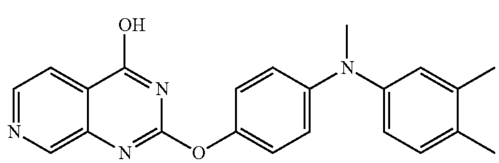 [SMILES: Cc1ccc(N(C)c2ccc(Oc3nc(O)c4ccncc4n3)cc2)cc1C] | 2-[4-(N,3,4-trimethylanilino)phenoxy]pyrido[3,4-d]pyrimidin-4-ol |
| 84 | 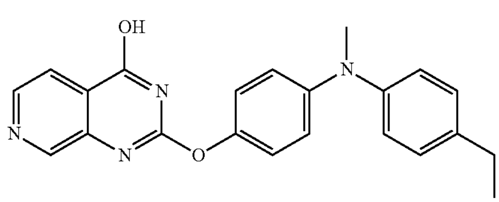 | 2-[4-(4-ethyl-N-methylanilino)phenoxy]pyrido[3,4-d]pyrimidin-4-ol |

TABLE 1-continued

| Ex | Structure | Name |
|---|---|---|
| 85 | 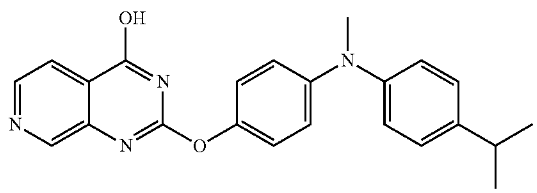 [SMILES: CC(C)c1ccc(N(C)c2ccc(Oc3nc(O)c4ccncc4n3)cc2)cc1] | 2-[4-(N-methyl-4-propan-2-ylanilino)phenoxy]pyrido[3,4-d]pyrimidin-4-ol |
| 86 | 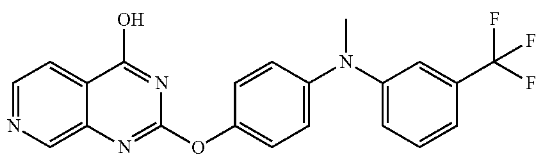 [SMILES: CN(c1ccc(Oc2nc(O)c3ccncc3n2)cc1)c1cccc(C(F)(F)F)c1] | 2-[4-[N-methyl-3-(trifluoromethyl)anilino]phenoxy]pyrido[3,4-d]pyrimidin-4-ol |
| 87 | 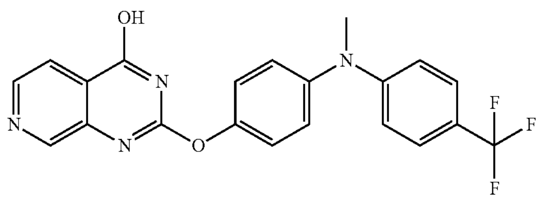 [SMILES: CN(c1ccc(Oc2nc(O)c3ccncc3n2)cc1)c1ccc(C(F)(F)F)cc1] | 2-[4-[N-methyl-4-(trifluoromethyl)anilino]phenoxy]pyrido[3,4-d]pyrimidin-4-ol |
| 88 | 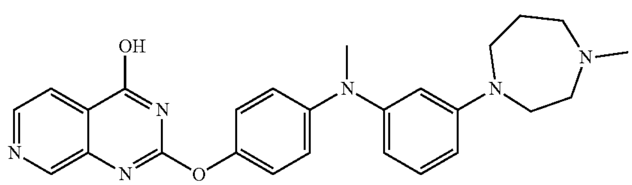 [SMILES: CN1CCCN(c2cccc(N(C)c3ccc(Oc4nc(O)c5ccncc5n4)cc3)c2)CC1] | 2-[4-[N-methyl-3-(4-methyl-1,4-diazepan-1-yl)anilino]phenoxy]pyrido[3,4-d]pyrimidin-4-ol |
| 89 | 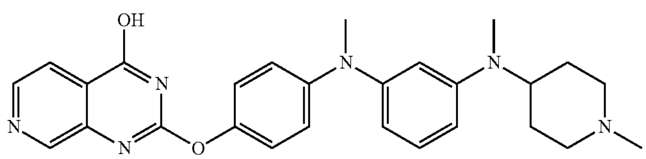 [SMILES: CN1CCC(N(C)c2cccc(N(C)c3ccc(Oc4nc(O)c5ccncc5n4)cc3)c2)CC1] | 2-[4-[N-methyl-3-[methyl-(1-methylpiperidin-4-yl)amino]anilino]phenoxy]pyrido[3,4-d]pyrimidin-4-ol |
| 90 | 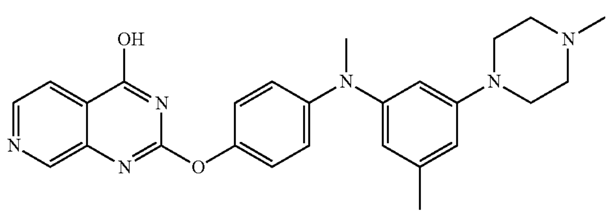 [SMILES: Cc1cc(N2CCN(C)CC2)cc(N(C)c2ccc(Oc3nc(O)c4ccncc4n3)cc2)c1] | 2-[4-[N,3-dimethyl-5-(4-methylpiperazin-1-yl)anilino]phenoxy]pyrido[3,4-d]pyrimidin-4-ol |
| 91 | 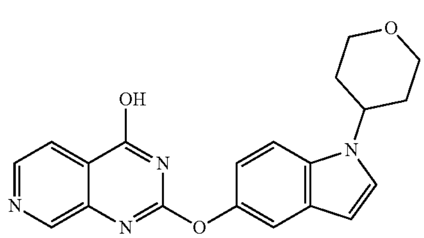 [SMILES: Oc1nc(Oc2ccc3c(ccn3C3CCOCC3)c2)nc2cnccc12] | 2-[1-(oxan-4-yl)indol-5-yl]oxypyrido[3,4-d]pyrimidin-4-ol |
| 92 | 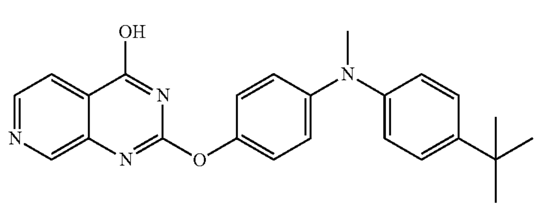 [SMILES: CN(c1ccc(Oc2nc(O)c3ccncc3n2)cc1)c1ccc(C(C)(C)C)cc1] | 2-[4-(4-tert-butyl-N-methylanilino)phenoxy]pyrido[3,4-d]pyrimidin-4-ol |

TABLE 1-continued

| Ex | Structure | Name |
|---|---|---|
| 93 | 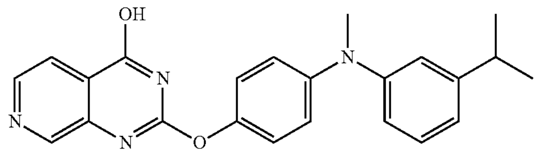 [SMILES: CC(C)c1cccc(N(C)c2ccc(Oc3nc(O)c4ccncc4n3)cc2)c1] | 2-[4-(N-methyl-3-propan-2-ylanilino)phenoxy]pyrido[3,4-d]pyrimidin-4-ol |
| 94 | 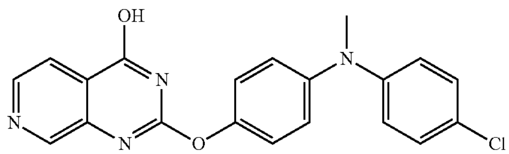 [SMILES: CN(c1ccc(Cl)cc1)c1ccc(Oc2nc(O)c3ccncc3n2)cc1] | 2-[4-(4-chloro-N-methylanilino)phenoxy]pyrido[3,4-d]pyrimidin-4-ol |
| 95 | 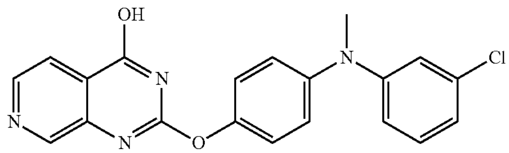 [SMILES: CN(c1ccc(Oc2nc(O)c3ccncc3n2)cc1)c1cccc(Cl)c1] | 2-[4-(3-chloro-N-methylanilino)phenoxy]pyrido[3,4-d]pyrimidin-4-ol |
| 96 | 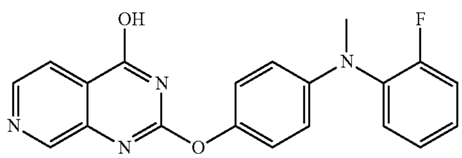 [SMILES: CN(c1ccc(Oc2nc(O)c3ccncc3n2)cc1)c1ccccc1F] | 2-[4-(3-fluoro-N-methylanilino)phenoxy]pyrido[3,4-d]pyrimidin-4-ol |
| 97 | 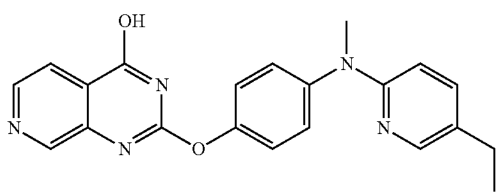 [SMILES: CCc1ccc(N(C)c2ccc(Oc3nc(O)c4ccncc4n3)cc2)nc1] | 2-[4-[(5-ethylpyridin-2-yl)-methylamino]phenoxy]pyrido[3,4-d]pyrimidin-4-ol |
| 98 | 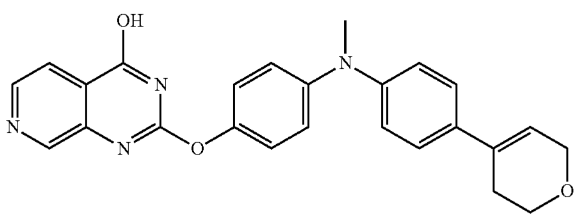 [SMILES: CN(c1ccc(Oc2nc(O)c3ccncc3n2)cc1)c1ccc(C2=CCOCC2)cc1] | 2-[4-[4-(3,6-dihydro-2H-pyran-4-yl)-N-methylanilino]phenoxy]pyrido[3,4-d]pyrimidin-4-ol |
| 99 | 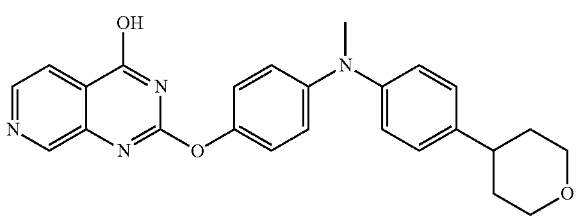 [SMILES: CN(c1ccc(Oc2nc(O)c3ccncc3n2)cc1)c1ccc(C2CCOCC2)cc1] | 2-[4-[N-methyl-4-(oxan-4-yl)anilino]phenoxy]pyrido[3,4-d]pyrimidin-4-ol |
| 100 | 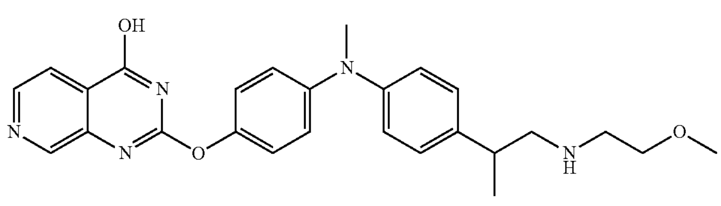 [SMILES: COCCNCC(C)c1ccc(N(C)c2ccc(Oc3nc(O)c4ccncc4n3)cc2)cc1] | 2-[4-[4-[1-(2-methoxyethylamino)propan-2-yl]-N-methylanilino]phenoxy]pyrido[3,4-d]pyrimidin-4-ol |

TABLE 1-continued

| Ex | Structure | Name |
| --- | --- | --- |
| 101 | 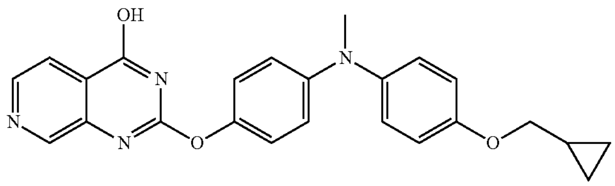 [SMILES: CN(c1ccc(OCC2CC2)cc1)c1ccc(Oc2nc(O)c3ccncc3n2)cc1] | 2-[4-[4-(cyclopropylmethoxy)-N-methylanilino]phenoxy]pyrido[3,4-d]pyrimidin-4-ol |
| 102 | 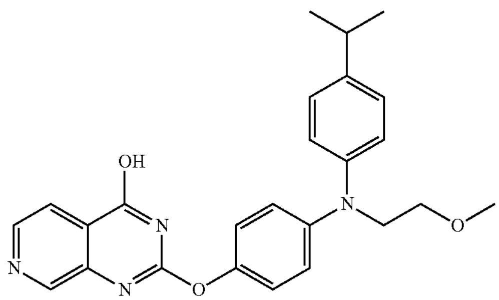 [SMILES: COCCN(c1ccc(Oc2nc(O)c3ccncc3n2)cc1)c1ccc(C(C)C)cc1] | 2-[4-[N-(2-methoxyethyl)-4-propan-2-ylanilino]phenoxy]pyrido[3,4-d]pyrimidin-4-ol |
| 103 | 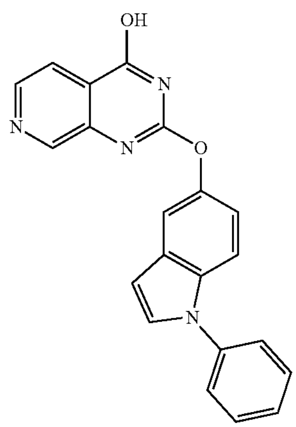 [SMILES: Oc1nc(Oc2ccc3c(ccn3-c3ccccc3)c2)nc2cnccc12] | 2-(1-phenylindol-5-yl)oxypyrido[3,4-d]pyrimidin-4-ol |
| 104 | 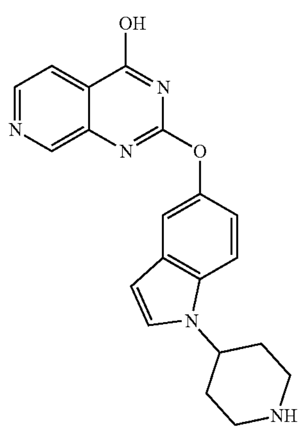 [SMILES: Oc1nc(Oc2ccc3c(ccn3C3CCNCC3)c2)nc2cnccc12] | 2-(1-piperidin-4-ylindol-5-yl)oxypyrido[3,4-d]pyrimidin-4-ol |

TABLE 1-continued

| Ex | Structure | Name |
|---|---|---|
| 105 | 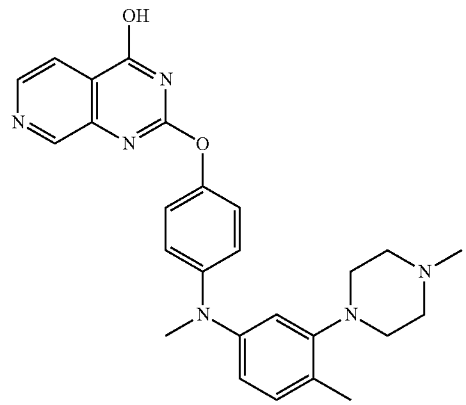 [SMILES: Cc1ccc(N(C)c2ccc(Oc3nc(O)c4ccncc4n3)cc2)cc1N1CCN(C)CC1] | 2-[4-[N,4-dimethyl-3-(4-methylpiperazin-1-yl)anilino]phenoxy]pyrido[3,4-d]pyrimidin-4-ol |
| 106 | 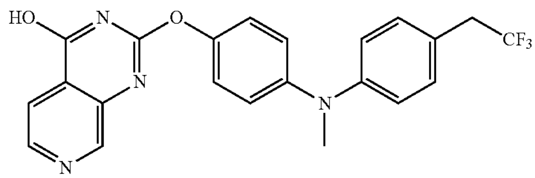 [SMILES: CN(c1ccc(CC(F)(F)F)cc1)c1ccc(Oc2nc(O)c3ccncc3n2)cc1] | 2-[4-[N-methyl-4-(2,2,2-trifluoroethyl)anilino]phenoxy]pyrido[3,4-d]pyrimidin-4-ol |
| 107 | 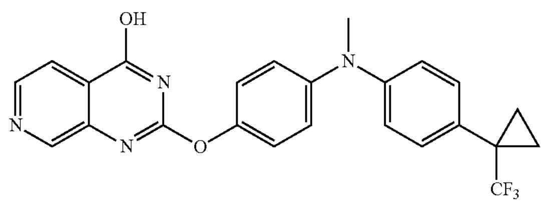 [SMILES: CN(c1ccc(Oc2nc(O)c3ccncc3n2)cc1)c1ccc(C2(C(F)(F)F)CC2)cc1] | 2-[4-[N-methyl-4-[1-(trifluoromethyl)cyclopropyl]anilino]phenoxy]pyrido[3,4-d]pyrimidin-4-ol |
| 108 | 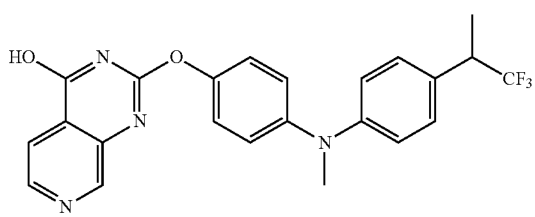 [SMILES: CC(c1ccc(N(C)c2ccc(Oc3nc(O)c4ccncc4n3)cc2)cc1)C(F)(F)F] | 2-[4-[N-methyl-4-(1,1,1-trifluoropropan-2-yl)anilino]phenoxy]pyrido[3,4-d]pyrimidin-4-ol |
| 109 | 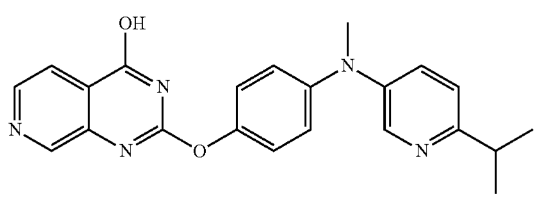 [SMILES: CC(C)c1ccc(N(C)c2ccc(Oc3nc(O)c4ccncc4n3)cc2)cn1] | 2-[4-[methyl-(6-propan-2-ylpyridin-3-yl)amino]phenoxy]pyrido[3,4-d]pyrimidin-4-ol |
| 110 | 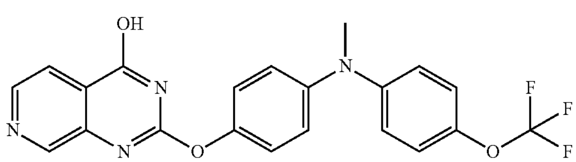 [SMILES: CN(c1ccc(Oc2nc(O)c3ccncc3n2)cc1)c1ccc(OC(F)(F)F)cc1] | 2-[4-[N-methyl-4-(trifluoromethoxy)anilino]phenoxy]pyrido[3,4-d]pyrimidin-4-ol |
| 111 | 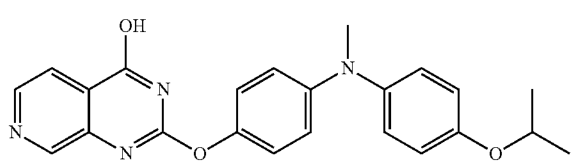 [SMILES: CC(C)Oc1ccc(N(C)c2ccc(Oc3nc(O)c4ccncc4n3)cc2)cc1] | 2-[4-(N-methyl-4-propan-2-yloxyanilino)phenoxy]pyrido[3,4-d]pyrimidin-4-ol |

TABLE 1-continued

| Ex | Structure | Name |
|---|---|---|
| 112 | 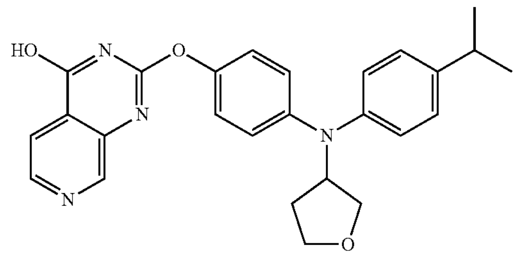 [SMILES: CC(C)c1ccc(N(c2ccc(Oc3nc(O)c4ccncc4n3)cc2)C2CCOC2)cc1] | 2-[4-[N-(oxolan-3-yl)-4-propan-2-ylanilino]phenoxy]pyrido[3,4-d]pyrimidin-4-ol |
| 113 | 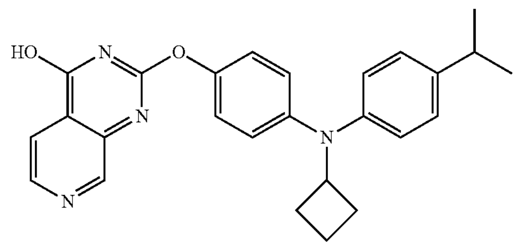 [SMILES: CC(C)c1ccc(N(c2ccc(Oc3nc(O)c4ccncc4n3)cc2)C2CCC2)cc1] | 2-[4-(N-cyclobutyl-4-propan-2-ylanilino)phenoxy]pyrido[3,4-d]pyrimidin-4-ol |
| 114 | 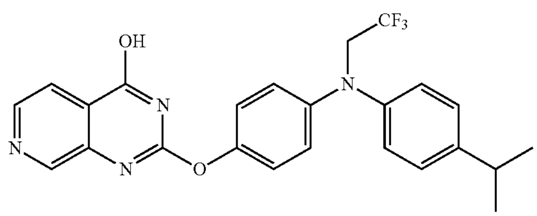 [SMILES: CC(C)c1ccc(N(CC(F)(F)F)c2ccc(Oc3nc(O)c4ccncc4n3)cc2)cc1] | 2-{4-[(4-isopropyl-phenyl)-(2,2,2-trifluoro-ethyl)-amino]-phenoxy}-pyrido[3,4-d]pyrimidin-4-ol |
| 115 | 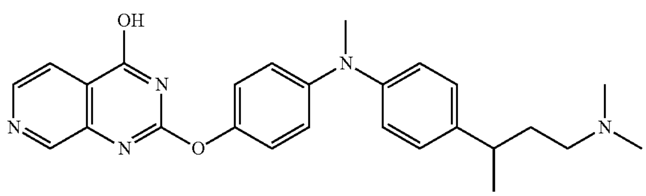 [SMILES: CC(CCN(C)C)c1ccc(N(C)c2ccc(Oc3nc(O)c4ccncc4n3)cc2)cc1] | 2-(4-{[4-(3-dimethylamino-1-methyl-propyl)-phenyl]-methyl-amino}-phenoxy)-pyrido[3,4-d]pyrimidin-4-ol |
| 116 | 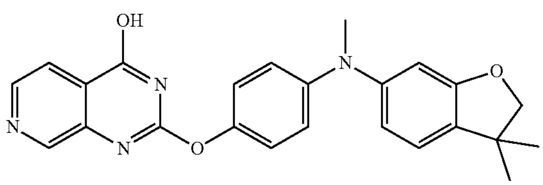 [SMILES: CN(c1ccc(Oc2nc(O)c3ccncc3n2)cc1)c1ccc2c(c1)OCC2(C)C] | (3,3-dimethyl-2,3-dihydro-benzofuran-6-yl)-methyl-[4-(4-methyl-pyrido[3,4-d]pyrimidin-2-yloxy)-phenyl]-amine |
| 117 | 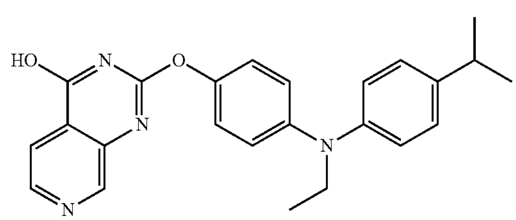 [SMILES: CCN(c1ccc(Oc2nc(O)c3ccncc3n2)cc1)c1ccc(C(C)C)cc1] | 2-(4-(ethyl(4-isopropylphenyl)amino)phenoxy)pyrido[3,4-d]pyrimidin-4-ol |
| 118 | 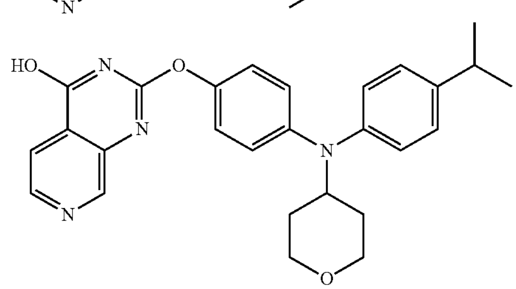 | 2-(4-((4-isopropylphenyl)(tetrahydro-2H-pyran-4-yl)amino)phenoxy)pyrido[3,4-d]pyrimidin-4-ol |

In some embodiments, the compound disclosed herein has a structure provided in Table 2.
TABLE 2
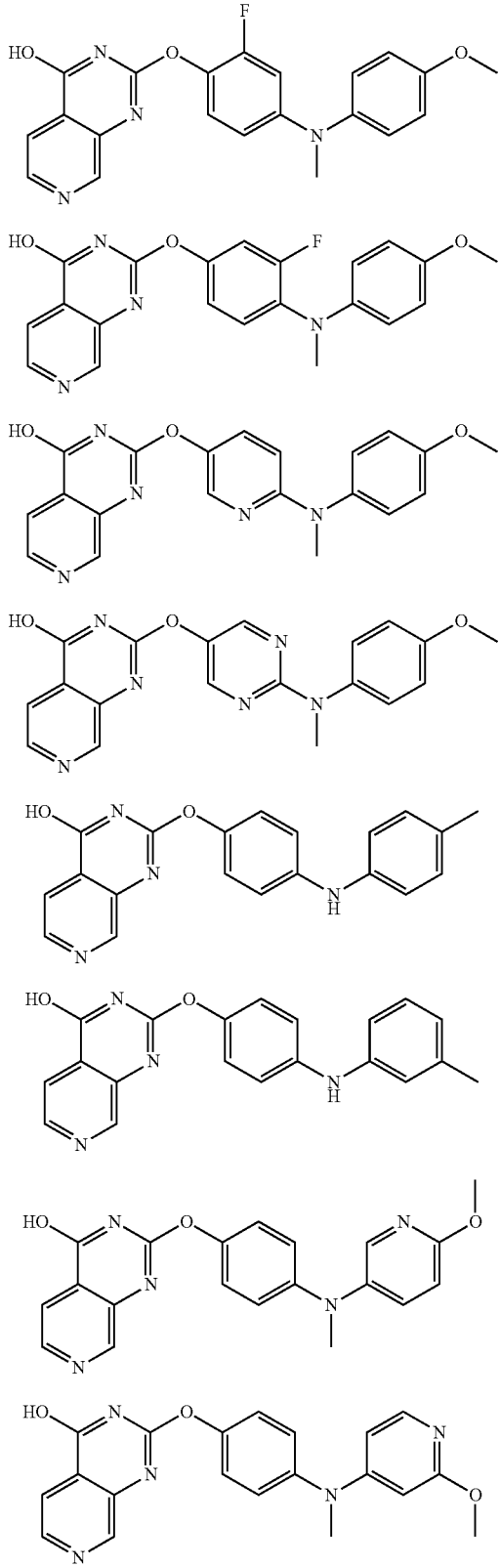
TABLE 2-continued
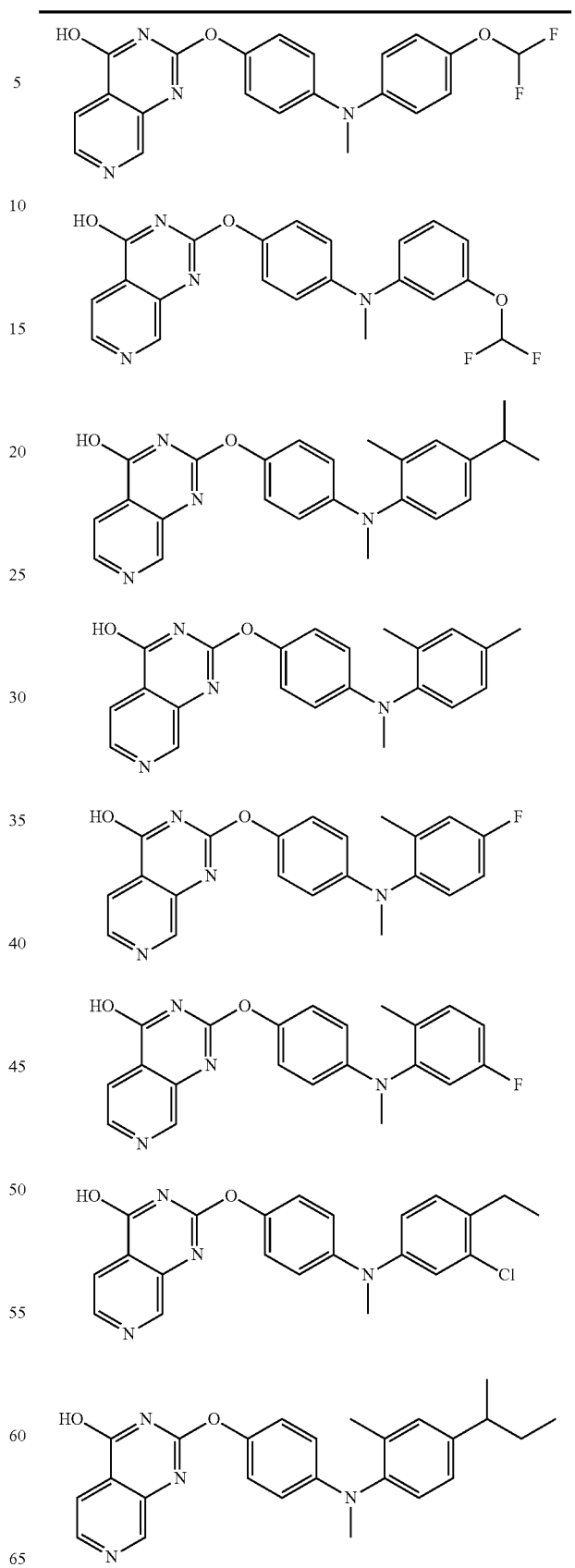

TABLE 2-continued

TABLE 2-continued
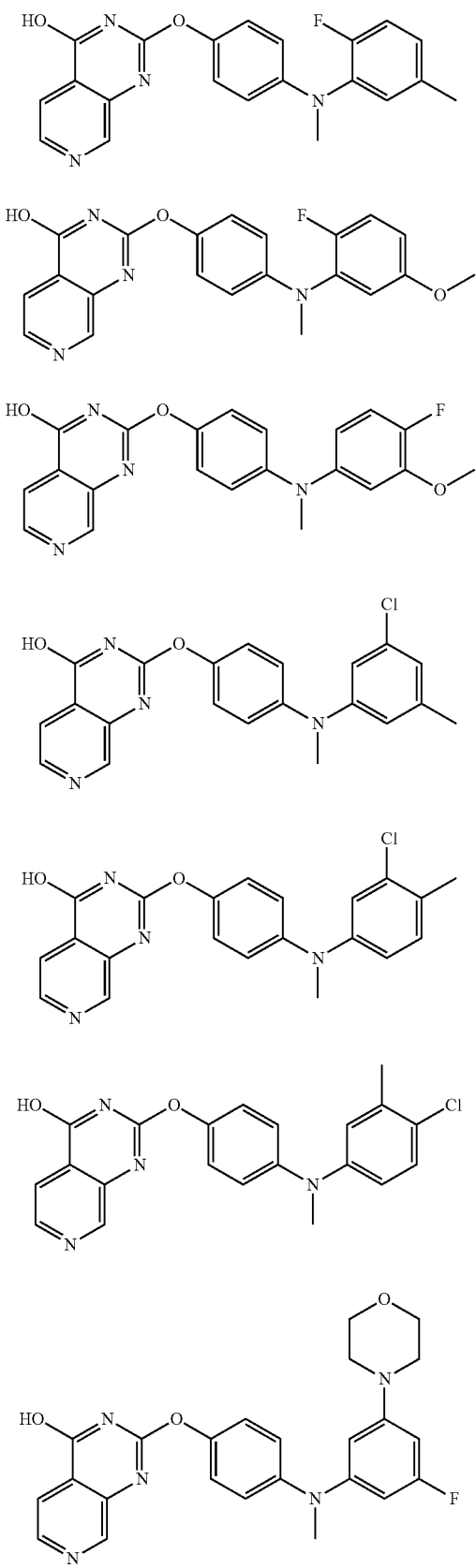
TABLE 2-continued
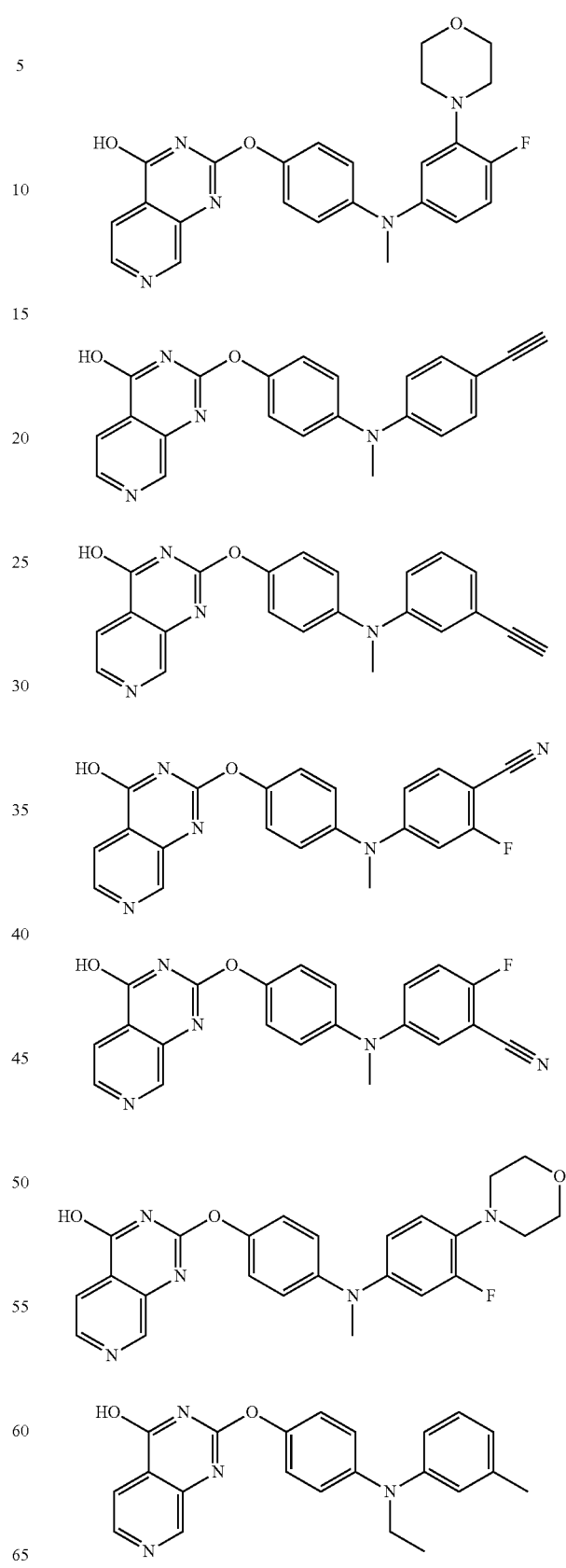

TABLE 2-continued
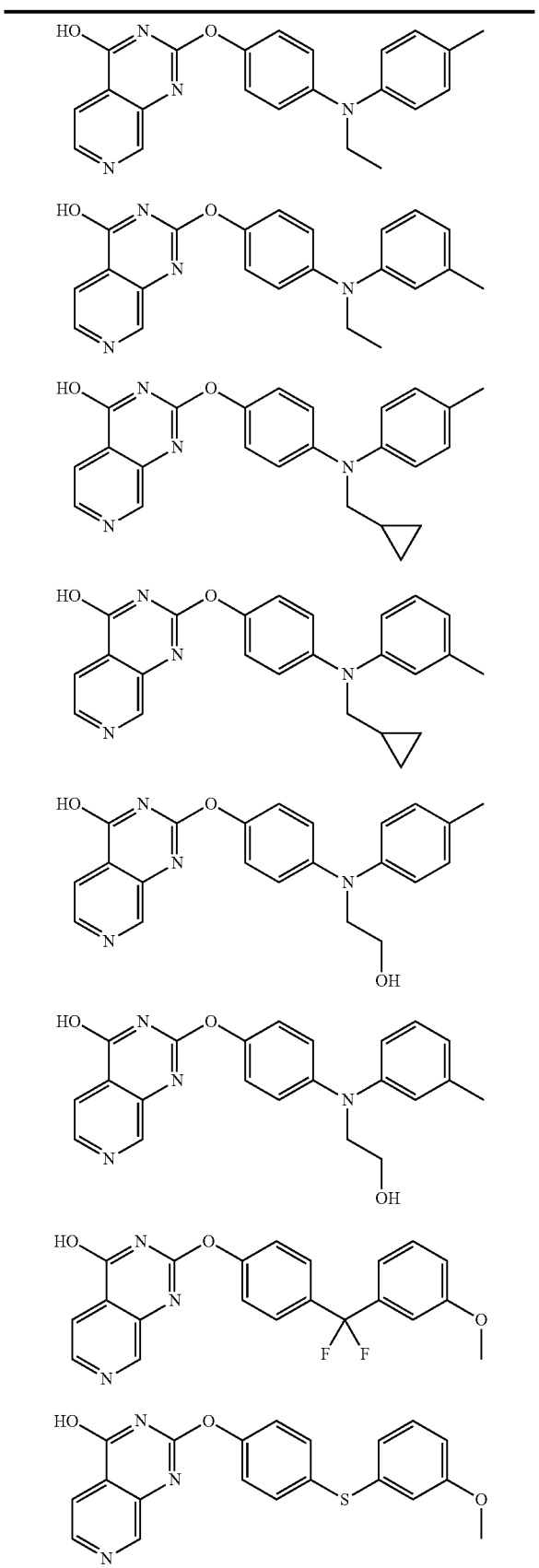
TABLE 2-continued
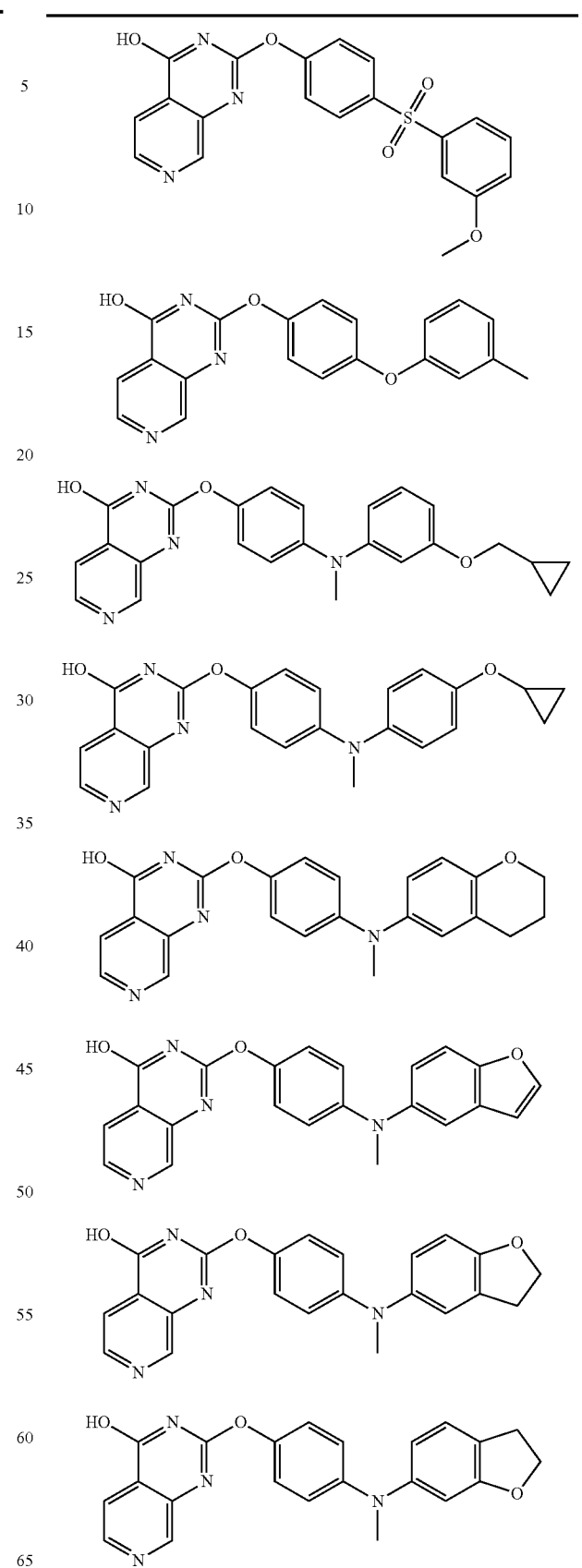

TABLE 2-continued
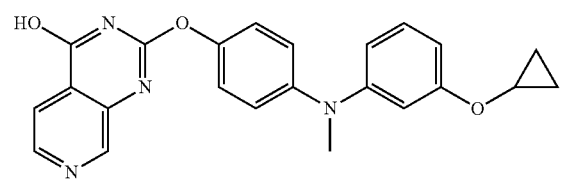 [SMILES: CN(c1ccc(Oc2nc(O)c3ccncc3n2)cc1)c1cccc(OC2CC2)c1]
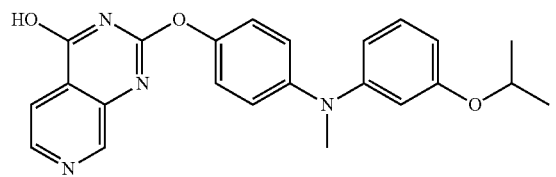 [SMILES: CC(C)Oc1cccc(N(C)c2ccc(Oc3nc(O)c4ccncc4n3)cc2)c1]
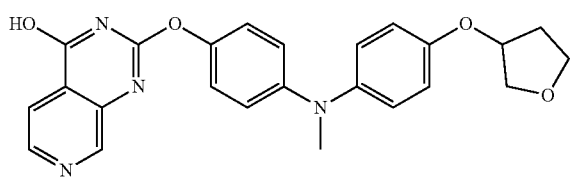 [SMILES: CN(c1ccc(Oc2nc(O)c3ccncc3n2)cc1)c1ccc(OC2CCOC2)cc1]
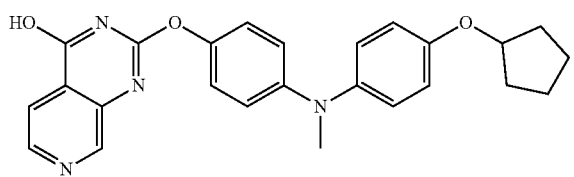 [SMILES: CN(c1ccc(Oc2nc(O)c3ccncc3n2)cc1)c1ccc(OC2CCCC2)cc1]
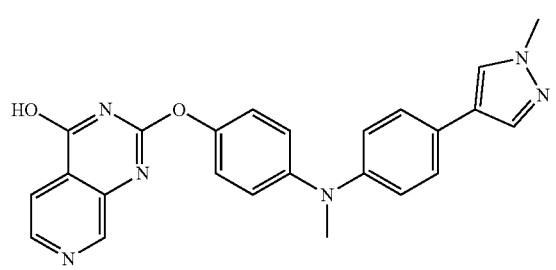 [SMILES: CN(c1ccc(Oc2nc(O)c3ccncc3n2)cc1)c1ccc(-c2cnn(C)c2)cc1]
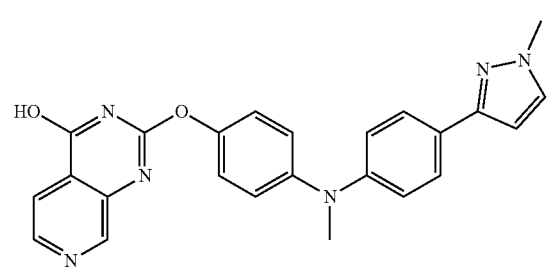 [SMILES: CN(c1ccc(Oc2nc(O)c3ccncc3n2)cc1)c1ccc(-c2ccn(C)n2)cc1]
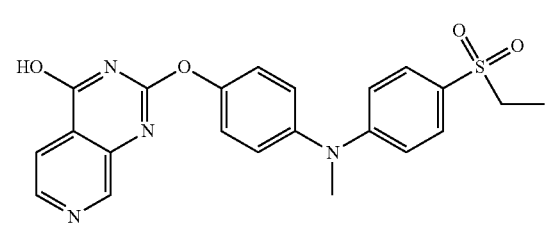 [SMILES: CCS(=O)(=O)c1ccc(N(C)c2ccc(Oc3nc(O)c4ccncc4n3)cc2)cc1]
TABLE 2-continued
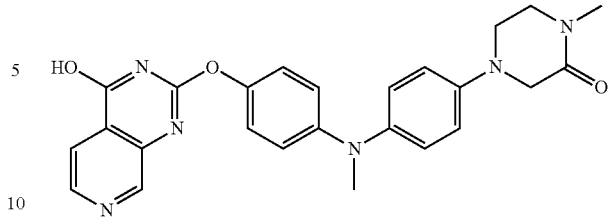
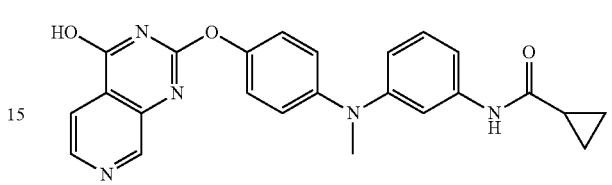
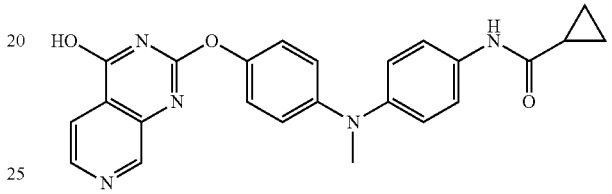
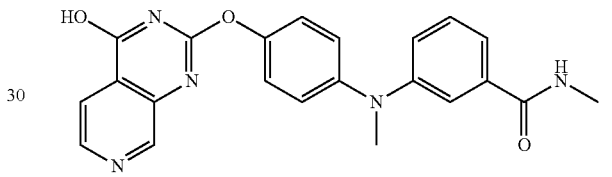
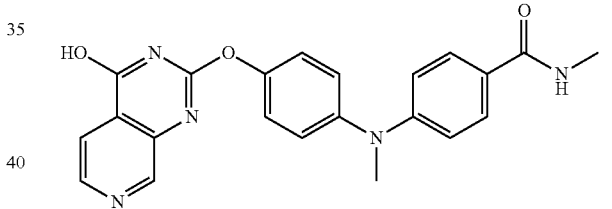
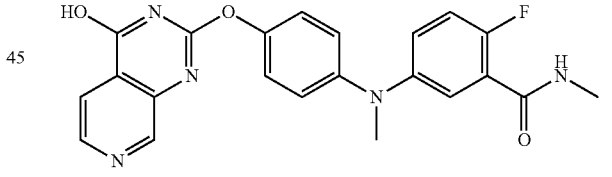
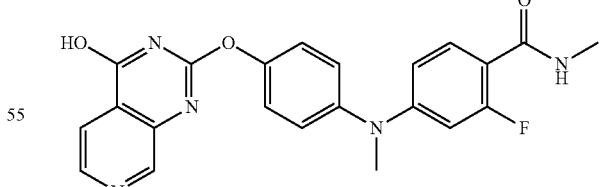
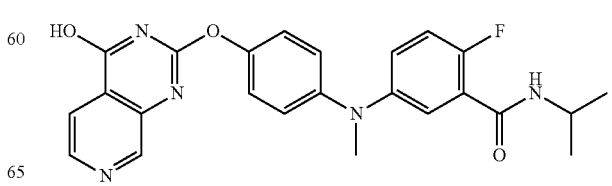

TABLE 2-continued
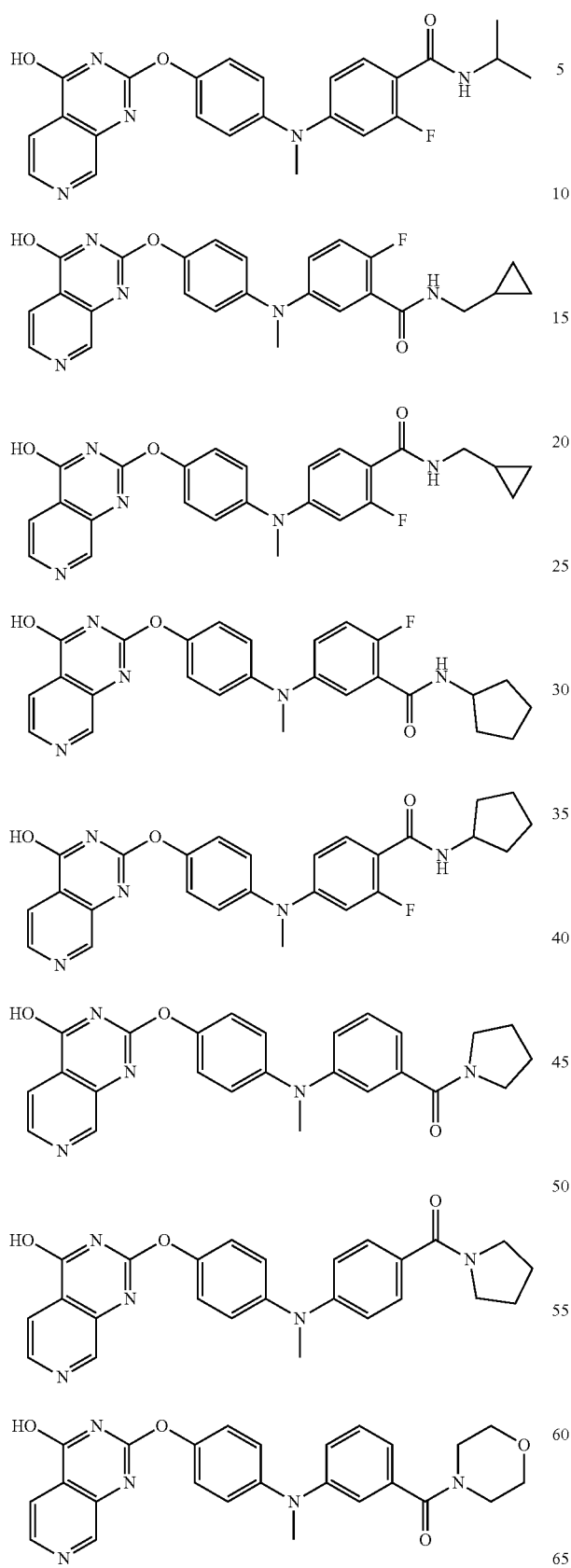
TABLE 2-continued
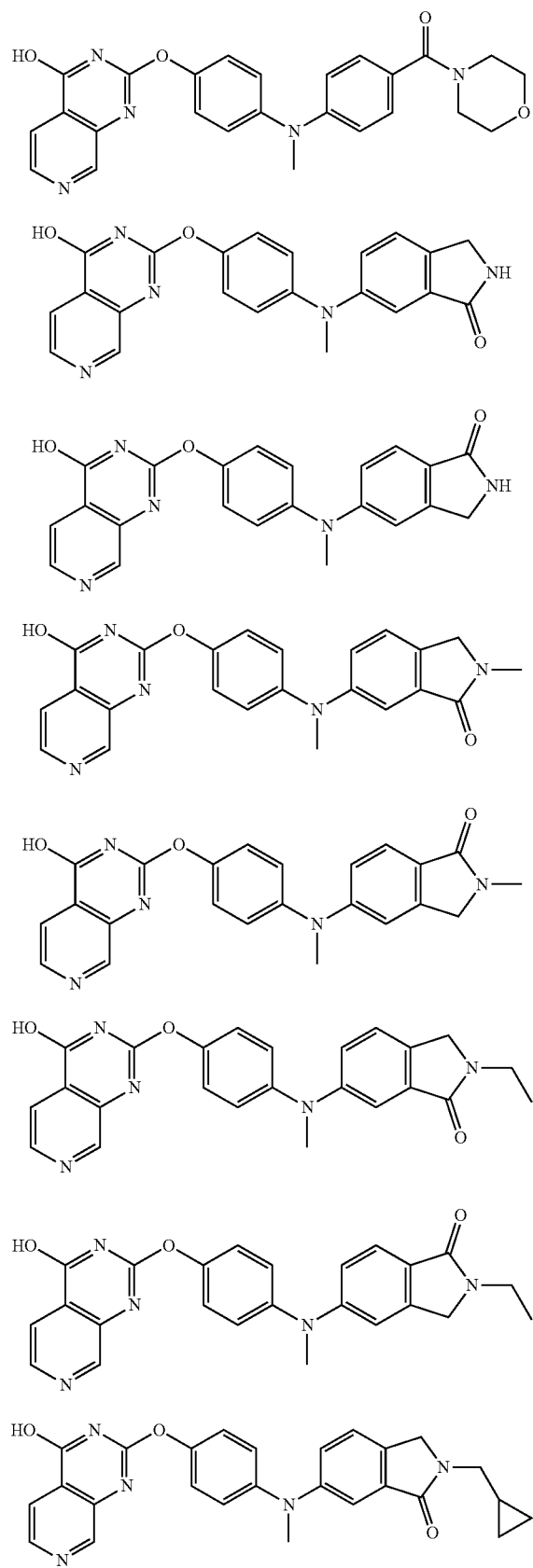

TABLE 2-continued
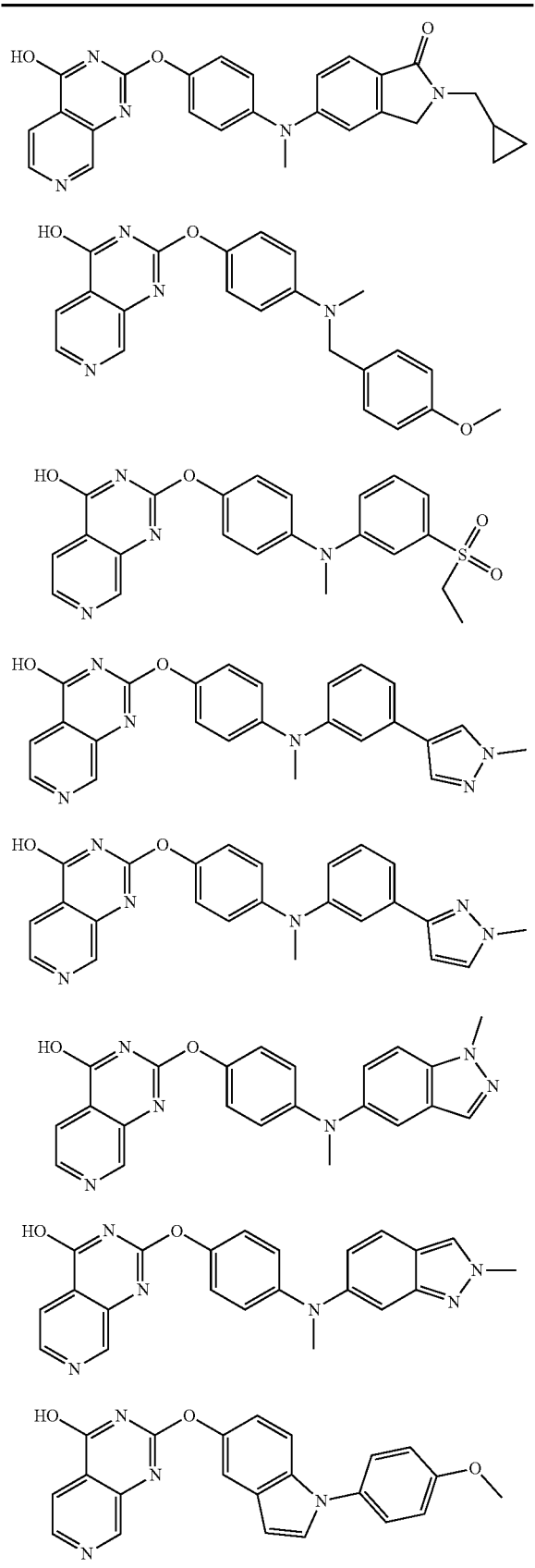
TABLE 2-continued
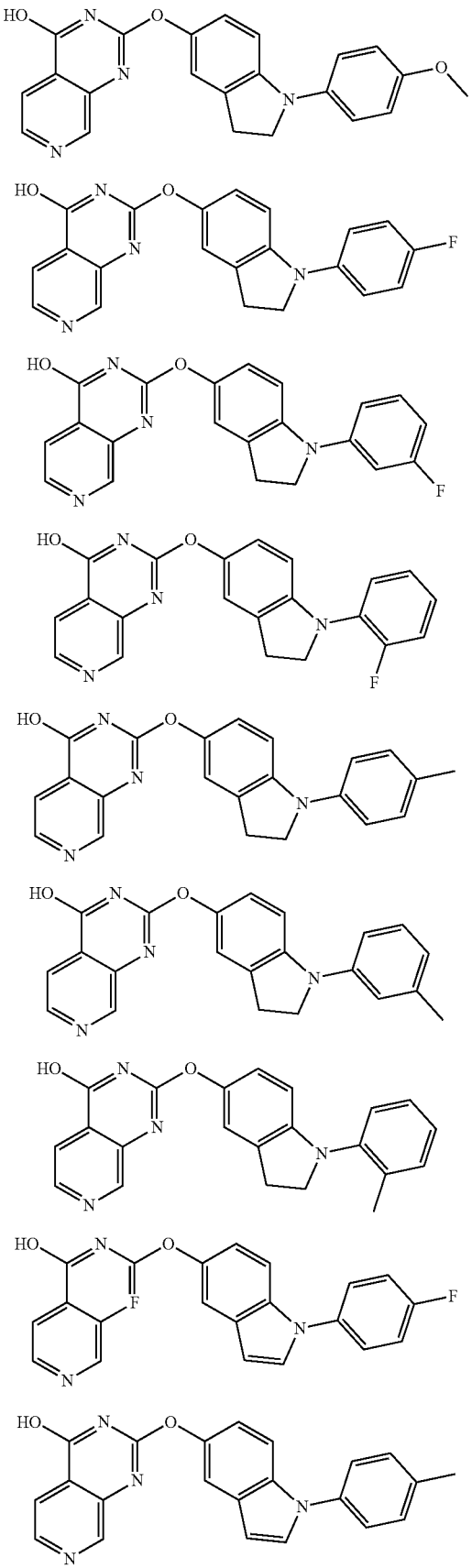

TABLE 2-continued
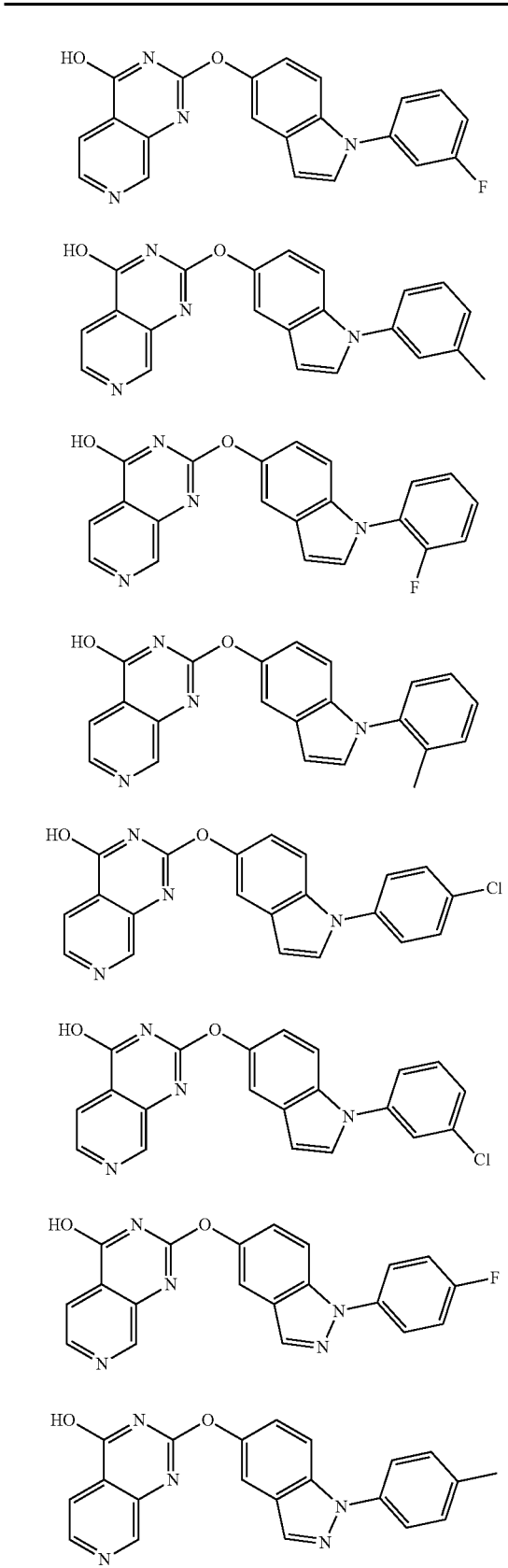
TABLE 2-continued
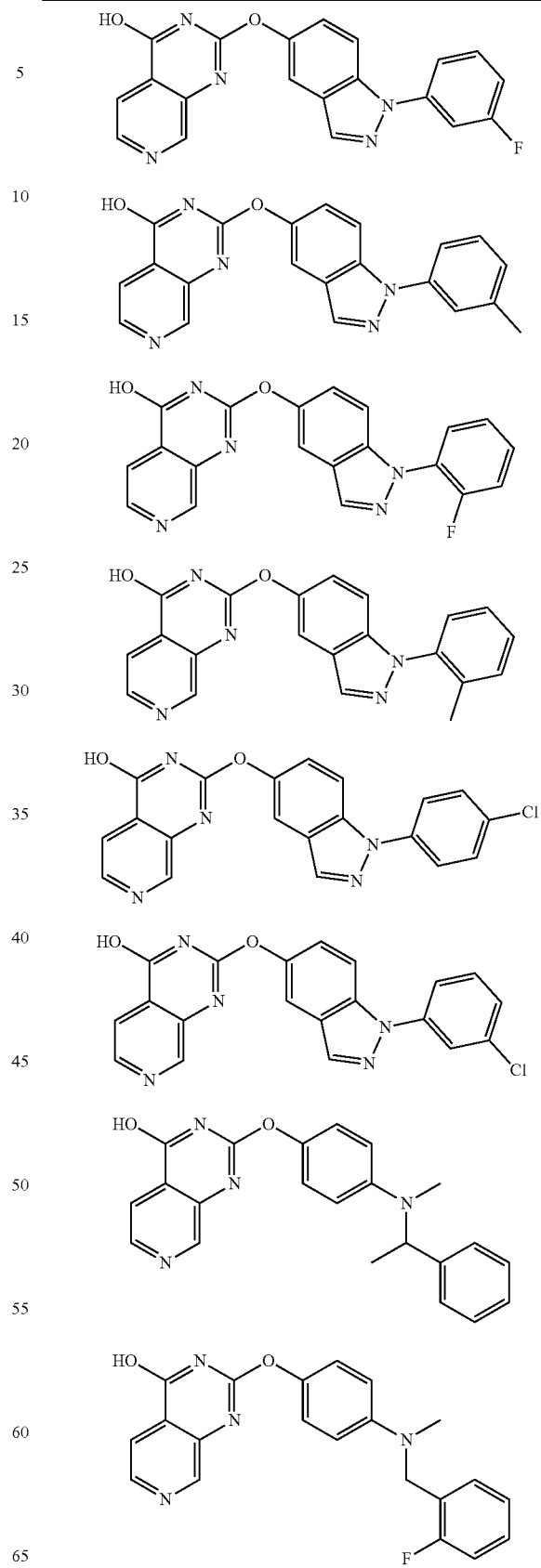

TABLE 2-continued
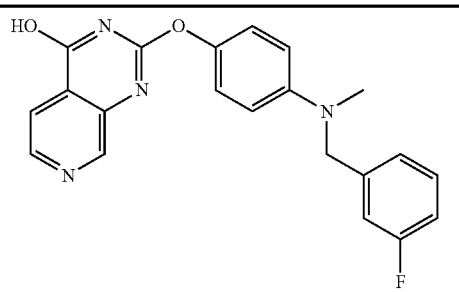
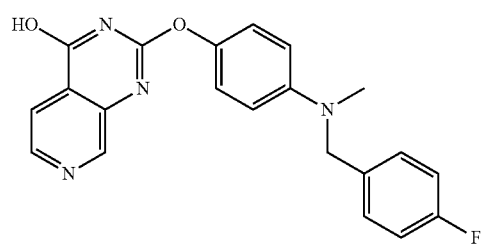 [SMILES: CN(Cc1ccc(F)cc1)c1ccc(Oc2nc(O)c3ccncc3n2)cc1]
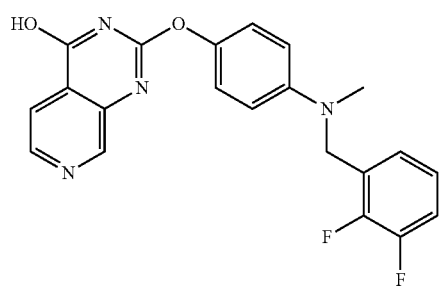 [SMILES: CN(Cc1cccc(F)c1F)c1ccc(Oc2nc(O)c3ccncc3n2)cc1]
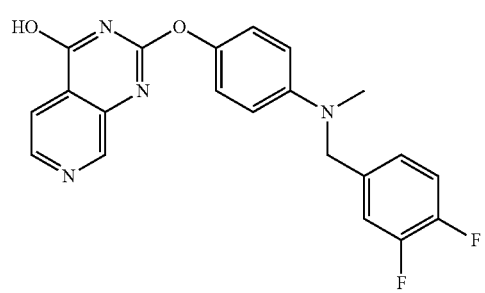 [SMILES: CN(Cc1ccc(F)c(F)c1)c1ccc(Oc2nc(O)c3ccncc3n2)cc1]
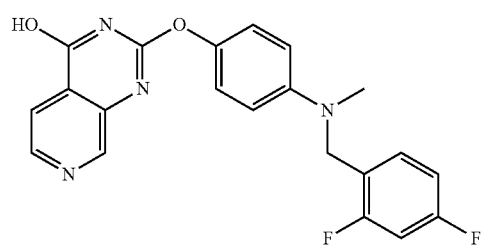 [SMILES: CN(Cc1ccc(F)cc1F)c1ccc(Oc2nc(O)c3ccncc3n2)cc1]
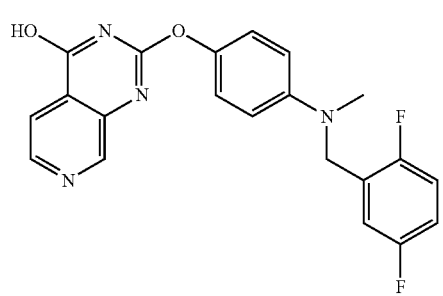
TABLE 2-continued
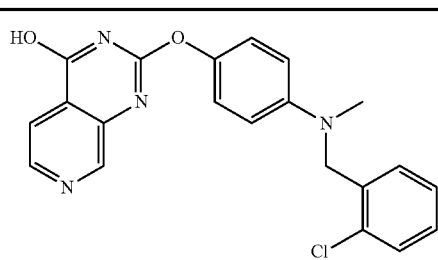
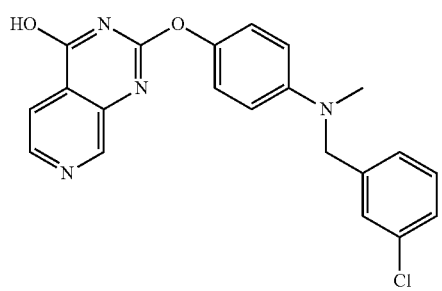
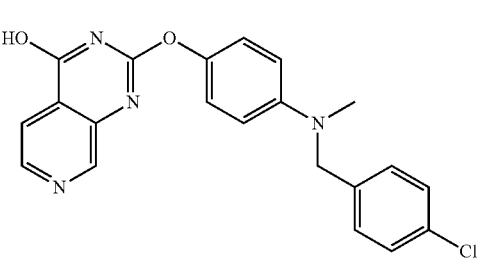 [SMILES: CN(Cc1ccc(Cl)cc1)c1ccc(Oc2nc(O)c3ccncc3n2)cc1]
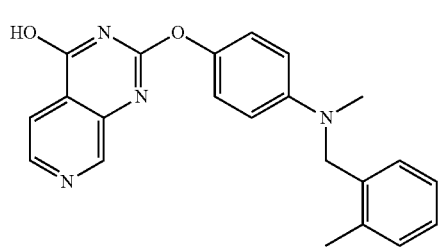 [SMILES: Cc1ccccc1CN(C)c1ccc(Oc2nc(O)c3ccncc3n2)cc1]
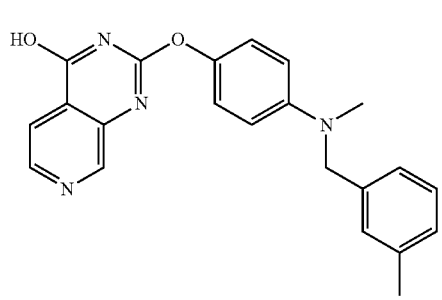 [SMILES: Cc1cccc(CN(C)c2ccc(Oc3nc(O)c4ccncc4n3)cc2)c1]
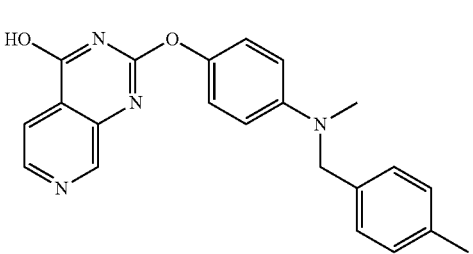

TABLE 2-continued
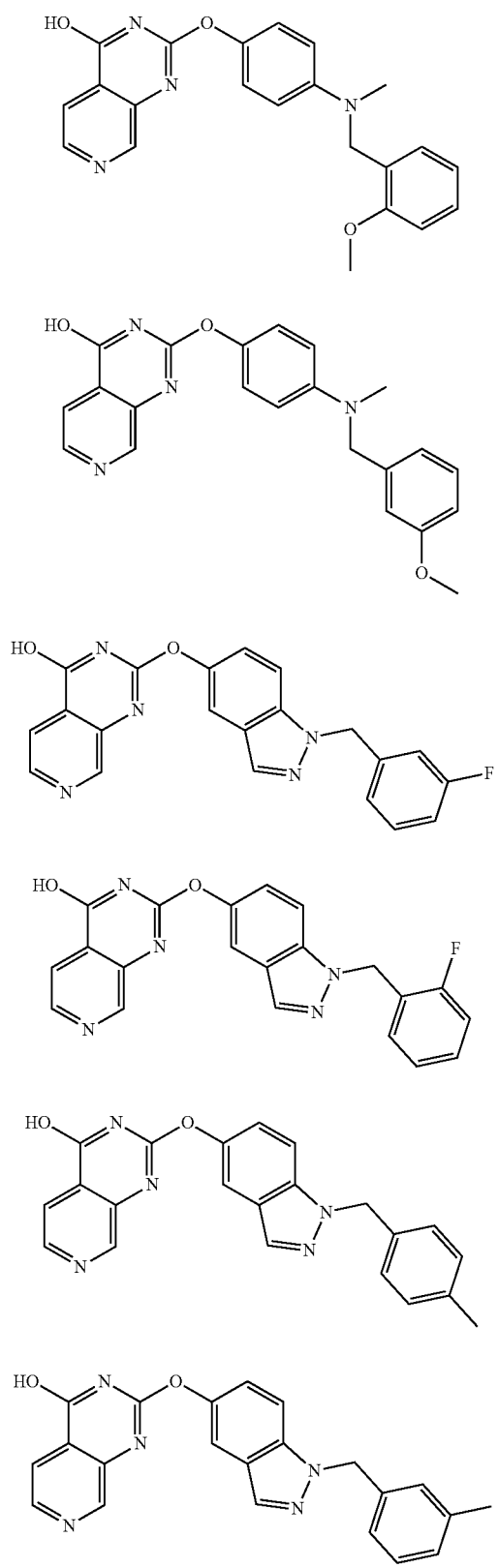
TABLE 2-continued
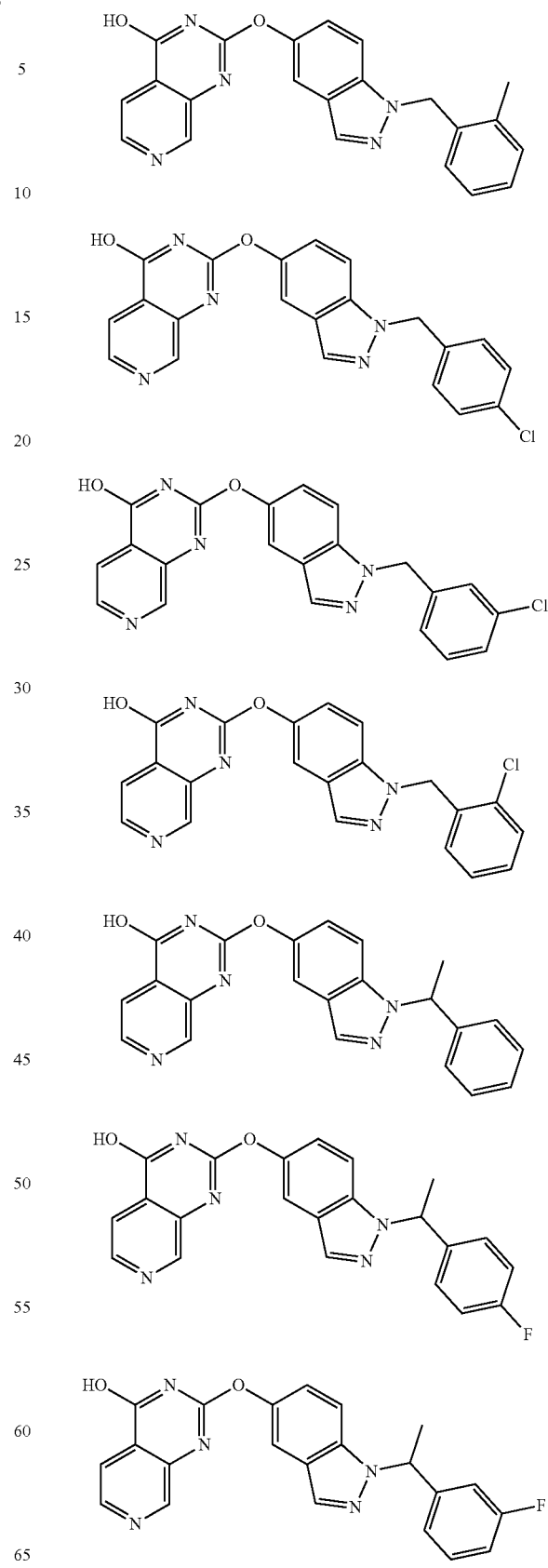

TABLE 2-continued
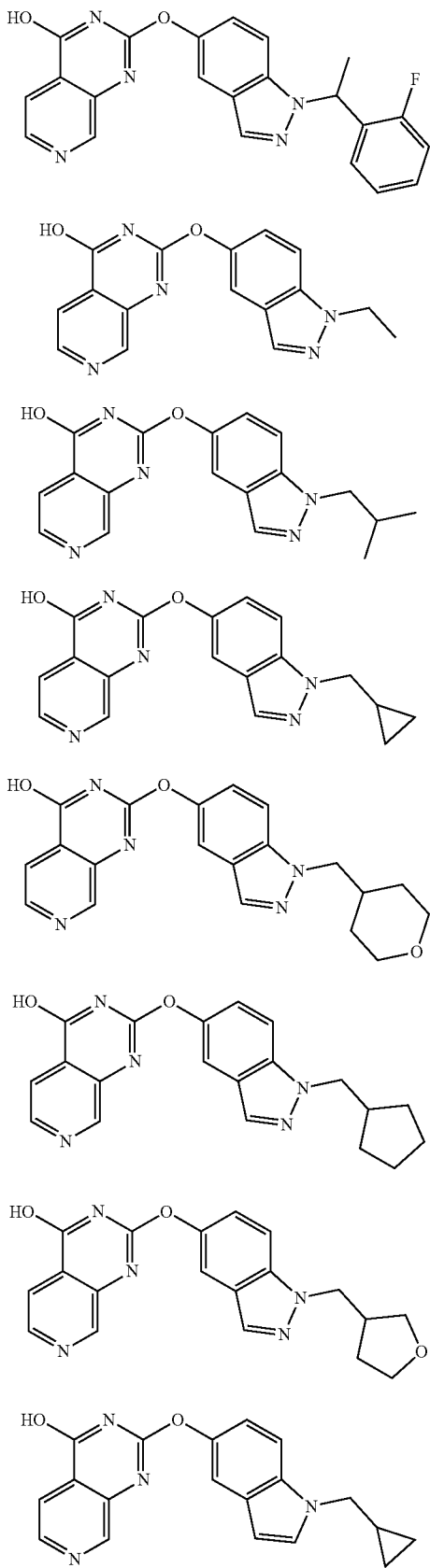
TABLE 2-continued
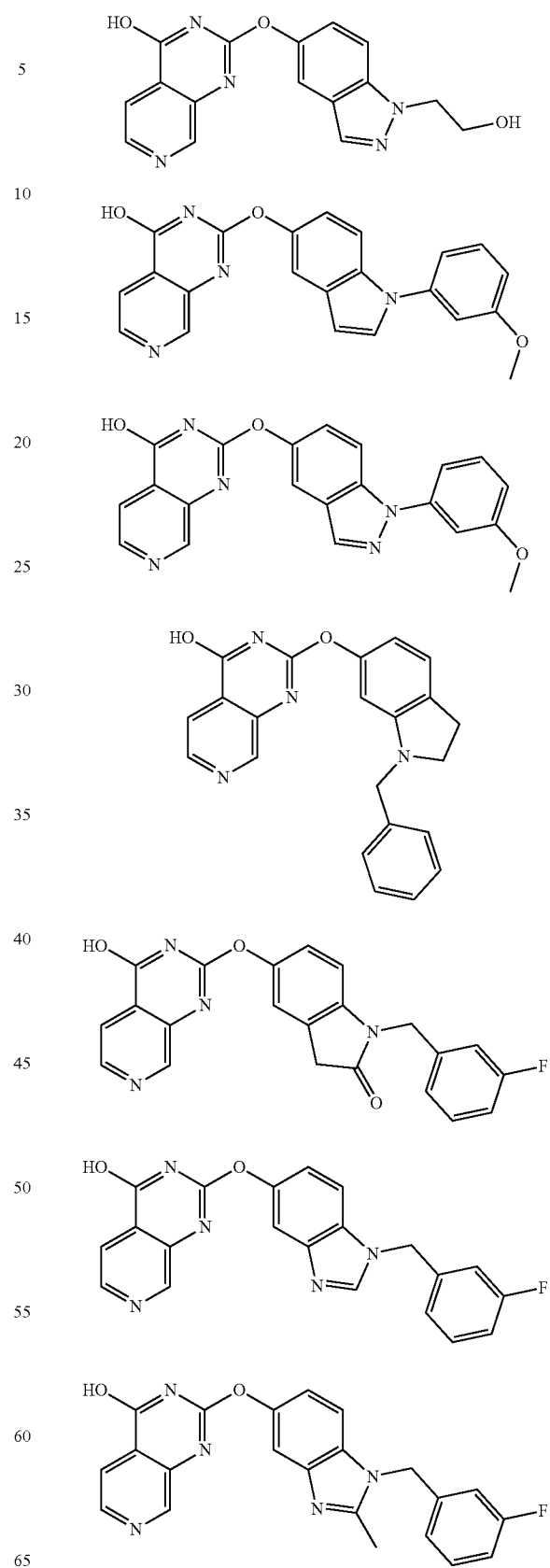

TABLE 2-continued
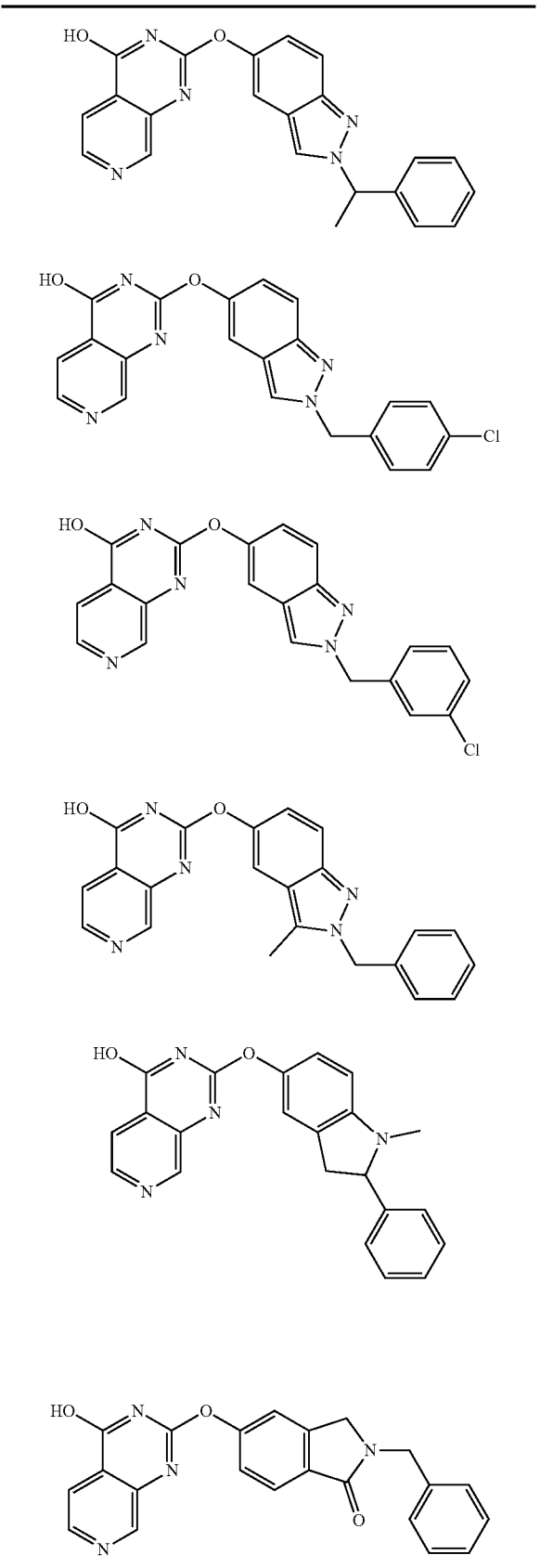
TABLE 2-continued
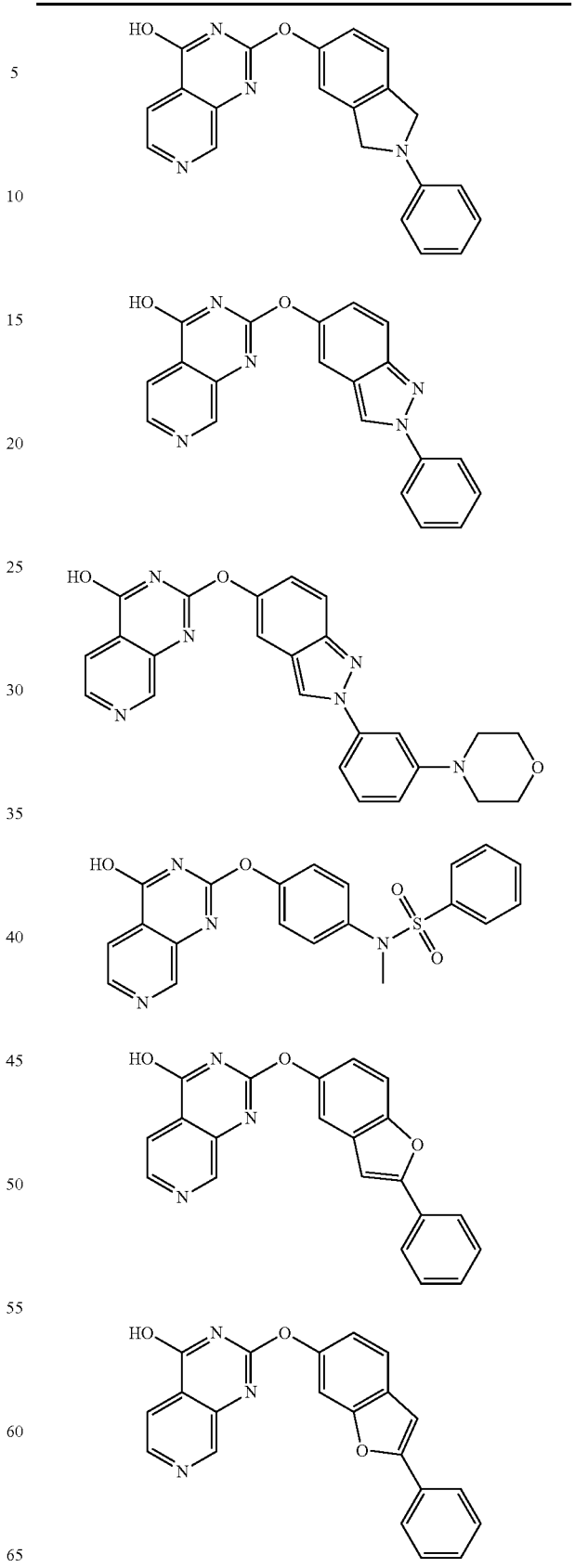

TABLE 2-continued
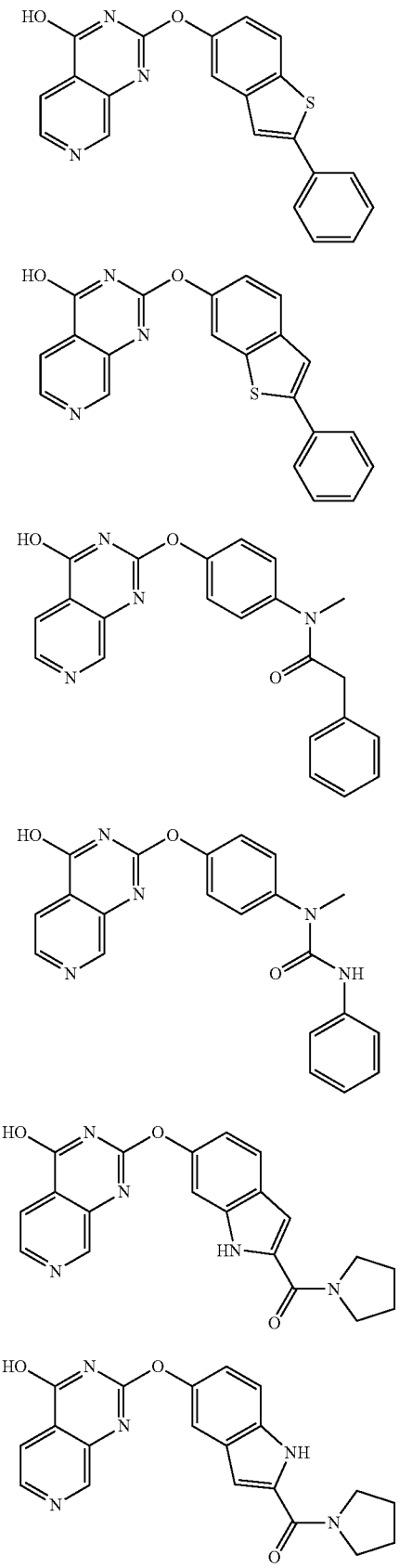
TABLE 2-continued
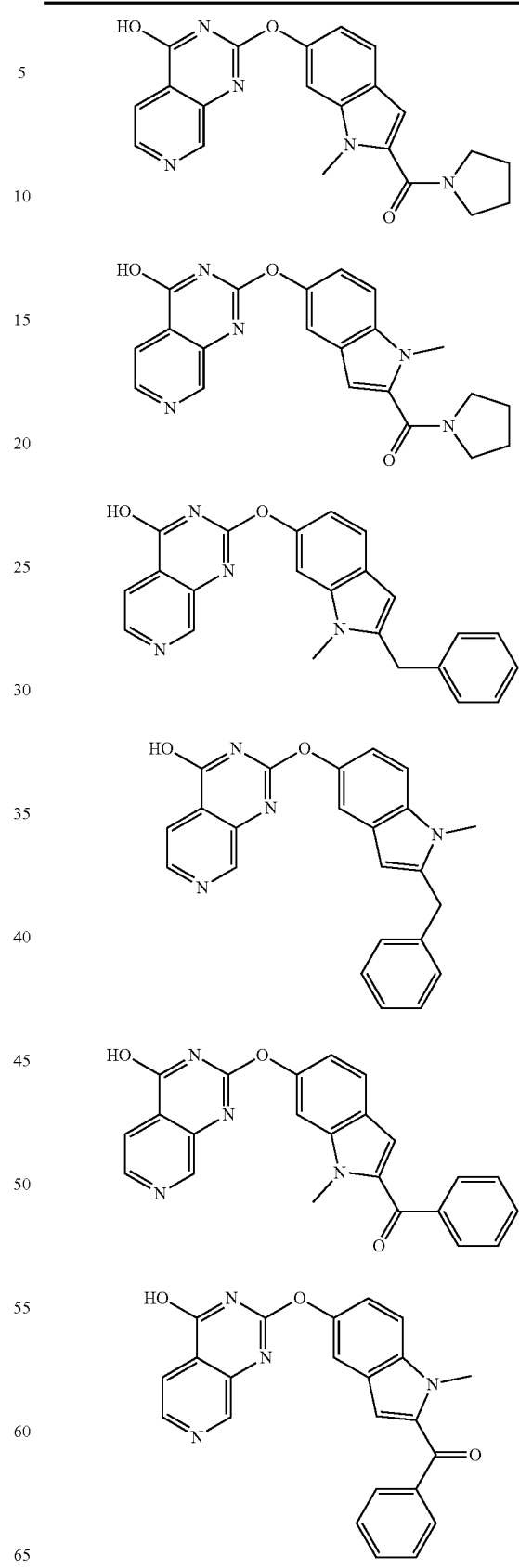

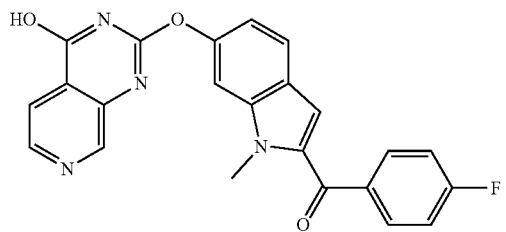 [SMILES: Cn1c(C(=O)c2ccc(F)cc2)cc2ccc(Oc3nc(O)c4ccncc4n3)cc21]
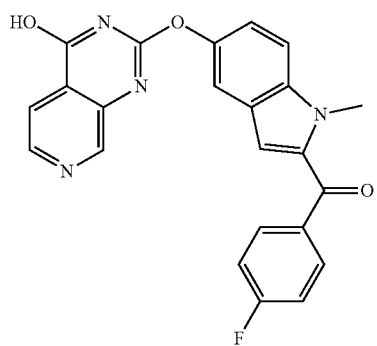 [SMILES: Cn1c(C(=O)c2ccc(F)cc2)cc2cc(Oc3nc(O)c4ccncc4n3)ccc21]
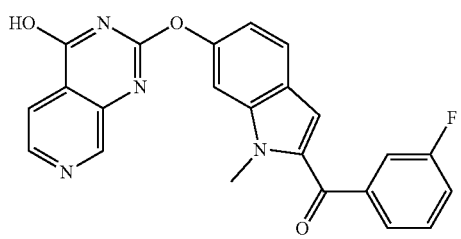 [SMILES: Cn1c(C(=O)c2cccc(F)c2)cc2ccc(Oc3nc(O)c4ccncc4n3)cc21]
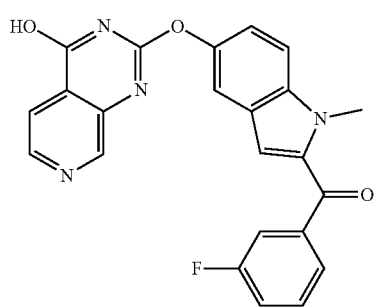 [SMILES: Cn1c(C(=O)c2cccc(F)c2)cc2cc(Oc3nc(O)c4ccncc4n3)ccc21]
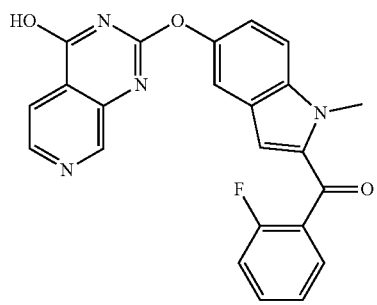 [SMILES: Cn1c(C(=O)c2ccccc2F)cc2cc(Oc3nc(O)c4ccncc4n3)ccc21]
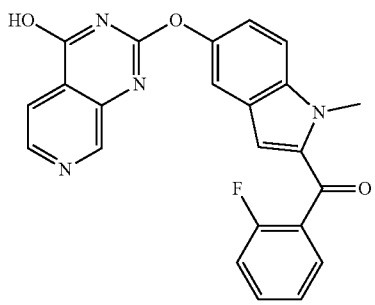 [SMILES: Cn1c(C(=O)c2ccccc2F)cc2cc(Oc3nc(O)c4ccncc4n3)ccc21]
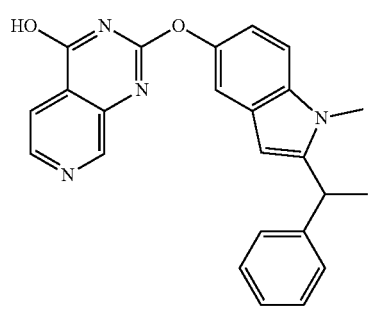 [SMILES: CC(c1ccccc1)c1cc2cc(Oc3nc(O)c4ccncc4n3)ccc2n1C]
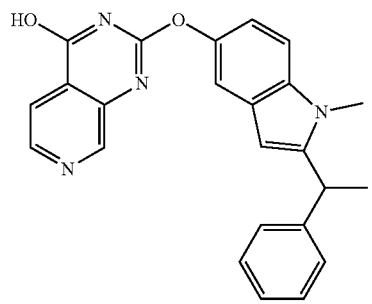 [SMILES: CC(c1ccccc1)c1cc2cc(Oc3nc(O)c4ccncc4n3)ccc2n1C]
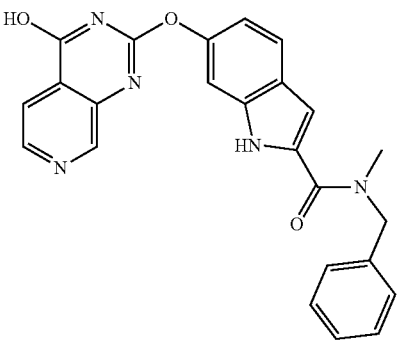 [SMILES: CN(Cc1ccccc1)C(=O)c1cc2ccc(Oc3nc(O)c4ccncc4n3)cc2[nH]1]
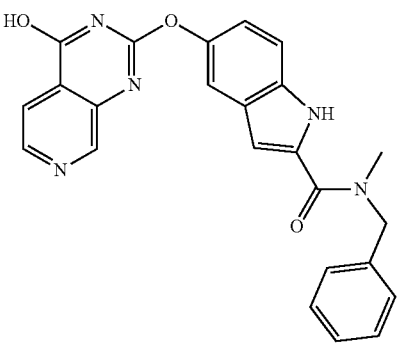 [SMILES: CN(Cc1ccccc1)C(=O)c1cc2cc(Oc3nc(O)c4ccncc4n3)ccc2[nH]1]

TABLE 2-continued
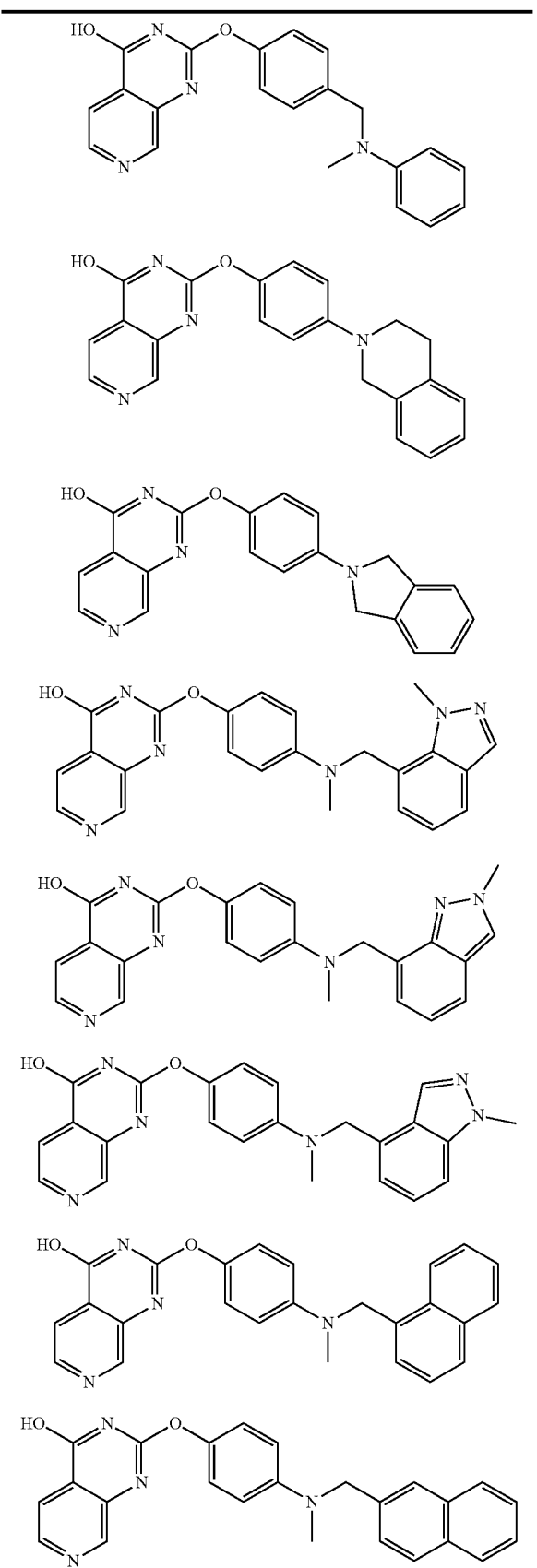
TABLE 2-continued
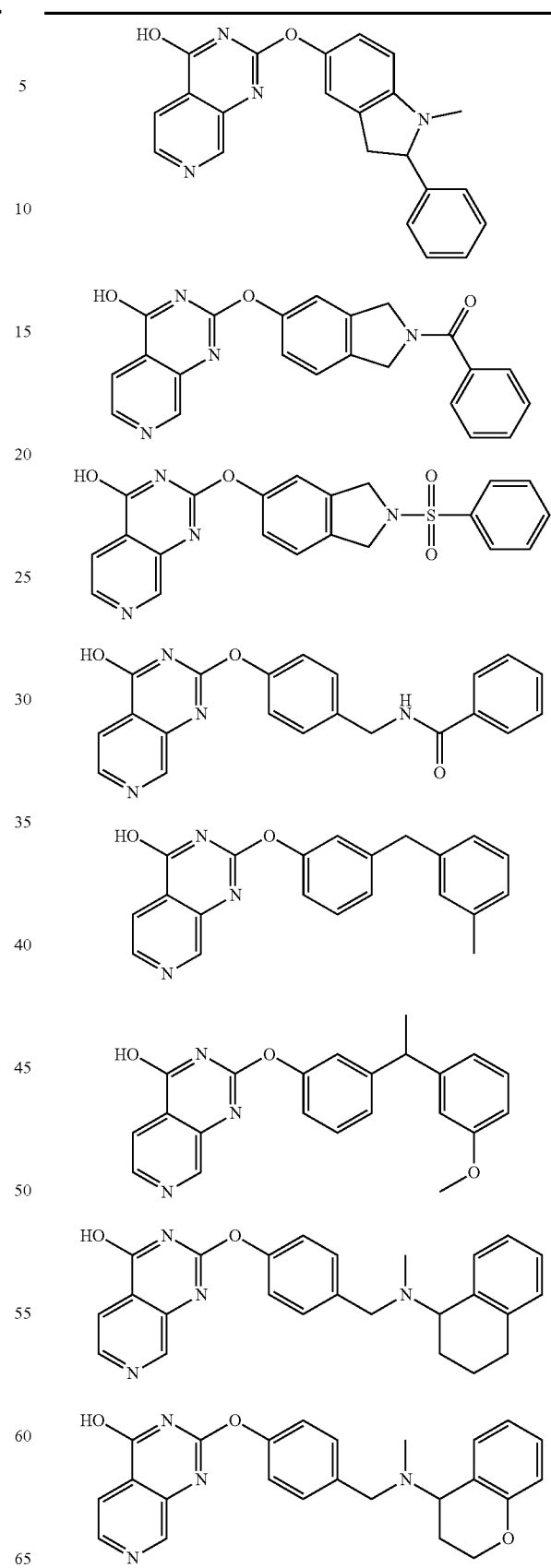

TABLE 2-continued
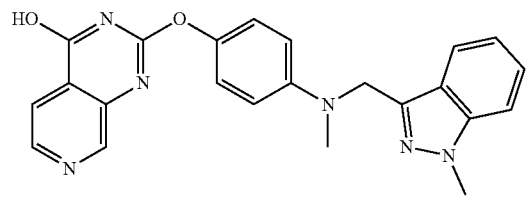 [SMILES: CN(Cc1nn(C)c2ccccc12)c1ccc(Oc2nc(O)c3ccncc3n2)cc1]
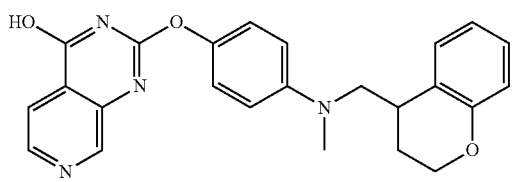 [SMILES: CN(CC1CCOc2ccccc21)c1ccc(Oc2nc(O)c3ccncc3n2)cc1]
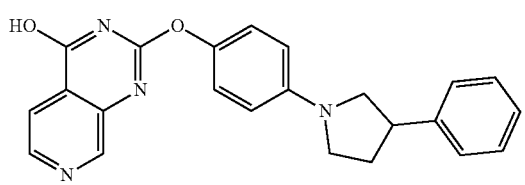 [SMILES: Oc1nc(Oc2ccc(N3CCC(c4ccccc4)C3)cc2)nc2cnccc12]
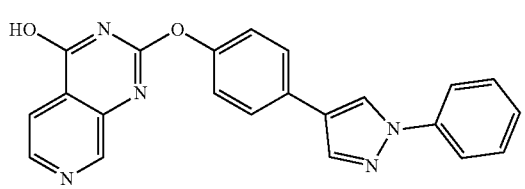 [SMILES: Oc1nc(Oc2ccc(-c3cnn(-c4ccccc4)c3)cc2)nc2cnccc12]
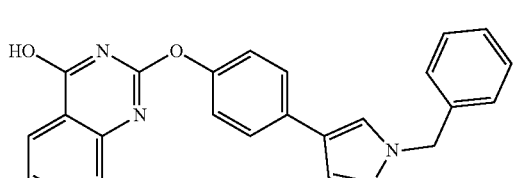
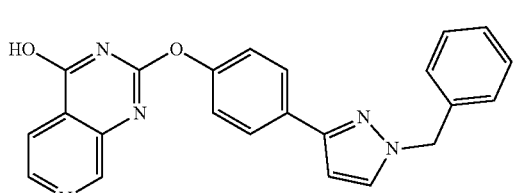
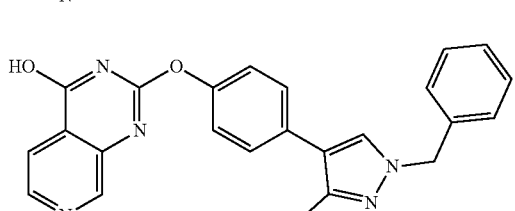
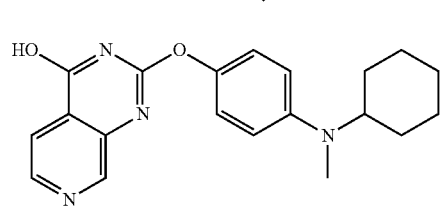
TABLE 2-continued
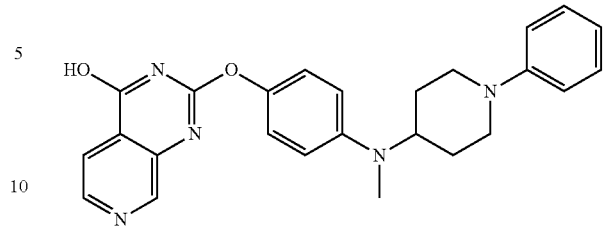
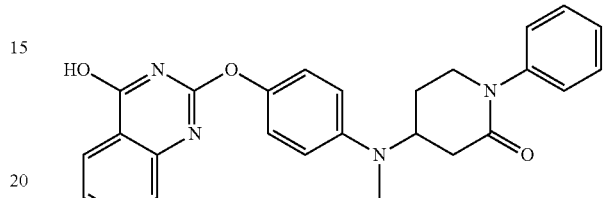
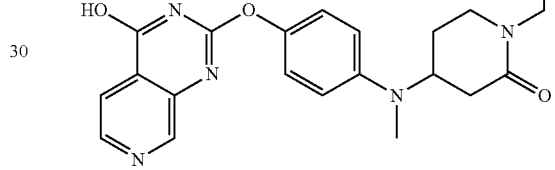
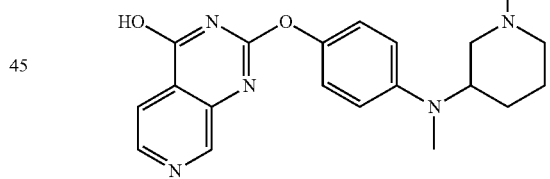
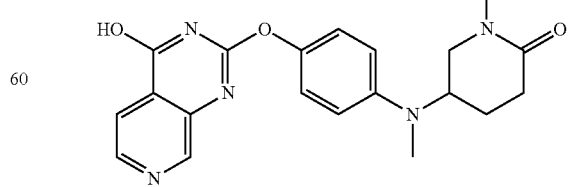

TABLE 2-continued
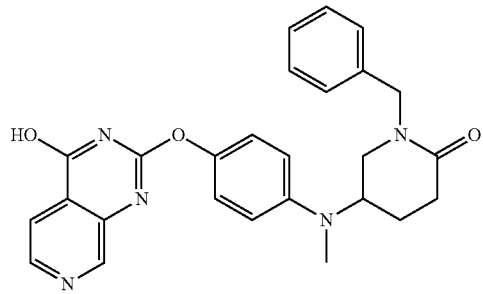 [SMILES: CN(c1ccc(Oc2nc(O)c3ccncc3n2)cc1)C1CCC(=O)N(Cc2ccccc2)C1]
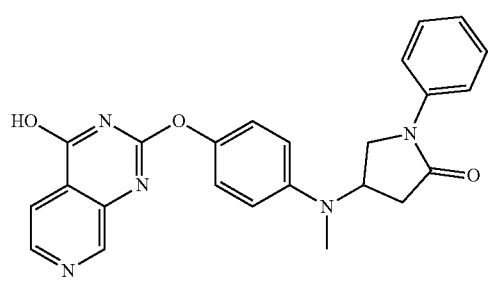 [SMILES: CN(c1ccc(Oc2nc(O)c3ccncc3n2)cc1)C1CC(=O)N(c2ccccc2)C1]
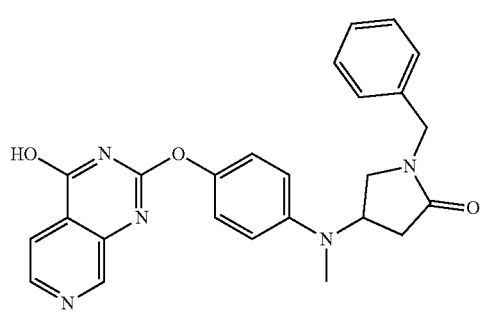 [SMILES: CN(c1ccc(Oc2nc(O)c3ccncc3n2)cc1)C1CC(=O)N(Cc2ccccc2)C1]
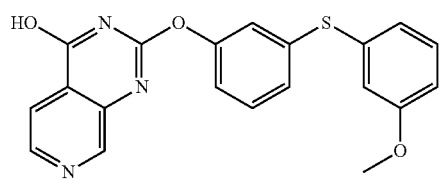 [SMILES: COc1cccc(Oc2cccc(Oc3nc(O)c4ccncc4n3)c2)c1]
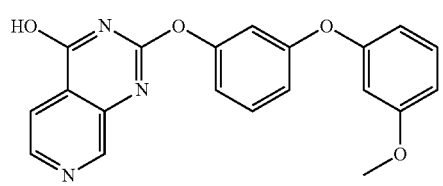
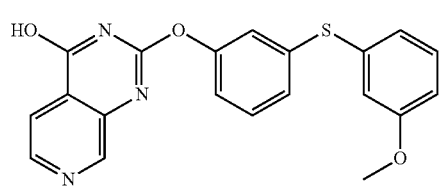
TABLE 2-continued
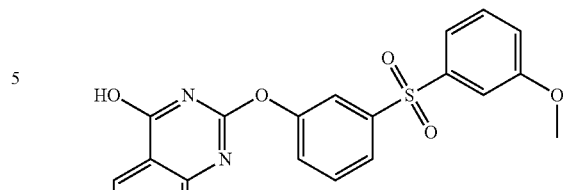
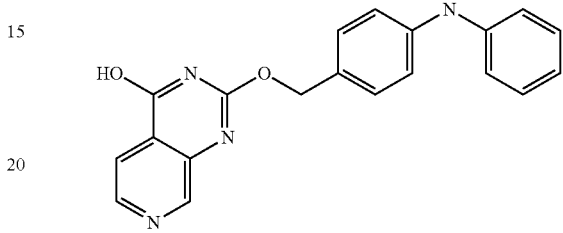
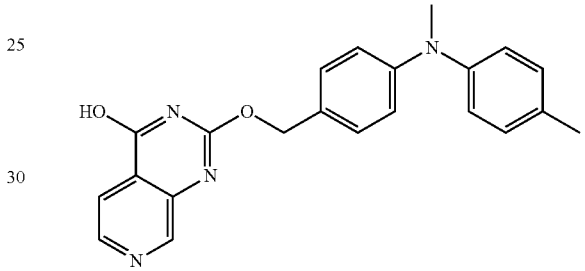
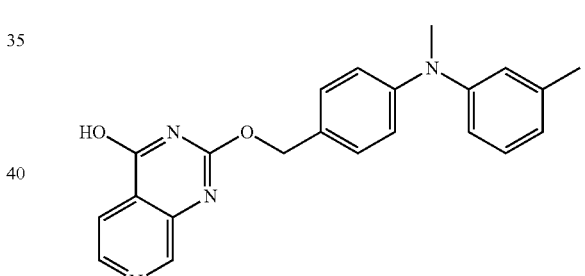
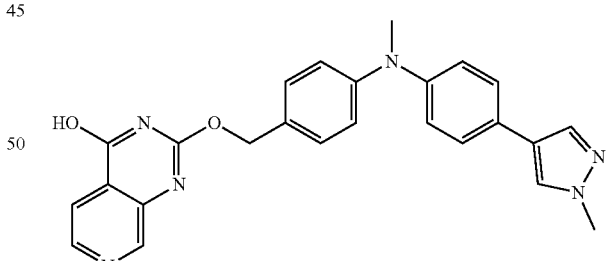
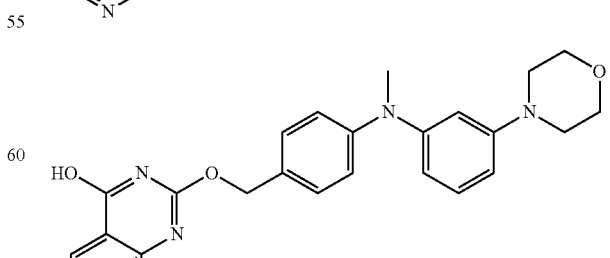

TABLE 2-continued
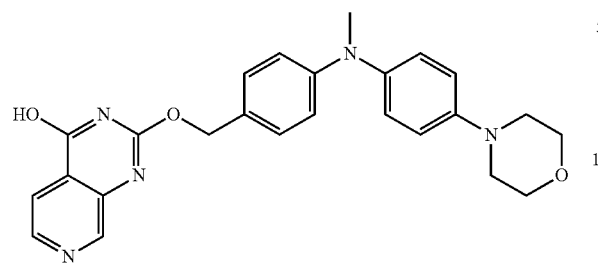
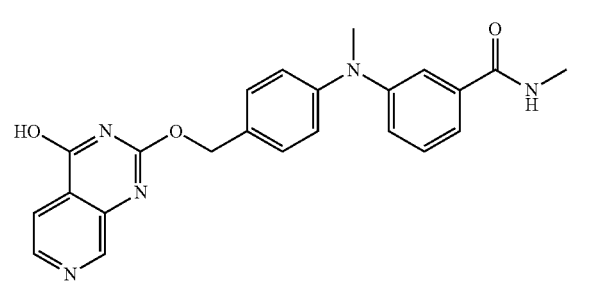
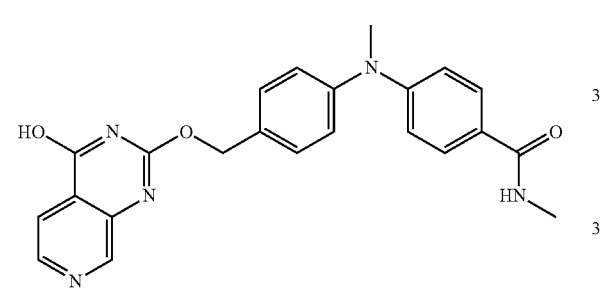 [SMILES: CN(c1ccc(COc2nc(O)c3ccncc3n2)cc1)c1ccc(N2CCOCC2)cc1]
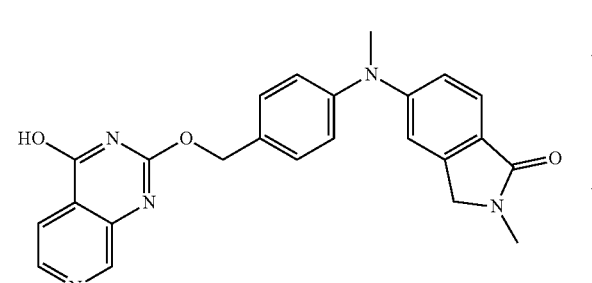
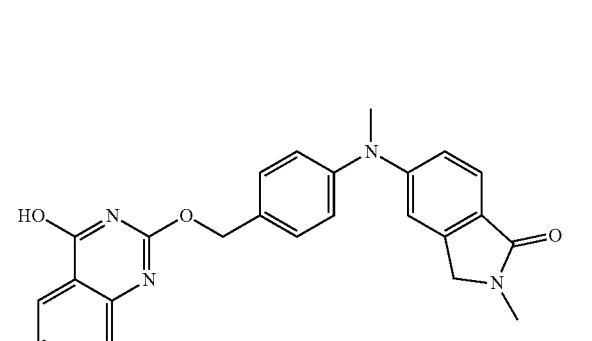
TABLE 2-continued
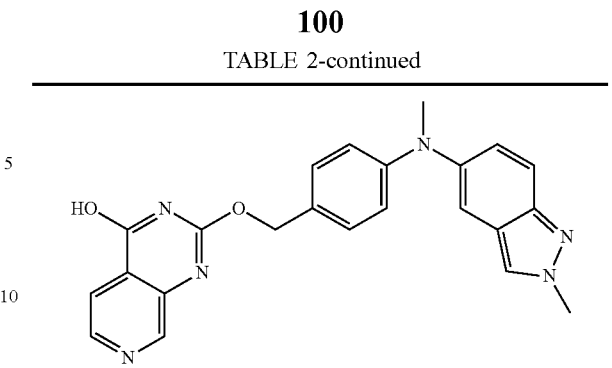
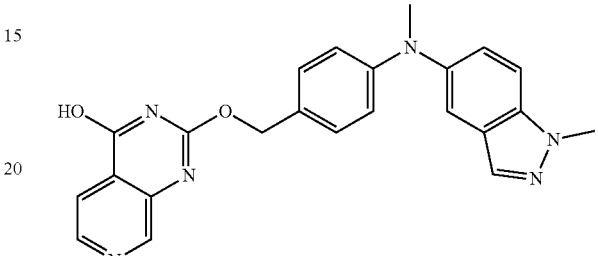
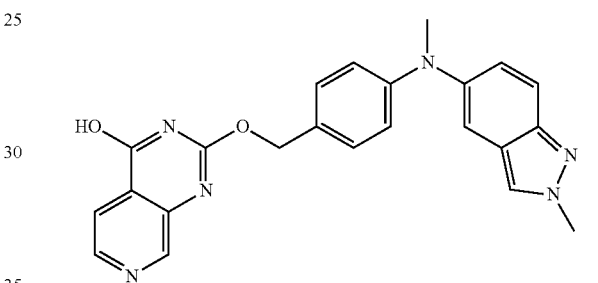
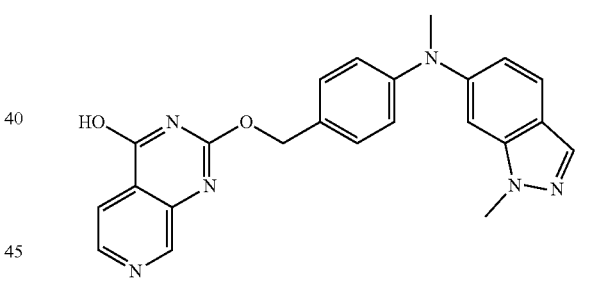
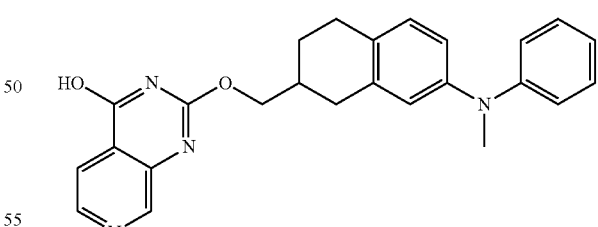
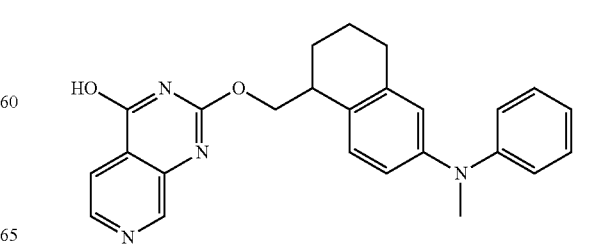

TABLE 2-continued
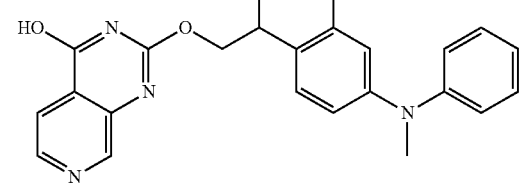
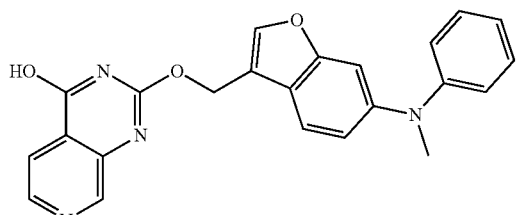
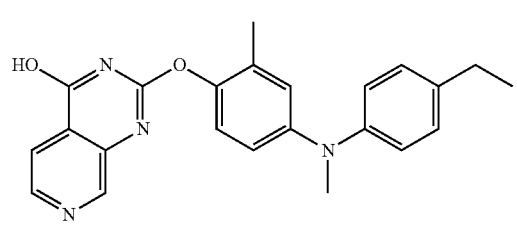 [SMILES: CCc1ccc(N(C)c2ccc(Oc3nc(O)c4ccncc4n3)c(C)c2)cc1]
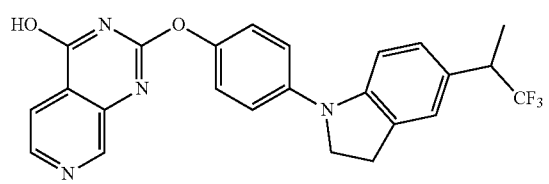 [SMILES: CC(c1ccc2c(c1)CCN2c1ccc(Oc2nc(O)c3ccncc3n2)cc1)C(F)(F)F]
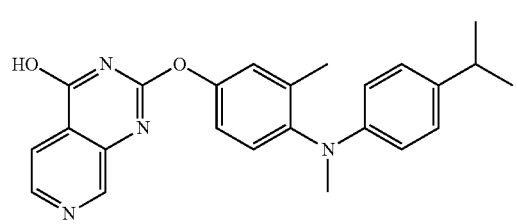 [SMILES: Cc1cc(Oc2nc(O)c3ccncc3n2)ccc1N(C)c1ccc(C(C)C)cc1]
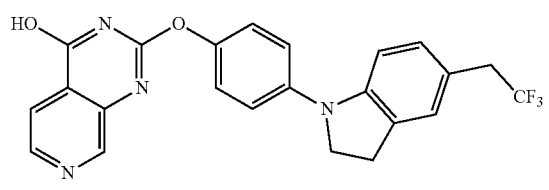 [SMILES: Oc1nc(Oc2ccc(N3CCc4cc(CC(F)(F)F)ccc43)cc2)nc2cnccc12]
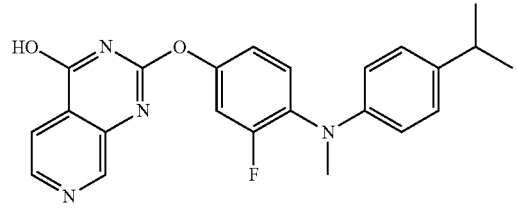
TABLE 2-continued
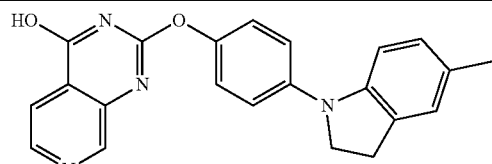
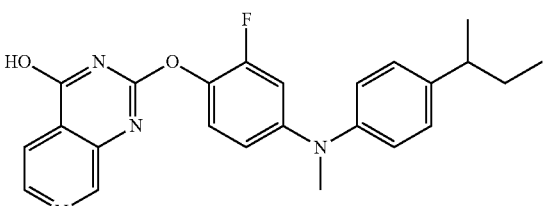
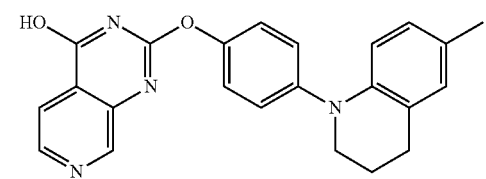 [SMILES: Cc1ccc2c(c1)CCCN2c1ccc(Oc2nc(O)c3ccncc3n2)cc1]
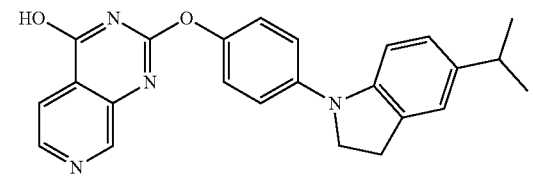 [SMILES: CC(C)c1ccc2c(c1)CCN2c1ccc(Oc2nc(O)c3ccncc3n2)cc1]
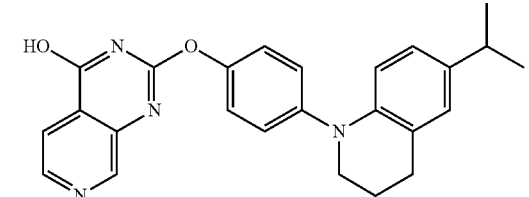
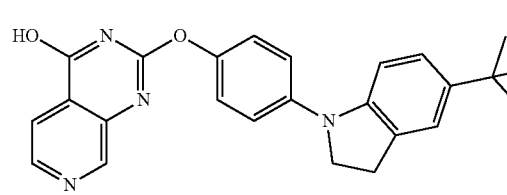
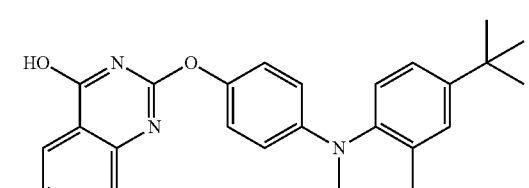
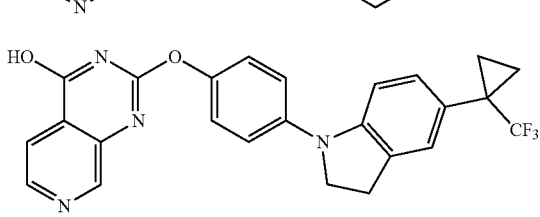

TABLE 2-continued
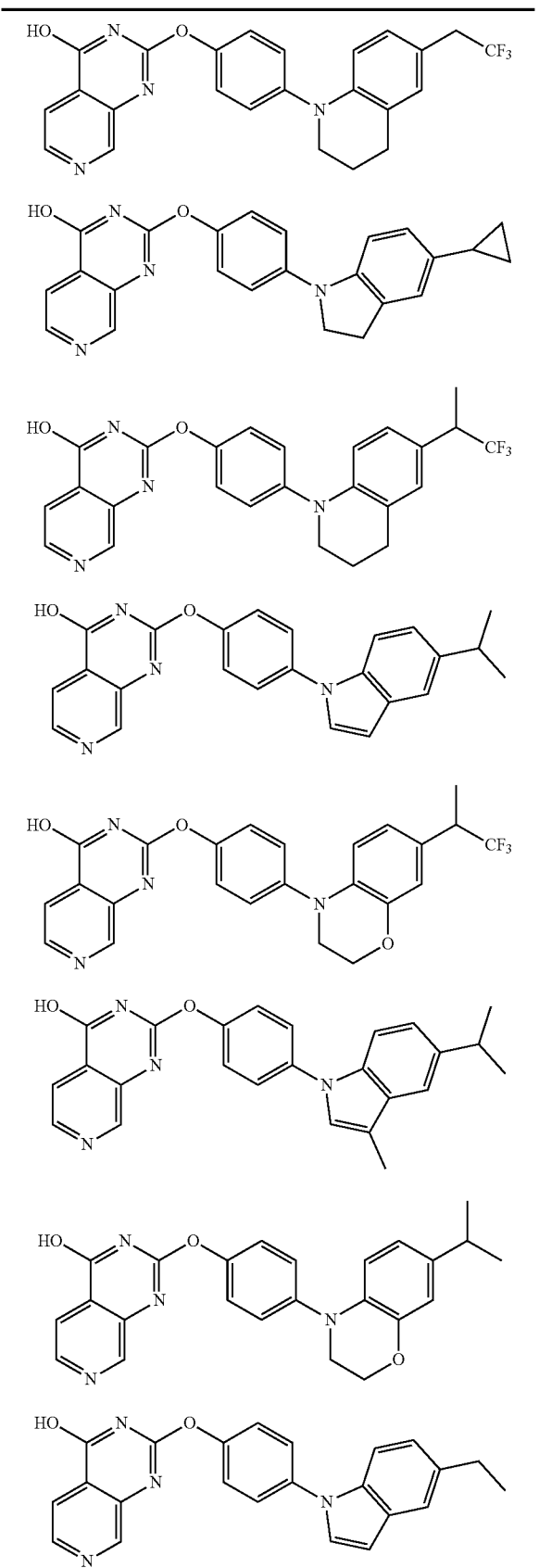
TABLE 2-continued
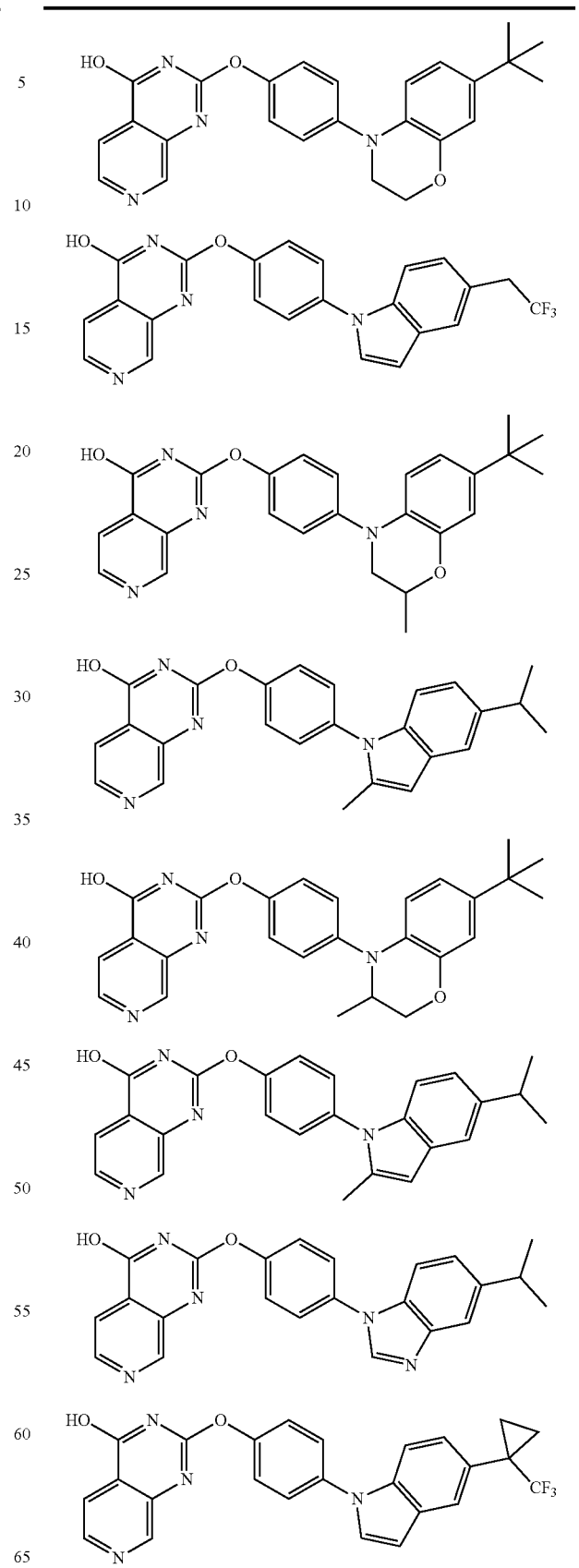

TABLE 2-continued

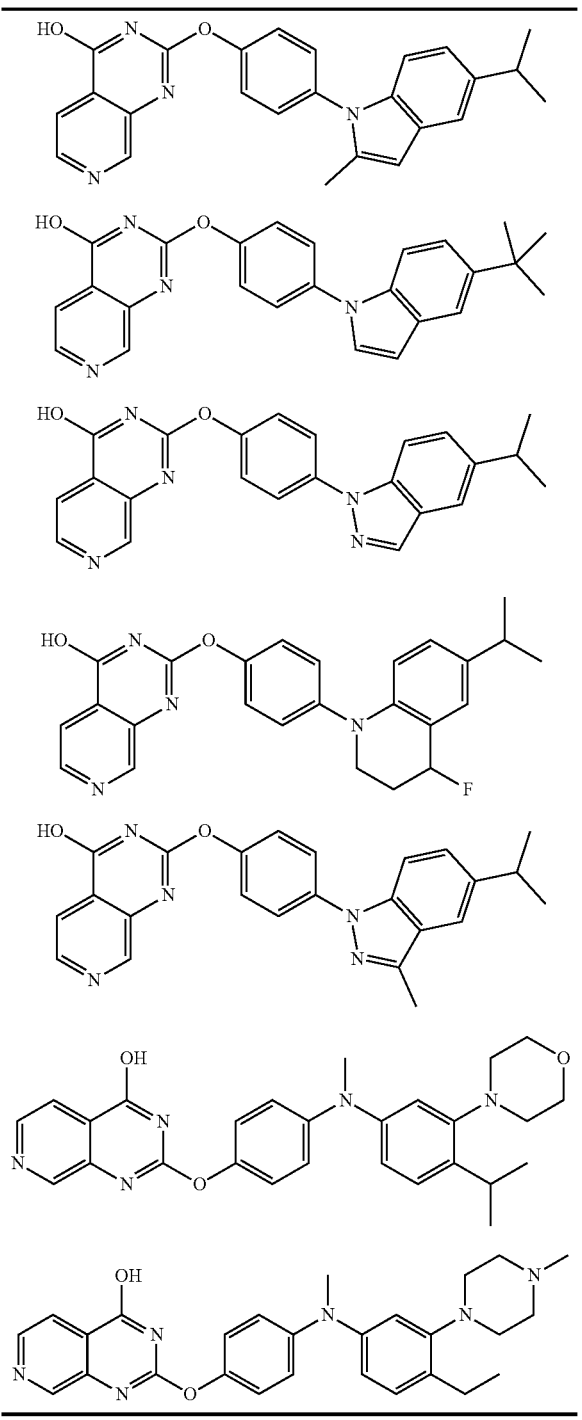

Preparation of the Substituted Pyrido[3,4-d]pyrimidin-4-one Derivative Compounds The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CT), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted pyrido[3,4-d]pyrimidin-4-one derivative compounds described herein is P. H. Stahl & C. G. Wermuth "Handbook of Pharmaceutical Salts", Verlag Helvetica Chimica Acta, Zurich, 2002.

The substituted pyrido[3,4-d]pyrimidin-4-one derivative compounds are prepared by the general synthetic routes described below in Scheme 1.

Scheme 1

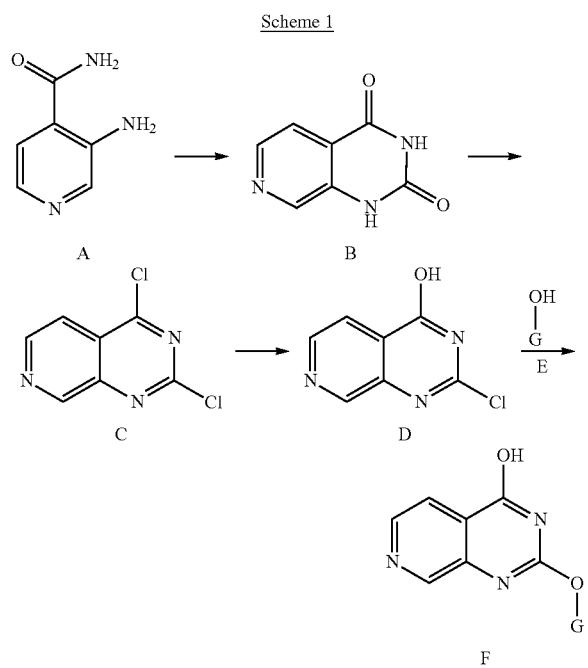

Referring to Scheme 1, compound A is converted to compound B by condensation with urea. The azaquinazolinedione compound B is converted to compound C using an appropriate chlorinating agent, such as POCl$_3$. Compound C is selectively hydrolyzed to form compound D under a variety of basic conditions, such as hydrolysis in a NaOH solution.

Nucleophilic substitution of the chloride in compound D is carried out with an alcohol, such as G-OH, under a variety of basic conditions to form compound F. For example, compound D can be treated with the sodium salt of the alcohol E. Additionally, compound D can be heated with the alcohol or phenol G-OH in the presence of CuI and CsCO$_3$ in an appropriate solvent to form compound F.

In each of the above reaction procedures or schemes, the various substituents may be selected from among the various substituents otherwise taught herein.

Pharmaceutical Compositions

In certain embodiments, a substituted pyrido[3,4-d]pyrimidin-4-one derivative compound as described by Formula (I)-(XI) is administered as a pure chemical. In other embodiments, the substituted pyrido[3,4-d]pyrimidin-4-one derivative compound as described by Formula (I)-(XI) is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, PA (2005)), the disclosure of which is hereby incorporated herein by reference, in its entirety.

Accordingly, provided herein is a pharmaceutical composition comprising at least one substituted pyrido[3,4-d] pyrimidin-4-one derivative compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I) or a pharmaceutically acceptable salt thereof. One embodiment provides a pharmaceutical composition comprising a pharmaceutically acceptable carrier and a compound of Formula (II) or a pharmaceutically acceptable salt thereof. One embodiment provides a pharmaceutical composition comprising a pharmaceutically acceptable carrier and a compound of Formula (III) or a pharmaceutically acceptable salt thereof. One embodiment provides a pharmaceutical composition comprising a pharmaceutically acceptable carrier and a compound of Formula (IV) or a pharmaceutically acceptable salt thereof. One embodiment provides a pharmaceutical composition comprising a pharmaceutically acceptable carrier and a compound of Formula (V) or a pharmaceutically acceptable salt thereof. One embodiment provides a pharmaceutical composition comprising a pharmaceutically acceptable carrier and a compound of Formula (VI) or a pharmaceutically acceptable salt thereof. One embodiment provides a pharmaceutical composition comprising a pharmaceutically acceptable carrier and a compound of Formula (VII) or a pharmaceutically acceptable salt thereof. One embodiment provides a pharmaceutical composition comprising a pharmaceutically acceptable carrier and a compound of Formula (VIII) or a pharmaceutically acceptable salt thereof. One embodiment provides a pharmaceutical composition comprising a pharmaceutically acceptable carrier and a compound of Formula (IX) or a pharmaceutically acceptable salt thereof. One embodiment provides a pharmaceutical composition comprising a pharmaceutically acceptable carrier and a compound of Formula (X) or a pharmaceutically acceptable salt thereof. One embodiment provides a pharmaceutical composition comprising a pharmaceutically acceptable carrier and a compound of Formula (XI) or a pharmaceutically acceptable salt thereof.

In certain embodiments, the substituted pyrido[3,4-d] pyrimidin-4-one derivative compound as described by Formula (I)-(XI) is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, 21$^{st}$ Ed. Mack Pub. Co., Easton, PA (2005)).

The dose of the composition comprising at least one substituted pyrido[3,4-d]pyrimidin-4-one derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

Oral doses can typically range from about 1.0 mg to about 1000 mg, one to four times, or more, per day.

Histone Demethylase

Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which can covalently modify histones at various sites.

Proteins can be post-translationally modified by methylation on amino groups of lysines and guanidino groups of arginines or carboxymethylated on aspartate, glutamate, or on the C-terminus of the protein. Post-translational protein methylation has been implicated in a variety of cellular processes such as RNA processing, receptor mediated signaling, and cellular differentiation. Post-translational protein methylation is widely known to occur on histones, such reactions known to be catalyzed by histone methyltransferases, which transfer methyl groups from S-adenyosyl methionine (SAM) to histones. Histone methylation is known to participate in a diverse range of biological processes including heterochromatin formation, X-chromosome inactivation, and transcriptional regulation (Lachner et al., (2003) J. Cell Sci. 116:2117-2124; Margueron et al., (2005) Curr. Opin. Genet. Dev. 15:163-176).

Unlike acetylation, which generally correlates with transcriptional activation, whether histone methylation leads to transcription activation or repression depends on the particular site of methylation and the degree of methylation (e.g., whether a particular histone lysine residue is mono-, di-, or tri-methylated). However, generally, methylation on H3K9, H3K27 and H4K20 is linked to gene silencing, while methylation on H3K4, H3K36, and H3K79 is generally associated with active gene expression. In addition, tri- and di-methylation of H3K4 generally marks the transcriptional start sites of actively transcribed genes, whereas mono-methylation of H3K4 is associated with enhancer sequences.

A "demethylase" or "protein demethylase," as referred to herein, refers to an enzyme that removes at least one methyl group from an amino acid side chain. Some demethylases act on histones, e.g., act as a histone H3 or H4 demethylase. For example, an H3 demethylase may demethylate one or more of H3K4, H3K9, H3K27, H3K36 and/or H3K79. Alternately, an H4 demethylase may demethylate histone H4K20. Demethylases are known which can demethylate either a mono-, di- and/or a tri-methylated substrate. Further, histone demethylases can act on a methylated core histone substrate, a mononucleosome substrate, a dinucleosome substrate and/or an oligonucleosome substrate, peptide substrate and/or chromatin (e.g., in a cell-based assay).

The first lysine demethylase discovered was lysine specific demethylase 1 (LSD1/KDM1), which demethylates both mono- and di-methylated H3K4 or H3K9, using flavin as a cofactor. A second class of Jumonji C (JmjC) domain containing histone demthylases were predicted, and confirmed when a H3K36 demethylase was found using a formaldehyde release assay, which was named JmjC domain containing histone demethylase 1 (JHDM1/KDM2A).

More JmjC domain-containing proteins were subsequently identified and they can be phylogenetically clustered into seven subfamilies: JHDM1, JHDM2, JHDM3, JMJD2, JARID, PHF2/PHF8, UTX/UTY, and JmjC domain only.

JMJD2 Family

The JMJD2 family of proteins are a family of histone-demethylases known to demethylate tri- and di-methylated H3-K9, and were the first identified histone tri-methyl demethylases. In particular, ectopic expression of JMJD2 family members was found to dramatically decrease levels of tri- and di-methylated H3-K9, while increasing levels of mono-methylated H3- K9, which delocalized Heterochromatin Protein 1 (HP1) and reduced overall levels of heterochromatin in vivo. Members of the JMJD2 subfamily of jumonji proteins include JMJD2C and its homologues JMJD2A, JMJD2B, JMJD2D and JMJD2E. Common structural features found in the JMJD2 subfamily of Jumonji proteins include the JmjN, JmjC, PHD and Tdr sequences.

JMJD2C, also known as GASC1 and KDM4C, is known to demethylate tri-methylated H3K9 and H3K36. Histone demethylation by JMJD2C occurs via a hydroxylation reaction dependent on iron and α-ketoglutarate, wherein oxidative decarboxylation of α-ketoglutarate by JMJD2C produces carbon dioxide, succinate, and ferryl and ferryl subsequently hydroxylates a methyl group of lysine H3K9, releasing formaldehyde. JMJD2C is known to modulate regulation of adipogenesis by the nuclear receptor PPARγ and is known to be involved in regulation of self-renewal in embryonic stem cells.

JARID Family

As used herein, a "JARID protein" includes proteins in the JARID1 subfamily (e.g., JARID1A, JARID1B, JARID1C and JARID1D proteins) and the JARID2 subfamily, as well as homologues thereof. A further description and listing of JARID proteins can be found in Klose et al. (2006) Nature Reviews/Genetics 7:715-727. The JARID1 family contains several conserved domains: JmjN, ARID, JmjC, PHD and a C5HC2 zing finger.

JARID1A, also called KDM5A or RBP2, was initially found as a binding partner of retinoblastoma (Rb) protein. JARID1A was subsequently found to function as a demethylase of tri- and di-methylated H3K4, and has been found to promote cell growth, while inhibiting senescence and differentiation. For instance, abrogation of JARID1A from mouse cells inhibits cell growth, induces senescence and differentiation, and causes loss of pluripotency of embryonic stem cells in vitro. JARID1A has been found to be overexpressed in gastric cancer and the loss of JARID1A has been found to reduce tumorigenesis in a mouse cancer model. Additionally, studies have demonstrated that loss of the retinoblastome binding protein 2 (RBP2) histone demethylase suppresses tumorigenesis in mice lacking Rb1 or Men1 (Lin et al. Proc. Natl. Acad. Sci. USA, Aug. 16, 2011, 108(33), 13379-86; doi: 10.1073/pnas.1110104108) and lead to the conclusion that RBP2-inhibitory drugs would have anti-cancer activity.

JARID1B, also referred to as KDM5B and PLU1, was originally found in experiments to discover genes regulated by the HER2 tyrosine kinase. JARID1B has consistently been found to be expressed in breast cancer cell lines, although restriction of JARID1B has been found in normal adult tissues, with the exception of the testis. In addition, 90% of invasive ductal carcinomas have been found to express JARID1B. In addition, JARID1B has been found to be up-regulated in prostate cancers, while having more limited expression in benign prostate, and has also been found to be up-regulated in bladder cancer and lung cancer (both SCLC and NSCLC). JARID1B has also been found to repress tumor suppressor genes such as BRCA1, CAV1 and 14-3-36, and knockdown of JARID1B was found to increase the levels of tri-methylated H3K4 at these genes.

In an additional embodiment is a method for inhibiting a histone-demethylase enzyme comprising contacting a histone demethylase enzyme with a compound of Formula (I) or a pharmaceutically acceptable salt thereof. In an additional embodiment is a method for inhibiting a histone-demethylase enzyme comprising contacting a histone demethylase enzyme with a compound of Formula (II) or a pharmaceutically acceptable salt thereof. In an additional embodiment is a method for inhibiting a histone-demethylase enzyme comprising contacting a histone demethylase enzyme with a compound of Formula (III) or a pharmaceutically acceptable salt thereof. In an additional embodiment is a method for inhibiting a histone-demethylase enzyme comprising contacting a histone demethylase enzyme with a compound of Formula (IV) or a pharmaceutically acceptable salt thereof. In an additional embodiment is a method for inhibiting a histone-demethylase enzyme comprising contacting a histone demethylase enzyme with a compound of Formula (V) or a pharmaceutically acceptable salt thereof. In an additional embodiment is a method for inhibiting a histone-demethylase enzyme comprising contacting a histone demethylase enzyme with a compound of Formula (VI) or a pharmaceutically acceptable salt thereof. In an additional embodiment is a method for inhibiting a histone-demethylase enzyme comprising contacting a histone demethylase enzyme with a compound of Formula (VII) or a pharmaceutically acceptable salt thereof. In an additional embodiment is a method for inhibiting a histone-demethylase enzyme comprising contacting a histone demethylase enzyme with a compound of Formula (VIII) or a pharmaceutically acceptable salt thereof. In an additional embodiment is a method for inhibiting a histone-demethylase enzyme comprising contacting a histone demethylase enzyme with a compound of Formula (IX) or a pharmaceutically acceptable salt thereof. In an additional embodiment is a method for inhibiting a histone-demethylase enzyme comprising contacting a histone demethylase enzyme with a compound of Formula (X) or a pharmaceutically acceptable salt thereof. In an additional embodiment is a method for inhibiting a histone-demethylase enzyme comprising contacting a histone demethylase enzyme with a compound of Formula (XI) or a pharmaceutically acceptable salt thereof.

In an additional embodiment is the method for inhibiting a histone-demethylase enzyme, wherein the histone-demethylase enzyme comprises a jumonji domain. In an additional embodiment is the method for inhibiting a histone-demethylase enzyme, wherein the histone-demethylase enzyme is JMJD2C.

Methods of Treatment

Disclosed herein are methods of modulating demethylation in a cell or in a subject, either generally or with respect to one or more specific target genes. Demethylation can be modulated to control a variety of cellular functions, including without limitation: differentiation; proliferation; apoptosis; tumorigenesis, leukemogenesis or other oncogenic transformation events; hair loss; or sexual differentiation. For example, in particular embodiments, the invention provides a method of treating a disease regulated by histone methylation and/or demethylation in a subject in need thereof by modulating the activity of a demethylase comprising a jumonji domain (e.g., a histone demethylase such as a JMJD2C protein).

In an additional embodiment is a method for treating cancer in subject in need thereof comprising administering a composition comprising a compound of Formula (I), or a pharmaceutically acceptable salt thereof. In an additional embodiment is a method for treating cancer in subject in need thereof comprising administering a composition comprising a compound of Formula (II), or a pharmaceutically acceptable salt thereof. In an additional embodiment is a method for treating cancer in subject in need thereof comprising administering a composition comprising a compound of Formula (III), or a pharmaceutically acceptable salt thereof. In an additional embodiment is a method for treating cancer in subject in need thereof comprising administering a composition comprising a compound of Formula (IV), or a pharmaceutically acceptable salt thereof. In an additional embodiment is a method for treating cancer in subject in need thereof comprising administering a composition comprising a compound of Formula (V), or a pharmaceutically acceptable salt thereof. In an additional embodiment is a method for treating cancer in subject in need thereof comprising administering a composition comprising a compound of Formula (VI), or a pharmaceutically acceptable salt thereof. In an additional embodiment is a method for treating cancer in subject in need thereof comprising administering a composition comprising a compound of Formula (VII), or a pharmaceutically acceptable salt thereof. In an additional embodiment is a method for treating cancer in subject in need thereof comprising administering a composition comprising a compound of Formula (VIII), or a pharmaceutically acceptable salt thereof. In an additional embodiment is a method for treating cancer in subject in need thereof comprising administering a composition comprising a compound of Formula (IX), or a pharmaceutically acceptable salt thereof. In an additional embodiment is a method for treating cancer in subject in need thereof comprising administering a composition comprising a compound of Formula (X), or a pharmaceutically acceptable salt thereof. In an additional embodiment is a method for treating cancer in subject in need thereof comprising administering a composition comprising a compound of Formula (XI), or a pharmaceutically acceptable salt thereof.

In a further embodiment is the method for treating cancer in a subject wherein the cancer is selected from prostate cancer, breast cancer, bladder cancer, lung cancer or melanoma.

In an additional embodiment is a method for inhibiting the growth of a tumor comprising administering a composition comprising a compound selected from any one of Formula (I)-(XI), or a pharmaceutically acceptable salt thereof, wherein the tumor is characterized by a loss of retinoblastoma gene (RB1) function.

In an additional embodiment is a method for inhibiting the growth of a tumor comprising administering a composition comprising a compound selected from any one of Formula (I)-(XI) or a pharmaceutically acceptable salt thereof, wherein the tumor is characterized by a loss of multiple endocrine neoplasia type 1 gene (Men1) function.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Preparation I: 2-Chloropyrido[3,4-d]pyrimidin-4-ol

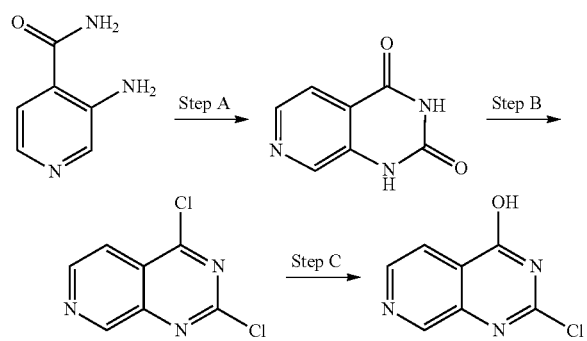

Step A: Pyrido[3,4-d]pyridine-2,4(1H,3H)-dione

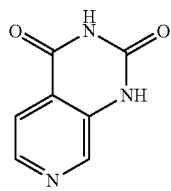

To a solution of 3-aminopyridine-4-carboxamide (5 g, 36.5 mmol) in THF (100 mL) was added triphosgene (11.9 g, 40.1 mmol) and TEA (7.4 g, 73 mmol). The reaction mixture was refluxed for 2 h. The solution was concentrated in vacuo and the residue was triturated in water. The solid was filtered and washed with water and THF. The solid was dried to afford 4.1 g (70%) of the title compound. $^1$H NMR (400 MHz, DMSO-d$_6$): δ 11.62 (s, 1H), 11.58 (s, 1H), 8.66 (s, 1H), 8.40 (d, 1H, J=5.2 Hz), 7.80 (d, 1H, J=5.2 Hz).

Step B: 2,4-Dichloropyrido[3,4-d]pyrimidine

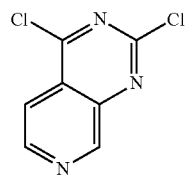 [SMILES: Clc1nc(Cl)c2ccncc2n1]

To a mixture of pyrido[3,4-d]pyridine-2,4(1H,3H)-dione (2 g, 12.3 mmol) in toluene (50 mL) was added DIEA (3.15 g, 25 mmol) and POCl$_3$ (9.5 g, 61.4 mmol). The reaction mixture was refluxed overnight. The solution was concentrated in vacuo and the residue was taken in ethyl acetate and washed with aq. NaHCO$_3$ and brine. The organics were dried and concentrated. The residue was purified by silica gel chromatography (25% EA:PE) to afford 1 g (41%) of the title compound. $^1$H NMR (400 MHz, DMSO-d$_6$): δ 9.50 (s, 1H), 8.90 (d, 1H, J=5.2 Hz), 8.02 (d, 1H, J=5.2 Hz).

Step C: 2-Chloropyrido[3,4-d]pyrimidin-4-ol

To a solution of 2,4-dichloropyrido[3,4-d]pyrimidine (1 g, 5 mmol) in THF (20 mL) was added a solution of NaOH (0.5 g, 12.5 mmol) in water (20 mL). The reaction mixture was stirred at r.t. for 2 h. The solution was adjusted to pH=2 using 5N HCl and the resulting precipitate was filtered and washed with water and THF, and dried to afford 0.8 g (88%) of the title compound.

$^1$H NMR (400 MHz, DMSO-d$_6$): δ 13.61 (s, 1H), 8.99 (s, 1H), 8.69 (d, 1H, J=5.2 Hz), 7.94 (d, 1H, J=5.2 Hz).

Preparation 1A: (4-Methoxy-phenyl)-pyridin-2-yl-amine

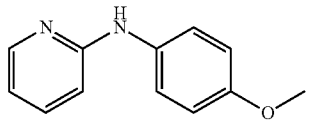

A mixture of 2-bromo-pyridine (2.00 g, 12.7 mmol), 4-methoxy-phenylamine (1.56 g, 12.7 mmol), Pd(OAc)$_2$ (290 mg, 1.27 mmol), BINAP (791 mg, 1.27 mmol) and t-BuOK (2.84 g, 25.3 mmol) in toluene (30 mL) was stirred under nitrogen atmosphere for 4 h at 125° C. The reaction mixture was concentrated. The residue was purified by silica gel chromatography (PE:EA 15:1) to give 1.78 g (70%) of the title compound. $^1$H NMR (400 MHz, CDCl$_3$): δ 3.81 (s, 3H), 6.47 (s, 1H), 6.67-6.68 (m, 2H), 6.88-6.92 (m, 2H), 7.21-7.26 (m, 2H), 7.41-7.45 (m, 1H), 8.14 (d, J=4.0 Hz, 1H). [M+H] Calc'd for C$_{19}$H$_{15}$N$_5$O$_2$, 201; Found, 201.

Preparation 1B:
(4-Methoxy-phenyl)-methyl-pyridin-2-yl-amine

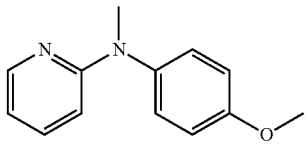 [SMILES: COc1ccc(N(C)c2ccccn2)cc1]

To a solution of (4-methoxy-phenyl)-pyridin-2-yl-amine (1.78 g, 8.9 mmol) in DMF (20 mL) was added t-BuOK (2.0 g, 17.8 mmol) at 0° C. After stirring for 30 min, MeI (2.53 g, 17.8 mmol) was added dropwise over 10 min and the reaction mixture was stirred at rt overnight. The reaction mixture was diluted with water (100 mL), extracted with DCM (30 mL*3). The combined organic layers were washed with water (150 mL*3), brine (150 mL), dried over $Na_2SO_4$, and concentrated to give 1.47 g (77%) of the title product. $^1$H NMR (400 MHz, $CDCl_3$): δ 3.42 (s, 3H), 3.83 (s, 3H), 6.37 (d, J=8.8 Hz, 1H), 6.54-6.57 (m, 1H), 6.93-6.95 (m, 2H), 7.16-7.19 (m, 2H), 7.26-7.28 (m, 1H), 8.19-8.21 (m, 1H). [M+H] Calc'd for $C_{13}H_{14}N_2O$, 215; Found, 215.

Preparation 1C:
4-(Methyl-pyridin-2-yl-amino)-phenol

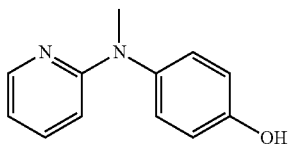

To a solution of (4-methoxy-phenyl)-methyl-pyridin-2-yl-amine (600 mg, 2.8 mmol) in DCM (12 mL) was added dropwise $BBr_3$ (28 mL, 28 mmol, 1M in DCM) at 0° C. The reaction mixture was stirred for 30 min and carefully quenched with MeOH at 0° C. The volatiles were concentrated in vacuo. The residue was dissolved in DCM (20 mL), washed with saturated $NaHCO_3$ solution (50 mL) and brine (50 mL), dried over $Na_2SO_4$, and concentrated to give 450 mg (80%) of the title product. $^1$H NMR (400 MHz, $CDCl_3$): δ 3.41 (s, 3H), 6.41 (d, J=8.8 Hz, 1H), 6.56-6.59 (m, 1H), 6.85-6.87 (m, 2H), 7.08-7.11 (m, 2H), 7.29-7.33 (m, 1H), 8.17-8.19 (m, 1H). [M+H] Calc'd for $C_{12}H_{12}N_2O$, 200; Found, 201.

Example 1: 2-[4-(Methyl-pyridin-2-yl-amino)-phenoxy]-pyrido[3,4-d]pyrimidin-4-ol

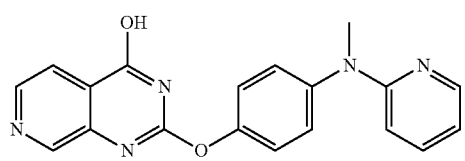 [SMILES: CN(c1ccc(Oc2nc(O)c3ccncc3n2)cc1)c1ccccn1]

A mixture of 2-chloro-pyrido[3,4-d]pyrimidin-4-ol (408 mg, 2.25 mmol), 4-(methyl-pyridin-2-yl-amino)-phenol (450 mg, 2.25 mmol), $Cs_2CO_3$ (734 mg, 2.25 mmol), and CuI (428 mg, 2.25 mmol) in DMF (5 mL) was stirred at 130° C. under nitrogen atmosphere overnight. The reaction mixture was concentrated. The residue was purified by HPLC to obtain 156 mg (20%) of the title product. $^1$H NMR (400 MHz, DMSO-$d_6$): δ 3.43 (s, 3H), 6.63 (d, J=7.2 Hz, 1H), 6.70-6.73 (m, 2H), 7.38-7.40 (m, 4H), 7.48-7.52 (m, 1H), 8.02-8.11 (m, 1H), 8.17 (d, J=4.0 Hz, 1H), 8.62-8.7 (m, 1H), 13.14 (s, 1H). [M+H] Calc'd for $C_{19}H_{15}N_5O_2$, 346; Found, 346.

Preparation 2A: 5-Benzyloxy-1-methyl-1H-indole

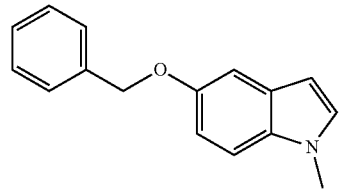 [SMILES: Cn1ccc2cc(OCc3ccccc3)ccc21]

To a solution of 5-benzyloxy-1H-indole (2.23 g, 10 mmol) in DMF (20 mL) at 0° C. was added NaH (480 mg, in mineral oil, 60%, 12 mmol) in portions and the mixture was stirred for 30 min. MeI was then added and the mixture was stirred at rt overnight. The reaction mixture was diluted with water (100 mL) and extracted with DCM (30 mL*3). Organics were dried over $Na_2SO_4$ and concentrated. The residue was purified by silica gel chromatography (PE:EA 50:1) to give 1.97 g (83%) of the title product. $^1$H NMR (400 MHz, $CDCl_3$): δ 3.77 (s, 3H), 5.11 (s, 2H), 6.39 (d, J=3.2 Hz, 1H), 6.97 (dd, J=2.4, 8.8 Hz, 1H), 7.01 (d, J=3.2 Hz, 1H), 7.17 (d, J=2.0 Hz, 1H), 7.22 (J=10.8 Hz, 1H), 7.31 (t, J=7.2 Hz, 1H), 7.39 (t, J=7.2 Hz, 2H), 7.48 (d, J=7.2 Hz, 2H). [M+H] Calc'd for $C_{16}H_{15}NO$, 238; Found, 238.

Preparation 2B: 1-Methyl-1H-indol-5-ol

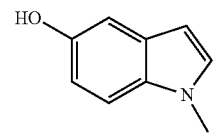

A mixture of 5-benzyloxy-1-methyl-1H-indole (1.97 g, 8.31 mmol) and Pd/C (0.5 g, 10% wet) in EtOH was stirred overnight under H2 atmosphere. The reaction mixture was filtered through a Celite pad. The filtrate was concentrated to give 1.2 g (98%) of the title product. $^1$H NMR (400 MHz, $CDCl_3$): δ 3.75 (s, 3H), 6.35 (d, J=2.8 Hz, 1H), 6.80 (dd, J=2.4, 8.8 Hz, 1H), 7.01-7.03 (m, 2H), 7.17 (d, J=8.8 Hz, 1H). [M+H] Calc'd for $C_9H_9NO$, 148; Found, 148.

Example 2: 2-(1-Methyl-1H-indol-5-yloxy)-pyrido[3,4-d]pyrimidin-4-ol

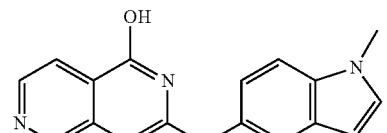

The title compound was prepared in 2.5% yield from 2-chloro-pyrido[3,4-d]pyrimidin-4-ol and 1-methyl-1H-indol-5-ol according to the preparation of Example 1. $^1$H NMR (400 MHz, DMSO-d$_6$): δ 3.83 (s, 3H), 6.45 (d, J=2.8 Hz, 1H), 7.07 (d, J=7.6 Hz, 1H), 7.40-7.43 (m, 2H), 7.48 (d, J=8.8 Hz, 1H), 7.84 (d, J=4.8 Hz, 1H), 8.44 (d, J=4.4 Hz, 1H), 8.59 (s, 1H). [M+H] Calc'd for C$_{16}$H$_{12}$N$_4$O$_2$, 293; Found, 293.

Preparation 3A: 5-Benzyloxy-1-phenethyl-1H-indole

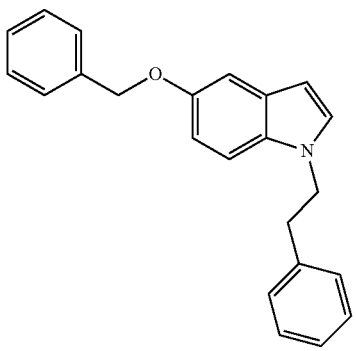 [SMILES: c1ccc(CCn2ccc3cc(OCc4ccccc4)ccc32)cc1]

A mixture of 5-benzyloxy-1H-indole (3.0 g, 13.5 mmol), (2-bromo-ethyl)-benzene (3.0 g, 16.1 mmol) and KOH (2.7 g, 40.4 mmol) in DMSO (25 mL) was stirred at 100° C. overnight. The reaction mixture was diluted with water (50 mL) and extracted with EA (20 mL*3). The organic layers were combined, washed with water (30 mL*3), washed with brine, dried over Na$_2$SO$_4$, and concentrated. The residue was purified by silica gel chromatography (PE:EA 50:1) to give 1.9 g (43%) of the title product. $^1$H NMR (400 MHz, CDCl$_3$): δ 3.08 (t, J=7.2 Hz, 2H), 4.29 (t, J=7.2 Hz, 2H), 5.10 (s, 2H), 6.33 (d, J=2.8 Hz, 1H), 6.88 (d, J=2.8 Hz, 1H), 6.94 (dd, J=2.8, 8.8 Hz, 1H), 7.07 (d, J=6.8 Hz, 2H), 7.16 (d, J=2.4 Hz, 1H), 7.21-7.26 (m, 4H), 7.31 (t, J=7.2 Hz, 1H), 7.38 (t, J=7.2 Hz, 2H), 7.47 (d, J=7.6 Hz, 2H). [M+H] Calc'd for C$_{23}$H$_{21}$NO, 328; Found, 328.

Preparation 3B: 1-Phenethyl-1H-indol-5-ol

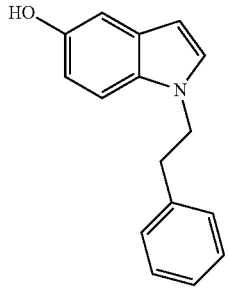 [SMILES: Oc1ccc2c(ccn2CCc2ccccc2)c1]

A mixture of 5-benzyloxy-1-phenethyl-1H-indole (1.9 g, 5.8 mmol) and Pd/C (0.5 g, 10% wet) in EtOH was stirred under H2 atmosphere overnight. The reaction mixture was filtered through a Celite pad. The filtrate was concentrated to give 1.2 g (87%) of the title product. $^1$H NMR (400 MHz, CDCl$_3$): δ 3.08 (t, J=7.2 Hz, 2H), 4.29 (t, J=7.2 Hz, 2H), 6.29 (d, J=2.8 Hz, 1H), 6.79 (dd, J=2.4, 8.8 Hz, 1H), 6.88 (d, J=2.8 Hz, 1H), 7.02 (d, J=2.4 Hz, 1H), 7.06-7.08 (m, 2H), 7.16-7.29 (m, 5H). [M+H] Calc'd for C$_{16}$H15NO, 238; Found, 238.

Example 3: 2-(1-Phenethyl-1H-indol-5-yloxy)-pyrido[3,4-d]pyrimidin-4-ol

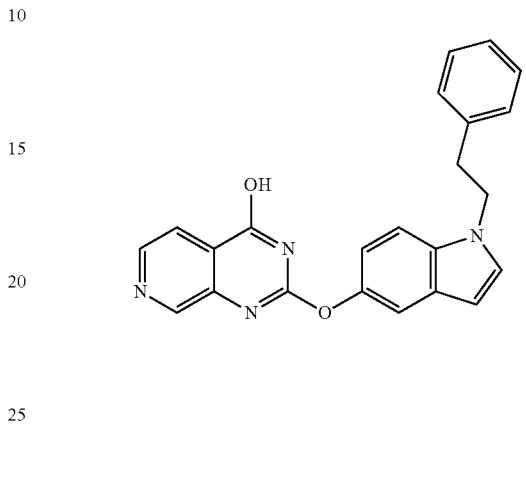

The title compound was prepared in 6% yield from 2-chloro-pyrido[3,4-d]pyrimidin-4-ol and 1-phenethyl-1H-indol-5-ol according to the procedure for the preparation of Example 1. $^1$H NMR (400 MHz, DMSO-d$_6$): δ 3.10 (t, J=7.0 Hz, 2H), 4.44 (t, J=7.0 Hz, 2H), 6.43 (s, 1H), 7.06 (d, J=7.6 Hz, 1H), 7.21-7.26 (m, 5H), 7.39 (s, 1H), 7.44 (s, 1H), 7.56 (d, J=8.8 Hz, 1H), 7.87 (t, J=2.0 Hz, 1H), 8.48 (d, J=4.8 Hz, 1H), 8.63 (s, 1H). [M+H] Calc'd for C$_{23}$H$_{18}$N$_4$O$_2$, 383; Found, 383.

Preparation 4A: 1-Benzyl-5-methoxy-1H-indole

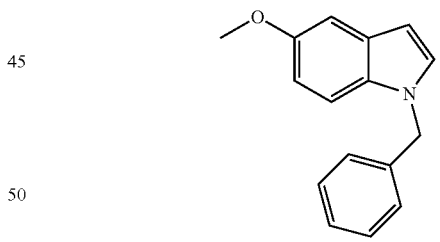

To a solution of 5-methoxy-1H-indole (1.50 g, 10 mmol) in DMF (20 mL) at 0° C. was added NaH (480 mg, in mineral oil, 60%, 12 mmol) in portions, and the mixture was stirred for 30 min. BnBr (2.09 g, 12 mmol) was then added and the mixture was stirred at rt overnight. The reaction mixture was diluted with water (100 mL) and extracted with DCM (30 mL*3). Organics were dried over Na$_2$SO$_4$ and concentrated. The residue was purified by silica gel chromatography (PE:EA 20:1) to give 2.40 g (99%) of the title product. [M+H] Calc'd for C$_{16}$H15NO, 238; Found, 238.

Example 4B: 1-Benzyl-1H-indol-5-ol

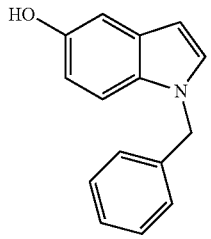 [SMILES: Oc1ccc2c(ccn2Cc2ccccc2)c1]

To a solution of 1-benzyl-5-methoxy-1H-indole (2.40 g, 10 mmol) in DCM (20 mL) was added BBr$_3$ (40 mL, 1.0 M in DCM, 40 mmol) in portions at 0° C., and the mixture was stirred at rt for 2 h. The reaction mixture was diluted with water (30 mL), basified to pH 5 with sat. Na$_2$CO$_3$, and extracted with DCM (30 mL*3). Organics were dried over Na$_2$SO$_4$ and concentrated. The residue was purified by silica gel chromatography (PE:EA 10:1) to give 1.20 g (53%) of the title product. [M+H] Calc'd for C$_{15}$H13NO, 224; Found, 224.

Example 4: 2-(1-Benzyl-1H-indol-5-yloxy)-pyrido[3,4-d]pyrimidin-4-ol

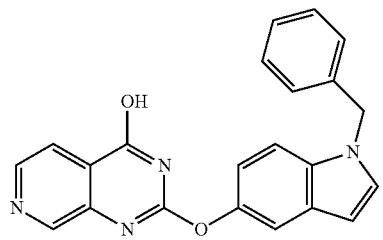 [SMILES: Oc1nc(Oc2ccc3c(ccn3Cc3ccccc3)c2)nc2cnccc12]

The title compound was prepared in 19% yield from 2-chloro-pyrido[3,4-d]pyrimidin-4-ol and 1-benzyl-1H-indol-5-ol according to the procedure for the preparation of Example 1. $^1$H NMR (300 MHz, DMSO-d$_6$): δ 5.45 (s, 2H), 6.53 (d, J=2.1 Hz, 1H), 7.04-7.08 (m, 1H), 7.24-7.36 (m, 5H), 7.49-7.55 (m, 2H), 7.63 (d, J=1.5 Hz, 1H), 7.85-7.89 (m, 1H), 8.15 (brs, 2H), 13.04 (s, 1H). [M+H] Calc'd for C$_{22}$H$_{16}$N$_4$O$_2$, 369; Found, 369.

Preparation 5A: 4-(Methyl-phenyl-amino)-phenol

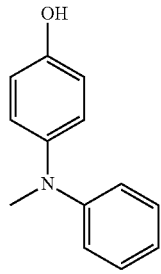

To a suspension of 4-bromo-phenol (2.00 g, 12 mmol), methyl-phenyl-amine (1.48 g, 14 mmol), Pd$_2$(dba)$_3$ (267 mg, 0.29 mmol) and 2-dicyclohexyphosphino-biphenyl (121 mg, 0.35 mmol) in toluene (40 mL) was added LiHMDS (25 mL, 1.0 M in THF, 25 mmol) in portions under nitrogen atmosphere. The reaction mixture was stirred at 65° C. overnight, acidified to pH 6 with 1N HCl, washed with brine (50 mL), dried over Na$_2$SO$_4$, filtered, and concentrated. The residue was purified by silica gel column (PE:EA 10:1) to give 2 g (87%) of the title product. [M+H] Calc'd for C$_{13}$H13NO, 200; Found, 200.

Example 5: 2-[4-(Methyl-phenyl-amino)-phenoxy]-pyrido[3,4-d]pyrimidin-4-ol

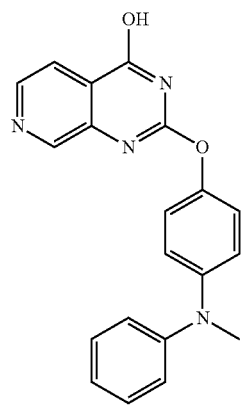 [SMILES: CN(c1ccccc1)c1ccc(Oc2nc(O)c3ccncc3n2)cc1]

The title compound was prepared in 18% yield from 2-chloro-pyrido[3,4-d]pyrimidin-4-ol and 4-(methyl-phenyl-amino)-phenol according to the procedure for the preparation of Example 1. $^1$H NMR (400 MHz, DMSO-d$_6$): δ 3.30 (s, 3H), 6.97-7.08 (m, 5H), 7.23-7.25 (m, 2H), 7.30-7.34 (m, 2H), 7.90-7.92 (m, 1H), 8.51-8.78 (m, 2H), 13.06 (s, 1H). [M+H] Calc'd for C$_{20}$H$_{16}$N$_4$O$_2$, 345; Found, 345.

Preparation 6A: 4-(Benzyl-methyl-amino)-phenol

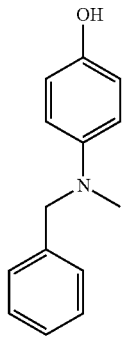 [SMILES: CN(Cc1ccccc1)c1ccc(O)cc1]

The title compound was prepared in 41% yield from 4-bromo-phenol and benzyl-methyl-amine according to the procedure of Preparation 5A. [M+H] Calc'd for C$_{14}$H$_{15}$NO, 214; Found, 214.

Example 6: 2-[4-(Benzyl-methyl-amino)-phenoxy]-pyrido[3,4-d]pyrimidin-4-ol

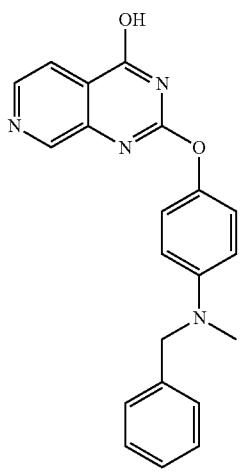 [SMILES: CN(Cc1ccccc1)c1ccc(Oc2nc(O)c3ccncc3n2)cc1]

The title compound was prepared in 5% yield from 2-chloro-pyrido[3,4-d]pyrimidin-4-ol and 4-(benzyl-methyl-amino)-phenol according to the procedure for the preparation of Example 1. $^1$H NMR (300 MHz, DMSO-d$_6$): δ 3.04 (s, 3H), 4.56 (s, 2H), 6.75-6.77 (m, 2H), 7.09-7.12 (m, 2H), 7.20-7.36 (m, 5H), 7.91-7.95 (m, 1H), 8.47-8.96 (m, 2H), 12.98 (s, 1H). [M+H] Calc'd for $C_{21}H_{15}N_4O_2$, 359; Found, 359.

Preparation 7A: 3-(Methyl-phenyl-amino)-phenol

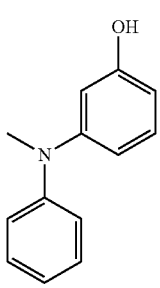

The title compound was prepared in 78% yield from 3-bromo-phenol and methyl-phenyl-amine according to the procedure of Preparation 5A. [M+H] Calc'd for $C_{13}H_{13}NO$, 200; Found, 200.

Example 7: 2-[3-(Methyl-phenyl-amino)-phenoxy]-pyrido[3,4-d]pyrimidin-4-ol

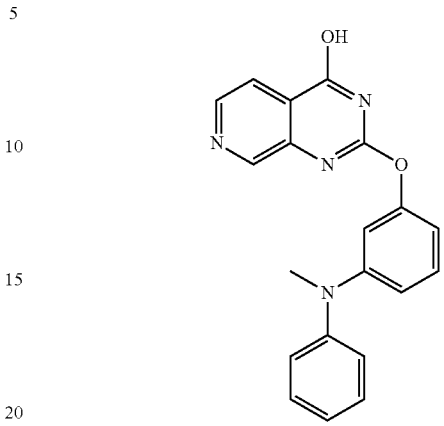

The title compound was prepared in 26% yield from 2-chloro-pyrido[3,4-d]pyrimidin-4-ol and 3-(methyl-phenyl-amino)-phenol according to the procedure for the preparation of Example 1. $^1$H NMR (400 MHz, DMSO-d$_6$): δ 3.31 (s, 3H), 6.79-6.86 (m, 3H), 7.05 (t, J=7.2 Hz, 1H), 7.17-7.19 (m, 2H), 7.32-7.36 (m, 3H), 7.88-7.95 (m, 1H), 8.45-8.73 (m, 2H), 13.03 (s, 1H). [M+H] Calc'd for $C_{20}H_{16}N_4O_2$, 345; Found, 345.

Example 8: 2-(1-Benzyl-1H-indol-6-yloxy)-pyrido[3,4-d]pyrimidin-4-ol

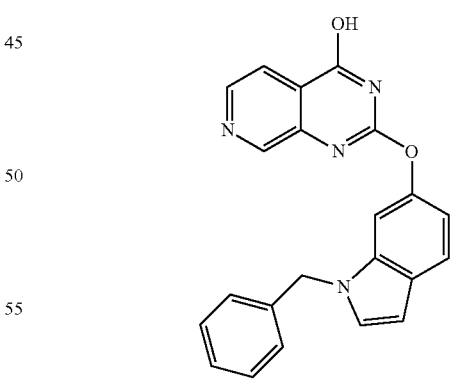

The title compound was prepared in 16% yield from 2-chloro-pyrido[3,4-d]pyrimidin-4-ol and 1-benzyl-1H-indol-6-ol according to the procedure for the preparation of Example 1. $^1$H NMR (400 MHz, DMSO-d$_6$): δ 5.41 (s, 2H), 6.55 (d, J=2.8 Hz, 1H), 6.98-7.01 (m, 1H), 7.23-7.32 (m, 5H), 7.50-7.52 (m, 1H), 7.57-7.62 (m, 2H), 7.87-7.94 (m, 1H), 8.52-8.63 (m, 2H), 13.07 (s, 1H). [M+H] Calc'd for $C_{22}H_{16}N_4O_2$, 369; Found, 369.

Preparation 9A: 3-(Benzyl-methyl-amino)-phenol

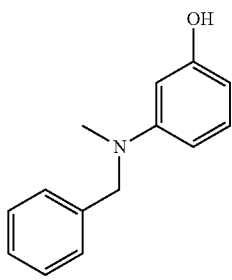 [SMILES: CN(Cc1ccccc1)c1cccc(O)c1]

The title compound was prepared in 24% yield from 3-bromo-phenol and benzyl-methyl-amine according to the procedure of Preparation 5A. [M+H] Calc'd for $C_{14}H_{15}NO$, 214; Found, 214.

Example 9: 2-[3-(Benzyl-methyl-amino)-phenoxy]-pyrido[3,4-d]pyrimidin-4-ol

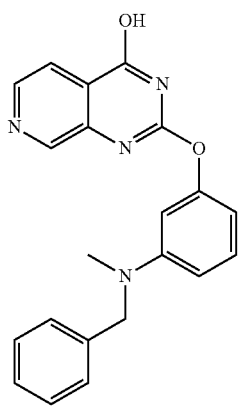 [SMILES: CN(Cc1ccccc1)c1cccc(Oc2nc(O)c3ccncc3n2)c1]

The title compound was prepared in 19% yield from 2-chloro-pyrido[3,4-d]pyrimidin-4-ol and 3-(benzyl-methyl-amino)-phenol according to the procedure for the preparation of Example 1. $^1$H NMR (400 MHz, DMSO-$d_6$): δ 3.03 (s, 3H), 4.59 (s, 2H), 6.55-6.57 (m, 1H), 6.64-6.69 (m, 2H), 7.23-7.32 (m, 7H), 7.92-8.20 (br, 2H), 13.02 (s, 1H). [M+H] Calc'd for $C_{21}H_{18}N_4O_2$, 359; Found, 359.

Preparation 10A:
3-Fluoro-4-(methyl-phenyl-amino)-phenol

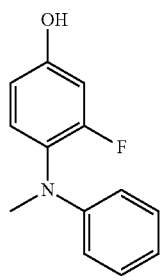 [SMILES: CN(c1ccccc1)c1ccc(O)cc1F]

The title compound was prepared in 18% yield from 4-bromo-3-fluoro-phenol and methyl-phenyl-amine according to the procedure of Preparation 5A. [M+H] Calc'd for $C_{13}H12FNO$, 218; Found, 218.

Example 10: 2-[3-Fluoro-4-(methyl-phenyl-amino)-phenoxy]-pyrido[3,4-d]pyrimidin-4-ol

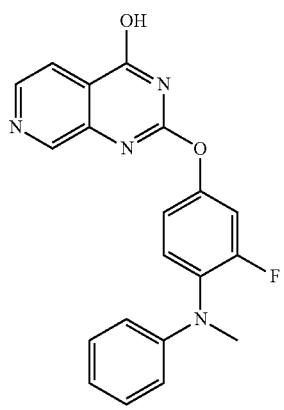 [SMILES: CN(c1ccccc1)c1ccc(Oc2nc(O)c3ccncc3n2)cc1F]

The title compound was prepared in 4% yield from 2-chloro-pyrido[3,4-d]pyrimidin-4-ol and 3-fluoro-4-(methyl-phenyl-amino)-phenol according to the procedure for the preparation of Example 5. $^1$H NMR (400 MHz, DMSO-$d_6$): δ 3.32 (s, 3H), 6.68-6.77 (m, 5H), 7.17-7.20 (m, 4H), 7.34-7.42 (m, 2H). [M+H] Calc'd for $C_{20}H_{15}FN_4O_2$, 363; Found, 363.

Preparation 11A: 1-Benzyl-6-methoxy-1H-indazole

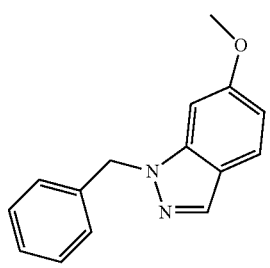 [SMILES: COc1ccc2cnn(Cc3ccccc3)c2c1]

The title compound was prepared in 62% yield from 6-methoxy-1H-indazole and bromomethyl-benzene according to the procedure of Preparation 4A. $^1$H NMR (400 MHz, CDCl$_3$): δ 3.85 (s, 3H), 5.53 (s, 2H), 6.76-6.78 (m, 1H), 6.98 (s, 1H), 7.26-7.37 (m, 5H), 7.47-7.49 (m, 1H), 7.78 (s, 1H). [M+H] Calc'd for $C_{15}H_{14}N_2O$, 239; Found, 239.

Preparation 11B: 1-Benzyl-1H-indazol-6-ol

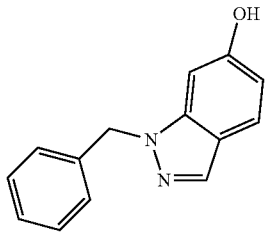 [SMILES: Oc1ccc2cnn(Cc3ccccc3)c2c1]

The title compound was prepared in 69% yield from 1-benzyl-6-methoxy-1H-indazole according to the procedure of Preparation 4B. $^1$H NMR (400 MHz, DMSO-d$_6$): δ 5.51 (s, 2H), 6.65-6.68 (m, 1H), 6.79 (s, 1H), 7.15-7.32 (m, 5H), 7.54 (d, J=8.8 Hz, 1H), 7.91 (s, 1H), 9.63 (s, 1H). [M+H] Calc'd for C$_{14}$H$_{12}$N$_2$O, 225; Found, 225.

Example 11: 2-(1-Benzyl-1H-indazol-6-yloxy)-pyrido[3,4-d]pyrimidin-4-ol

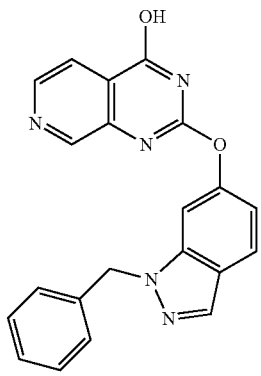 [SMILES: Oc1nc(Oc2ccc3cnn(Cc4ccccc4)c3c2)nc2cnccc12]

The title compound was prepared in 16% yield from 2-chloro-pyrido[3,4-d]pyrimidin-4-ol and 1-benzyl-1H-indazol-6-ol according to the procedure for the preparation of Example 1. $^1$H NMR (300 MHz, DMSO-d$_6$): δ 5.64 (s, 2H), 7.13-7.16 (m, 1H), 7.25-7.33 (m, 5H), 7.79-7.91 (m, 3H), 8.17 (m, 1H), 8.44-8.78 (m, 2H), 13.20 (s, 1H). [M+H] Calc'd for C$_{21}$H$_{15}$N$_5$O$_2$, 370; Found, 370.

Preparation 12A: 2-Benzyl-6-methoxy-1H-indazole

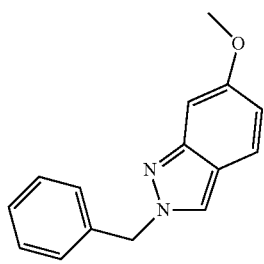 [SMILES: COc1ccc2cn(Cc3ccccc3)nc2c1]

The title compound was prepared in 31% yield from 6-methoxy-1H-indazole and bromomethyl-benzene according to the procedure of Preparation 4A. [M+H] Calc'd for C$_{15}$H$_{14}$N$_2$O, 239; Found, 239.

Preparation 12B: 2-Benzyl-1H-indazol-6-ol

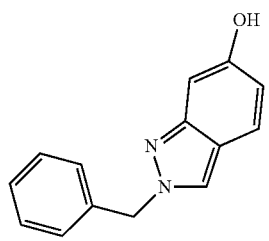 [SMILES: Oc1ccc2cn(Cc3ccccc3)nc2c1]

The title compound was prepared in 74% yield from 2-benzyl-6-methoxy-1H-indazole according to the procedure of Preparation 4B. [M+H] Calc'd for C$_{14}$H$_{12}$N$_2$O, 225; Found, 225.

Example 12: 2-(2-Benzyl-2H-indazol-6-yloxy)-pyrido[3,4-d]pyrimidin-4-ol

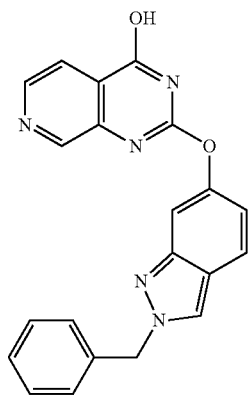 [SMILES: Oc1nc(Oc2ccc3cn(Cc4ccccc4)nc3c2)nc2cnccc12]

The title compound was prepared in 1% yield from 2-chloro-pyrido[3,4-d]pyrimidin-4-ol and 2-benzyl-1H-indazol-6-ol according to the procedure for the preparation of Example 1. $^1$H NMR (300 MHz, DMSO-d$_6$): δ 5.66 (s, 2H), 7.01-7.05 (m, 1H), 7.29-7.37 (m, 5H), 7.52 (s, 1H), 7.79-7.88 (m, 2H), 8.49-8.65 (m, 3H), 13.11 (s, 1H). [M+H] Calc'd for C$_{21}$H$_{15}$N$_5$O$_2$, 370; Found, 370.

Preparation 13A: 4-[Methyl(2-phenylethyl)amino]phenol

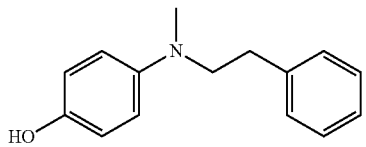 [SMILES: CN(CCc1ccccc1)c1ccc(O)cc1]

To a solution of 4-bromophenol (2.0 g, 11.56 mmol) and methyl(2-phenylethyl)amine (1.88 g, 13.9 mmol) in toluene (20 mL) was added Pd$_2$(dba)$_3$ (110 mg, 0.12 mmol) and dicyclohexyl(2-phenylphenyl)phosphine (98 mg, 0.28 mmol), then LiHMDS (25.4 mL, 25.4 mmol) was added under nitrogen. The mixture was stirred overnight at 65° C. under nitrogen. The reaction mixture was filtered and concentrated. The residue was purified by prep-HPLC to give the 1.52 g (58%) of the title product. [M+H] Calc'd for $C_{15}H_{17}NO$, 228; Found, 228.

Example 13: 2-{4-[Methyl(2-phenylethyl)amino]phenoxy}pyridino[3,4-d]pyrimidin-4-ol

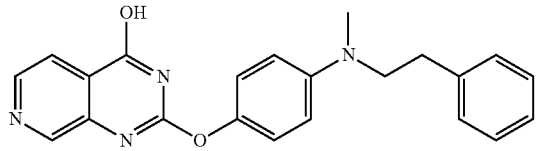 [SMILES: CN(CCc1ccccc1)c1ccc(Oc2nc(O)c3ccncc3n2)cc1]

The title compound was prepared in 17% yield from 2-chloro-pyrido[3,4-d]pyrimidin-4-ol and 4-[methyl(2-phenylethyl)amino]phenol according to the procedure for the preparation of Example 1. $^1$H NMR (400 MHz, DMSO-d$_6$): δ 2.82 (t, J=7.6 Hz, 2H), 2.90 (s, 3H), 3.56 (t, J=7.8 Hz, 2H), 6.76 (d, J=9.2 Hz, 2H), 7.13 (d, J=8.8 Hz, 2H), 7.20-7.23 (m, 1H), 7.28-7.31 (m, 4H), 7.86 (d, J=4.8 Hz, 1H), 8.49 (d, J=4.8 Hz, 1H), 8.68 (s, 1H). [M+H] Calc'd for $C_{22}H_{20}N_4O_2$, 373; Found, 373.

Preparation 14A and 15A:
5-Methoxy-2-benzyl-2H-indazole and
5-methoxy-1-benzyl-1H-indazole

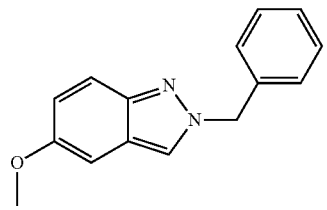

14A

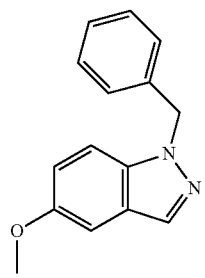

15A

To a solution of 5-methoxy-1H-indazole (1.0 g, 6.76 mmol) in DMF (10 mL) was added Cs$_2$CO$_3$ (2.2 g, 6.76 mmol) and BnBr (1.38 g, 8.1 mmol). The mixture was stirred at rt for 3 h, diluted with water (100 mL), and extracted with EA. Organics were washed with brine, dried over Na$_2$SO$_4$, and concentrated. The residue was purified by prep-HPLC to give 576 mg of the product 14A (54%) and 863 mg of the product 15A (36%). 14A: $^1$H NMR (400 MHz, CDCl$_3$): δ 3.81 (s, 3H), 5.56 (s, 2H), 6.84 (d, J=2.4 Hz, 1H), 6.99 (dd, J=2.0, 7.2 Hz, 1H), 7.25-7.28 (m, 2H), 7.31-7.37 (m, 3H), 7.61 (d, J=9.6 Hz, 1H), 7.75 (s, 1H). 15A: $^1$H NMR (400 MHz, CDCl$_3$): δ 3.84 (s, 3H), 5.57 (s, 2H), 7.00 (dd, J=2.8, 6.4 Hz, 1H), 7.08 (d, J=2.0 Hz, 1H), 7.17-7.19 (m, 1H), 7.21-7.29 (m, 5H), 7.94 (s, 1H).

Preparation 14B: 2-Benzyl-2H-indazol-5-ol

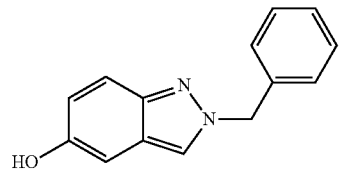 [SMILES: Oc1ccc2nn(Cc3ccccc3)cc2c1]

The title compound was prepared in 47% yield from 5-methoxy-2-benzyl-2H-indazole according to the procedure of Preparation 1C. [M+H] Calc'd for $C_{14}H_{12}N_2O$, 225; Found, 225.

Example 14: 2-[2-Benzyl-2H-indazol-5-yloxy]pyridino[3,4-d]pyrimidin-4-ol

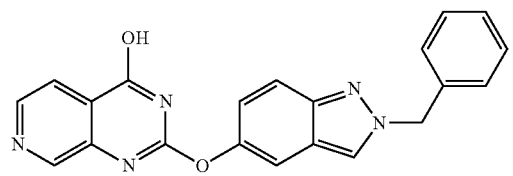 [SMILES: Oc1nc(Oc2ccc3nn(Cc4ccccc4)cc3c2)nc2cnccc12]

The title compound was prepared in 16% yield from 2-chloro-pyrido[3,4-d]pyrimidin-4-ol and 2-benzyl-2H-indazol-5-ol according to the procedure for the preparation of Example 1. $^1$H NMR (400 MHz, DMSO-d$_6$): δ 5.66 (s, 2H), 7.19 (d, J=7.2 Hz, 1H), 7.32-7.37 (m, 5H), 7.59 (d, J=1.6 Hz, 1H), 7.66 (d, J=9.6 Hz, 1H), 7.84 (d, J=4.8 Hz, 1H), 8.45 (d, J=4.8 Hz, 1H), 8.52 (s, 1H), 8.62 (s, 1H). [M+H] Calc'd for $C_{21}H_{15}N_5O_2$, 370; Found, 370.

Preparation 15B: 1-Benzyl-1H-indazol-5-ol

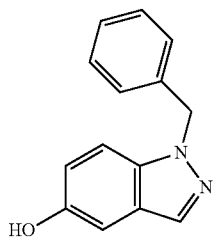 [SMILES: Oc1ccc2c(cnn2Cc2ccccc2)c1]

The title compound was prepared in 75% yield from 5-methoxy-1-benzyl-1H-indazole according to the procedure of Preparation 1C. [M+H] Calc'd for $C_{14}H_{12}N_2O$, 225; Found, 225.

Example 15: 2-(1-Benzyl-1H-indazol-5-yloxy)-pyridino[3,4-d]pyrimidin-4-ol

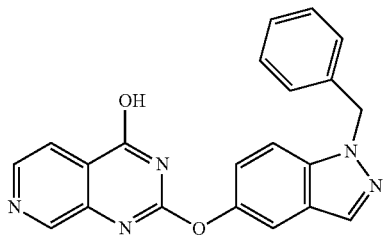 [SMILES: Oc1nc(Oc2ccc3c(cnn3Cc3ccccc3)c2)nc2cnccc12]

The title compound was prepared in 16% yield from 2-chloro-pyrido[3,4-d]pyrimidin-4-ol and 1-benzyl-1H-indazol-5-ol according to the procedure for the preparation of Example 1. $^1$H NMR (300 MHz, DMSO-$d_6$): δ 5.71 (s, 2H), 7.22-7.41 (m, 9H), 7.78-7.83 (m, 2H), 7.16 (s, 1H), 13.12 (s, 1H). [M+H] Calc'd for $C_{21}H_{15}N_5O_2$, 370; Found, 370.

Preparation 16A: 4-[(4-Methoxy-phenyl)-methyl-amino]-phenol

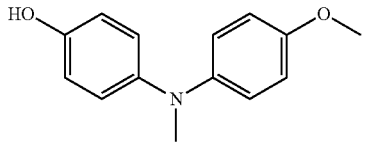 [SMILES: COc1ccc(N(C)c2ccc(O)cc2)cc1]

The title compound was prepared in 34% yield from 4-bromo-phenol and benzyl-methyl-amine according to the Preparation 5A. [M+H] Calc'd for $C_{14}H_{15}NO_2$, 230; Found, 230.

Example 16: 2-{4-[(4-Methoxy-phenyl)-methyl-amino]-phenoxy}-pyrido[3,4-d]pyrimidin-4-ol

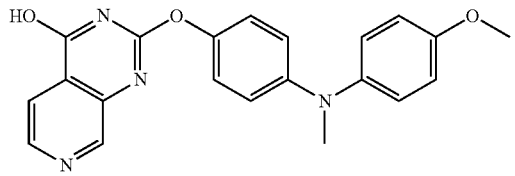 [SMILES: COc1ccc(N(C)c2ccc(Oc3nc(O)c4ccncc4n3)cc2)cc1]

The title compound was prepared in 15% yield from 2-chloro-pyrido[3,4-d]pyrimidin-4-ol and 1-benzyl-1H-indazol-5-ol according to the procedure for the preparation of Example 1. $^1$H NMR (400 MHz, DMSO-$d_6$): δ 3.26 (s, 3H), 3.73 (s, 3H), 6.76 (d, J=9.2 Hz, 2H), 6.97 (d, J=9.2 Hz, 2H), 7.12-7.16 (m, 4H), 7.89 (s, 1H), 8.52 (s, 1H), 8.75 (s, 1H), 13.02 (s, 1H). [M+H] Calc'd for $C_{21}H_{18}N_4O_3$, 375; Found, 375.

Preparation 17A: 4-[(3-Methoxy-phenyl)-methyl-amino]-phenol

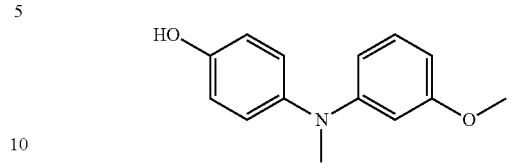

The title compound was prepared in 34% yield from 4-bromo-phenol and benzyl-methyl-amine according to the procedure of Preparation 5A. [M+H] Calc'd for $C_{14}H_{15}NO_2$, 230; Found, 230.

Example 17: 2-{4-[(3-Methoxy-phenyl)-methyl-amino]-phenoxy}-pyrido[3,4-d]pyrimidin-4-ol

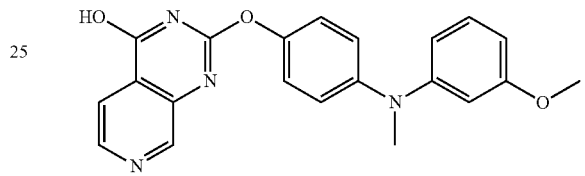

The title compound was prepared in 5% yield from 2-chloro-pyrido[3,4-d]pyrimidin-4-ol and 1-benzyl-1H-indazol-5-ol according to the procedure for preparation of Example 1. $^1$H NMR (400 MHz, DMSO-$d_6$): δ 3.29 (s, 3H), 3.73 (s, 3H), 6.54-6.61 (m, 3H), 7.08-7.27 (m, 5H), 7.89 (s, 1H), 8.52 (s, 1H), 8.71 (s, 1H), 13.08 (s, 1H). [M+H] Calc'd for $C_{21}H_{18}N_4O_3$, 375; Found, 375.

Preparation 18A: Methyl-(4-morpholin-4-yl-phenyl)-amine

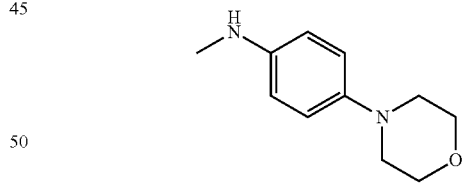

A solution of 4-morpholin-4-yl-phenylamine (4 g, 22.5 mmol) in HCOOH (40 mL) was heated at 110° C. overnight. The solution was diluted with water (100 mL) and extracted with DCM (30 mL×3). Organics were washed with $H_2O$ and brine, dried over $Na_2SO_4$, and concentrated in vacuo. To the residue in THF (100 mL) at 0° C. was added a 2M LiAlH$_4$ solution (33 mL), and the mixture was stirred at rt for 2 h. $H_2O$ (3 mL) was added at 0° C., followed by 10% NaOH solution (6 mL). The mixture was filtered and the filtrate was extracted with DCM (50 mL×2). The extracts were washed with brine, dried over $Na_2SO_4$, concentrated in vacuo. The residue was purified by silica gel chromatography (PE:EA 2:1) to give 4 g (93%) of the title compound. [M+H] Calc'd for $C_{11}H_{16}N_2O$, 193; Found, 193.

Preparation 18B: 4-[Methyl-(4-morpholin-4-yl-phenyl)-amino]-phenol

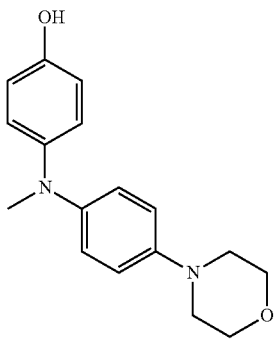 [SMILES: CN(c1ccc(O)cc1)c1ccc(N2CCOCC2)cc1]

The title compound was prepared in 34% yield from 4-bromo-phenol and methyl-(4-morpholin-4-yl-phenyl)-amine according to the procedure of Preparation 5A. [M+H] Calc'd for $C_{17}H_{20}N_2O_2$, 285; Found, 285.

Example 18: 2-{4-[Methyl-(4-morpholin-4-yl-phenyl)-amino]-phenoxy}-pyrido[3,4-d]pyrimidin-4-ol

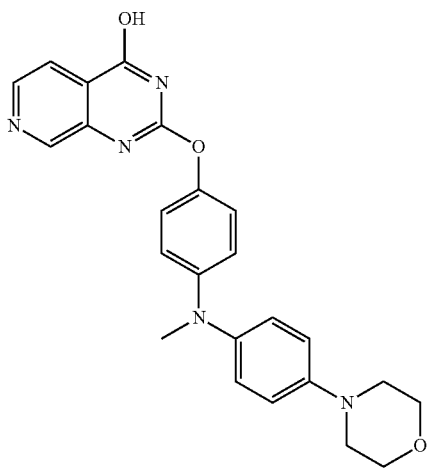 [SMILES: CN(c1ccc(Oc2nc(O)c3ccncc3n2)cc1)c1ccc(N2CCOCC2)cc1]

The title compound was prepared in 2% yield from 2-chloro-pyrido[3,4-d]pyrimidin-4-ol and 4-[methyl-(4-morpholin-4-yl-phenyl)-amino]-phenol according to the procedure for the preparation of Example 1. $^1$H NMR (300 MHz, DMSO-$d_6$): δ 3.05-3.10 (m, 4H), 3.19 (s, 3H), 3.73-3.78 (m, 4H), 6.75 (d, J=9.2 Hz, 2H), 6.97 (d, J=9.2 Hz, 2H), 7.06-7.12 (m, 4H), 7.86 (d, J=5.2 Hz, 1H), 8.49-8.53 (m, 1H), 8.69 (s, 1H), 13.03 (s, 1H). [M+H] Calc'd for $C_{24}H_{55}N_5O_3$, 430; Found, 430.

Preparation 19A: Methyl-(3-morpholin-4-yl-phenyl)-amine

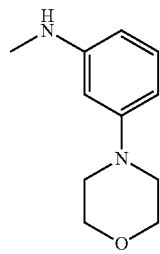

The title compound was prepared in 90% yield from 3-morpholin-4-yl-phenylamine according to the procedure of Preparation 18. [M+H] Calc'd for $C_{11}H_{16}N_2O$, 193; Found, 193.

Preparation 19B: 4-[Methyl-(3-morpholin-4-yl-phenyl)-amino]-phenol

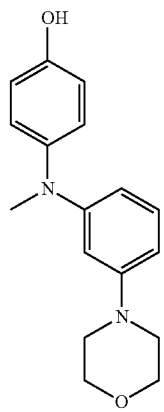 [SMILES: CN(c1ccc(O)cc1)c1cccc(N2CCOCC2)c1]

The title compound was prepared in 45% yield from 4-bromo-phenol and methyl-(3-morpholin-4-yl-phenyl)-amine according to the procedure of preparation of 5A. [M+H] Calc'd for $C_{17}H_{20}N_2O_2$, 285; Found, 285.

Example 19: 2-{4-[Methyl-(3-morpholin-4-yl-phenyl)-amino]-phenoxy}-pyrido[3,4-d]pyrimidin-4-ol

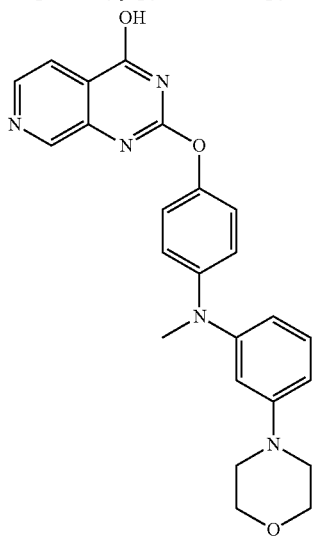

The title compound was prepared in 3% yield from 2-chloro-pyrido[3,4-d]pyrimidin-4-ol and 4-[methyl-(3-morpholin-4-yl-phenyl)-amino]-phenol according to the procedure for the preparation of Example 1. $^1$H NMR (300 MHz, DMSO-$d_6$): δ 3.06-3.09 (m, 4H), 3.29 (s, 3H), 3.71-3.73 (m, 4H), 6.53-6.55 (m, 1H), 6.62-6.64 (m, 2H), 6.97-6.99 (m, 2H), 7.16-7.21 (m, 3H), 7.87 (d, J=5.2 Hz, 1H), 8.51 (d, J=4.8 Hz, 1H), 8.69 (s, 1H), 13.03 (s, 1H). [M+H] Calc'd for $C_{24}H_{55}N_5O_3$, 430; Found, 430.

Preparation 20: 4-(Methyl-p-tolyl-amino)-phenol

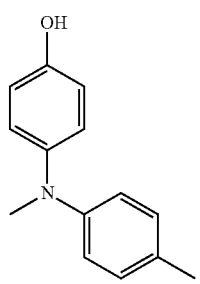

The title compound was prepared in 53% yield from 4-bromo-phenol and methyl-p-tolyl-amine according to the procedure of preparation 5A. [M+H] Calc'd for $C_{14}H_{15}NO$, 214; Found 214.

Example 20: 2-[4-(Methyl-p-tolyl-amino)-phenoxy]-pyrido[3,4-d]pyrimidin-4-ol

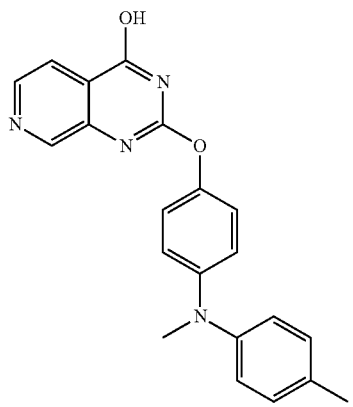 [SMILES: Cc1ccc(N(C)c2ccc(Oc3nc(O)c4ccncc4n3)cc2)cc1]

The title compound was prepared in 18% yield from 2-chloro-pyrido[3,4-d]pyrimidin-4-ol and 4-(methyl-p-tolyl-amino)-phenol according to the procedure for the preparation of Example 1. $^1$H NMR (400 MHz, DMSO-$d_6$): δ 2.33 (s, 3H), 3.26 (s, 3H), 6.90 (d, J=8.8 Hz, 2H), 6.99 (d, J=9.6 Hz, 2H), 7.15-7.22 (m, 4H), 7.86 (d, J=5.2 Hz, 1H), 8.50 (d, J=4.8 Hz, 1H), 8.69 (s, 1H), 13.07 (s, 1H). [M+H] Calc'd for $C_{21}H_{18}N_4O_2$, 359; Found, 359.

Preparation 21: 4-(Methyl-m-tolyl-amino)-phenol

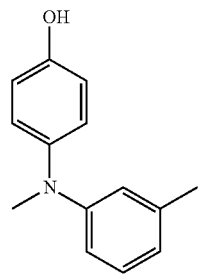

The title compound was prepared in 53% yield from 4-bromo-phenol and methyl-m-tolyl-amine according to the procedure of Preparation 5A. [M+H] Calc'd for $C_{14}H_{15}NO$, 214; Found 214.

Example 21: 2-[4-(Methyl-m-tolyl-amino)-phenoxy]-pyrido[3,4-d]pyrimidin-4-ol

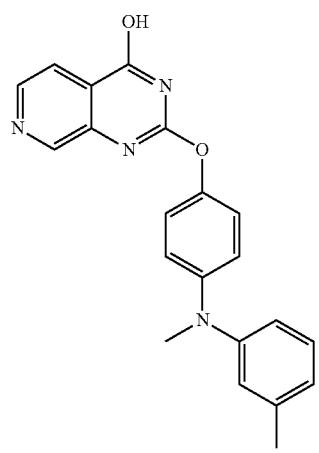 [SMILES: Cc1cccc(N(C)c2ccc(Oc3nc(O)c4ccncc4n3)cc2)c1]

The title compound was prepared in 15% yield from 2-chloro-pyrido[3,4-d]pyrimidin-4-ol and 4-(methyl-m-tolyl-amino)-phenol according to the procedure for the preparation of Example 1. $^1$H NMR (400 MHz, DMSO-$d_6$): δ 2.28 (s, 3H), 3.29 (s, 3H), 6.82-6.88 (m, 3H), 7.01 (d, J=8.8 Hz, 2H), 7.19-7.23 (m, 3H), 7.87 (d, J=4.8 Hz, 1H), 8.51 (d, J=4.8 Hz, 1H), 8.71 (s, 1H). [M+H] Calc'd for $C_{21}H_{18}N_4O_2$, 359; Found, 359.

Preparation 22A: (3-chloro-phenyl)-(4-methoxy-phenyl)-methyl-amine

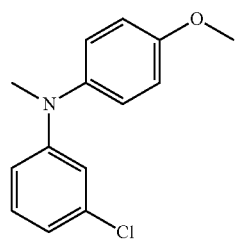

To a solution of (3-chloro-phenyl)-methyl-amine (10 g, 71 mmol) in toluene was added 1-bromo-4-methoxy-benzene (14.0 g, 74.5 mmol), biphenyl-2-yl-dicyclohexyl-phosphane (270 mg, 0.71 mmol), Pd$_2$(dba)$_3$ (650 mg, 0.71 mmol), t-BuOK (12.0 g, 106.5 mmol) and the mixture was refluxed overnight under nitrogen atmosphere. The reaction mixture was cooled to RT and the solvent was concentrated. The residue was purified by silica gel chromatography (PE:EA, 50:1) to give 15 g (86%) of the title compound. [M+H] Calc'd for $C_{14}H_{14}ClNO$, 248; Found, 248.

Preparation 22B: (4-methoxy-phenyl)-methyl-[3-(4-methyl-piperazin-1-yl)-phenyl]-amine

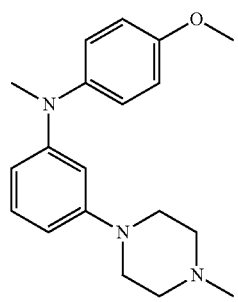

To a solution of ((3-chloro-phenyl)-(4-methoxy-phenyl)-methyl-amine (2.0 g, 8.1 mmol) in toluene was added 1-methyl-piperazine (0.97 g, 9.7 mmol), biphenyl-2-yl-dicyclohexyl-phosphane (155 mg, 0.4 mmol), Pd$_2$(dba)$_3$ (450 mg, 0.48 mmol), t-BuOK (2.5 g, 22.3 mmol) and the mixture was refluxed overnight under nitrogen atmosphere. The reaction mixture was cooled to RT and the solvent was concentrated. The residue was purified by silica gel chromatography (DCM:MeOH, 20:1) to give 1.1 g (48%) of the title compound. [M+H] Calc'd for $C_{19}H_{25}N_3O$, 312; Found, 312.

Preparation 22C: 4-{methyl-[3-(4-methyl-piperazin-1-yl)-phenyl]-amino}-phenol

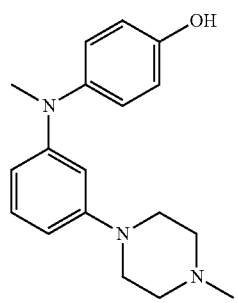

To a solution of (4-methoxy-phenyl)-methyl-[3-(4-methyl-piperazin-1-yl)-phenyl]-amine (1.0 g, 3.2 mmol) in DCM (10 mL) was added BBr$_3$ (20 mL, 1M) at −20° C. and the mixture was stirred at RT for 1 h. The mixture was then warmed to 0° C., quenched with MeOH and the PH of the solution was neutralized with aqueous NaHCO$_3$. The organic layer was washed brine, dried over Na$_2$SO$_4$ and concentrated. The residue was purified by silica gel chromatography (DCM:MeOH, 10:1) to give 370 mg (39%) of the title compound. [M+H] Calc'd for $C_{18}H_{23}N_3O$, 298; Found, 298.

Example 22: 2-(4-{methyl-[3-(4-methyl-piperazin-1-yl)-phenyl]-amino}-phenoxy)-pyrido[3,4-d]pyrimidin-4-ol

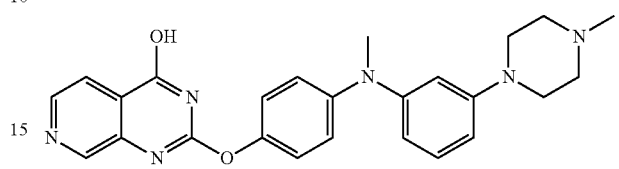

A mixture of 2-chloro-pyrido[3,4-d]pyrimidin-4-ol (200 mg, 1.1 mmol), 4-{methyl-[3-(4-methyl-piperazin-1-yl)-phenyl]-amino}-phenol (370 mg, 1.24 mmol), Cs$_2$CO$_3$ (400 mg, 1.22 mmol), and CuI (230 mg, 1.22 mmol) in DMF (10 mL) was stirred overnight at 130° C. under nitrogen atmosphere. The reaction mixture was concentrated and the residue was purified by prep-HPLC to give 30 mg (6%) of the title product. $^1$H NMR (400 MHz, DMSO-d$_6$): δ 2.24 (s, 3H), 2.47-2.49 (m, 4H), 3.10-3.12 (m, 4H), 3.26 (s, 3H), 6.49 (d, J=10.0 Hz, 1H), 6.60 (d, J=9.2 Hz, 2H), 6.96-7.17 (m, 5H), 7.84 (d, J=6.8 Hz, 1H), 8.46 (d, J=6.8 Hz, 1H), 8.67 (s, 1H). [M+H] Calc'd for $C_{25}H_{26}N_6O_2$, 443; Found, 443.

Preparation 23A: (1-{3-[(4-methoxy-phenyl)-methyl-amino]-phenyl}-piperidin-4-yl)-carbamic acid tert-butyl ester

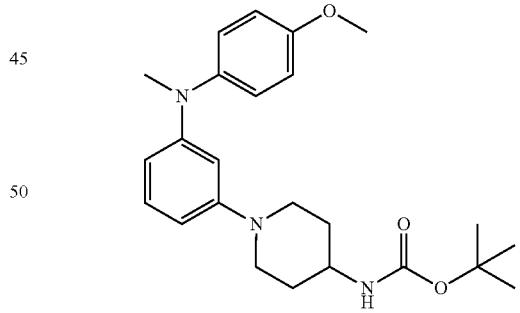

To a solution of ((3-chloro-phenyl)-(4-methoxy-phenyl)-methyl-amine (3.0 g, 12.1 mmol) in toluene was added piperidin-4-yl-carbamic acid tert-butyl ester (3.65 g, 18.2 mmol), S-Phos (250 mg, 0.61 mmol), Pd$_2$(dba)$_3$ (670 mg, 0.73 mmol), t-BuOK (2.74 g, 24.5 mmol) and the mixture was stirred overnight at 95° C. under nitrogen atmosphere. The reaction mixture was cooled to RT and the solvent was concentrated. The residue was purified by silica gel chromatography (DCM:MeOH, 10:1) to give 0.65 g (27%) of the title compound. [M+H] Calc'd for $C_{24}H_{33}N_3O_3$, 412; Found, 412.

Preparation 23B: 4-{[3-(4-amino-piperidin-1-yl)-phenyl]-methyl-amino}-phenol

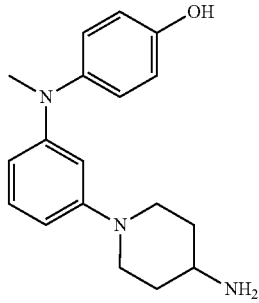 [SMILES: CN(c1ccc(O)cc1)c1cccc(N2CCC(N)CC2)c1]

Example 23: 2-(4-{[4-(4-amino-piperidin-1-yl)-phenyl]-methyl-amino}-phenoxy)-pyrido[3,4-d]pyrimidin-4-ol

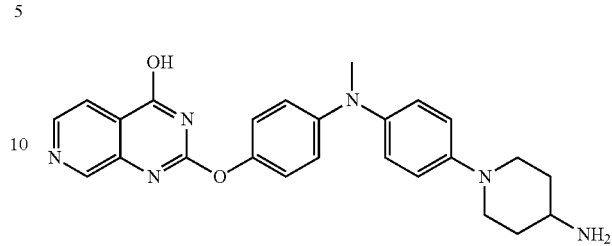

A mixture of 2-chloro-pyrido[3,4-d]pyrimidin-4-ol (150 mg, 0.83 mmol), (1-{3-[(4-hydroxy-phenyl)-methyl-amino]-phenyl}-piperidin-4-yl)-carbamic acid tert-butyl ester (400 mg, 1.24 mmol), $Cs_2CO_3$ (300 mg, 0.92 mmol), and CuI (175 mg, 0.92 mmol) in DMF (10 mL) was stirred overnight at 130° C. under nitrogen atmosphere. The reaction mixture was concentrated. The residue was purified by silica gel chromatography (DCM:MeOH, 10:1) to give 30 mg of boc protected product, which was subsequently taken in DCM (10 mL). TFA (2 mL) was added to the solution and the mixture was stirred at RT for 1 h. The solvent was concentrated and the residue was purified by preparative HPLC to give 10 mg (3%) of the title product. [M+H] Calc'd for $C_{25}H_{26}N_6O_2$, 443; Found, 443.

To a solution of (1-{3-[(4-methoxy-phenyl)-methyl-amino]-phenyl}-piperidin-4-yl)-carbamic acid tert-butyl ester (650 mg, 1.58 mmol) in DCM (10 mL) was added $BBr_3$ (10 mL, 1 M) at −20° C. and the mixture was stirred at RT for 1 h. The mixture was then warmed to 0° C., quenched with MeOH and the PH of the solution was neutralized with aqueous $NaHCO_3$. The residue was purified by silica gel chromatography (DCM:MeOH, 10:1) to give 360 mg (77%) of the title compound. [M+H] Calc'd for $C_{18}H_{23}N_3O$, 298; Found, 298.

Preparation 23B: (1-{3-[(4-hydroxy-phenyl)-methyl-amino]-phenyl}-piperidin-4-yl)-carbamic acid tert-butyl ester

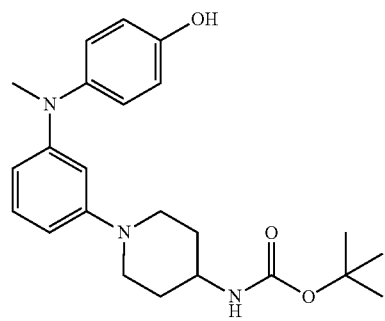 [SMILES: CN(c1ccc(O)cc1)c1cccc(N2CCC(NC(=O)OC(C)(C)C)CC2)c1]

Preparation 24A: N-(4-methoxy-phenyl)-N-methyl-2-phenyl-acetamide

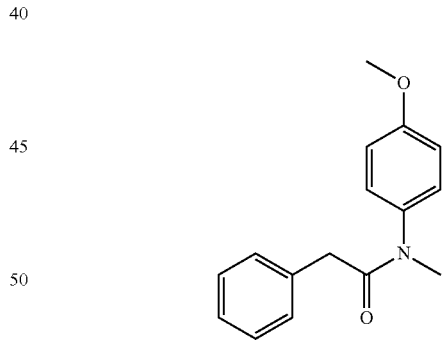

To a solution of compound 4-{[3-(4-amino-piperidin-1-yl)-phenyl]-methyl-amino}-phenol (360 mg, 1.21 mmol) in MeOH (5 mL) was added was added 1N NaOH (2.42 mL) and $(Boc)_2O$ (287 mg, 1.32 mmol) and the mixture was stirred at RT for 2 h. The reaction mixture was diluted with water and extracted with DCM (3×). The organics were concentrated and the residue was purified by silica gel chromatography (PE:EA, 5:1) to give 400 mg (83%) of the title compound. [M+H] Calc'd for $C_{23}H_{31}N_3O_3$, 398; Found, 398.

Phenyl-acetyl chloride (2.0 g, 1.31 mmol) was added at 0° C. to a solution of (4-methoxy-phenyl)-methyl-amine (1.5 g, 1.1 mmol) and TEA (2.2 g, 2.2 mmol) in DCM (20 mL). The mixture was stirred at RT for 2 h and quenched with $NH_4Cl$. The mixture was concentrated and the residue was purified by silica gel chromatography (PE:EA, 5:1) to give 2.0 g (71%) of the title compound. [M+H] Calc'd for $C_{16}H_{17}NO_2$, 256; Found, 256.

Preparation 24B:
N-(4-hydroxy-phenyl)-N-methyl-2-phenyl-acetamide

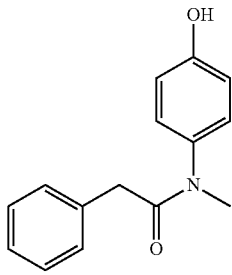 [SMILES: CN(C(=O)Cc1ccccc1)c1ccc(O)cc1]

To a solution of N-(4-methoxy-phenyl)-N-methyl-2-phenyl-acetamide (2.0 g, 10 mmol) in DCM (20 mL) was added BBr$_3$ (40 mL, 1.0 M in DCM, 40 mmol) in portions at 0° C., and the mixture was stirred at RT for 2 h. The reaction mixture was diluted with water (30 mL), basified to pH 5 with sat. Na$_2$CO$_3$ and extracted with DCM (30 mL*3). The combined organics were dried over Na$_2$SO$_4$ and concentrated. The residue was purified by silica gel chromatography (PE:EA, 2:1) to give 1.5 g (94%) of the title product. [M+H] Calc'd for C$_{15}$H$_{15}$NO$_2$, 242; Found, 242.

Example 24: N-[4-(4-hydroxy-pyrido[3,4-d]pyrimidin-2-yloxy)-phenyl]-N-methyl-2-phenyl-acetamide

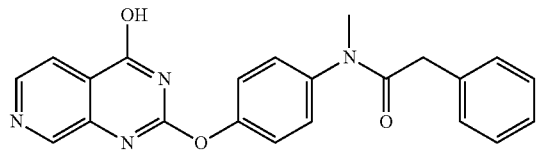 [SMILES: CN(C(=O)Cc1ccccc1)c1ccc(Oc2nc(O)c3ccncc3n2)cc1]

The title compound was prepared in 28% yield from 2-chloro-pyrido[3,4-d]pyrimidin-4-ol and N-(4-hydroxyphenyl)-N-methyl-2-phenyl-acetamide according to the procedure for the preparation of Example 1. $^1$H NMR (400 MHz, DMSO-d$_6$): δ 3.20 (s, 2H), 3.44 (s, 3H), 7.05-7.40 (m, 9H), 7.87 (d, J=6.8 Hz, 1H), 8.50 (d, J=6.8 Hz, 1H), 8.67 (s, 1H), 13.07 (s, 1H). [M+H] Calc'd for C$_{22}$H$_{18}$N$_4$O$_3$, 387; Found, 387.

Preparation 25A:
1-(4-methoxy-phenyl)-3-phenyl-piperidine

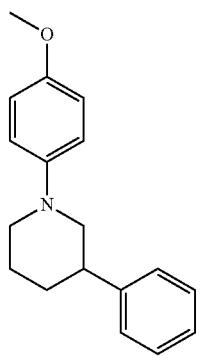 [SMILES: COc1ccc(N2CCCC(c3ccccc3)C2)cc1]

To a solution of 1-bromo-4-methoxy-benzene (0.5 g, 2.9 mmol) in toluene was added 3-phenyl-piperidine (0.5 g, 3.2 mmol), S-Phos (60 mg, 0.15 mmol), Pd$_2$(dba)$_3$ (160 mg, 0.17 mmol), t-BuOK (0.81 g, 7.23 mmol) and the mixture was stirred overnight at 95° C. under nitrogen atmosphere. The reaction mixture was cooled to RT and the solvent was concentrated. The residue was purified by silica gel chromatography (PE:EA, 10:1) to give 0.5 g (52%) of the title compound. [M+H] Calc'd for C$_{18}$H$_{21}$NO, 268; Found, 268.

Preparation 25B: 4-(3-phenyl-piperidin-1-yl)-phenol

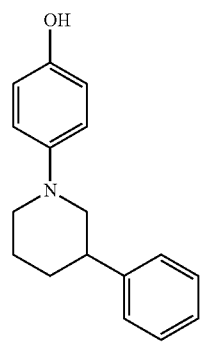 [SMILES: Oc1ccc(N2CCCC(c3ccccc3)C2)cc1]

The title compound was prepared in 53% yield from 1-(4-methoxy-phenyl)-3-phenyl-piperidine according to the procedure of Preparation 22C. [M+H] Calc'd for C$_{17}$H$_{19}$NO, 254; Found 254.

Example 25: 2-[4-(3-phenyl-piperidin-1-yl)-phenoxy]-pyrido[3,4-d]pyrimidin-4-ol

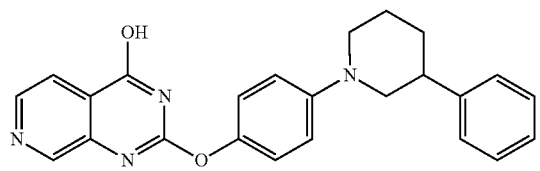

The title compound was prepared in 15% yield from 2-chloro-pyrido[3,4-d]pyrimidin-4-ol and 4-(3-phenyl-piperidin-1-yl)-phenol according to the procedure for the preparation of Example 1. $^1$H NMR (400 MHz, DMSO-d$_6$): δ 1.62-1.94 (m, 4H), 2.72-2.83 (m, 3H), 3.69-3.76 (m, 2H), 7.00 (d, J=12.0 Hz, 2H), 7.13 (d, J=12.0 Hz, 2H), 7.19-7.35 (m, 5H), 7.84 (d, J=7.6 Hz, 1H), 8.47 (d, J=7.2 Hz, 1H), 8.65 (s, 1H). [M+H] Calc'd for C$_{24}$H$_{22}$N$_4$O$_2$, 399; Found, 399.

Preparation 26A:
4-(4-benzyloxy-phenyl)-2-phenyl-morpholine

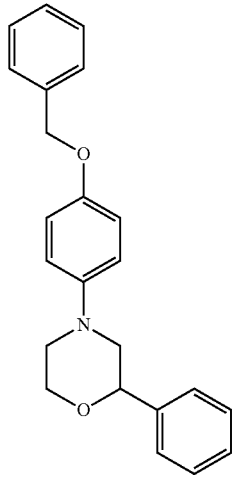 [SMILES: c1ccc(COc2ccc(N3CCOC(c4ccccc4)C3)cc2)cc1]

The title compound was prepared in 80% yield from 2-phenylmorpholine and 1-(benzyloxy)-4-bromobenzene according to the procedure of Preparation 25A. [M+H] Calc'd for $C_{23}H_{23}NO_2$, 346 Found, 346.

Preparation 26B:
4-(2-phenyl-morpholin-4-yl)-phenol

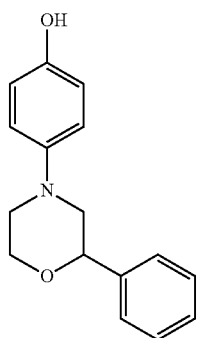

To a solution of 4-(4-benzyloxy-phenyl)-2-phenyl-morpholine (1.5 g, 3.9 mmol) in MeOH (20 mL) was added Pd/C (0.15 g), and the mixture was stirred overnight under H2 atmosphere. The reaction mixture was filtered and the filtrate was concentrated to give 0.99 g (99%) of the title compound. [M+H] Calc'd for $C_{16}H_{17}NO_2$, 256; Found, 256.

Example 26: 2-[4-(2-phenyl-morpholin-4-yl)-phenoxy]-pyrido[3,4-d]pyrimidin-4-ol

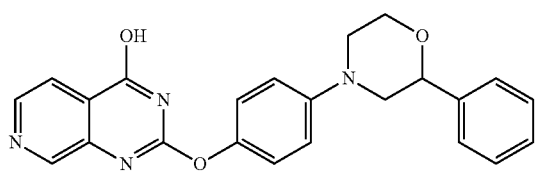

The title compound was prepared in 32% yield from 2-chloro-pyrido[3,4-d]pyrimidin-4-ol and 4-(2-phenyl-morpholin-4-yl)-phenol according to the procedure for the preparation of Example 1. $^1$H NMR (400 MHz, DMSO-d$_6$): δ 2.25-2.63 (m, 1H), 2.79-2.87 (m, 1H), 3.27-3.86 (m, 3H), 4.09-4.14 (m, 1H), 4.62-4.66 (m, 1H), 7.06 (d, J=12.8 Hz, 2H), 7.17 (d, J=12.4 Hz, 2H), 7.29-7.48 (m, 5H), 7.84 (d, J=7.6 Hz, 1H), 8.47 (d, J=7.2 Hz, 1H), 8.65 (s, 1H), 13.07 (s, 1H). [M+H] Calc'd for $C_{23}H_{20}N_4O_3$, 401; Found, 401.

Preparation 27A:
(5-bromo-pyridin-3-yl)-methyl-carbamic acid tert-butyl ester

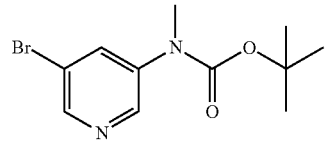 [SMILES: CN(C(=O)OC(C)(C)C)c1cncc(Br)c1]

A solution of (5-bromo-pyridin-3-yl)-carbamic acid tert-butyl ester (3.4 g, 12.5 mmol) in THF (10 mL) was added to a solution of NaH (0.75 g, 18.8 mmol, 60% in mineral oil) in THF (15 mL) and the mixture was stirred at RT for 10 min. CH$_3$I (2.13 g, 15.0 mmol) was added and the mixture was stirred at RT for 2 h. The reaction was quenched with aqueous NH$_4$Cl and extracted with EtOAc (3×). The organics were combined, dried over Na$_2$SO$_4$ and concentrated. The residue was purified by silica gel chromatography (PE:EA, 10:1) to give 2.7 g (76%) of the title compound. [M+H] Calc'd for $C_{11}H_{15}BrN_2O_2$, 287; Found, 287.

Preparation 27B:
methyl-(5-morpholin-4-yl-pyridin-3-yl)-amine

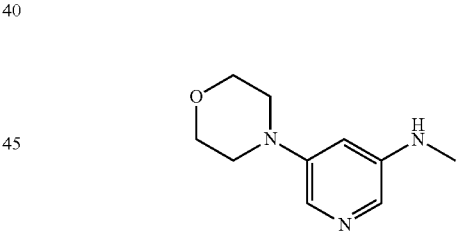

To a solution of (5-bromo-pyridin-3-yl)-methyl-carbamic acid tert-butyl ester (200 mg, 0.7 mmol) in toluene was added morpholine (120 mg, 1.4 mmol), BINAP (87 mg, 0.14 mmol), Pd(OAc)$_2$ (16 mg, 0.07 mmol), Cs$_2$CO$_3$ (2.5 g, 2.1 mmol) and the mixture was refluxed overnight under N$_2$ atmosphere. The solvent was concentrated and the residue was purified by silica gel chromatography (PE:EA, 1:1) to give boc-protected product, which was dissolved in DCM (2 mL). TFA was added to the solution and the mixture was stirred at RT for 1 h. The solution was concentrated to give 100 mg (74%) of the title compound as the TFA salt. [M+H] Calc'd for $C_{10}H_{15}N_3O$, 194; Found, 194.

Preparation 27C: 4-[methyl-(5-morpholin-4-yl-pyridin-3-yl)-amino]-phenol

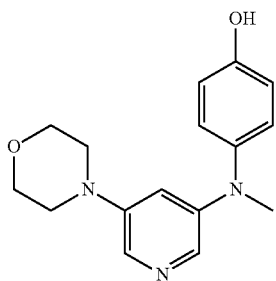 [SMILES: CN(c1ccc(O)cc1)c1cncc(N2CCOCC2)c1]

The title compound was prepared in 34% yield from 4-bromo-phenol and methyl-(5-morpholin-4-yl-pyridin-3-yl)-amine according to the procedure of Preparation 5A. [M+H] Calc'd for $C_{16}H_{19}N_3O_2$, 286; Found, 286.

Example 27: 2-{4-[methyl-(5-morpholin-4-yl-pyridin-3-yl)-amino]-phenoxy}-pyrido[3,4-d]pyrimidin-4-ol

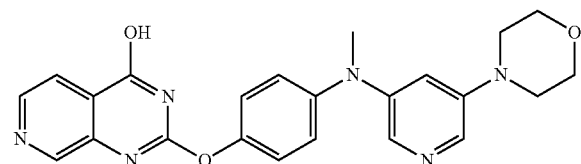

The title compound was prepared in 10% yield from 2-chloro-pyrido[3,4-d]pyrimidin-4-ol and 4-[methyl-(5-morpholin-4-yl-pyridin-3-yl)-amino]-phenol according to the procedure for the preparation of Example 1. $^1$H NMR (400 MHz, DMSO-$d_6$): δ 3.12-3.13 (m, 4H), 3.20 (s, 3H), 3.71-3.73 (m, 4H), 6.90 (s, 1H), 7.07-7.09 (m, 2H), 7.23-7.26 (m, 2H), 7.75 (s, 1H), 7.86-7.90 (m, 2H), 8.49 (s, 1H), 8.67 (s, 1H). [M+H] Calc'd for $C_{23}H_{22}N_6O_3$, 431; Found, 431.

Preparation 28A: 1,2,3,4-tetrahydro-naphthalene-1-carboxylic acid (4-methoxy-phenyl)-methyl-amide

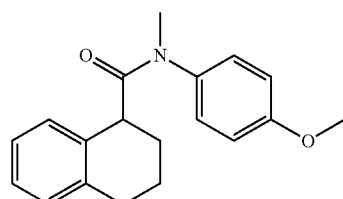

SOCl$_2$ (2 mL) was added to a solution of 1,2,3,4-tetrahydro-naphthalene-1-carboxylic acid (0.6 g, 3.4 mmol) in DCM (10 mL) and the mixture was refluxed for 2 h. The solvent was concentrated and the residue was added to a mixture of (4-methoxy-phenyl)-methyl-amine (470 mg, 3.4 mmol) and TEA (2 mL) in DCM (10 mL). The reaction mixture was stirred at RT for 5 h and quenched with 1N HCl (10 mL). The organic layer was separated, washed with water, washed with brine, dried over Na$_2$SO$_4$ and concentrated. The residue was purified by silica gel chromatography (PE:EA, 4:1) to give 630 mg (63%) of the title compound. [M+H] Calc'd for $C_{19}H_{21}NO_2$, 296; Found, 296.

Preparation 28B: (4-methoxy-phenyl)-methyl-(1,2,3,4-tetrahydro-naphthalen-1-ylmethyl)-amine

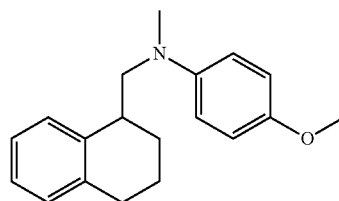

To a solution of 1,2,3,4-tetrahydro-naphthalene-1-carboxylic acid (4-methoxy-phenyl)-methyl-amide (600 mg, 2.0 mmol) in THF (10 mL) was added BH$_3$ (8 mL, 1N in Me$_2$S). The mixture was stirred at 40° C. for 2 h, cooled to RT and quenched with MeOH. The solution was adjusted to PH=9 with 1N NaOH and extracted with EA (3×). The organics were combined, washed with water, washed with brine, dried over Na$_2$SO$_4$ and concentrated. The residue was purified by silica gel chromatography (PE:EA, 10:1) to give 300 mg (53%) of the title compound. [M+H] Calc'd for $C_{19}H_{23}NO$, 282; Found, 282.

Preparation 28C: 4-[methyl-(1,2,3,4-tetrahydro-naphthalen-1-ylmethyl)-amino]-phenol

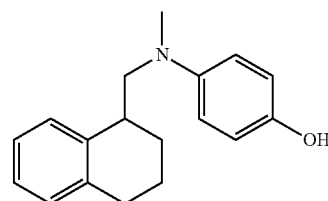

The title compound was prepared in 82% yield from 4-bromo-phenol and (4-methoxy-phenyl)-methyl-(1,2,3,4-tetrahydro-naphthalen-1-ylmethyl)-amine according to the procedure of Preparation 5A. [M+H] Calc'd for $C_{19}H_{21}NO$, 268; Found, 268.

Example 28: 2-{4-[methyl-(1,2,3,4-tetrahydro-naphthalen-1-ylmethyl)-amino]-phenoxy}-pyrido[3,4-d]pyrimidin-4-ol

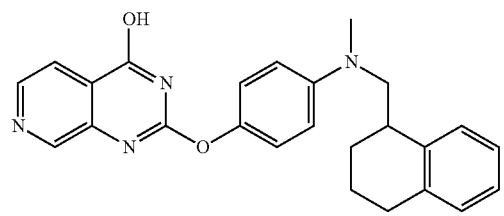 [SMILES: CN(CC1CCCc2ccccc21)c1ccc(Oc2nc(O)c3ccncc3n2)cc1]

The title compound was prepared in 20% yield from 2-chloro-pyrido[3,4-d]pyrimidin-4-ol and 4-[methyl-(1,2,3,4-tetrahydro-naphthalen-1-ylmethyl)-amino]-phenol according to the procedure for the preparation of Example 1. $^1$H NMR (400 MHz, DMSO-$d_6$): δ 1.65-1.89 (m, 4H), 2.67-2.74 (m, 2H), 2.96 (s, 3H), 3.29-3.56 (m, 3H), 6.78 (d, J=11.2 Hz, 2H), 7.07-7.22 (m, 6H), 7.86 (s, 1H), 8.49 (s, 1H), 8.67 (s, 1H), 12.99 (s, 1H). [M+H] Calc'd for $C_{25}H_{24}N_4O_2$, 413; Found, 413.

Preparation 29A: 2-(4-bromo-phenyl)-propionic acid methyl ester

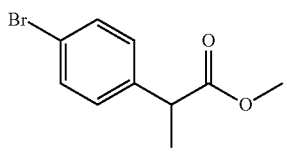

To a solution of (4-bromo-phenyl)-acetic acid methyl ester (1.0 g, 4.37 mmol) in THF was added LDA (4.4 mL, 1N) at −78° C. under $N_2$ atmosphere and the mixture was stirred at this temperature for 10 min. $CH_3I$ (0.74 g, 5.2 mmol) was added and the mixture was stirred at RT for 1 h, quenched with aqueous $NH_4Cl$ and extracted with EA (3×). The organics were combined, washed with water, washed with brine, dried over $Na_2SO_4$ and concentrated. The residue was purified by silica gel chromatography (PE:EA, 20:1) to give 0.6 g (57%) of the title compound. [M+H] Calc'd for $C_{10}H_{11}BrO_2$, 242; Found, 242.

Preparation 29B: 2-{4-[(4-benzyloxy-phenyl)-methyl-amino]-phenyl}-propionic acid methyl ester

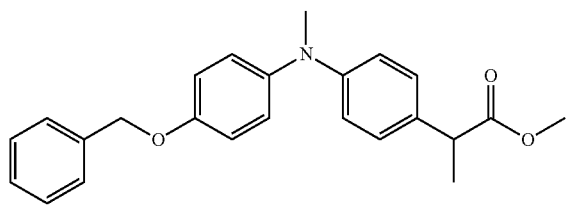 [SMILES: COC(=O)C(C)c1ccc(N(C)c2ccc(OCc3ccccc3)cc2)cc1]

To a solution of 2-(4-bromo-phenyl)-propionic acid methyl ester (0.6 g, 2.47 mmol) in toluene was added (4-benzyloxy-phenyl)-methyl-amine (526 mg, 2.47 mmol), X-Phos (140 mg, 0.29 mmol), Pd(OAc)$_2$ (33 mg, 0.15 mmol), Cs$_2$CO$_3$ (3.2 g, 9.8 mmol) and the mixture was refluxed overnight. The solvent was concentrated and the residue was purified by silica gel chromatography (PE:EA, 10:1) to give 0.7 g (76%) of the title compound. [M+H] Calc'd for $C_{24}H_{25}NO_3$, 376; Found, 376.

Preparation 29C: 2-{4-[(4-benzyloxy-phenyl)-methyl-amino]-phenyl}-propan-1-ol

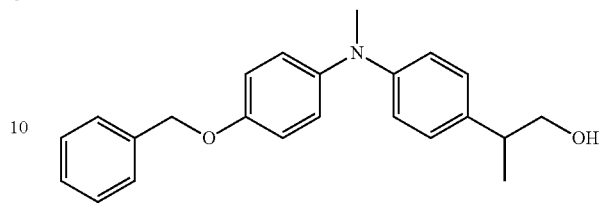

To a solution of 2-{4-[(4-benzyloxy-phenyl)-methyl-amino]-phenyl}-propionic acid methyl ester (0.7 g, 1.87 mmol) in THF (15 mL) was added LAH (1.6 mL, 1N) at 0° C. under $N_2$ atmosphere and the mixture was stirred at this temperature for 2 h. The reaction was warmed to RT, quenched with water and extracted with EA (3×). The organics were combined, washed with brine, dried over $Na_2SO_4$ and concentrated to give 0.6 g (92%) of the title compound. [M+H] Calc'd for $C_{23}H_{25}NO_2$, 348; Found, 348.

Preparation 29D: (4-benzyloxy-phenyl)-[4-(2-methoxy-1-methyl-ethyl)-phenyl]-methyl-amine

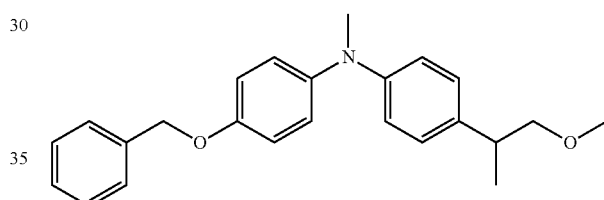

To a solution of 2-{4-[(4-benzyloxy-phenyl)-methyl-amino]-phenyl}-propan-1-ol (1.5 g, 4.3 mmol) in DMF (20 mL) was added NaH (0.32 g, 7.8 mmol, 60% in mineral oil) at 0° C. After stirring for 30 min, MeI (0.92 g, 6.5 mmol) was added dropwise over 10 min and the reaction mixture was stirred at RT for 3 h. The reaction mixture was diluted with water (100 mL), extracted with EA (10 mL*3). The combined organic were washed with water (150 mL*3), brine (150 mL), dried over $Na_2SO_4$, and concentrated to give 1.47 g (77%) of the title product. [M+H] Calc'd for $C_{24}H_{27}NO_2$, 362; Found, 362.

Preparation 29E: 4-{[4-(2-methoxy-1-methyl-ethyl)-phenyl]-methyl-amino}-phenol

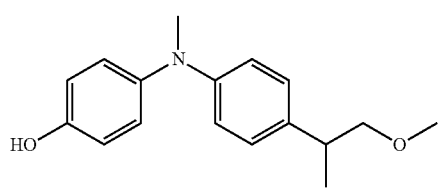 [SMILES: COCC(C)c1ccc(N(C)c2ccc(O)cc2)cc1]

The title compound was prepared in 100% yield from (4-benzyloxy-phenyl)-[4-(2-methoxy-1-methyl-ethyl)-phenyl]-methyl-amine according to the procedure of Preparation 26B. [M+H] Calc'd for $C_{17}H_{21}NO_2$, 272 Found, 272.

Example 29: 2-(4-{[4-(2-methoxy-1-methyl-ethyl)-phenyl]-methyl-amino}-phenoxy)-pyrido[3,4-d]pyrimidin-4-ol

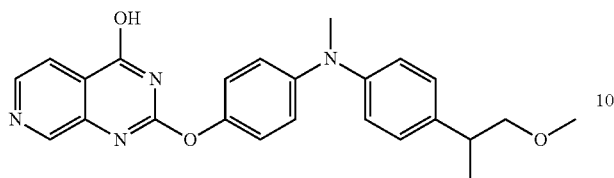

The title compound was prepared in 20% yield from 2-chloro-pyrido[3,4-d]pyrimidin-4-ol and 4-{[4-(2-methoxy-1-methyl-ethyl)-phenyl]-methyl-amino}-phenol according to the procedure for the preparation of Example 1. $^1$H NMR (400 MHz, DMSO-$d_6$): δ 1.17 (t, J=9.2 Hz, 3H), 2.91-2.95 (m, 1H), 3.20 (s, 3H), 3.30 (s, 3H), 3.35-3.38 (m, 2H), 6.93 (d, J=12.0 Hz, 2H), 7.01 (m, J=11.2 Hz, 2H), 7.16-7.19 (m, 4H), 7.86 (d, J=6.4 Hz, 1H), 8.48 (d, J=6.4 Hz, 1H), 8.67 (s, 1H). [M+H] Calc'd for $C_{24}H_{24}N_4O_3$, 417; Found, 417.

Preparation 30A: methanesulfonic acid 2-{4-[(4-benzyloxy-phenyl)-methyl-amino]-phenyl}-propyl ester

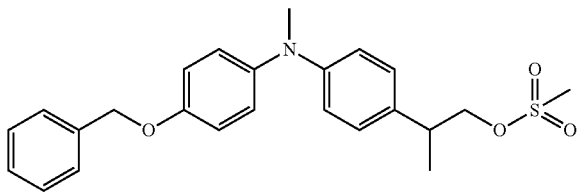 [SMILES: CC(COS(C)(=O)=O)c1ccc(N(C)c2ccc(OCc3ccccc3)cc2)cc1]

To a solution of 2-{4-[(4-benzyloxy-phenyl)-methyl-amino]-phenyl}-propan-1-ol (1.5 g, 4.32 mmol) in DCM (20 mL) was added TEA (0.72 g, 6.5 mmol) and MsCl (0.65 g, 5.6 mmol) at 0° C. and the mixture was stirred at RT for 2 h. The reaction mixture was washed with aqueous NH$_4$Cl, washed with brine, dried over Na$_2$SO$_4$ and concentrated. The residue was purified by silica gel chromatography (PE:EA, 3:1) to give 1.4 g (76%) of the title compound. [M+H] Calc'd for $C_{24}H_{27}NO_4S$, 426; Found, 426.

Preparation 30B: 3-{4-[(4-benzyloxy-phenyl)-methyl-amino]-phenyl}-butyronitrile

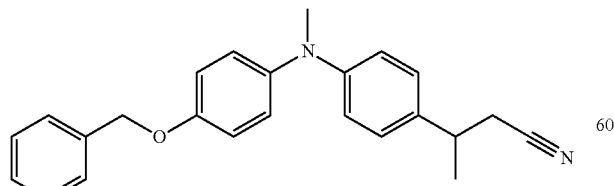

To a solution of methanesulfonic acid 2-{4-[(4-benzyloxy-phenyl)-methyl-amino]-phenyl}-propyl ester (1.35 g, 3.17 mmol) in DMSO (20 mL) was added KCN (0.4 g, 6.34 mmol) and 18-crown-6 (0.84 g, 3.17 mmol), and the mixture was stirred overnight at 65° C. The reaction mixture was cooled to RT, quenched with water and extracted with EA (3×). The combined organics were washed with brine, dried over Na$_2$SO$_4$ and concentrated. The residue was purified by silica gel chromatography (PE:EA, 5:1) to give 0.56 g (50%) of the title compound. [M+H] Calc'd for $C_{24}H_{24}N_2O$, 357; Found, 357.

Preparation 30C: 3-{4-[(4-hydroxy-phenyl)-methyl-amino]-phenyl}-butyronitrile

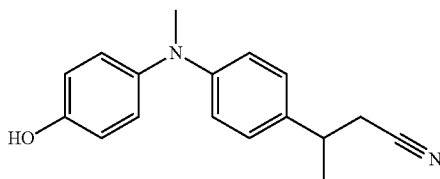 [SMILES: CC(CC#N)c1ccc(N(C)c2ccc(O)cc2)cc1]

The title compound was prepared in 88% yield from 3-{4-[(4-benzyloxy-phenyl)-methyl-amino]-phenyl}-butyronitrile according to the procedure of Preparation 26B. [M+H] Calc'd for $C_{17}H_{18}N_2O$, 267 Found, 267.

Example 30: 3-(4-{[4-(4-hydroxy-pyrido[3,4-d]pyrimidin-2-yloxy)-phenyl]-methyl-amino}-phenyl)-butyronitrile

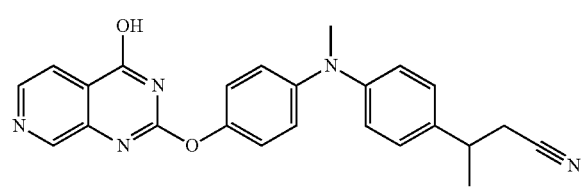 [SMILES: CC(CC#N)c1ccc(N(C)c2ccc(Oc3nc(O)c4ccncc4n3)cc2)cc1]

The title compound was prepared in 17% yield from 2-chloro-pyrido[3,4-d]pyrimidin-4-ol and 3-{4-[(4-hydroxy-phenyl)-methyl-amino]-phenyl}-butyronitrile according to the procedure for the preparation of Example 1. $^1$H NMR (400 MHz, DMSO-$d_6$): δ 1.28 (d, J=9.2 Hz, 3H), 2.77 (d, J=9.2 Hz, 2H), 3.05-3.09 (m, 1H), 3.27 (s, 3H), 6.95-6.99 (m, 4H), 7.19-7.27 (m, 4H), 7.86 (d, J=6.8 Hz, 1H), 8.49 (d, J=6.4 Hz, 1H), 8.70 (s, 1H). [M+H] Calc'd for $C_{24}H_{21}N_5O_2$, 412; Found, 412.

Preparation 31A: 1-cyclopentyl-5-methoxy-1H-indole

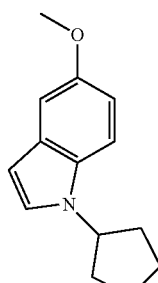

To a solution of 5-methoxy-1H-indole (1.5 g, 10 mmol) in DMF (20 mL) at 0° C. was added NaH (480 mg, in mineral oil, 60%, 12 mmol) in portions and the mixture was stirred for 30 min. Bromo-cyclopentane (2.3 g, 15 mmol) was then added and the mixture was stirred overnight at 90° C. The reaction mixture was diluted with water (100 mL) and extracted with DCM (30 mL*3). The organics were combined, dried over $Na_2SO_4$ and concentrated. The residue was purified by silica gel chromatography (PE:EA, 20:1) to give 450 mg (21%) of the title product. [M+H] Calc'd for $C_{14}H_{17}NO$, 216; Found, 216.

Preparation 31B: 1-cyclopentyl-1H-indol-5-ol

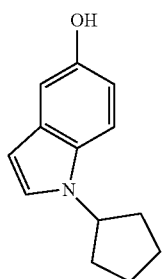

The title compound was prepared in 21% yield from 1-cyclopentyl-5-methoxy-1H-indole according to the procedure for the preparation of Example 4B. [M+H] Calc'd for $C_{13}H_{15}NO$, 202; Found, 202.

Example 31: 2-(1-cyclopentyl-1H-indol-5-yloxy)-pyrido[3,4-d]pyrimidin-4-ol

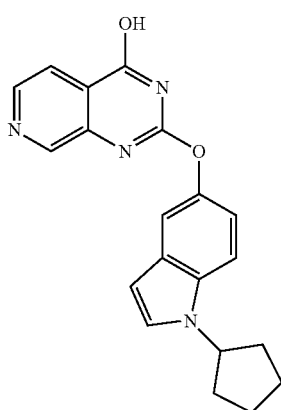 [SMILES: Oc1nc(Oc2ccc3c(ccn3C3CCCC3)c2)nc2cnccc12]

The title compound was prepared in 3% yield from 2-chloro-pyrido[3,4-d]pyrimidin-4-ol and 1-cyclopentyl-1H-indol-5-ol according to the procedure for the preparation of Example 1. $^1$H NMR (400 MHz, DMSO-$d_6$): δ 1.72-1.76 (m, 2H), 1.87-1.91 (m, 4H), 2.15-2.21 (m, 2H), 4.92 (t, J=6.4 Hz, 1H), 6.49 (d, J=3.2 Hz, 1H), 7.08 (dd, J=1.6, 7.2 Hz, 1H), 7.45 (d, J=1.6 Hz, 1H), 7.54-7.59 (m, 2H), 7.88 (s, 1H), 8.51 (brs, 1H), 8.64 (brs, 1H). [M+H] Calc'd for $C_{20}H_{18}N_4O_2$, 347; Found, 347.

Preparation 32A: 5-benzyloxy-1-phenyl-1H-indole

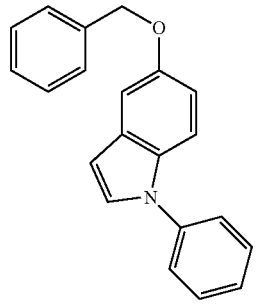 [SMILES: c1ccc(COc2ccc3c(ccn3-c3ccccc3)c2)cc1]

A mixture of iodobenzene (1.83 g, 8.97 mmol), 5-benzyloxy-1H-indole (2.0 g, 8.97 mmol), CuI (171 mg, 0.90 mmol) and $Cs_2CO_3$ (5.8 g, 17.94 mmol) in DMF (17 mL) was heated overnight at 120° C. The reaction mixture was filtered and the filtrate was concentrated. The residue was purified by flash chromatography (PE:EA, 15:1 to 10:1) to give 1.29 g (49%) of the title compound. [M+H] Calc'd for $C_{21}H17NO$, 300; Found, 300.

Preparation 32B: 1-phenyl-1H-indol-5-ol

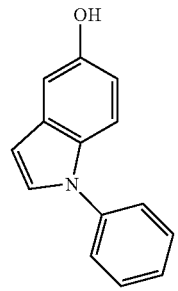 [SMILES: Oc1ccc2c(ccn2-c2ccccc2)c1]

To a solution of 5-benzyloxy-1-phenyl-1H-indole (100 mg, 0.33 mmol) in EtOH (20 mL) was added Pd/C (20 mg) and the mixture was stirred overnight at RT under H2 atmosphere. The reaction mixture was filtered on celite and concentrated to give 70 mg (100%) of the title crude product. [M+H] Calc'd for $C_{14}H_{11}NO$, 210; Found, 210.

Preparation 32C: 1-phenyl-2,3-dihydro-1H-indol-5-ol

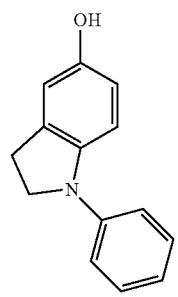 [SMILES: Oc1ccc2c(c1)CCN2c1ccccc1]

To a solution of 1-phenyl-1H-indol-5-ol (500 mg, 2.4 mmol) in AcOH (10 mL) was added NaBH$_3$CN (1.2 g, 19.1 mmol) and the reaction mixture was stirred overnight at RT. The reaction was diluted with water, basified to pH 8 with sat. Na$_2$CO$_3$ and extracted with EA (3×). The combined organics were washed with brine, dried over Na$_2$SO$_4$, filtered and concentrated to give 200 mg (40%) of the title crude product. [M+H] Calc'd for C$_{15}$H15NO, 226; Found, 226.

Example 32: 2-(1-phenyl-2,3-dihydro-1H-indol-5-yloxy)-pyrido[3,4-d]pyrimidin-4-ol

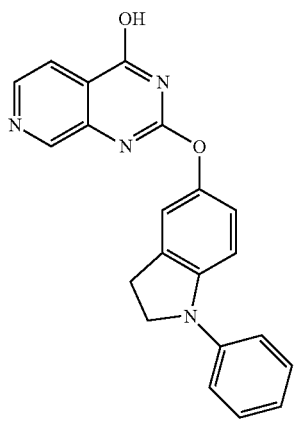 [SMILES: Oc1nc(Oc2ccc3c(c2)CCN3c2ccccc2)nc2cnccc12]

The title compound was prepared in 16% yield from 2-chloro-pyrido[3,4-d]pyrimidin-4-ol and 1-phenyl-2,3-dihydro-1H-indol-5-ol according to the procedure for the preparation of Example 1. $^1$H NMR (400 MHz, DMSO-d$_6$): δ 3.14 (t, J=8.0 Hz, 2H), 4.00 (t, J=8.4 Hz, 2H), 6.97 (d, J=6.8 Hz, 2H), 7.11 (d, J=8.4 Hz, 1H), 7.16 (s, 1H), 7.27 (d, J=8.0 Hz, 2H), 7.35-7.39 (m, 2H), 7.87 (d, J=4.8 Hz, 1H), 8.50 (d, J=5.2 Hz, 1H), 8.70 (s, 1H), 13.04 (brs, 1H). [M+H] Calc'd for C$_{21}$H$_{16}$N$_4$O$_2$, 357; Found, 357.

Preparation 33A: 6-(tert-butyl-dimethyl-silanyloxy)-1,2,3,4-tetrahydro-quinoline

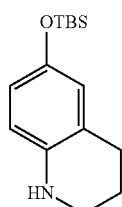

To a solution of 1,2,3,4-tetrahydro-quinolin-6-ol (1.0 g, 6.7 mmol) and imidazole (1.4 g, 20.1 mmol) in DCM (20 mL) was added TBSCl (1.7 g, 7.4 mmol) at ice-bath temperature, and the reaction was stirred at RT for 3 h. The reaction was diluted with water and extracted with EA (3×). The combined organics were washed with brine, dried over Na$_2$SO$_4$, filtered and concentrated. The residue was purified by silica gel chromatography (PE:EA, 20:1) to give 1.7 g (97%) of the title product.

Preparation 33B: 6-(tert-butyl-dimethyl-silanyloxy)-1-phenyl-1,2,3,4-tetrahydro-quinoline

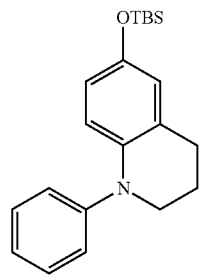 [SMILES: CC(C)(C)[Si](C)(C)Oc1ccc2c(c1)CCCN2c1ccccc1]

To a suspension of 6-(tert-butyl-dimethyl-silanyloxy)-1,2,3,4-tetrahydro-quinoline (100 mg, 0.38 mmol), iodo-benzene (78 mg, 0.38 mmol), BINAP (24 mg, 0.038 mmol) and Cs$_2$CO$_3$ (248 mg, 0.76 mmol) in toluene (10 mL) was added Pd$_2$(dba)$_3$ (18 mg, 0.019 mmol) under N$_2$ atmosphere. The reaction was stirred at reflux overnight, filtered and the filtrate was concentrated. The residue was purified by silica gel chromatography (PE) to give 100 mg (78%) of the title product. [M+H] Calc'd for C$_{21}$H$_{29}$NOSi, 340; Found, 340.

Preparation 33C: 1-phenyl-1,2,3,4-tetrahydro-quinolin-6-ol

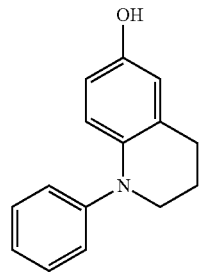 [SMILES: Oc1ccc2c(c1)CCCN2c1ccccc1]

To a solution 6-(tert-butyl-dimethyl-silanyloxy)-1-phenyl-1,2,3,4-tetrahydro-quinoline (700 mg, 2.1 mmol) in THF (20 mL) was added TBAF (4.1 mL, 1.0 M in THF, 4.1 mmol) at RT and the reaction was stirred at RT for 30 min. The reaction was diluted with water, extracted with EA (3×). The combined organics were washed with brine, dried over Na$_2$SO$_4$, filtered and concentrated. The residue was purified by silica gel chromatography (PE:EA, 6:1) to give 250 mg (54%) of the title product. [M+H] Calc'd for C$_{15}$H$_{15}$NO, 226; Found, 226.

Example 33: 2-(1-phenyl-1,2,3,4-tetrahydro-quinolin-6-yloxy)-pyrido[3,4-d]pyrimidin-4-ol

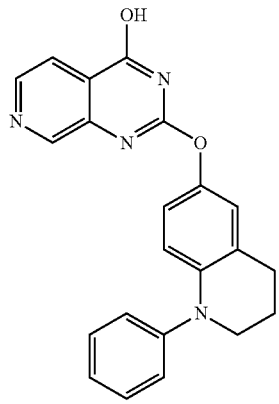 [SMILES: Oc1nc(Oc2ccc3c(c2)CCCN3c2ccccc2)nc2cnccc12]

The title compound was prepared in 26% yield from 2-chloro-pyrido[3,4-d]pyrimidin-4-ol and 1-phenyl-1,2,3,4-tetrahydro-quinolin-6-ol according to the procedure for the preparation of Example 1. $^1$H NMR (300 MHz, DMSO-$d_6$): δ 1.96-1.98 (m, 2H), 2.80 (t, J=6.0 Hz, 2H), 3.57 (t, J=6.0 Hz, 2H), 6.61 (d, J=9.0 Hz, 1H), 6.84 (d, J=8.4 Hz, 1H), 6.98 (s, 1H), 7.08-7.12 (m, 1H), 7.24 (d, J=7.8 Hz, 2H), 7.34-7.39 (m, 2H), 7.84 (d, J=2.7 Hz, 1H), 8.48 (brs, 1H), 8.68 (brs, 1H). [M+H] Calc'd for $C_{22}H_{18}N_4O_2$, 371; Found, 371.

Preparation 34A: 2-chloro-5-isopropenyl-pyridine

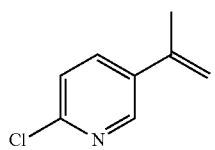

To a suspension of 2-chloro-5-iodo-pyridine (100 mg, 0.42 mmol), 2-isopropenyl-4,4,5,5-tetramethyl-[1,3,2]dioxaborolane (75 mg, 0.42 mmol), S-Phos (17 mg, 0.042 mmol) and $K_3PO_4$ (178 mg, 0.84 mmol) in toluene (10 mL) was added $Pd_2(dba)_3$ (8 mg, 0.008 mmol) under $N_2$ atmosphere. The reaction was stirred at reflux overnight, filtered and the filtrate was concentrated. The residue was purified by silica gel chromatography (PE:EA, 50:1) to give 30 mg (47%) of the title product. [M+H] Calc'd for $C_8H_8ClN$, 154; Found, 154.

Preparation 34B: (5-isopropenyl-pyridin-2-yl)-(4-methoxy-phenyl)-methyl-amine

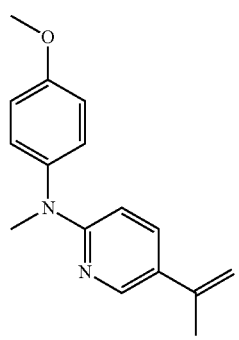 [SMILES: C=C(C)c1ccc(N(C)c2ccc(OC)cc2)nc1]

The title compound was prepared in 77% yield from 2-chloro-5-isopropenyl-pyridine and (4-methoxy-phenyl)-methyl-amine according to the procedure of Preparation 34A. [M+H] Calc'd for $C_{16}H_{18}N_2O$, 255; Found, 255.

Preparation 34C: (5-isopropyl-pyridin-2-yl)-(4-methoxy-phenyl)-methyl-amine

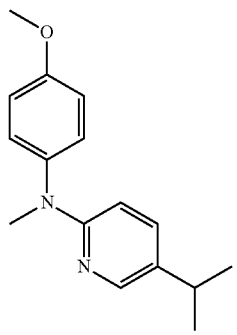 [SMILES: COc1ccc(N(C)c2ccc(C(C)C)cn2)cc1]

The title compound was prepared in 99% yield from (5-isopropenyl-pyridin-2-yl)-(4-methoxy-phenyl)-methyl-amine according to the procedure of Preparation 32B. [M+H] Calc'd for $C_{16}H_{20}N_2O$, 257; Found, 257.

Preparation 34D: 4-[(5-isopropyl-pyridin-2-yl)-methyl-amino]-phenol

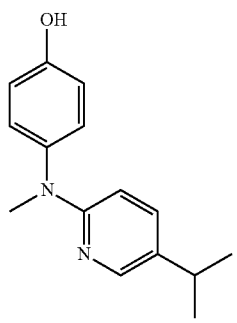 [SMILES: CC(C)c1ccc(N(C)c2ccc(O)cc2)nc1]

The title compound was prepared in 59% yield from (5-isopropyl-pyridin-2-yl)-(4-methoxy-phenyl)-methyl-amine according to the procedure of Preparation 4B. [M+H] Calc'd for $C_{15}H_{18}N_2O$, 243; Found, 243.

Example 34: 2-{4-[(5-isopropyl-pyridin-2-yl)-methyl-amino]-phenoxy}-pyrido[3,4-d]pyrimidin-4-ol

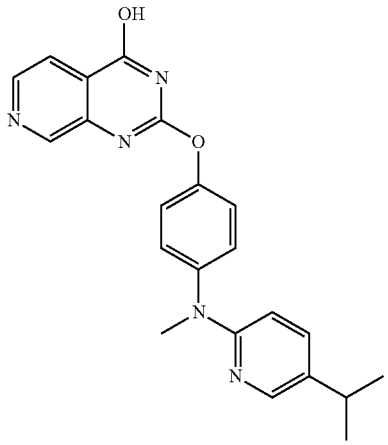 [SMILES: CC(C)c1ccc(N(C)c2ccc(Oc3nc(O)c4ccncc4n3)cc2)nc1]

The title compound was prepared in 28% yield from 2-chloro-pyrido[3,4-d]pyrimidin-4-ol and 4-[(5-isopropyl-pyridin-2-yl)-methyl-amino]-phenol according to the procedure for the preparation of Example 1. $^1$H NMR (300 MHz, DMSO-$d_6$): δ 1.16 (d, J=6.6 Hz, 6H), 2.77-2.82 (m, 1H), 3.38 (s, 3H), 6.62 (d, J=8.7 Hz, 1H), 7.34 (s, 4H), 7.41 (dd, J=2.7, 9.0 Hz, 1H), 7.87 (d, J=5.1 Hz, 1H), 8.04 (d, J=2.1 Hz, 1H), 8.51 (d, J=3.9 Hz, 1H), 8.72 (s, 1H), 13.12 (s, 1H). [M+H] Calc'd for $C_{22}H_{21}N_5O_2$, 388; Found, 388.

Preparation 35A: (4-isopropyl-3-nitro-phenyl)-(4-methoxy-phenyl)-methyl-amine

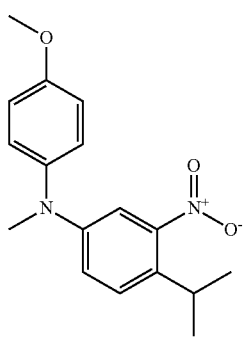 [SMILES: COc1ccc(N(C)c2ccc(C(C)C)c([N+](=O)[O-])c2)cc1]

The title compound was prepared in 81% yield from (4-methoxy-phenyl)-methyl-amine and 4-bromo-1-isopropyl-2-nitro-benzene according to the procedure of Preparation 27B. [M+H] Calc'd for $C_{17}H_{20}N_2O_3$, 301; Found, 301.

Preparation 35B: 4-isopropyl-$N_1$-(4-methoxy-phenyl)-$N_1$-methyl-benzene-1,3-diamine

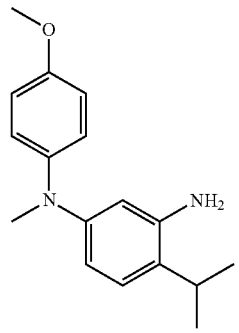 [SMILES: COc1ccc(N(C)c2ccc(C(C)C)c(N)c2)cc1]

The title compound was prepared in 96% yield from (4-isopropyl-3-nitro-phenyl)-(4-methoxy-phenyl)-methyl-amine according to the procedure of Preparation 32B. [M+H] Calc'd for $C_{17}H_{22}N_2O$, 271; Found, 271.

Preparation 35C: (4-isopropyl-3-morpholin-4-yl-phenyl)-(4-methoxy-phenyl)-methyl-amine

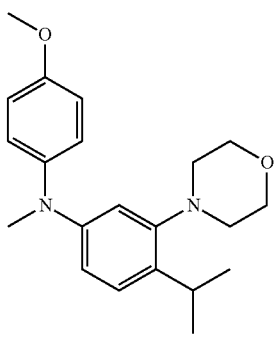 [SMILES: COc1ccc(N(C)c2ccc(C(C)C)c(N3CCOCC3)c2)cc1]

To a suspension of 4-isopropyl-$N_1$-(4-methoxy-phenyl)-$N_1$-methyl-benzene-1,3-diamine (2.0 g, 7.4 mmol), $K_2CO_3$ (5.1 g, 37.1 mmol) and NaI (2.0 g) in DMF (100 mL) was added 1-chloro-2-(2-chloro-ethoxy)-ethane (1.1 g, 7.4 mmol) and the reaction was stirred overnight at RT. The reaction was diluted with water and extracted with EA (3×). The combined organics were washed with brine, dried over $Na_2SO_4$, filtered and concentrated. The residue was purified by silica gel chromatography (PE:EA, 20:1) to give 1.5 g (60%) of the title product. [M+H] Calc'd for $C_{21}H_{28}N_2O_2$, 341; Found, 341.

Preparation 35D: 4-[(4-isopropyl-3-morpholin-4-yl-phenyl)-methyl-amino]-phenol

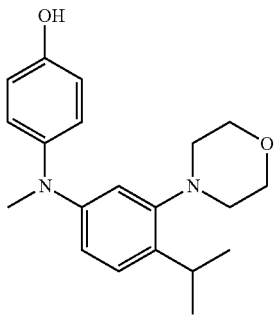 [SMILES: CC(C)c1ccc(N(C)c2ccc(O)cc2)cc1N1CCOCC1]

The title compound was prepared in 59% yield from (4-isopropyl-3-morpholin-4-yl-phenyl)-(4-methoxy-phenyl)-methyl-amine according to the procedure of Preparation 4B. [M+H] Calc'd for $C_{20}H_{26}N_2O_2$, 327; Found, 327.

Example 35: 2-{4-[(4-isopropyl-3-morpholin-4-yl-phenyl)-methyl-amino]-phenoxy}-pyrido[3,4-d]pyrimidin-4-ol

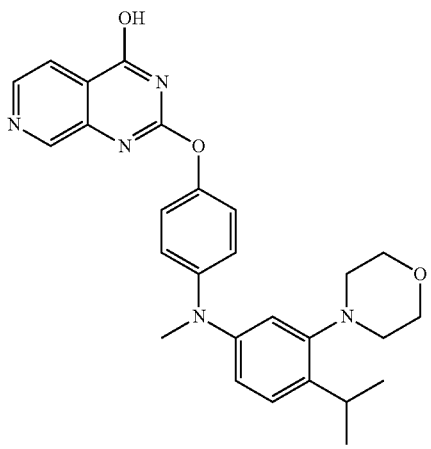 [SMILES: CC(C)c1ccc(N(C)c2ccc(Oc3nc(O)c4ccncc4n3)cc2)cc1N1CCOCC1]

The title compound was prepared in 23% yield from 2-chloro-pyrido[3,4-d]pyrimidin-4-ol and 4-[(5-isopropyl-pyridin-2-yl)-methyl-amino]-phenol according to the procedure for the preparation of Example 1. $^1$H NMR (400 MHz, DMSO-$d_6$): δ 1.17 (d, J=6.8 Hz, 6H), 2.78 (t, J=4.0 Hz, 4H), 3.28 (s, 3H), 3.34-3.41 (m, 1H), 3.72 (t, J=4.0 Hz, 4H), 6.84-6.86 (m, 2H), 6.96 (d, J=8.0 Hz, 2H), 7.18-7.25 (m, 3H), 7.88 (d, J=5.2 Hz, 1H), 8.51 (d, J=5.2 Hz, 1H), 8.70 (s, 1H), 13.06 (brs, 1H). [M+H] Calc'd for $C_{27}H_{29}N_5O_3$, 472; Found, 472.

Preparation 36A: 1-[4-(4-benzyloxy-phenylamino)-phenyl]-ethanone

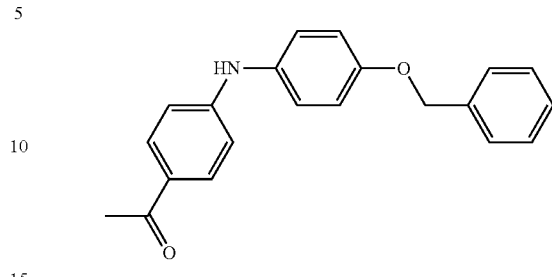

A mixture of 1-(4-bromo-phenyl)-ethanone (10 g, 0.05 mol), 4-benzyloxy-phenylamine (12 g, 0.06 mol), X-Phos (1.2 g, 2.5 mmol), Pd$_2$(dba)$_3$ (1.16 g, 1.26 mmol) and K$_3$PO$_4$ (16 g, 0.075 mol) in toluene (200 mL) was refluxed overnight under N$_2$ atmosphere. The reaction mixture was filtered and the filtrate was concentrated. The residue was purified by silica gel chromatography (PE:EA, 5:1) to give 11.7 g of the title product. [M+H] Calc'd for $C_{21}H_{19}NO_2$, 318; Found, 318.

Preparation 36B: 1-{4-[(4-benzyloxy-phenyl)-methyl-amino]-phenyl}-ethanone

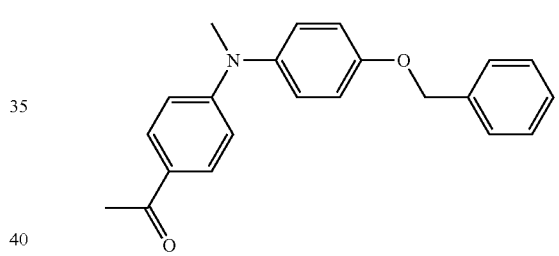

The title compound was prepared in 68% yield from 1-[4-(4-benzyloxy-phenylamino)-phenyl]-ethanone according to the procedure of Preparation 27A. [M+H] Calc'd for $C_{22}H_{21}NO_2$, 332 Found, 332.

Preparation 36C: 1-{4-[(4-benzyloxy-phenyl)-methyl-amino]-phenyl}-ethanol

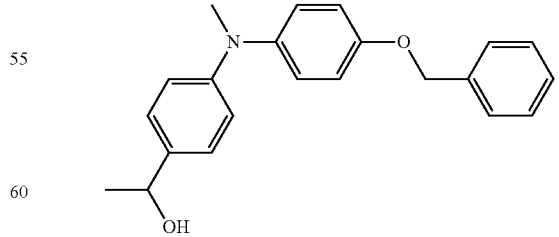

The title compound was prepared in 99% yield from 1-{4-[(4-benzyloxy-phenyl)-methyl-amino]-phenyl}-ethanone according to the procedure of Preparation 29C. [M+H] Calc'd for $C_{22}H_{23}NO_2$, 334 Found, 334.

Preparation 36D: (4-benzyloxy-phenyl)-[4-(1-methoxy-ethyl)-phenyl]-methyl-amine

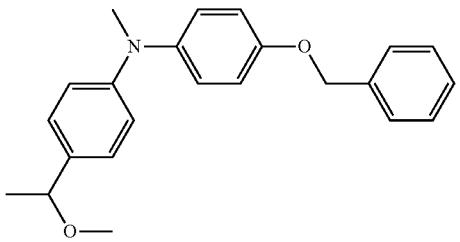 [SMILES: COC(C)c1ccc(N(C)c2ccc(OCc3ccccc3)cc2)cc1]

The title compound was prepared in 45% yield from 1-[4-(4-benzyloxy-phenylamino)-phenyl]-ethanone according to the procedure of Preparation 29D. [M+H] Calc'd for $C_{23}H_{25}NO_2$, 348 Found, 348.

Preparation 36E: 4-{[4-(1-methoxy-ethyl)-phenyl]-methyl-amino}-phenol

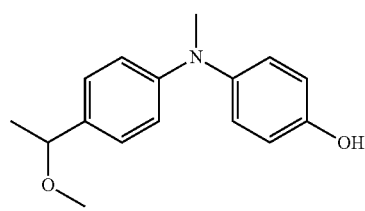 [SMILES: COC(C)c1ccc(N(C)c2ccc(O)cc2)cc1]

To a solution of (4-benzyloxy-phenyl)-[4-(1-methoxy-ethyl)-phenyl]-methyl-amine (0.947 g, 2.73 mmol) in THE (20 mL) was added Pd/C (0.10 g) and the mixture was stirred overnight under H2 atmosphere. The reaction mixture was filtered on celite and the filtrate was concentrated to give 0.34 g (50%) of the title compound. [M+H] Calc'd for $C_{16}H_{19}NO_2$, 258; Found, 258.

Example 36: 2-(4-{[4-(1-methoxy-ethyl)-phenyl]-methyl-amino}-phenoxy)-pyrido[3,4-d]pyrimidin-4-ol

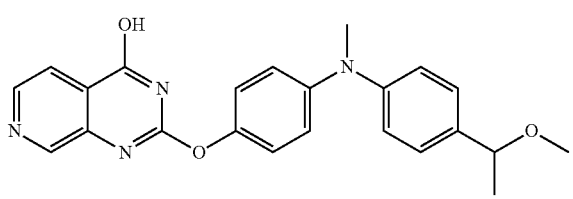 [SMILES: COC(C)c1ccc(N(C)c2ccc(Oc3nc(O)c4ccncc4n3)cc2)cc1]

The title compound was prepared in 23% yield from 2-chloro-pyrido[3,4-d]pyrimidin-4-ol and 4-{[4-(1-methoxy-ethyl)-phenyl]-methyl-amino}-phenol according to the procedure for the preparation of Example 1. $^1$H NMR (300 MHz, DMSO-d$_6$): δ 1.41 (d, J=6.6 Hz, 3H), 3.07 (s, 3H), 3.27 (s, 3H), 4.23-4.25 (m, 1H), 7.01-7.04 (m, 4H), 7.20-7.24 (m, 4H), 7.86 (d, J=5.1 Hz, 1H), 8.50 (d, J=5.1 Hz, 1H), 8.69 (s, 1H). [M+H] Calc'd for $C_{23}H_{22}N_4O_3$, 403; Found, 403.

Preparation 37A: methanesulfonic acid 2-{4-[(4-benzyloxy-phenyl)-methyl-amino]-phenyl}-propyl ester

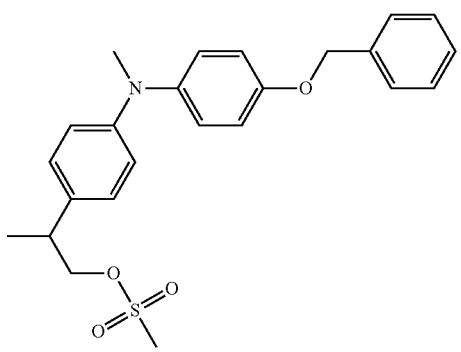 [SMILES: CC(COS(C)(=O)=O)c1ccc(N(C)c2ccc(OCc3ccccc3)cc2)cc1]

The title compound was prepared in 60% yield from 2-{4-[(4-benzyloxy-phenyl)-methyl-amino]-phenyl}-propan-1-ol according to the procedure of Preparation 30A. [M+H] Calc'd for $C_{24}H_{27}NO_4S$, 426; Found, 426.

Preparation 37B: [4-(2-amino-isopropyl)phenyl]methyl[4-(phenylmethoxy)phenyl]amine

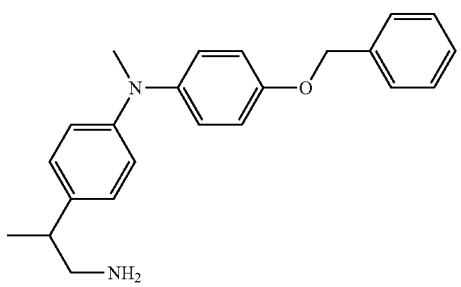 [SMILES: CC(CN)c1ccc(N(C)c2ccc(OCc3ccccc3)cc2)cc1]

A solution of methanesulfonic acid 2-{4-[(4-benzyloxy-phenyl)-methyl-amino]-phenyl}-propyl ester (3.5 g, 8.24 mmol) in NH$_3$/THF (20 mL) was stirred overnight at 148° C. in a sealed tube. The reaction mixture was concentrated and the residue was purified by silica gel chromatography (DCM:MeOH, 10:1) to give 1.71 g (60%) of the title product. [M+H] Calc'd for $C_{23}H_{26}N_2O$, 347; Found, 347.

Preparation 37C: (2-{4-[(4-benzyloxy-phenyl)-methyl-amino]-phenyl}-propyl)-carbamic acid tert-butyl ester

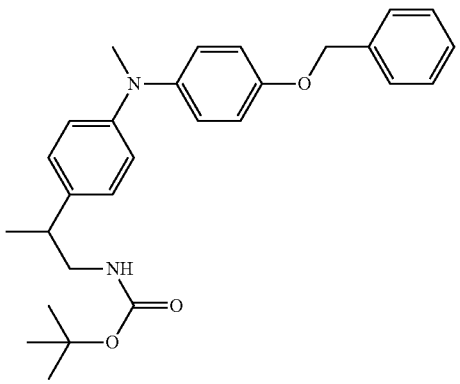 [SMILES: CC(CNC(=O)OC(C)(C)C)c1ccc(N(C)c2ccc(OCc3ccccc3)cc2)cc1]

A solution of [4-(2-amino-isopropyl)phenyl]methyl[4-(phenylmethoxy)phenyl]amine (1.7 g, 4.91 mmol), (Boc)$_2$O (1.29 g, 5.90 mmol) and TEA (744 mg, 7.37 mmol) in THF (20 mL) was stirred for 2 h at RT. The reaction mixture was concentrated and the residue was purified by silica gel chromatography (PE:EA, 10:1) to give 1.67 g (76%) of the title product. [M+H] Calc'd for $C_{28}H_{34}N_2O_3$, 447; Found, 447.

Preparation 37D: (2-{4-[(4-hydroxy-phenyl)-methyl-amino]-phenyl}-propyl)-carbamic acid tert-butyl ester

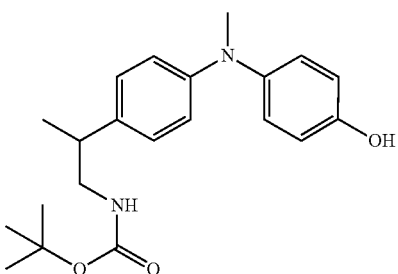 [SMILES: CC(CNC(=O)OC(C)(C)C)c1ccc(N(C)c2ccc(O)cc2)cc1]

The title compound was prepared in 88% yield from (2-{4-[(4-benzyloxy-phenyl)-methyl-amino]-phenyl}-propyl)-carbamic acid tert-butyl ester according to the procedure of Preparation 36E. [M+H] Calc'd for $C_{21}H_{28}N_2O_3$, 357; Found, 357.

Example 37: 2-(4-{[4-(2-amino-1-methyl-ethyl)-phenyl]-methyl-amino}-phenoxy)-pyrido[3,4-d]pyrimidin-4-ol

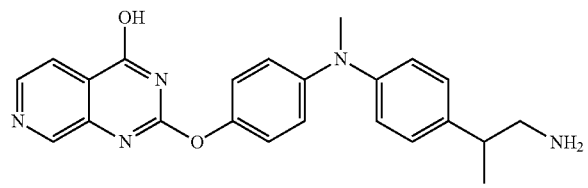 [SMILES: CC(CN)c1ccc(N(C)c2ccc(Oc3nc(O)c4ccncc4n3)cc2)cc1]

The title compound was prepared in 3.3% yield from 2-chloro-pyrido[3,4-d]pyrimidin-4-ol and (2-{4-[(4-hydroxy-phenyl)-methyl-amino]-phenyl}-propyl)-carbamic acid tert-butyl ester according to the procedure of Example 23. $^1$H NMR (300 MHz, CD3OD-d$_4$): δ 1.28 (d, J=6.3 Hz, 3H), 2.73-2.96 (m, 2H), 3.32 (s, 3H), 3.41-3.50 (m, 1H), 7.04-7.08 (m, 4H), 7.17-7.24 (m, 4H), 7.98 (d, J=4.8 Hz, 1H), 8.47 (d, J=4.8 Hz, 1H), 8.73 (s, 1H). [M+H] Calc'd for $C_{23}H_{23}N_5O_2$, 402; Found, 4 02.

Preparation 38A: (4-{2-[(2-methoxyethyl)amino]-isopropyl}phenyl)methyl[4 (phenylmethoxy)phenyl]amine

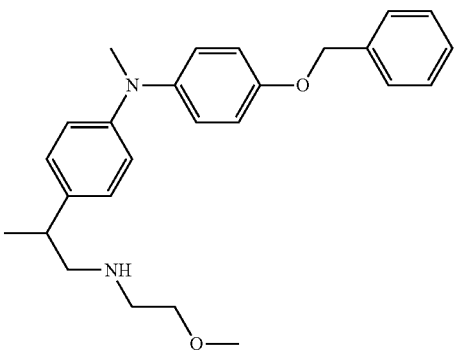 [SMILES: COCCNCC(C)c1ccc(N(C)c2ccc(OCc3ccccc3)cc2)cc1]

A mixture of methanesulfonic acid 2-{4-[(4-benzyloxy-phenyl)-methyl-amino]-phenyl}-propyl ester (1.22 g, 2.88 mmol), 2-methoxy-ethylamine (1.08 g, 14.4 mmol) and NaHCO$_3$ (720 mg, 8.64 mmol) in ACN (20 mL) was stirred overnight at 70° C. The reaction mixture was concentrated and the residue was purified by silica gel chromatography (DCM:MeOH, 10:1) to give 1.14 g (100%) of the title product. [M+H] Calc'd for $C_{26}H_{32}N_2O_2$, 405; Found, 405.

Preparation 38B: (4-{2-[(2-methoxyethyl)methyl-amino]-isopropyl}phenyl)methyl[4-(phenylmethoxy)phenyl]amine

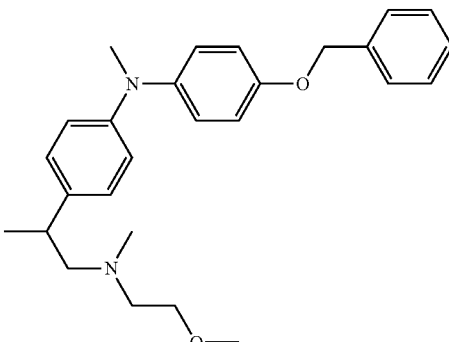

The title compound was prepared in 25% yield from (4-{2-[(2-methoxyethyl)amino]-isopropyl}phenyl)methyl[4 (phenylmethoxy)phenyl]amine according to the procedure of Preparation 27A. [M+H] Calc'd for $C_{27}H_{34}N_2O_2$, 419 Found, 419.

Preparation 38C: 4-[(4-{2-[(2-methoxy-ethyl)-methyl-amino]-1-methyl-ethyl}-phenyl)-methyl-amino]-phenol

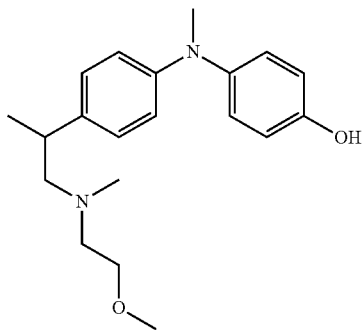 [SMILES: COCCN(C)CC(C)c1ccc(N(C)c2ccc(O)cc2)cc1]

The title compound was prepared in 100% yield from (4-{2-[(2-methoxyethyl)methylamino]-isopropyl}phenyl)methyl[4-(phenylmethoxy)phenyl]amine according to the procedure of Preparation 36E. [M+H] Calc'd for $C_{20}H_{28}N_2O_2$, 329; Found, 329.

Example 38: 2-{4-[(4-{2-[(2-methoxy-ethyl)-methyl-amino]-1-methyl-ethyl}-phenyl)-methyl-amino]-phenoxy}-pyrido[3,4-d]pyrimidin-4-ol

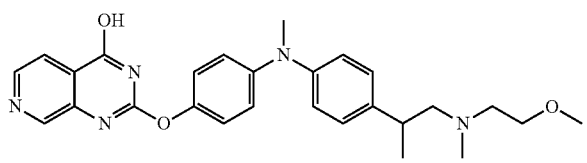 [SMILES: COCCN(C)CC(C)c1ccc(N(C)c2ccc(Oc3nc(O)c4ccncc4n3)cc2)cc1]

The title compound was prepared in 23% yield from 2-chloro-pyrido[3,4-d]pyrimidin-4-ol and 4-[(4-{2-[(2-methoxy-ethyl)-methyl-amino]-1-methyl-ethyl}-phenyl)-methyl-amino]-phenol according to the procedure for the preparation of Example 1. $^1$H NMR (300 MHz, CD3OD-d$_4$): δ 1.12-1.14 (m, 3H), 2.59-2.60 (m, 1H), 2.72 (s, 3H), 3.04-3.66 (m, 12H), 6.94-7.12 (m, 8H), 7.90-7.95 (m, 1H), 8.34-8.35 (m, 1H), 8.73-8.74 (m, 1H). [M+H] Calc'd for $C_{27}H_{31}N_5O_3$, 474; Found, 474.

Preparation 39A: 1-(4-bromo-phenyl)-1-cyclopropyl-ethanol

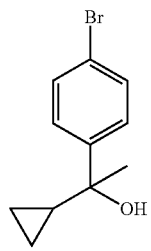

To a solution of (4-bromo-phenyl)-cyclopropyl-methanone (225 mg, 1 mmol) in THF (10 mL) was added CH$_3$MgBr (0.4 mL, 1.1 mmol) at 0° C., and the mixture was stirred for 2 h at RT. The reaction was quenched with aqueous NH$_4$Cl, extracted with EA (3×), dried over Na$_2$SO$_4$, filtered and concentrated. The residue was purified by silica gel chromatography (PE:EA, 10:1) to give 179 mg (75%) of the title product. [M+H] Calc'd for $C_{11}H_{13}BrO$, 241; Found, 241.

Preparation 39B: 1-bromo-4-(1-cyclopropyl-ethyl)-benzene

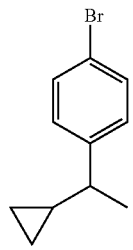

To a solution of 1-(4-bromo-phenyl)-1-cyclopropyl-ethanol (138 mg, 0.575 mmol) in DCM (5 mL) at −78° C. was added under N$_2$ atmosphere Et$_3$SiH (87 mg, 0.75 mmol) and TFA (131 mg, 1.15 mmol) and the mixture was stirred overnight at RT. The reaction was quenched with aqueous NaHCO$_3$, extracted with EA (3×), dried over Na$_2$SO$_4$, filtered and concentrated. The residue was purified by silica gel chromatography (PE) to give 120 mg (94%) of the title product. [M+H] Calc'd for $C_{11}H_{13}Br$, 225; Found, 225.

Preparation 39C: [4-(1-cyclopropyl-ethyl)-phenyl]-methyl-amine

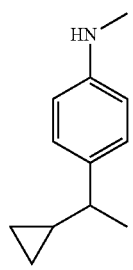

A mixture of 1-bromo-4-(1-cyclopropyl-ethyl)-benzene (3.7 g, 16.52 mmol) and Cu (53 mg, 0.825 mmol) in a methylamine solution (40 wt. % in H$_2$O, 35 mL) was stirred overnight at 100° C. in a sealed tube. The reaction was cooled to RT, diluted with H$_2$O and extracted with EA (3×). The combined organics were washed with brine, dried over Na$_2$SO$_4$, filtered and concentrated. The residue was purified by silica gel chromatography (PE:EA, 10:1) to give 440 mg (15%) of the title product. [M+H] Calc'd for $C_{12}H_{17}N$, 176; Found, 176.

Preparation 39D: 4-{[4-(1-cyclopropyl-ethyl)-phenyl]-methyl-amino}-phenol

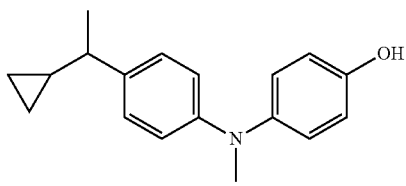 [SMILES: CC(c1ccc(N(C)c2ccc(O)cc2)cc1)C1CC1]

The title compound was prepared in 35% yield from [4-(1-cyclopropyl-ethyl)-phenyl]-methyl-amine according to the procedure of Preparation 5A. [M+H] Calc'd for $C_{18}H_{21}NO$, 268; Found, 268.

Example 39: 2-(4-{[4-(1-cyclopropyl-ethyl)-phenyl]-methyl-amino}-phenoxy)-pyrido[3,4-d]pyrimidin-4-ol

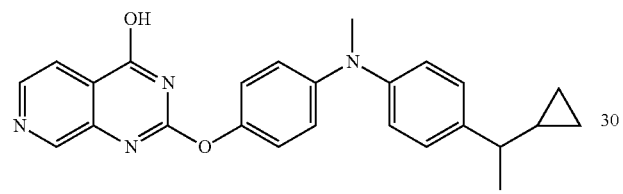

The title compound was prepared in 15% yield from 2-chloro-pyrido[3,4-d]pyrimidin-4-ol and 4-{[4-(1-cyclopropyl-ethyl)-phenyl]-methyl-amino}-phenol according to the procedure for the preparation of Example 1. $^1$H NMR (300 MHz, DMSO-$d_6$): δ 0.10-0.20 (m, 2H), 0.35-0.38 (m, 1H), 0.46-0.50 (m, 1H), 0.89-0.93 (m, 1H), 1.25 (d, J=6.9 Hz, 3H), 1.91-1.97 (m, 1H), 3.23 (s, 3H), 6.93 (d, J=9.0 Hz, 2H), 7.04 (d, J=8.7 Hz, 2H), 7.16-7.25 (m, 4H), 7.86 (d, J=4.5 Hz, 1H), 8.49 (d, J=4.5 Hz, 1H), 8.69 (s, 1H), 13.02 (s, 1H). [M+H] Calc'd for $C_{25}H_{24}N_4O_2$, 413; Found, 413.

Preparation 40A: 3-(4-methoxy-phenylamino)-benzonitrile

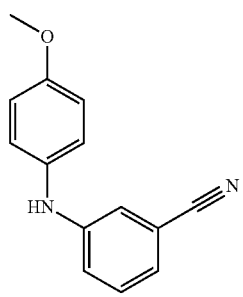 [SMILES: COc1ccc(Nc2cccc(C#N)c2)cc1]

The title compound was prepared in 55% yield from 1-bromo-4-methoxy-benzene and 3-amino-benzonitrile according to the procedure of Preparation 1A. [M+H] Calc'd for $C_{14}H_{12}N_2O$, 225; Found, 225.

Preparation 40B: 3-[(4-methoxy-phenyl)-methyl-amino]-benzonitrile

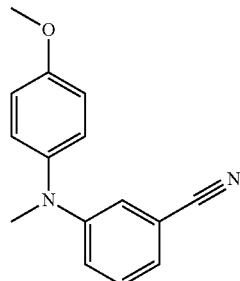

The title compound was prepared in 67% yield from 3-(4-methoxy-phenylamino)-benzonitrile according to the procedure of Preparation 1B. [M+H] Calc'd for $C_{15}H_{14}N_2O$, 239; Found, 239.

Preparation 40C: 3-[(4-hydroxy-phenyl)-methyl-amino]-benzonitrile

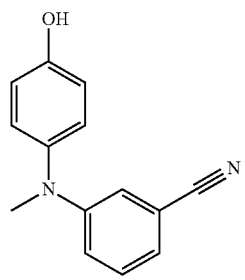 [SMILES: CN(c1ccc(O)cc1)c1cccc(C#N)c1]

The title compound was prepared in 39% yield from 3-[(4-methoxy-phenyl)-methyl-amino]-benzonitrile according to the procedure of Preparation 4B. [M+H] Calc'd for $C_{14}H_{12}N_2O$, 225; Found, 225.

Example 40: 3-{[4-(4-hydroxy-pyrido[3,4-d]pyrimidin-2-yloxy)-phenyl]-methyl-amino}-benzonitrile

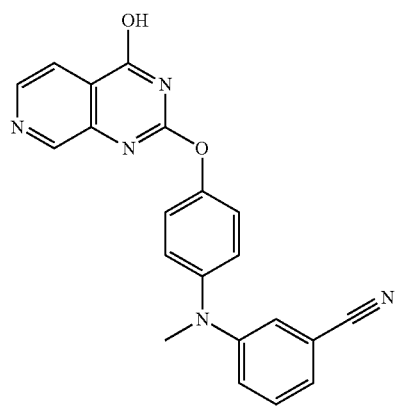

The title compound was prepared in 37% yield from 2-chloro-pyrido[3,4-d]pyrimidin-4-ol and 3-[(4-hydroxyphenyl)-methyl-amino]-benzonitrile according to the procedure for the preparation of Example 1. $^1$H NMR (300 MHz, DMSO-d$_6$): δ 3.30 (s, 3H), 7.16-7.29 (m, 5H), 7.35-7.44 (m, 3H), 7.89 (d, J=5.1 Hz, 1H), 8.53 (d, J=4.8 Hz, 1H), 8.72 (s, 1H). [M+H] Calc'd for $C_{21}H_{15}N_5O_2$, 370; Found, 370.

Preparation 41A:
1-methyl-4-(3-nitro-benzyl)-piperazine

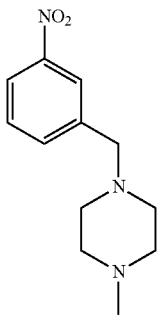

A mixture of 1-bromomethyl-3-nitro-benzene (5.0 g, 23 mmol), 1-methyl-piperazine (2.3 g, 23 mmol) and K$_2$CO$_3$ (6.4 g, 46 mmol) in DMF (80 mL) was stirred overnight at RT. The reaction mixture was diluted with water and the mixture was extracted with EA (3×). The combined organics were washed with brine, dried over Na$_2$SO$_4$, filtered and concentrated to give 3.2 g (59%) of the title product without further purification. [M+H] Calc'd for $C_{12}H_{17}N_3O_2$, 236; Found, 236.

Preparation 41B:
3-(4-methyl-piperazin-1-ylmethyl)-phenylamine

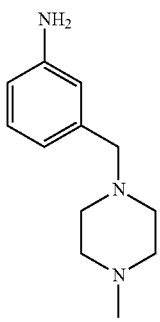

A mixture of 1-methyl-4-(3-nitro-benzyl)-piperazine (3.20 g, 13.6 mmol), Fe (7.60 g, 136 mmol), NH$_4$Cl (364 mg, 6.81 mmol) in EtOH (40 mL) and H$_2$O (10 mL) was stirred for 2 h at 80° C. The mixture was concentrated, redissolved in methanol and filtered through celite. The filtrate concentrated to give 1.3 g (46%) of the title product without further purification. [M+H] Calc'd for $C_{12}H_{19}N_3$, 206; Found, 206.

Preparation 41C: methyl-[3-(4-methyl-piperazin-1-ylmethyl)-phenyl]-amine

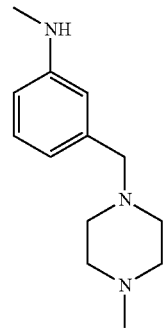 [SMILES: CNc1cccc(CN2CCN(C)CC2)c1]

The title compound was prepared in 57% yield from 3-(4-methyl-piperazin-1-ylmethyl)-phenylamine according to the procedure of Preparation 18A.

Preparation 41D: (4-benzyloxy-phenyl)-methyl-[3-(4-methyl-piperazin-1-ylmethyl)-phenyl]-amine

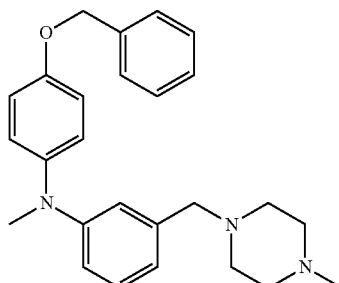

To a solution of methyl-[3-(4-methyl-piperazin-1-ylmethyl)-phenyl]-amine (1.0 g, 4.6 mmol) in toluene (5 mL) was added 1-benzyloxy-4-bromo-benzene (1.26 g, 4.79 mmol), biphenyl-2-yl-dicyclohexyl-phosphane (16 mg, 0.046 mmol), Pd$_2$(dba)$_3$ (42 mg, 0.046 mmol) and t-BuOK (767 mg, 6.85 mmol), and the mixture was stirred overnight at 110° C. under N$_2$ atmosphere. The reaction mixture was filtered and concentrated. The residue was purified by silica gel chromatography (PE:EA, 20:1) to give 1.29 g (70%) of the title compound. [M+H] Calc'd for $C_{26}H_{31}N_3O$, 402; Found, 402.

Preparation 41E: 4-{methyl-[3-(4-methyl-piperazin-1-ylmethyl)-phenyl]-amino}-phenol

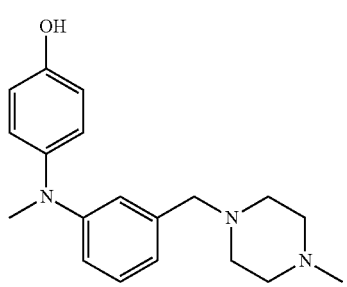 [SMILES: CN1CCN(Cc2cccc(N(C)c3ccc(O)cc3)c2)CC1]

The title compound was prepared in 36% yield from (4-benzyloxy-phenyl)-methyl-[3-(4-methyl-piperazin-1-yl-methyl)-phenyl]-amine according to the procedure of Preparation 36E. [M+H] Calc'd for $C_{19}H_{25}N_3O$, 312; Found, 312.

Example 41: 2-(4-{methyl-[3-(4-methyl-piperazin-1-ylmethyl)-phenyl]-amino}-phenoxy)-pyrido[3,4-d]pyrimidin-4-ol

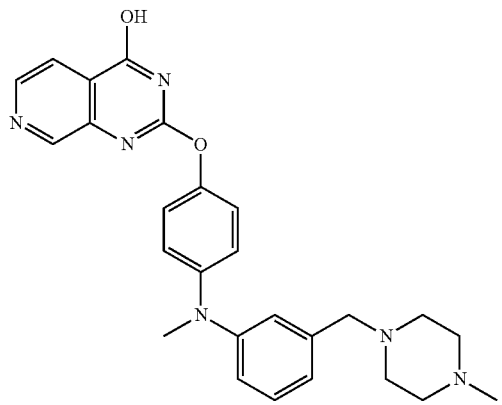 [SMILES: CN1CCN(Cc2cccc(N(C)c3ccc(Oc4nc(O)c5ccncc5n4)cc3)c2)CC1]

The title compound was prepared in 8% yield from 2-chloro-pyrido[3,4-d]pyrimidin-4-ol and 4-{methyl-[3-(4-methyl-piperazin-1-ylmethyl)-phenyl]-amino}-phenol according to the procedure for the preparation of Example 1. $^1$H NMR (300 MHz, DMSO-$d_6$): δ 2.29 (s, 3H), 2.38-2.57 (m, 8H), 3.20 (s, 3H), 3.44 (s, 2H), 6.86-7.04 (m, 5H), 7.16-7.26 (m, 3H), 7.82 (d, J=5.1 Hz, 1H), 8.44 (d, J=5.1 Hz, 1H), 8.67 (s, 1H). [M+H] Calc'd for $C_{26}H_{28}N_6O_2$, 457; Found, 457.

Preparation 42A: (4-bromo-phenoxy)-tert-butyl-dimethyl-silane

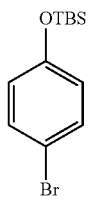

The title compound was prepared in 90% yield from 4-bromo-phenol according to the procedure of Preparation 33A. [M+H] Calc'd for $C_{12}H_{19}BrOSi$, 288; Found, 288.

Preparation 42B: [4-(tert-butyl-dimethyl-silanyloxy)-phenyl]-(4-cyclopropyl-phenyl)-methyl-amine

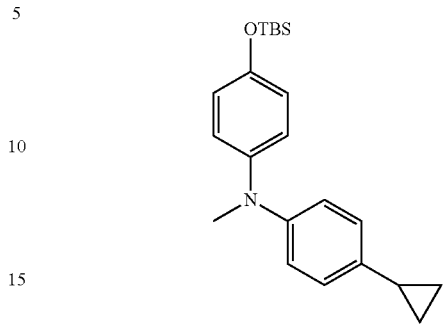

The title compound was prepared in 38% yield from (4-bromo-phenoxy)-tert-butyl-dimethyl-silane and (4-cyclopropyl-phenyl)-methyl-amine according to the procedure of Preparation 41D. [M+H] Calc'd for $C_{22}H_{31}NOSi$, 354; Found, 354.

Preparation 42C: 4-[(4-cyclopropyl-phenyl)-methyl-amino]-phenol

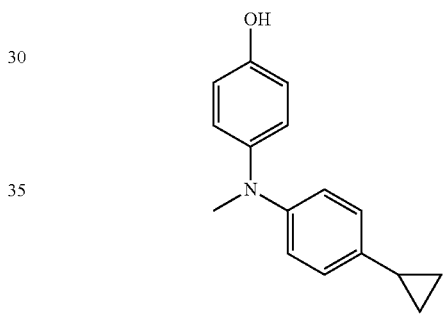

The title compound was prepared in 28% yield from [4-(tert-butyl-dimethyl-silanyloxy)-phenyl]-(4-cyclopropyl-phenyl)-methyl-amine according to the procedure of Preparation 33C. [M+H] Calc'd for $C_{16}H_{17}NO$, 240; Found, 240.

Example 42: 2-{4-[(4-cyclopropyl-phenyl)-methyl-amino]-phenoxy}-pyrido[3,4-d]pyrimidin-4-ol

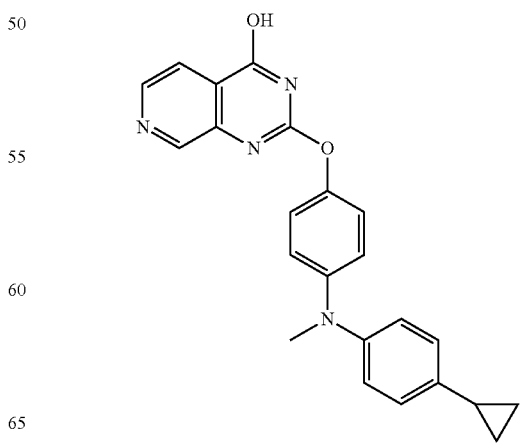

The title compound was prepared in 3% yield from 2-chloro-pyrido[3,4-d]pyrimidin-4-ol and 4-[(4-cyclopropyl-phenyl)-methyl-amino]-phenol according to the procedure for the preparation of Example 1. $^1$H NMR (300 MHz, DMSO-$d_6$): δ 0.60-0.63 (m, 2H), 0.86-0.90 (i, 2H), 1.86-1.88 (i, 1H), 3.23 (s, 3H), 6.88-7.16 (i, 8H), 7.84-7.86 (i, 1H), 8.47-8.49 (i, 1H), 8.68 (s, 1H). [M+H] Calc'd for $C_{23}H_{20}N_4O_2$, 385; Found, 385.

| Ex | Structure (prepared by procedure of cited Example) | MS (ESI) m/z | NMR spectrum data |
|---|---|---|---|
| 43 | Prepared by the procedure of Example 1 | 360 | $^1$H NMR (400 MHz, DMSO-$d_6$): δ 2.15 (s, 3H), 3.36 (s, 3H), 6.61 (d, J = 11.6 Hz, 1H), 7.32-7.34 (m, 5H), 7.87 (d, J = 6.4 Hz, 1H), 7.99 (s, 1H), 8.50 (d, J = 6.8 Hz, 1H), 8.72 (s, 1H). |
| 44 | Prepared by the procedure of Example 1 | 388 | $^1$H NMR (400 MHz, DMSO-$d_6$): δ 2.89 (s, 6H), 3.20 (s, 3H), 6.69 (d, J = 12.4 Hz, 2H), 6.78 (d, J = 12.4 Hz, 2H), 7.04-7.09 (m, 4H), 7.86 (d, J = 6.4 Hz, 1H), 8.50 (d, J = 6.8 Hz, 1H), 8.68 (s, 1H). |
| 45 | Prepared by the procedure of Example 22 | 457 | $^1$H NMR (400 MHz, DMSO-$d_6$): δ 2.89 (s, 3H), 3.41 (s, 3H), 3.42-3.46 (m, 4H), 3.72 (s, 2H), 6.51 (d, J = 7.6 Hz, 1H), 6.60 (d, J = 8.4 Hz, 2H), 6.99-7.20 (m, 5H), 7.86 (d, J = 5.2 Hz, 1H), 8.48 (d, J = 5.6 Hz, 1H), 8.86 (s, 1H). |
| 46 | Prepared by the procedure of Example 22 | 443 | $^1$H NMR (400 MHz, DMSO-$d_6$): δ 2.23 (s, 3H), 2.47-2.49 (m, 4H), 3.10-3.12 (m, 4H), 3.21 (s, 3H), 6.74 (d, J = 12.0 Hz, 2H), 6.95 (d, J = 12.0 Hz, 2H), 7.02-7.09 (m, 4H), 7.82 (d, J = 6.8 Hz, 1H), 8.45 (d, J = 6.8 Hz, 1H), 8.67 (s, 1H). |
| 47 | Prepared by the procedure of Example 1 | 388 | $^1$H NMR (400 MHz, DMSO-$d_6$): δ 2.87 (s, 6H), 3.32 (s, 3H), 6.38-6.44 (m, 3H), 6.93-6.96 (m, 2H), 7.13-7.17 (m, 3H), 7.86 (d, J = 6.4 Hz, 1H), 8.47 (d, J = 6.8 Hz, 1H), 8.68 (s, 1H). |
| 48 | Prepared by the procedure of Example 22 | 414 | $^1$H NMR (400 MHz, DMSO-$d_6$): δ 1.96 (m, 4H), 3.20 (s, 4H), 3.32 (s, 3H), 6.57-6.66 (m, 4H), 7.03-7.08 (m, 4H), 7.86 (d, J = 4.8 Hz, 1H), 8.50 (d, J = 4.8 Hz, 1H), 8.69 (s, 1H), 12.99 (s, 1H). |

-continued

| Ex | Structure (prepared by procedure of cited Example) | MS (ESI) m/z | NMR spectrum data |
|---|---|---|---|
| 49 | (Prepared by the procedure of Example 22) | 414 | $^1$H NMR (400 MHz, DMSO-$d_6$): δ 1.96 (m, 4H), 3.20 (m, 4H), 3.32 (s, 3H), 6.25-6.35 (m, 3H), 6.94-7.18 (m, 5H), 7.87 (d, J = 4.8 Hz, 1H), 8.51 (d, J = 4.8 Hz, 1H), 8.69 (s, 1H), 13.00 (s, 1H). |
| 50 | (Prepared by the procedure of Example 23) | 443 | $^1$H NMR (400 MHz, CD$_3$OD): δ 1.91-2.95 (m, 2H), 2.19-2.25 (m, 2H), 3.25-3.45 (m, 6H), 3.74-3.78 (m, 2H), 6.81-6.90 (m, 2H), 7.15-7.33 (m, 6H), 8.11 (d, J = 6.4 Hz, 1H), 8.53 (d, J = 6.4 Hz, 1H), 8.81 (s, 1H). |
| 51 | (Prepared by the procedure of Example 5) | 373 | $^1$H NMR (400 MHz, DMSO-$d_6$): δ 1.50 (d, J = 9.2 Hz, 3H), 2.69 (s, 3H), 5.14-5.16 (m, 1H), 6.85 (d, J = 9.6 Hz, 2H), 7.10 (d, J = 9.2 Hz, 2H), 7.24-7.37 (m, 5H), 7.80 (d, J = 6.8 Hz, 1H), 8.48 (d, J = 7.2 Hz, 1H), 8.67 (s, 1H), 13.05 (s, 1H). |
| 52 | (Prepared by the procedure of Example 5) | 373 | $^1$H NMR (400 MHz, DMSO-$d_6$): δ 1.50 (d, J = 9.2 Hz, 3H), 2.69 (s, 3H), 5.14-5.16 (m, 1H), 6.85 (d, J = 9.6 Hz, 2H), 7.10 (d, J = 9.2 Hz, 2H), 7.24-7.37 (m, 5H), 7.80 (d, J = 6.8 Hz, 1H), 8.48 (d, J = 7.2 Hz, 1H), 8.67 (s, 1H), 13.05 (s, 1H). |
| 53 | (Prepared by the procedure of Example 1) | 377 | $^1$H NMR (400 MHz, DMSO-$d_6$): δ 2.14 (s, 3H), 3.25 (s, 3H), 6.69-6.77 (m, 2H), 7.08-7.26 (m, 5H), 7.86 (d, J = 6.4 Hz, 1H), 8.48 (d, J = 6.8 Hz, 1H), 8.67 (s, 1H). |
| 54 | (Prepared by the procedure of Example 25) | 385 | $^1$H NMR (400 MHz, DMSO-$d_6$): δ 1.96-2.06 (m, 2H), 2.47-2.49 (m, 1H), 3.36-3.53 (m, 3H), 3.67-3.70 (m, 1H), 6.59 (d, J = 12.4 Hz, 2H), 7.08 (d, J = 12.4 Hz, 2H), 7.22-7.34 (m, 5H), 7.82 (d, J = 6.8 Hz, 1H), 8.43 (d, J = 6.8 Hz, 1H), 8.63 (s, 1H). |

-continued

| Ex | Structure (prepared by procedure of cited Example) | MS (ESI) m/z | NMR spectrum data |
|---|---|---|---|
| 55 | 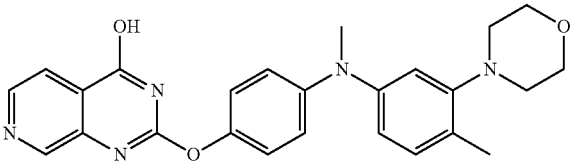<br>Prepared by the procedure of Example 18 | 444 | $^1$H NMR (300 MHz, DMSO-$d_6$): δ 2.19 (s, 3H), 2.77-2.80 (m, 4H), 3.24 (s, 3H), 3.68-3.71 (m, 4H), 6.69-6.73 (m, 2H), 6.80 (d, J = 12.0 Hz, 2H), 7.09-7.14 (m, 3H), 7.81 (d, J = 6.4 Hz, 1H), 8.43 (d, J = 6.0 Hz, 1H), 8.65 (s, 1H). |
| 56 | Prepared by the procedure of Example 1 | 423 | $^1$H NMR (300 MHz, DMSO-$d_6$): δ 3.18 (s, 3H), 3.35 (s, 3H), 7.17-7.50 (m, 8H), 7.87 (d, J = 6.4 Hz, 1H), 8.50 (d, J = 6.0 Hz, 1H), 8.70 (s, 1H). |
| 57 | Prepared by the procedure of Example 1 | 423 | $^1$H NMR (300 MHz, DMSO-$d_6$): δ 3.08 (s, 3H), 3.35 (s, 3H), 6.89 (d, J = 12.0 Hz, 2H), 7.37-7.44 (m, 4H), 7.68 (d, J = 12.0 Hz, 2H), 7.87 (d, J = 6.4 Hz, 1H), 8.51 (d, J = 6.0 Hz, 1H), 8.71 (s, 1H). |
| 58 | 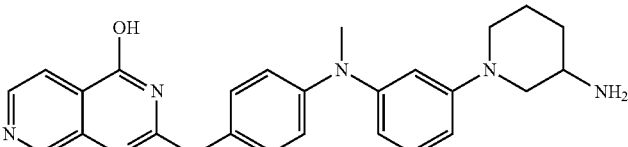<br>Prepared by the procedure of Example 23 | 443 | $^1$H NMR (400 MHz, CD$_3$OD): δ 1.70-1.81 (m, 2H), 1.93-2.04 (m, 2H), 3.11-3.23 (m, 3H), 3.32 (s, 3H), 3.45-3.49 (m, 2H), 6.66-6.77 (m, 2H), 7.02-7.24 (m, 6H), 8.19 (d, J = 6.8 Hz, 1H), 8.53 (d, J = 6.4 Hz, 1H), 8.83 (s, 1H). |
| 59 | 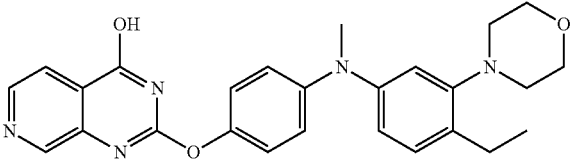<br>Prepared by the procedure of Example 18 | 458 | $^1$H NMR (300 MHz, DMSO-$d_6$): δ 1.17 (t, J = 10.0 Hz, 3H), 2.60 (q, J = 10.0 Hz, 2H), 2.76-2.79 (m, 4H), 3.30 (s, 3H), 3.68-3.71 (m, 4H), 6.79 (d, J = 9.2 Hz, 2H), 6.93 (d, J = 9.2 H, 2H), 7.14-7.17 (m, 3H), 7.85 (d, J = 6.8 Hz, 1H), 8.49 (d, J = 7.2 Hz, 1H), 8.67 (s, 1H). |
| 60 | 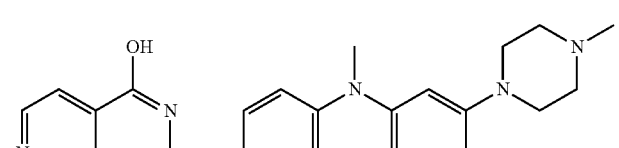<br>Prepared by the procedure of Example 18 | 471 | $^1$H NMR (300 MHz, DMSO-$d_6$): δ 1.16 (t, J = 10.0 Hz, 3H), 2.25 (s, 3H), 2.48-2.62 (m, 6H), 2.76-2.79 (m, 4H), 3.25 (s, 3H), 6.77 (d, J = 8.0 Hz, 2H), 6.93 (d, J = 8.0 Hz, 2H), 7.14-7.17 (m, 3H), 7.84 (d, J = 6.4 Hz, 1H), 8.47 (d, J = 6.4 Hz, 1H), 8.66 (s, 1H). |
| 61 | 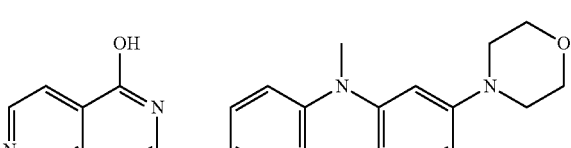<br>Prepared by the procedure of Example 18 | 431 | $^1$H NMR (300 MHz, DMSO-$d_6$): δ 3.28-3.36 (m, 7H), 3.66-3.69 (m, 4H), 6.03-6.07 (m, 2H), 7.32-7.42 (m, 4H), 7.77 (d, J = 7.6 Hz, 1H), 7.89 (d, J = 7.6 Hz, 1H), 8.53 (d, J = 7.6 Hz, 1H), 8.71 (s, 1H), 13.15 (s, 1H). |

| Ex | Structure (prepared by procedure of cited Example) | MS (ESI) m/z | NMR spectrum data |
|---|---|---|---|
| 62 | Prepared by the procedure of Example 28 | 399 | ¹H NMR (300 MHz, DMSO-$d_6$): δ 1.82-1.86 (m, 1H), 2.07-2.17 (m, 1H), 2.77-2.84 (m, 1H), 2.95-3.02 (m, 1H), 3.30-3.36 (m, 4H), 3.52-3.55 (m, 1H), 3.67-3.72 (m, 1H), 6.79 (d, J = 9.6 Hz, 1H), 7.12-7.30 (m, 6H), 7.80 (d, J = 5.2 Hz, 1H), 8.50 (d, J = 5.2 Hz, 1H), 8.68 (s, 1H), 13.00 (s, 1H). |
| 63 | Prepared by the procedure of Example 18 | 401 | ¹H NMR (300 MHz, DMSO-$d_6$): δ 0.85 (d, J = 8.4 Hz, 6H), 1.75-1.82 (m, 1H), 2.38 (d, J = 7.6 Hz, 2H), 3.22 (s, 3H), 6.93 (d, J = 11.6 Hz, 2H), 7.01 (d, J = 10.8 Hz, 2H), 7.11 (d, J = 11.2 Hz, 2H), 7.17 (d, J = 11.6 Hz, 1H), 7.85 (d, J = 7.2 Hz, 1H), 8.49 (d, J = 6.0 Hz, 1H), 8.68 (s, 1H), 13.01 (s, 1H). |
| 64 | Prepared by the procedure of Example 26 | 403 | ¹H NMR (300 MHz, DMSO-$d_6$): δ 1.40 (s, 6H), 3.26 (s, 3H), 4.93 (s, 1H), 6.93 (d, J = 11.6 Hz, 2H), 7.03 (d, J = 11.2 Hz, 2H), 7.17 (d, J = 12.0 Hz, 2H), 7.41 (d, J = 11.6 Hz, 1H), 7.85 (d, J = 6.8 Hz, 1H), 8.49 (d, J = 6.8 Hz, 1H), 8.68 (s, 1H), 13.01 (s, 1H). |
| 65 | Prepared by the procedure of Example 18 | 460 | ¹H NMR (300 MHz, DMSO-$d_6$): δ 1.12 (t, J = 10.0 Hz, 3H), 2.52-2.60 (m, 2H), 2.87 (s, 6H), 3.28 (s, 3H), 3.51 (t, J = 6.0 Hz, 2H), 4.26 (t, J = 6.0 Hz, 2H), 6.66-6.74 (m, 2H), 6.94 (d, J = 11.6 Hz, 2H), 7.10-7.19 (m, 3H), 7.87 (d, J = 6.4 Hz, 1H), 8.50 (d, J = 6.0 Hz, 1H), 8.68 (s, 1H). |
| 66 | Prepared by the procedure of Example 18 | 447 | ¹H NMR (300 MHz, DMSO-$d_6$): δ 1.11 (t, J = 10.0 Hz, 3H), 2.47-2.52 (m, 2H), 3.26 (s, 3H), 3.32 (s, 3H), 3.63 (t, J = 6.0 Hz, 2H), 4.03 (t, J = 6.0 Hz, 2H), 6.59-6.66 (m, 2H), 6.94 (d, J = 11.6 Hz, 2H), 7.06-7.17 (m, 3H), 7.87 (d, J = 6.4 Hz, 1H), 8.48 (d, J = 6.0 Hz, 1H), 8.67 (s, 1H). |
| 67 | Prepared by the procedure of Example 29 | 431 | ¹H NMR (400 MHz, DMSO-$d_6$): δ 1.22 (s, 6H), 3.20 (s, 3H), 3.30 (s, 3H), 3.32 (s, 2H), 6.93 (d, J = 11.6 Hz, 2H), 7.01 (d, J = 11.2 Hz, 2H), 7.19 (d, J = 11.6 Hz, 2H), 7.31 (d, J = 11.2 Hz, 2H), 7.86 (d, J = 6.4 Hz, 1H), 8.48 (d, J = 6.4 Hz, 1H), 8.67 (s, 1H). |

| Ex | Structure (prepared by procedure of cited Example) | MS (ESI) m/z | NMR spectrum data |
|---|---|---|---|
| 68 | (Structure) Prepared by the procedure of Example 29 | 417 | ¹H NMR (400 MHz, DMSO-$d_6$): δ 1.20 (s, 6H), 3.25 (s, 3H), 3.38 (s, 2H), 6.93 (d, J = 12.0 Hz, 2H), 7.01 (d, J = 11.2 Hz, 2H), 7.16 (d, J = 12.0 Hz, 2H), 7.31 (d, J = 11.2 Hz, 2H), 7.84 (d, J = 6.8 Hz, 1H), 8.48 (d, J = 6.4 Hz, 1H), 8.67 (s, 1H). |
| 69 | (Structure) Prepared by the procedure of Example 29 | 387 | ¹H NMR (400 MHz, DMSO-$d_6$): δ 0.88 (t, J = 9.6 Hz, 3H), 1.53-1.57 (m, 2H), 2.49 (J = 6.8 Hz, 2H), 3.24 (s, 3H), 6.93 (d, J = 11.2 Hz, 2H), 7.01 (d, J = 11.2 Hz, 2H), 7.12-7.17 (m, 4H), 7.85 (d, J = 6.4 Hz, 1H), 8.48 (d, J = 6.4 Hz, 1H), 8.67 (s, 1H). |
| 70 | (Structure) Prepared by the procedure of Example 30 | 416 | ¹H NMR (400 MHz, DMSO-$d_6$): δ 1.25 (d, J = 8.4 Hz, 3H), 2.71 (s, 3H), 3.08 (d, J = 8.4 Hz, 2H), 3.21-3.23 (m, 1H), 3.32 (s, 3H), 7.05-7.26 (m, 8H), 7.24 (d, J = 7.2 Hz, 1H), 8.55 (d, J = 7.2 Hz, 1H), 8.87 (s, 1H). |
| 71 | (Structure) Prepared by the procedure of Example 30 | 416 | ¹H NMR (400 MHz, DMSO-$d_6$): δ 1.18 (d, J = 7.2 Hz, 3H), 1.76-1.79 (m, 2H), 2.52-2.58 (m, 1H), 2.69-2.72 (m, 2H), 3.23 (s, 3H), 6.88-7.11 (m, 8H), , 7.67 (d, J = 4.8 Hz, 1H), 8.19 (d, J = 4.8 Hz, 1H), 8.57 (s, 1H). |
| 72 | (Structure) Prepared by the procedure of Example 30 | 430 | ¹H NMR (400 MHz, DMSO-$d_6$): δ 1.18 (d, J = 7.2 Hz, 3H), 1.76-1.79 (m, 2H), 2.48 (s, 3H), 2.58-2.72 (m, 3H), 3.26 (s, 3H), 6.88-7.11 (m, 8H), 7.67 (d, J = 7.2 Hz, 1H), 8.20 (d, J = 7.2 Hz, 1H), 8.57 (s, 1H). |
| 73 | (Structure) Prepared by the procedure of Example 5 | 443 | ¹H NMR (300 MHz, DMSO-$d_6$): δ 3.23 (s, 3H), 4.68-4.77 (m, 2H), 6.82 (d, J = 11.6 Hz, 2H), 7.06-7.15 (m, 6H), 7.87 (d, J = 6.4 Hz, 1H), 8.48 (d, J = 6.0 Hz, 1H), 8.67 (s, 1H), 13.01 (s, 1H). |

| Ex | Structure (prepared by procedure of cited Example) | MS (ESI) m/z | NMR spectrum data |
|---|---|---|---|
| 74 | Prepared by the procedure of Example 5 | 417 | $^1$H NMR (400 MHz, DMSO-$d_6$): δ 0.96 (d, J = 9.2 Hz, 6H), 1.94-2.01 (m, 1H), 3.20 (s, 3H), 3.71 (d, J = 8.4 Hz, 2H), 6.75 (d, J = 12.4 Hz, 2H), 6.94 (d, J = 12.0 Hz, 2H), 7.06-7.10 (m, 4H), 7.81 (d, J = 6.4 Hz, 1H), 8.43 (d, J = 6.4 Hz, 1H), 8.64 (s, 1H). |
| 75 | Prepared by the procedure of Example 5 | 431 | $^1$H NMR (400 MHz, DMSO-$d_6$): δ 0.96 (s, 9H), 3.21 (s, 3H), 3.60 (s, 2H), 6.74 (d, J = 12.4 Hz, 2H), 6.94 (d, J = 12.0 Hz, 2H), 7.06-7.10 (m, 4H), 7.84 (d, J = 6.8 Hz, 1H), 8.43 (d, J = 6.4 Hz, 1H), 8.66 (s, 1H). |
| 76 | Prepared by the procedure of Example 26 | 399 | $^1$H NMR (400 MHz, DMSO-$d_6$): δ 0.17-0.20 (m, 2H), 0.43-0.48 (m, 2H), 0.92-0.96 (m, 1H), 2.44 (s, 3H), 3.27 (d, J = 9.2 Hz, 2H), 6.94 (d, J = 12.0 Hz, 2H), 7.03 (d, J = 12.0 Hz, 2H), 7.15-7.23 (m, 4H), 7.86 (d, J = 6.8 Hz, 1H), 8.49 (d, J = 7.2 Hz, 1H), 8.68 (s, 1H), 13.02 (s, 1H). |
| 77 | Prepared by the procedure of Example 5 | 401 | $^1$H NMR (300 MHz, DMSO-$d_6$): δ 0.77 (t, J = 7.2 Hz, 3H), 1.17 (d, J = 7.2 Hz, 3H), 1.50-1.55 (m, 2H), 2.48-2.55 (m, 1H), 3.27 (d, J = 13.5 Hz, 3H), 6.92 (d, J = 9.3 Hz, 2H), 7.03 (d, J = 9.0 Hz, 2H), 7.15-7.29 (m, 4H), 7.86 (d, J = 5.1 Hz, 1H), 8.49 (d, J = 5.4 Hz, 1H), 8.68 (s, 1H), 13.02 (s, 1H). |
| 78 | Prepared by the procedure of Example 5 | 401 | $^1$H NMR (300 MHz, DMSO-$d_6$): δ 0.77 (t, J = 7.2 Hz, 3H), 1.17 (d, J = 7.2 Hz, 3H), 1.50-1.55 (m, 2H), 2.48-2.55 (m, 1H), 3.27 (d, J = 13.5 Hz, 3H), 6.92 (d, J = 9.3 Hz, 2H), 7.03 (d, J = 9.0 Hz, 2H), 7.15-7.29 (m, 4H), 7.86 (d, J = 5.1 Hz, 1H), 8.49 (d, J = 5.4 Hz, 1H), 8.68 (s, 1H), 13.02 (s, 1H). |
| 79 | Prepared by the procedure of Example 22 | 442 | H NMR (300 MHz, DMSO-$d_6$): δ 2.22 (s, 3H), 3.08-3.11 (m, 4H), 3.25 (s, 3H), 3.32-2.39 (m, 4H), 6.48 (d, J = 8.4 Hz, 1H), 6.93-6.96 (m, 2H), 6.94 (d, J = 9.3 Hz, 2H), 7.13-7.17 (m, 3H), 7.83 (d, J = 5.1 Hz, 1H), 8.46 (d, J = 5.1 Hz, 1H), 8.66 (s, 1H). |

| Ex | Structure (prepared by procedure of cited Example) | MS (ESI) m/z | NMR spectrum data |
|---|---|---|---|
| 80 | Prepared by the procedure of Example 5 | 358 | H NMR (300 MHz, DMSO-d$_6$): δ 1.17 (t, J = 2.1 Hz, 3H), 3.74-3.81 (m, 2H), 6.95-7.03 (m, 5H), 7.20-7.23 (m, 2H), 7.31 (t, J = 7.2 Hz, 2H), 7.87 (d, J = 5.1 Hz, 1H), 8.51 (d, J = 5.1 Hz, 1H), 8.71 (s, 1H). |
| 81 | Prepared by the procedure of Example 1 | 369 | H NMR (300 MHz, DMSO-d$_6$): δ 3.39 (s, 3H), 6.81 (d, J = 2.4 Hz, 2H), 7.33-7.43 (m, 4H), 7.54-7.59 (m, 2H), 7.87 (d, J = 4.8 Hz, 1H), 8.51 (brs, 1H), 8.71 (brs, 1H), 13.13 (brs, 1H). |
| 82 | Prepared by the procedure of Example 5 | 398 | H NMR (300 MHz, DMSO-d$_6$): δ 3.29 (s, 3H), 4.13 (s, 3H), 6.82 (d, J = 9.3 Hz, 2H), 7.03 (d, J = 9.3 Hz, 1H), 7.13 (d, J = 9.0 Hz, 2H), 7.42 (s, 1H), 7.57 (d, J = 9.0 Hz, 1H), 7.85 (d, J = 5.1 Hz, 1H), 8.23 (s, 1H), 8.49 (d, J = 4.5 Hz, 1H), 8.68 (s, 1H). |
| 83 | Prepared by the procedure of Example 18 | 372 | H NMR (300 MHz, DMSO-d$_6$): δ 2.17 (d, J = 2.4 Hz, 6H), 3.22 (s, 3H), 6.83-6.87 (m, 4H), 7.08-7.14 (m, 3H), 7.83 (d, J = 4.8 Hz, 1H), 8.47 (d, J = 5.1 Hz, 1H), 8.66 (s, 1H). |
| 84 | Prepared by the procedure of Example 18 | 372 | $^1$H NMR (300 MHz, DMSO-d$_6$): δ 1.16 (t, J = 7.2 Hz, 3H), 2.55-2.60 (m, 2H), 3.23 (s, 3H), 6.90 (d, J = 8.4 Hz, 2H), 7.03 (d, J = 8.4 Hz, 2H), 7.14-7.18 (m, 4H), 7.85 (d, J = 5.7 Hz, 1H), 8.48 (d, J = 5.7 Hz, 1H), 8.67 (s, 1H). |
| 85 | Prepared by the procedure of Example 18 | 386 | $^1$H NMR (300 MHz, DMSO-d$_6$): δ 1.18 (d, J = 7.5 Hz, 6H), 2.80-2.89 (m, 1H), 3.24 (s, 3H), 6.92 (d, J = 9.3 Hz, 2H), 7.02 (d, J = 9.3 Hz, 2H), 7.14-7.21 (m, 4H), 7.84 (d, J = 5.1 Hz, 1H), 8.47 (d, J = 5.1 Hz, 1H), 8.67 (s, 1H). |
| 86 | Prepared by the procedure of Example 5 | 412 | $^1$H NMR (300 MHz, DMSO-d$_6$): δ 3.31 (s, 3H), 7.10-7.15 (m, 3H), 7.23 (d, J = 9.0 Hz, 2H), 7.35 (d, J = 9.0 Hz, 2H), 7.44 (t, J = 7.8 Hz, 1H), 7.87 (d, J = 5.1 Hz, 1H), 8.50 (d, J = 4.5 Hz, 1H), 8.69 (s, 1H). |

| Ex | Structure (prepared by procedure of cited Example) | MS (ESI) m/z | NMR spectrum data |
|---|---|---|---|
| 87 | *Prepared by the procedure of Example 5* | 412 | $^1$H NMR (300 MHz, DMSO-d$_6$): δ 3.32 (s, 3H), 6.94 (d, J = 6.6 Hz, 2H), 7.34 (d, J = 6.6 Hz, 2H), 7.40 (d, J = 6.3 Hz, 2H), 7.53 (d, J = 6.6 Hz, 2H), 7.90 (d, J = 3.6 Hz, 1H), 8.53 (d, J = 3.9 Hz, 1H), 8.73 (s, 1H). |
| 88 | *Prepared by the procedure of Example 22* | 456 | $^1$H NMR (300 MHz, DMSO-d$_6$): δ 1.86-1.89 (m, 2H), 2.32 (s, 3H), 2.48-2.53 (m, 2H), 2.67 (m, 2H), 3.24 (s, 3H), 3.31-3.38 (m, 2H), 3.47-3.48 (m, 2H), 6.30-6.39 (m, 3H), 6.93 (d, J = 8.7 Hz, 2H), 7.08-7.13 (m, 3H), 7.80 (d, J = 4.5 Hz, 1H), 8.42 (d, J = 5.1 Hz, 1H), 8.64 (s, 1H). |
| 89 | *Prepared by the procedure of Example 22* | 470 | $^1$H NMR (300 MHz, DMSO-d$_6$): δ 1.56-1.59 (m, 2H), 1.71-1.76 (m, 2H), 2.14-2.21 (m, 2H), 2.25 (s, 3H), 2.66 (s, 3H), 2.92 (d, J = 11.7 Hz, 2H), 3.23 (s, 3H), 3.36-3.38 (m, 1H), 6.34-6.37 (m, 1H), 6.43-6.49 (m, 2H), 6.91-6.94 (m, 2H), 7.07-7.13 (m, 3H), 7.81 (d, J = 5.1 Hz, 1H), 8.42 (d, J = 5.1 Hz, 1H), 8.65 (s, 1H). |
| 90 | *Prepared by the procedure of Example 22* | 456 | $^1$H NMR (300 MHz, DMSO-d$_6$): δ 2.21 (s, 3H), 2.24 (s, 3H), 2.49-2.50 (m, 4H), 3.09-3.10 (m, 4H), 3.24 (s, 3H), 6.35 (s, 1H), 6.45 (d, J = 4.8 Hz, 2H), 6.93 (d, J = 8.7 Hz, 2H), 7.17 (d, J = 9.0 Hz, 2H), 7.86 (d, J = 4.8 Hz, 1H), 8.49 (d, J = 5.1 Hz, 1H), 8.68 (s, 1H). |
| 91 | *Prepared by the procedure of Example 31* | 363 | $^1$H NMR (300 MHz, DMSO-d$_6$): δ 1.92-2.08 (m, 4H), 3.58 (t, J = 8.7 Hz, 2H), 4.00-4.03 (m, 2H), 4.64-4.71 (m, 1H), 9.49 (s, 1H), 7.05 (d, J = 1.5 Hz, 1H), 7.42 (s, 1H), 7.61-7.63 (m, 2H), 7.82 (d, J = 3.9 Hz, 1H), 8.43 (d, J = 3.9 Hz, 1H), 8.60 (s, 1H). |
| 92 | *Prepared by the procedure of Example 18* | 400 | $^1$H NMR (400 MHz, DMSO-d$_6$): δ 1.28 (s, 9H), 3.27 (s, 3H), 6.95 (d, J = 8.0 Hz, 2H), 7.05 (d, J = 8.0 Hz, 2H), 7.18 (d, J = 8.0 Hz, 2H), 7.36 (d, J = 8.0 Hz, 2H), 7.87 (s, 1H), 8.47 (m, 1H), 8.72 (m, 1H), 13.05 (s, 1H). |

-continued

| Ex | Structure (prepared by procedure of cited Example) | MS (ESI) m/z | NMR spectrum data |
|---|---|---|---|
| 93 | Prepared by the procedure of Example 18 | 386 | ¹H NMR (300 MHz, DMSO-d₆): δ 1.20 (d, J = 6.8 Hz, 6H), 2.85 (m, 1H), 3.29 (s, 3H), 6.89-7.01 (m, 5H), 7.20-7.25 (m, 3H), 7.88 (s, 1H), 8.52-8.73 (m, 2H), 13.07 (s, 1H). |
| 94 | Prepared by the procedure of Example 18 | 379 | ¹H NMR (300 MHz, DMSO-d₆): δ 3.28 (s, 3H), 6.99 (d, J = 9.0 Hz, 2H), 7.13 (d, J = 9.0 Hz, 2H), 7.26 (d, J = 9.0 Hz, 2H), 7.30 (d, J = 9.0 Hz, 2H), 7.86 (d, J = 5.1 Hz, 1H), 8.49 (d, J = 5.1 Hz, 1H), 8.70 (s, 1H). |
| 95 | Prepared by the procedure of Example 18 | 379 | ¹H NMR (300 MHz, DMSO-d₆): δ 3.32 (s, 3H), 6.85-6.92 (m, 3H), 7.21-7.26 (m, 3H), 7.34 (d, J = 5.1 Hz, 2H), 7.89 (d, J = 3.9 Hz, 1H), 8.52 (d, J = 3.9 Hz, 1H), 8.72 (s, 1H), 13.11 (s, 1H). |
| 96 | Prepared by the procedure of Example 18 | 363 | ¹H NMR (300 MHz, DMSO-d₆): δ 3.36 (s, 3H), 6.70 (d, J = 8.1 Hz, 2H), 7.13 (d, J = 8.1 Hz, 2H), 7.29-7.40 (m, 4H), 7.85 (s, 1H), 8.47-8.49 (br, 1H), 8.65-8.70 (br 1H). |
| 97 | Prepared by the procedure of Example 34 | 374 | ¹H NMR (300 MHz, DMSO-d₆): δ 1.14 (t, J = 7.5 Hz, 3H), 2.45-2.47 (m, 2H), 3.36 (s, 3H), 8.64 (d, J = 8.7 Hz, 1H), 7.36-7.40 (m, 5H), 7.89 (d, J = 5.1 Hz, 1H), 8.03 (s, 1H), 8.53 (d, J = 4.5 Hz, 1H), 874 (s, 1H), 13.16 (s, 1H). |
| 98 | Prepared by the procedure of Example 34 | 427 | ¹H NMR (300 MHz, DMSO-d₆): δ 2.43-2.50 (m, 2H), 3.23 (s, 3H), 3.80-3.84 (m, 2H), 4.21-4.22 (m, 2H), 6.16 (s, 1H), 7.01-7.10 (m, 4H), 7.24-7.41 (m, 4H), 7.88 (d, J = 4.8 Hz, 1H), 8.52 (d, J = 5.1 Hz, 1H), 8.72 (s, 1H), 13.02 (s, 1H). |
| 99 | Prepared by the procedure of Example 34 | 429 | H NMR (300 MHz, DMSO-d₆): δ 1.65-1.68 (m, 4H), 2.49-2.51 (m, 1H), 3.26 (s, 3H), 3.40-3.41 (m, 2H), 3.91-3.94 (m, 2H), 6.93-7.05 (m, 4H), 7.16-7.22 (m, 4H), 7.85 (d, J = 5.1 Hz, 1H), 8.49 (d, J = 5.1 Hz, 1H), 8.68 (s, 1H), 13.07 (s, 1H). |

| Ex | Structure (prepared by procedure of cited Example) | MS (ESI) m/z | NMR spectrum data |
|---|---|---|---|
| 100 | Prepared by the procedure of Example 37 | 460 | ¹H NMR (300 MHz, CD3OD-d₄): 1.19-1.26 (m, 3H), 2.64-2.70 (m, 1H), 3.07-3.66 (m, 12H), 7.07-7.20 (m, 8H), 8.00-8.05 (m, 1H), 8.47-8.50 (m, 1H), 8.75-8.77 (m, 1H). |
| 101 | Prepared by the procedure of Example 5 | 415 | ¹H NMR (300 MHz, DMSO-d₆): δ 0.29-0.31 (m, 2H), 0.54-0.57 (m, 2H), 1.20-1.21 (m, 1H), 3.21 (s, 3H), 3.79 (d, J = 7.2 Hz, 2H), 6.74 (d, J = 9.0 Hz, 2H), 6.94 (d, J = 8.7 Hz, 2H), 7.09-7.12 (m, 4H), 7.85 (d, J = 5.1 Hz, 1H), 8.48 (d, J = 5.1 Hz, 1H), 8.67 (s, 1H), 13.00 (s, 1H). |
| 102 | Prepared by the procedure of Example 5 | 413 | ¹H NMR (300 MHz, CD3OD-d₄): δ 1.25 (d, J = 6.9 Hz, 6H), 2.86-2.88 (m, 1H), 3.34 (s, 3H), 3.60 (t, J = 6.0 Hz, 2H), 3.90 (t, J = 5.7 Hz, 2H), 6.95 (d, J = 9.0 Hz, 2H), 7.06-7.13 (m, 4H), 7.20 (d, J = 8.7 Hz, 2H), 7.98 (d, J = 5.1 Hz, 1H), 8.47 (d, J = 5.1 Hz, 1H), 8.75 (s, 1H). |
| 103 | Prepared by the procedure of Example 32 | 355 | 1H NMR (400 MHz, DMSO-d6): δ 6.75 (d, J = 2.4 Hz, 1H), 7.16 (d, J = 8.4 Hz, 1H), 7.44 (t, J = 6.4 Hz, 1H), 7.61-7.65 (m, 6H), 7.76 (d, J = 3.2 Hz, 1H), 7.89 (s, 1H), 8.50-8.67 (m, 2H), 13.10 (s, 1H). |

| Ex | Structure (prepared by procedure of cited Example) | MS (ESI) m/z | NMR spectrum data |
|---|---|---|---|
| 104 | (structure shown) Prepared by the procedure of Example 31 | 362 | 1H NMR (400 MHz, DMSO-d6): δ 1.63-1.88 (m, 4H), 2.58-2.67 (m, 2H), 3.01-3.10 (m, 2H), 4.27-4.30 (m, 1H), 6.46 (d, J = 2.0 Hz, 1H), 7.01 (d, J = 8.8 Hz, 1H), 7.29 (s, 1H), 7.37 (d, J = 2.5 Hz, 1H), 7.62 (d, J = 8.8 Hz, 1H), 7.71 (d, J = 4.8 Hz, 1H), 8.25 (d, J = 4.8 Hz, 1H), 8.64 (s, 1H). |
| 105 | (structure shown) Prepared by the procedure of Example 23 | 457 | 1H NMR (300 MHz, DMSO-d6): δ 2.18 (s, 3H), 2.25 (s, 3H), 2.48-2.49 (m, 4H), 2.80-2.85 (m, 4H), 3.24 (s, 3H), 6.69-6.73 (m, 2H), 6.90 (d, J = 5.7 Hz, 2H), 7.09-7.14 (m, 3H), 7.83 (d, J = 5.1 Hz), 8.46 (d, J = 5.1 Hz), 8.66 (s, 1H). |
| 106 | (structure shown) Prepared by the procedure of Example 39 | 426 | $^1$H NMR (400 MHz, DMSO-d$_6$): δ ppm 3.28-3.31 (m, 3 H) 3.49-3.63 (m, 2 H) 6.98-7.06 (m, 2 H) 7.08-7.15 (m, 2 H) 7.26 (br. s., 4 H) 7.81-7.94 (m, 1 H) 8.44-8.58 (m, 1 H) 8.65-8.79 (m, 1 H) 12.78-13.25 (s, 1 H) |
| 107 | (structure shown) Prepared by the procedure of Example 39 | 452 | $^1$H NMR (400 MHz, DMSO-d$_6$): δ ppm 1.02-1.13 (m, 2 H) 1.22-1.38 (m, 2 H) 2.48-2.50 (m, 3 H) 6.95-7.03 (m, 2 H) 7.13-7.19 (m, 2 H) 7.27-7.39 (m, 4 H) 7.85-7.93 (m, 1 H) 8.47-8.57 (m, 1 H) 8.70-8.75 (m, 1 H) 13.02-13.18 (s, 1 H) |

-continued

| Ex | Structure (prepared by procedure of cited Example) | MS (ESI) m/z | NMR spectrum data |
|---|---|---|---|
| 108 | Prepared by the procedure of Example 5 | 440 | ¹H NMR (400 MHz, DMSO-d$_6$): δ ppm 1.38-1.47 (m, 3 H) 3.29-3.31 (s, 3 H) 3.62-3.79 (m, 1 H) 6.98-7.07 (m, 2 H) 7.09-7.17 (m, 2 H) 7.23-7.36 (m, 4 H) 7.84-7.93 (s, 1 H) 8.45-8.59 (s, 1 H) 8.65-8.79 (s, 1 H) 12.98-13.20 (s, 1 H) |
| 109 | Prepared by the procedure of Example 5 | 387 | ¹H NMR (400 MHz, DMSO-d$_6$): δ ppm 1.19-1.27 (m, 6 H) 2.47-2.49 (m, 3 H) 2.93-3.09 (m, 1 H) 7.02-7.09 (m, 2 H) 7.21-7.30 (m, 3 H) 7.40-7.49 (m, 1 H) 7.85-7.93 (m, 1 H) 8.23-8.32 (m, 1 H) 8.48-8.58 (m, 1 H) 8.66-8.77 (m, 1 H) 13.01-13.16 (s, 1 H) |
| 110 | Prepared by the procedure of Example 26 | 429 | H NMR (300 MHz, DMSO-d$_6$): δ ppm 3.29 (s, 3 H) 7.02-7.05 (m, 2 H) 7.13-7.16 (m, 2 H) 7.23-7.30 (m, 4 H) 7.86-7.88 (m, 1 H) 8.50-8.52 (m, 1 H) 8.70 (s, 1 H) 13.10 (s, 1 H) |
| 111 | Prepared by the procedure of Example 5 | 403 | H NMR (300 MHz, DMSO-d$_6$): δ ppm 1.25 (d, J = 8.0 Hz, 6H), 3.21 (s, 3 H), 4.51-4.59 (m, 1H), 6.75 (d, J = 12.0 Hz, 2H), 6.92 (d, J = 12.0 Hz, 2H), 7.08-7.13 (m, 4 H), 7.85 (d, J = 6.8 Hz, 1 H), 8.48 (d, J = 6.8 Hz, 1 H) 8.67 (s, 1 H) 12.98 (s, 1 H) |
| 112 | Prepared by the procedure of Example 47 | 422 | ¹H NMR (400 MHz, DMSO-d$_6$): δ 1.20 (d, J = 8.0 Hz, 6H), 1.81-1.83 (m, 1H), 2.19-2.21 (m, 1H), 2.87-2.92 (m, 1H), 3.58-3.65 (m, 3H), 3.90-3.95 (m, 1H), 4.58-4.62 (m, 1H), 6.76 (d, J = 12.0 Hz, 2H), 6.97 (d, J = 12.0 Hz, 2H), 7.19 (d, J = 12.0 Hz, 2H), 7.25 (d, J = 12.0 Hz, 2H), 7.87 (d, J = 6.4 Hz, 1H), 8.52 (dd, J = 2.0 Hz, 3.2 Hz, 1H), 8.69 (s, 1H), 13.02 (s, 1H). |
| 113 | Prepared by the procedure of Example 47 | 426 | 1H NMR (300 MHz, DMSO-d$_6$): δ 1.22 (d, J = 7.2 Hz, 6H), 1.58-1.77 (m, 4H), 2.20-2.24 (m, 2H), 2.87-2.91 (m, 1H), 4.29 (t, J = 7.8 Hz, 1H), 6.71 (d, J = 8.7 Hz, 2H), 6.92 (d, J = 8.1 Hz, 2H), 7.14 (d, J = 8.7 Hz, 2H), 7.26 (d, J = 8.1 Hz, 2H), 7.86 (d, J = 4.8 Hz, 1H), 8.48-8.50 (m, 1H), 8.69 (s, 1H), 13.01 (brs, 1H). |

Preparation 114A: 2,2,2-trifluoro-N-(4-isopropyl-phenyl)-acetamide

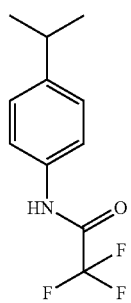 [SMILES: CC(C)c1ccc(NC(=O)C(F)(F)F)cc1]

To a solution of 4-isopropyl-phenylamine (1.0 g, 7.4 mmol) in DCM (60 ml) was added pyridine (1.8 g, 22.2 mmol) and TFAA (1.9 g, 8.9 mmol) at 0° C., and the mixture was stirred for 2 h at RT. The reaction was quenched with aqueous NaHCO$_3$ and the mixture was extracted with EA (80 mL×3). The combined organics were dried over MgSO$_4$ and concentrated in vacuo. The resulting residue was purified by silica gel column chromatography (PE:EtOAc, 30:1) to give the title compound (1.6 g, 94%) as a yellow oil. [M+H] Calc'd for C$_{11}$H$_{12}$F$_3$NO, 232; Found, 232.

Preparation 114B: (4-isopropyl-phenyl)-(2,2,2-trifluoro-ethyl)-amine

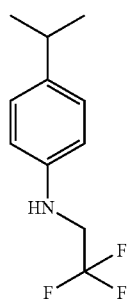

To a solution of 2,2,2-trifluoro-N-(4-isopropyl-phenyl)-acetamide (1.6 g, 7.0 mmol) in THF (70 mL) was added DMSB (7 mL, 14.0 mmol) and the mixture was refluxed for 2 h. The reaction was quenched with H$_2$O (70 mL), extracted with ether (80 mL×3). The combined organics were dried over MgSO$_4$ and concentrated in vacuo. The resulting residue was purified by silica gel column chromatography (PE:EtOAc, 50:1) to give the title compound (800 mg, 53%) as a yellow oil. [M+H] Calc'd for C$_{11}$H$_{14}$F$_3$N, 218; Found, 218.

Preparation 114C: 4-[(4-isopropyl-phenyl)-(2,2,2-trifluoro-ethyl)-amino]-phenol

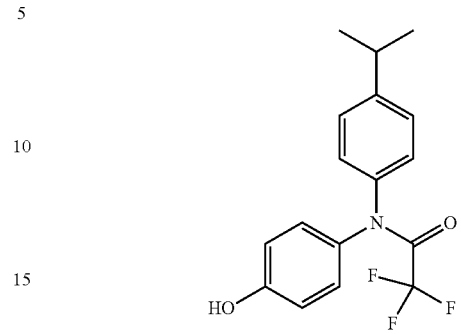

The title compound was prepared in 73% yield from 2-chloro-pyrido[3,4-d]pyrimidin-4-ol and (4-isopropyl-phenyl)-(2,2,2-trifluoro-ethyl)-amine according to the procedure of Preparation 33C. [M+H] Calc'd for C$_{17}$H$_{18}$F$_3$NO, 310; Found, 310.

Example 114: 2-{4-[(4-isopropyl-phenyl)-(2,2,2-trifluoro-ethyl)-amino]-phenoxy}-pyrido[3,4-d]pyrimidin-4-ol

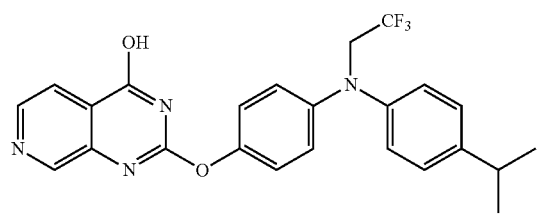 [SMILES: CC(C)c1ccc(N(CC(F)(F)F)c2ccc(Oc3nc(O)c4ccncc4n3)cc2)cc1]

The title compound was prepared in 11% yield from 2-chloro-pyrido[3,4-d]pyrimidin-4-ol and 4-[(4-isopropyl-phenyl)-(2,2,2-trifluoro-ethyl)-amino]-phenol according to the procedure for the preparation of Example 1; $^1$H NMR (300 MHz, DMSO-d$_6$): δ 1.20-1.22 (m, 6H), 2.88-2.89 (m, 1H), 4.59-4.62 (m, 2H), 6.94 (d, J=5.4 Hz, 2H), 7.07-7.10 (d, J=8.4 Hz, 2H), 7.25 (m, 4H), 7.86-7.88 (d, J=4.5 Hz, 1H), 8.51 (d, J=5.1 Hz, 1H), 8.70 (s, 1H). [M+H] Calc'd for C$_{24}$H$_{21}$F$_3$N$_4$O$_2$, 455; Found, 455.

Preparation 115A: [4-(3-amino-1-methylpropyl)phenyl]methyl[4-(phenylmethoxy)phenyl]amine

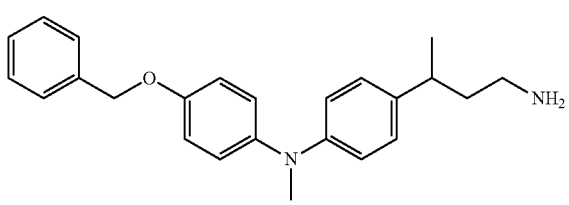 [SMILES: CC(CCN)c1ccc(N(C)c2ccc(OCc3ccccc3)cc2)cc1]

To a solution of 3-{4-[(4-benzyloxy-phenyl)-methyl-amino]-phenyl}-butyronitrile (1.0 g, 2.8 mmol) in THF (10 mL) was added LAH (2.3 mL, 2.4M) at 0° C., and the mixture was stirred at RT for 2 h. The reaction was quenched with water and extracted with EA (3×). The combined organics were dried over MgSO₄ and concentrated to give 0.68 g (68%) of the title compound. [M+H] Calc'd for C₂₄H₂₈N₂O, 361; Found, 361.

Preparation 115B: (3-{4-[(4-benzyloxy-phenyl)-methyl-amino]-phenyl}-butyl)-carbamic acid tert-butyl ester

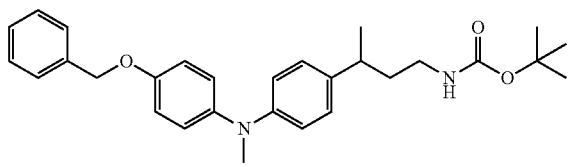 [SMILES: CC(CCNC(=O)OC(C)(C)C)c1ccc(N(C)c2ccc(OCc3ccccc3)cc2)cc1]

To a solution of [4-(3-amino-1-methylpropyl)phenyl] methyl[4-(phenylmethoxy)phenyl]amine (0.68 g, 1.9 mmol) in DCM (5 mL) was added (Boc)₂O (0.5 g, 2.3 mmol) and TEA (0.38 g, 3.8 mmol), and the mixture was stirred at RT for 2 h. The reaction was quenched with aqueous NH₄Cl and extracted with DCM (3×). The combined organics were dried over MgSO₄ and concentrated to give 0.83 g (95%) of the title compound. [M+H] Calc'd for C₂₉H₃₆N₂O₃, 461; Found, 461.

Preparation 115C: (3-{4-[(4-benzyloxy-phenyl)-methyl-amino]-phenyl}-butyl)-methyl-carbamic acid tert-butyl ester

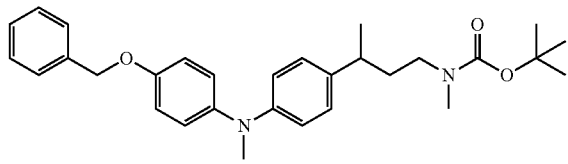 [SMILES: CC(CCN(C)C(=O)OC(C)(C)C)c1ccc(N(C)c2ccc(OCc3ccccc3)cc2)cc1]

To a solution of (3-{4-[(4-benzyloxy-phenyl)-methyl-amino]-phenyl}-butyl)-carbamic acid tert-butyl ester (1.9 g, 4.1 mmol) in THF (20 mL) was added NaH (0.25 g, 6.15 mmol) at 0° C., and the mixture was stirred at RT for 30 min at 0° C. CH₃I (0.7 g, 4.92 mmol) was added and the mixture was stirred at 45° C. for 2 h. The reaction was quenched with aqueous NH₄Cl and extracted with EA (3×). The combined organics were dried over MgSO₄ and concentrated. The residue was purified by silica gel chromatography (EA:PE, 1:10) give 1.2 g (61%) of the title compound. [M+H] Calc'd for C₃₀H₃₈N₂O₃, 475; Found, 475.

Preparation 115D: 4-{[4-(3-dimethylamino-1-methyl-propyl)-phenyl]-methyl-amino}-phenol

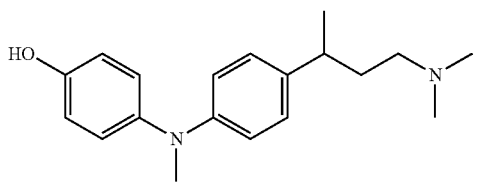 [SMILES: CC(CCN(C)C)c1ccc(N(C)c2ccc(O)cc2)cc1]

To a solution of (3-{4-[(4-benzyloxy-phenyl)-methyl-amino]-phenyl}-butyl)-methyl-carbamic acid tert-butyl ester (0.89 g, 1.88 mmol) in THF (10 mL) was added LAH (1.2 mL, 2.4M) at 0° C., and the mixture was refluxed overnight. The reaction was quenched with water and extracted with EA (3×). The combined organics were dried over MgSO₄ and concentrated. The residue was dissolved in MeOH and Pd/C (30 mg) was added. The mixture was stirred overnight at RT under H2 atmosphere and filtered. The filtrate was concentrated and the residue was purified by silica gel chromatography (MeOH:DCM, 1:10) to give 0.4 g (72%) of the title compound. [M+H] Calc'd for C₁₉H₂₆N₂O, 299; Found, 299.

Example 115: 2-(4-{[4-(3-dimethylamino-1-methyl-propyl)-phenyl]-methyl-amino}-phenoxy)-pyrido[3,4-d]pyrimidin-4-ol

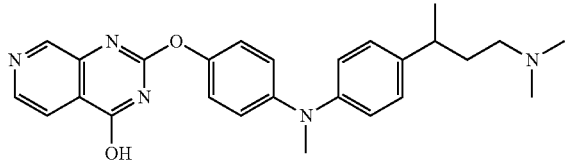 [SMILES: CC(CCN(C)C)c1ccc(N(C)c2ccc(Oc3nc(O)c4ccncc4n3)cc2)cc1]

The title compound was prepared in 5% yield from 2-chloro-pyrido[3,4-d]pyrimidin-4-ol and N-(4-hydroxy-phenyl)-N-methyl-2-phenyl-acetamide according to the procedure for the preparation of Example 1. ¹H NMR (400 MHz, DMSO-d₆): δ1.02 (d, J=8.4 Hz, 3H), 2.25-2.27 (m, 1H), 2.44-2.52 (m, 1H), 2.67-2.73 (m, 1H), 2.88 (d, J=26.0 Hz, 6H), 3.04-3.08 (m, 2H), 3.30 (s, 3H), 7.00-7.20 (m, 8H), 7.87 (d, J=6.8 Hz, 1H), 8.50 (d, J=6.8 Hz, 1H), 8.67 (s, 1H). [M+H] Calc'd for C₂₆H₂₉N₅O₂, 444; Found, 444.

Preparation 116A:
1-bromo-2-(2-methyl-allyloxy)-4-nitro-benzene

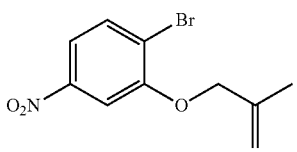

To a solution of 2-bromo-5-nitro-phenol (0.5 g, 2.3 mmol) in acetone (20 mL) was added 3-bromo-2-methyl-propene (465 mg, 3.4 mmol) and K₂CO₃ (633 mg, 4.6 mmol), and the mixture was refluxed overnight. The reaction mixture was cooled to RT and the solvent was concentrated. The residue was dissolved in EA, washed with water, washed with brine. The organics were concentrated and purified by silica gel chromatography (EA:PE, 1:20) to give 0.5 g (80%) of the title compound. [M+H] Calc'd for C₁₀H₁₀BrNO₃, 271; Found, 271.

Preparation 116B: [4-bromo-3-(2-methyl-allyloxy)-phenyl]-carbamic acid tert-butyl ester

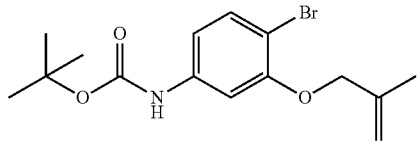 [SMILES: C=C(C)COc1cc(NC(=O)OC(C)(C)C)ccc1Br]

To a solution of 1-bromo-2-(2-methyl-allyloxy)-4-nitrobenzene (3.1 g, 114 mmol) in methanol (100 mL) was added iron powder (1.95 g, 343 mmol) and NH$_4$Cl (2.0 g, 37 mmol), and the mixture was refluxed overnight, the solvent was concentrated. The residue was adjusted with aqueous NaHCO$_3$ to PH-8, extracted with EA (3×). The combined organics were dried and concentrated. The residue was dissolved in THF (50 mL), (Boc)$_{20}$ (3.0 g, 137 mmol) and TEA (2.5 g, 228 mmol) were added, and the mixture was refluxed overnight. The reaction mixture was cooled to RT and the solvent was concentrated. The residue was purified by silica gel chromatography (EA:PE, 1:20) to give 3.0 g (77%) of the title compound. [M+H] Calc'd for C$_{15}$H$_{20}$BrNO$_3$, 342; Found, 342.

Preparation 116C: (3,3-dimethyl-2,3-dihydro-benzofuran-6-yl)-carbamic acid tert-butyl ester

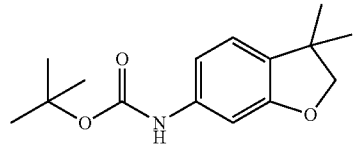 [SMILES: CC(C)(C)OC(=O)Nc1ccc2c(c1)OCC2(C)C]

To a solution of [4-bromo-3-(2-methyl-allyloxy)-phenyl]-carbamic acid tert-butyl ester (340 mg, 1 mmol) in toluene (10 mL) was added was AIBI (16.5 mg, 0.1 mmol) and tributytin hydride (360 mg, 1.2 mmol), and the mixture was stirred overnight at 110° C. The reaction mixture was cooled to RT, EA and 10% KF solution were added and the mixture was stirred for 2 h. The organic layer was washed with water, washed with brine and concentrated. The residue was purified by silica gel chromatography (PE:EA, 20:1) to give 150 mg (57%) of the title compound. [M+H] Calc'd for C$_{15}$H$_{21}$NO$_3$, 264; Found, 264.

Preparation 116D: (3,3-dimethyl-2,3-dihydro-benzofuran-6-yl)-methyl-amine

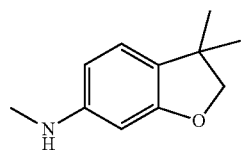

To a solution of (3,3-dimethyl-2,3-dihydro-benzofuran-6-yl)-carbamic acid tert-butyl ester (1.0 g, 3.8 mmol) in DMF (10 mL) was added NaH (0.23 g, 5.7 mmol) at 0° C., an dthe mixture was stirred for 30 min at 0° C. CH$_3$I (0.65 g, 4.5 mmol) was added and the mixture was stirred at RT for 2 h, quenched with aqueous NH$_4$Cl, and extracted with EA (3×). The combined organics were washed with water, washed with brine, dried and concentrated. The residue was dissolved in DCM (10 mL), TFA (2 mL) was added and the mixture was stirred at RT for 1 h. The organics were concentrated and the residue was purified by silica gel chromatography (EA:PE, 1:20) to give 600 mg (94%) of the title compound. [M+H] Calc'd for C$_{11}$H$_{15}$NO, 178; Found, 178.

Preparation 116E: 4-[(3,3-dimethyl-2,3-dihydrobenzofuran-6-yl)-methyl-amino]-phenol

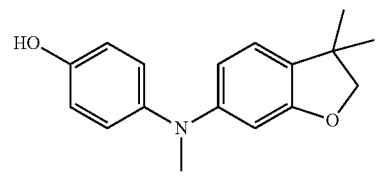 [SMILES: CN(c1ccc(O)cc1)c1ccc2c(c1)OCC2(C)C]

A solution of (3,3-dimethyl-2,3-dihydro-benzofuran-6-yl)-methyl-amine (300 mg, 1.7 mmol), 1-benzyloxy-4-bromo-benzene (535 mg, 2.0 mmol), S-Phos (35 mg, 0.085 mmol), Pd$_2$(dba)$_3$ (80 mg, 0.085 mmol), t-BuOK (475 mg, 4.25 mmol) in toluene (10 mL) was refluxed overnight under nitrogen atmosphere. The solvent was concentrated and the residue was purified by silica gel chromatography (EA:PE, 1:20) to give (4-benzyloxy-phenyl)-(3,3-dimethyl-2,3-dihydro-benzofuran-6-yl)-methyl-amine (600 mg, 99%). This benzyl protected product was in turn dissolved in THF/MeOH and Pd/C (50 mg) was added. The mixture was stirred overnight at RT under H$_2$ atmosphere. The mixture was filtered on celite and the filtrate was concentrated. The residue was purified by silica gel chromatography (EA:PE, 1:10) to give 430 mg (94%) of the title compound. [M+H] Calc'd for C$_{17}$H$_{19}$NO$_2$, 270; Found, 270.

Example 116: (3,3-dimethyl-2,3-dihydro-benzofuran-6-yl)-methyl-[4-(4-methyl-pyrido [3,4-d]pyrimidin-2-yloxy)-phenyl]-amine

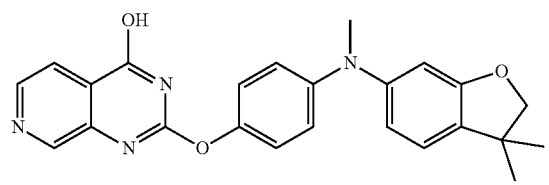 [SMILES: CN(c1ccc(Oc2nc(O)c3ccncc3n2)cc1)c1ccc2c(c1)OCC2(C)C]

The title compound was prepared in 48% yield from 2-chloro-pyrido[3,4-d]pyrimidin-4-ol and N-(4-hydroxyphenyl)-N-methyl-2-phenyl-acetamide according to the procedure for the preparation of Example 1. $^1$H NMR (400 MHz, DMSO-d$_6$): δ 1.26 (s, 6H), 3.22 (s, 3H), 4.19 (s, 2H), 6.46-6.57 (m, 2H), 6.97 (d, J=7.6 Hz, 1H), 7.10 (d, J=10.8 Hz, 1H), 7.19 (d, J=10.8 Hz, 2H), 7.86 (d, J=6.0 Hz, 1H), 8.50 (d, J=6.0 Hz, 1H), 8.69 (s, 1H), 13.04 (s, 1H). [M+H] Calc'd for C$_{22}$H$_{18}$N$_4$O$_3$, 387; Found, 387.

Preparation 117A: 4-(benzyloxy)-N-(4-isopropylphenyl)aniline

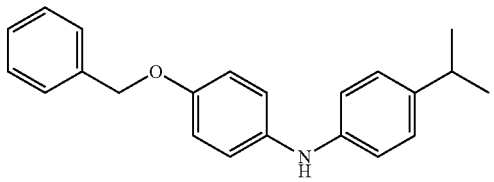 [SMILES: CC(C)c1ccc(Nc2ccc(OCc3ccccc3)cc2)cc1]

A mixture of 4-(benzyloxy)aniline (7.8 g, 39.03 mmol), 1-bromo-4-isopropylbenzene (8.5 g, 42.93 mmol), X-Phos (2.3 g, 4.68 mmol), Pd(OAc)$_2$ (0.53 g, 2.34 mmol) and Cs$_2$CO$_3$ (50.9 g, 156.12 mmol) in toluene (150 mL) was purged with N$_2$ and then reflux overnight. The reaction mixture was cooled to RT and filtered. The filtrate was concentrated and purified by silica column chromatography (PE:EA, 20:1) to give 7.1 g (57%) of the title compound. $^1$H NMR (CDCl$_3$, 300 MHz): δ 1.23 (d, J=6.9 Hz, 6H), 2.77-2.92 (m, 1H), 5.04 (s, 2H), 6.87-6.94 (m, 4H), 7.01-7.04 (m, 2H), 7.08-7.10 (m, 2H), 7.31-7.46 (m, 5H). [M+H] Calc'd for C$_{22}$H23NO, 318; Found, 318.

Preparation 117B: 4-(benzyloxy)-N-ethyl-N-(4-isopropylphenyl)aniline

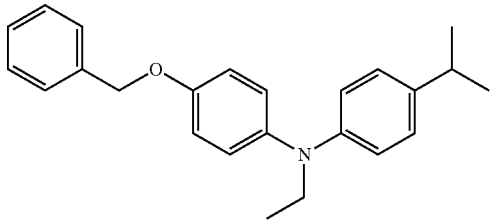 [SMILES: CCN(c1ccc(OCc2ccccc2)cc1)c1ccc(C(C)C)cc1]

To a solution of compound 4-(benzyloxy)-N-(4-isopropylphenyl)aniline (0.5 g, 1.58 mmol) in DMF (5 mL) was added NaH (189 mg, 4.73 mmol) and the mixture was stirred at 0° C. for 30 min. Iodoethane (761 mg, 4.9 mmol) was then added and the reaction mixture was stirred overnight at RT. The mixture was quenched with aqueous NH$_4$Cl solution and extracted with ethyl acetate (3×10 mL). The combined organic layers were washed with water (3×10 mL), washed with brine (10 mL), dried over Na$_2$SO$_4$ and concentrated to give 350 mg (64%) of the title compound as brown liquid. $^1$H NMR (CDCl$_3$, 300 MHz): δ 1.19 (t, J=6.9 Hz, 3H), 1.22 (d, J=6.9 Hz, 6H), 2.76-2.90 (m, 1H), 3.69 (q, J=6.9 Hz, 2H), 5.06 (s, 2H), 6.72-6.76 (m, 2H), 6.93-6.98 (m, 2H), 7.00-7.08 (m, 4H), 7.31-7.47 (m, 5H). [M+H] Calc'd for C$_{24}$H$_{27}$NO, 346; Found, 346.

Preparation 117C: 4-(ethyl(4-isopropylphenyl)amino)phenol

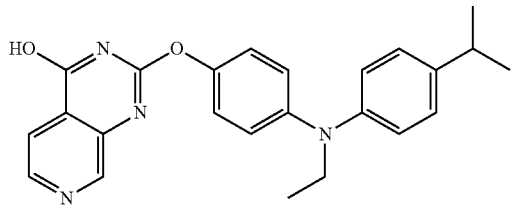 [SMILES: CCN(c1ccc(Oc2nc(O)c3ccncc3n2)cc1)c1ccc(C(C)C)cc1]

The title compound was prepared in 85% yield from 4-(benzyloxy)-N-ethyl-N-(4-isopropylphenyl)aniline according to the procedure of Preparation 26B. [M+H] Calc'd for C$_{17}$H$_{21}$NO, 256 Found, 256.

Example 117: 2-(4-(ethyl(4-isopropylphenyl)amino)phenoxy)pyrido[3,4-d]pyrimidin-4-ol The title compound was prepared in 5% yield from 2-chloro-pyrido[3,4-d]pyrimidin-4-ol and 4-(ethyl(4-isopropylphenyl)amino)phenol according to the procedure for the preparation of Example 1. $^1$H NMR (400 MHz, CDCl$_3$): δ 1.23-1.28 (m, 9H), 2.87-2.94 (m, 1H), 3.77 (q, J=6.8 Hz, 2H), 6.88 (d, J=8.0 Hz, 2H), 7.05-7.11 (m, 4H), 7.20 (d, J=8.0 Hz, 2H), 8.01 (brs, 1H), 8.59 (brs, 1H), 8.93 (s, 1H), 9.69 (brs, 1H). [M+H] Calc'd for C$_{24}$H$_{24}$N$_4$O$_2$, 401; Found, 401.

Preparation 118A: N-(4-isopropylphenyl)tetrahydro-2H-pyran-4-amine

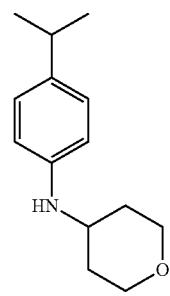 [SMILES: CC(C)c1ccc(NC2CCOCC2)cc1]

To a solution of compound 4-isopropylaniline (1.0 g, 7.4 mmol), dihydro-2H-pyran-4(3H)-one (1.5 g, 14.8 mmol) in DMF (10 mL) was added AcOH (2 mL). After stirring at RT for 30 min, the reaction mixture was cooled to 0° C., and sodium triacetoxyborohydride (3.2 g, 14.8 mmol) was added slowly. The mixture was stirred at RT for 2 h and then cooled to 0° C., quenched with Na$_2$CO$_3$ solution and extracted with EA (2×20 mL). The combined organics were washed with water (2×10 mL), washed with brine, dried over Na$_2$SO$_4$ and concentrated. The residue was purified by silica column chromatography (PE:EA=10:1) to give 1.5 g (93%) of the title compound as colorless oil. $^1$H NMR (CDCl$_3$, 300 MHz): δ 1.20 (d, J=7.2 Hz, 6H), 1.39-1.53 (m, 2H), 2.00-2.05 (m, 2H), 2.75-2.85 (m, 1H), 3.41-3.55 (m, 3H), 3.96-4.03 (m, 2H), 6.57 (d, J=8.4 Hz, 2H), 7.04 (d, J=8.4 Hz, 2H). [M+H] Calc'd for C$_{14}$H$_{21}$NO, 220; Found, 220.

Preparation 118B: 4-((4-isopropylphenyl)(tetra-hydro-2H-pyran-4-yl)amino)phenol

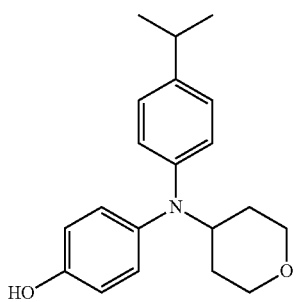 [SMILES: CC(C)c1ccc(N(c2ccc(O)cc2)C2CCOCC2)cc1]

The title compound was prepared in 30% yield from N-(4-isopropylphenyl)tetrahydro-2H-pyran-4-amine according to the procedure of Preparation 5A. [M+H] Calc'd for C$_{20}$H$_{25}$NO$_2$, 312 Found, 312.

Example 118: 2-(4-((4-isopropylphenyl)(tetrahydro-2H-pyran-4-yl)amino)phenoxy)pyrido[3,4-d]pyrimidin-4-ol

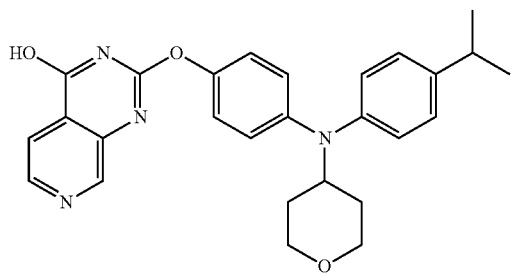 [SMILES: CC(C)c1ccc(N(c2ccc(Oc3nc(O)c4ccncc4n3)cc2)C2CCOCC2)cc1]

The title compound was prepared in 8% yield from 2-chloro-pyrido[3,4-d]pyrimidin-4-ol and 4-((4-isopropylphenyl)(tetrahydro-2H-pyran-4-yl)amino)phenol according to the procedure for the preparation of Example 1. $^1$H NMR (400 MHz, CDCl$_3$): δ 1.28 (d, J=6.8 Hz, 6H), 1.54-1.66 (m, 2H), 1.91-1.92 (m, 2H), 2.90-2.97 (m, 1H), 3.50-3.57 (m, 2H), 4.01-4.12 (m, 3H), 6.71 (d, J=9.2 Hz, 2H), 6.97 (d, J=8.4 Hz, 2H), 7.08 (d, J=9.2 Hz, 2H), 7.24 (d, J=8.4 Hz, 2H), 8.02 (d, J=4.8 Hz, 1H), 8.58 (d, J=4.8 Hz, 1H), 8.90 (s, 1H), 9.09 (brs, 1H). [M+H] Calc'd for C$_{27}$H$_{28}$N$_4$O$_3$, 457; Found, 457.

II. Biological Evaluation

Example 1: In Vitro Enzyme Inhibition Assay

This assay determines the ability of a test compound to inhibit JMJD2C demethylase activity. Baculovirus expressed JMJD2C (GenBank Accession #BC143571, AA 2-372) was purchased from BPS Bioscience (Cat #50105).

JMJD2C Assay

The ability of test compounds to inhibit the activity of JMJD2C was determined in 384-well plate format under the following reaction conditions: 0.3 nM JMJD2C, 300 nM H3K9me3-biotin labeled peptide (Anaspec cat #64360), 2 μM alpha-ketoglutaric acid in assay buffer of 50 mM HEPES, pH7.3, 0.005% Brij35, 0.5 mM TCEP, 0.2 mg/ml BSA, 50 μM sodium L-ascorbate, and 2 μM ammonium iron(II) sulfate. Reaction product was determined quantitatively by TR-FRET after the addition of detection reagent Phycolink Streptavidin-allophycocyanin (Prozyme) and Europium-anti-di-methylated histone H3 lysine 9 (H3K9me2) antibody (PerkinElmer) in the presence of 5 mM EDTA in LANCE detection buffer (PerkinElmer) at a final concentration of 50 nM and 1 nM, respectively.

The assay reaction was initiated by the following: 2 μl of the mixture of 900 nM H3K9me3-biotin labeled peptide and 6 μM alpha-ketoglutaric acid with 2 μl of 11-point serial diluted inhibitor in 3% DMSO were added to each well of the plate, followed by the addition of 2 μl of 0.9 nM JMJD2C to initiate the reaction. The reaction mixture was incubated at room temperature for 30 minutes, and terminated by the addition of 6 μl of 5 mM EDTA in LANCE detection buffer containing 100 nM Phycolink Streptavidin-allophycocyanin and 2 nM Europium-anti-H3K9me2 antibody. Plates were read by EnVisionMultilabel Reader in TR-FRET mode (excitation at 320 nm, emission at 615 nm and 665 nm) after 1 hour incubation at room temperature. A ratio was calculated (665/615) for each well and fitted to determine inhibition constant (IC$_{50}$).

The ability of the compounds disclosed herein to inhibit demethylase activity was quantified and the respective IC$_{50}$ value was determined. Table 3 provides the IC$_{50}$ values of various compounds disclosed herein.

TABLE 3

| Example | Name | JMJD2C IC$_{50}$ |
|---|---|---|
| 1 | 2-[4-(methyl-pyridin-2-yl-amino)-phenoxy]-pyrido[3,4-d]pyrimidin-4-ol | B |
| 2 | 2-(1-methyl-1H-indol-5-yloxy)-pyrido[3,4-d]pyrimidin-4-ol | B |
| 3 | 2-(1-phenethyl-1H-indol-5-yloxy)-pyrido[3,4-d]pyrimidin-4-ol | B |
| 4 | 2-(1-benzyl-1H-indol-5-yloxy)-pyrido[3,4-d]pyrimidin-4-ol | B |
| 5 | 2-[4-(methyl-phenyl-amino)-phenoxy]-pyrido[3,4-d]pyrimidin-4-ol | B |
| 6 | 2-[4-(benzyl-methyl-amino)-phenoxy]-pyrido[3,4-d]pyrimidin-4-ol | B |
| 7 | 2-[3-(methyl-phenyl-amino)-phenoxy]-pyrido[3,4-d]pyrimidin-4-ol | C |

TABLE 3-continued

| Example | Name | JMJD2C IC$_{50}$ |
|---|---|---|
| 8 | 2-(1-benzyl-1H-indol-6-yloxy)-pyrido[3,4-d]pyrimidin-4-ol | C |
| 9 | 2-[3-(benzyl-methyl-amino)-phenoxy]-pyrido[3,4-d]pyrimidin-4-ol | C |
| 10 | 2-[3-fluoro-4-(methyl-phenyl-amino)-phenoxy]-pyrido[3,4-d]pyrimidin-4-ol | B |
| 11 | 2-(1-benzyl-1H-indazol-6-yloxy)-pyrido[3,4-d]pyrimidin-4-ol | B |
| 12 | 2-(2-benzyl-2H-indazol-6-yloxy)-pyrido[3,4-d]pyrimidin-4-ol | B |
| 13 | 2-{4-[methyl(2-phenylethyl)amino]phenoxy}pyridino[3,4-d]pyrimidin-4-ol | B |
| 14 | 2-[2-benzyl-2H-indazol-5-yloxy]pyridino[3,4-d]pyrimidin-4-ol | B |
| 15 | 2-(1-benzyl-1H-indazol-5-yloxy)-pyridino[3,4-d]pyrimidin-4-ol | B |
| 16 | 2-{4-[(4-methoxy-phenyl)-methyl-amino]-phenoxy}-pyrido[3,4-d]pyrimidin-4-ol | B |
| 17 | 2-{4-[(3-methoxy-phenyl)-methyl-amino]-phenoxy}-pyrido[3,4-d]pyrimidin-4-ol | B |
| 18 | 2-{4-[methyl-(4-morpholin-4-yl-phenyl)-amino]-phenoxy}-pyrido[3,4-d]pyrimidin-4-ol | B |
| 19 | 2-{4-[methyl-(3-morpholin-4-yl-phenyl)-amino]-phenoxy}-pyrido[3,4-d]pyrimidin-4-ol | B |
| 20 | 2-[4-(methyl-p-tolyl-amino)-phenoxy]-pyrido[3,4-d]pyrimidin-4-ol | B |
| 21 | 2-[4-(methyl-m-tolyl-amino)-phenoxy]-pyrido[3,4-d]pyrimidin-4-ol | B |
| 22 | 2-(4-{methyl-[3-(4-methyl-piperazin-1-yl)-phenyl]-amino}-phenoxy)-pyrido[3,4-d]pyrimidin-4-ol | A |
| 23 | 2-(4-{[4-(4-amino-piperidin-1-yl)-phenyl]-methyl-amino}-phenoxy)-pyrido[3,4-d]pyrimidin-4-ol | B |
| 24 | N-[4-(4-hydroxy-pyrido[3,4-d]pyrimidin-2-yloxy)-phenyl]-N-methyl-2-phenyl-acetamide | B |
| 25 | 2-[4-(3-phenyl-piperidin-1-yl)-phenoxy]-pyrido[3,4-d]pyrimidin-4-ol | B |
| 26 | 2-[4-(2-phenyl-morpholin-4-yl)-phenoxy]-pyrido[3,4-d]pyrimidin-4-ol | B |
| 27 | 2-{4-[methyl-(5-morpholin-4-yl-pyridin-3-yl)-amino]-phenoxy}-pyrido[3,4-d]pyrimidin-4-ol | B |
| 28 | 2-{4-[methyl-(1,2,3,4-tetrahydro-naphthalen-1-ylmethyl)-amino]-phenoxy}-pyrido[3,4-d]pyrimidin-4-ol | A |
| 29 | 2-(4-{[4-(2-methoxy-1-methyl-ethyl)-phenyl]-methyl-amino}-phenoxy)-pyrido[3,4-d]pyrimidin-4-ol | B |
| 30 | 3-(4-{[4-(4-hydroxy-pyrido[3,4-d]pyrimidin-2-yloxy)-phenyl]-methyl-amino}-phenyl)-butyronitrile | B |
| 31 | 2-(1-cyclopentyl-1H-indol-5-yloxy)-pyrido[3,4-d]pyrimidin-4-ol | C |
| 32 | 2-(1-phenyl-2,3-dihydro-1H-indol-5-yloxy)-pyrido[3,4-d]pyrimidin-4-ol | B |
| 33 | 2-(1-phenyl-1,2,3,4-tetrahydro-quinolin-6-yloxy)-pyrido[3,4-d]pyrimidin-4-ol | C |
| 34 | 2-{4-[(5-isopropyl-pyridin-2-yl)-methyl-amino]-phenoxy}-pyrido[3,4-d]pyrimidin-4-ol | A |
| 35 | 2-{4-[(4-isopropyl-3-morpholin-4-yl-phenyl)-methyl-amino]-phenoxy}-pyrido[3,4-d]pyrimidin-4-ol | B |
| 36 | 2-(4-{[4-(1-methoxy-ethyl)-phenyl]-methyl-amino}-phenoxy)-pyrido[3,4-d]pyrimidin-4-ol | B |
| 37 | 2-(4-{[4-(2-amino-1-methyl-ethyl)-phenyl]-methyl-amino}-phenoxy)-pyrido[3,4-d]pyrimidin-4-ol | A |
| 38 | 2-{4-[(4-{2-[(2-methoxy-ethyl)-methyl-amino]-1-methyl-ethyl}-phenyl)-methyl-amino]-phenoxy}-pyrido[3,4-d]pyrimidin-4-ol | B |
| 39 | 2-(4-{[4-(1-cyclopropyl-ethyl)-phenyl]-methyl-amino}-phenoxy)-pyrido[3,4-d]pyrimidin-4-ol | C |
| 40 | 3-{[4-(4-hydroxy-pyrido[3,4-d]pyrimidin-2-yloxy)-phenyl]-methyl-amino}-benzonitrile | B |
| 41 | 2-(4-{methyl-[3-(4-methyl-piperazin-1-ylmethyl)-phenyl]-amino}-phenoxy)-pyrido[3,4-d]pyrimidin-4-ol | A |
| 42 | 2-{4-[(4-cyclopropyl-phenyl)-methyl-amino]-phenoxy}-pyrido[3,4-d]pyrimidin-4-ol | B |
| 43 | 2-[4-[methyl-(5-methylpyridin-2-yl)amino]phenoxy]pyrido[3,4-d]pyrimidin-4-ol | B |
| 44 | 2-[4-[4-(dimethylamino)-N-methylanilino]phenoxy]pyrido[3,4-d]pyrimidin-4-ol | A |
| 45 | 4-[3-[4-(4-hydroxypyrido[3,4-d]pyrimidin-2-yl)oxy-N-methylanilino]phenyl]-1-methylpiperazin-2-one | B |
| 46 | 2-[4-[N-methyl-4-(4-methylpiperazin-1-yl)anilino]phenoxy]pyrido[3,4-d]pyrimidin-4-ol | B |
| 47 | 2-[4-[3-(dimethylamino)-N-methylanilino]phenoxy]pyrido[3,4-d]pyrimidin-4-ol | B |
| 48 | 2-[4-(N-methyl-3-pyrrolidin-1-ylanilino)phenoxy]pyrido[3,4-d]pyrimidin-4-ol | B |

TABLE 3-continued

| Example | Name | JMJD2C IC$_{50}$ |
|---|---|---|
| 49 | 2-[4-(N-methyl-4-pyrrolidin-1-ylanilino)phenoxy]pyrido[3,4-d]pyrimidin-4-ol | C |
| 50 | 2-[4-[3-(4-aminopiperidin-1-yl)-N-methylanilino]phenoxy]pyrido[3,4-d]pyrimidin-4-ol | A |
| 51 | 2-[4-[methyl-[(1S)-1-phenylethyl]amino]phenoxy]pyrido[3,4-d]pyrimidin-4-ol | B |
| 52 | 2-[4-[methyl-[(1R)-1-phenylethyl]amino]phenoxy]pyrido[3,4-d]pyrimidin-4-ol | B |
| 53 | 2-[4-(3-fluoro-N,4-dimethylanilino)phenoxy]pyrido[3,4-d]pyrimidin-4-ol | B |
| 54 | 2-[4-(3-phenylpyrrolidin-1-yl)phenoxy]pyrido[3,4-d]pyrimidin-4-ol | C |
| 55 | 2-[4-(N,4-dimethyl-3-morpholin-4-ylanilino)phenoxy]pyrido[3,4-d]pyrimidin-4-ol | B |
| 56 | 2-[4-(N-methyl-3-methylsulfonylanilino)phenoxy]pyrido[3,4-d]pyrimidin-4-ol | B |
| 57 | 2-[4-(N-methyl-4-methylsulfonylanilino)phenoxy]pyrido[3,4-d]pyrimidin-4-ol | B |
| 58 | 2-[4-[3-(3-aminopiperidin-1-yl)-N-methylanilino]phenoxy]pyrido[3,4-d]pyrimidin-4-ol | A |
| 59 | 2-[4-(4-ethyl-N-methyl-3-morpholin-4-ylanilino)phenoxy]pyrido[3,4-d]pyrimidin-4-ol | A |
| 60 | 2-[4-[4-ethyl-N-methyl-3-(4-methylpiperazin-1-yl)anilino]phenoxy]pyrido[3,4-d]pyrimidin-4-ol | A |
| 61 | 2-[4-[methyl-(2-morpholin-4-ylpyridin-4-yl)amino]phenoxy]pyrido[3,4-d]pyrimidin-4-ol | A |
| 62 | 2-[4-[2,3-dihydro-1H-inden-1-ylmethyl(methyl)amino]phenoxy]pyrido[3,4-d]pyrimidin-4-ol | B |
| 63 | 2-[4-[N-methyl-4-(2-methylpropyl)anilino]phenoxy]pyrido[3,4-d]pyrimidin-4-ol | B |
| 64 | 2-[4-[4-(2-hydroxypropan-2-yl)-N-methylanilino]phenoxy]pyrido[3,4-d]pyrimidin-4-ol | B |
| 65 | 2-[4-[3-[2-(dimethylamino)ethoxy]-4-ethyl-N-methylanilino]phenoxy]pyrido[3,4-d]pyrimidin-4-ol | A |
| 66 | 2-[4-[4-ethyl-3-(2-methoxyethoxy)-N-methylanilino]phenoxy]pyrido[3,4-d]pyrimidin-4-ol | C |
| 67 | 2-[4-[4-(1-methoxy-2-methylpropan-2-yl)-N-methylanilino]phenoxy]pyrido[3,4-d]pyrimidin-4-ol | C |
| 68 | 2-[4-[4-(1-hydroxy-2-methylpropan-2-yl)-N-methylanilino]phenoxy]pyrido[3,4-d]pyrimidin-4-ol | B |
| 69 | 2-[4-(N-methyl-4-propylanilino)phenoxy]pyrido[3,4-d]pyrimidin-4-ol | C |
| 70 | 2-[4-[N-methyl-4-[1-(methylamino)propan-2-yl]anilino]phenoxy]pyrido[3,4-d]pyrimidin-4-ol | A |
| 71 | 2-[4-[4-(4-aminobutan-2-yl)-N-methylanilino]phenoxy]pyrido[3,4-d]pyrimidin-4-ol | A |
| 72 | 2-[4-[N-methyl-4-[4-(methylamino)butan-2-yl]anilino]phenoxy]pyrido[3,4-d]pyrimidin-4-ol | A |
| 73 | 2-[4-[N-methyl-4-(2,2,2-trifluoroethoxy)anilino]phenoxy]pyrido[3,4-d]pyrimidin-4-ol | B |
| 74 | 2-[4-[N-methyl-4-(2-methylpropoxy)anilino]phenoxy]pyrido[3,4-d]pyrimidin-4-ol | C |
| 75 | 2-[4-[4-(2,2-dimethylpropoxy)-N-methylanilino]phenoxy]pyrido[3,4-d]pyrimidin-4-ol | C |
| 76 | 2-[4-[4-(cyclopropylmethyl)-N-methylanilino]phenoxy]pyrido[3,4-d]pyrimidin-4-ol | C |
| 77 | 2-[4-[4-[(2S)-butan-2-yl]-N-methylanilino]phenoxy]pyrido[3,4-d]pyrimidin-4-ol | C |
| 78 | 2-[4-[4-[(2R)-butan-2-yl]-N-methylanilino]phenoxy]pyrido[3,4-d]pyrimidin-4-ol | C |
| 79 | 2-[4-[N-methyl-3-(4-methylpiperazin-1-yl)anilino]phenoxy]pyrido[3,4-d]pyrimidin-4-ol | A |
| 80 | 2-[4-(N-ethylanilino)phenoxy]pyrido[3,4-d]pyrimidin-4-ol | B |
| 81 | 4-[4-(4-hydroxypyrido[3,4-d]pyrimidin-2-yl)oxy-N-methylanilino]benzonitrile | B |
| 82 | 2-[4-[methyl-(2-methylindazol-5-yl)amino]phenoxy]pyrido[3,4-d]pyrimidin-4-ol | B |
| 83 | 2-[4-(N,3,4-trimethylanilino)phenoxy]pyrido[3,4-d]pyrimidin-4-ol | C |
| 84 | 2-[4-(4-ethyl-N-methylanilino)phenoxy]pyrido[3,4-d]pyrimidin-4-ol | B |
| 85 | 2-[4-(N-methyl-4-propan-2-ylanilino)phenoxy]pyrido[3,4-d]pyrimidin-4-ol | C |
| 86 | 2-[4-[N-methyl-3-(trifluoromethyl)anilino]phenoxy]pyrido[3,4-d]pyrimidin-4-ol | C |

TABLE 3-continued

| Example | Name | JMJD2C IC$_{50}$ |
|---|---|---|
| 87 | 2-[4-[N-methyl-4-(trifluoromethyl)anilino]phenoxy]pyrido[3,4-d]pyrimidin-4-ol | C |
| 88 | 2-[4-[N-methyl-3-(4-methyl-1,4-diazepan-1-yl)anilino]phenoxy]pyrido[3,4-d]pyrimidin-4-ol | A |
| 89 | 2-[4-[N-methyl-3-[methyl-(1-methylpiperidin-4-yl)amino]anilino]phenoxy]pyrido[3,4-d]pyrimidin-4-ol | A |
| 90 | 2-[4-[N,3-dimethyl-5-(4-methylpiperazin-1-yl)anilino]phenoxy]pyrido[3,4-d]pyrimidin-4-ol | A |
| 91 | 2-[1-(oxan-4-yl)indol-5-yl]oxypyrido[3,4-d]pyrimidin-4-ol | B |
| 92 | 2-[4-(4-tert-butyl-N-methylanilino)phenoxy]pyrido[3,4-d]pyrimidin-4-ol | B |
| 93 | 2-[4-(N-methyl-3-propan-2-ylanilino)phenoxy]pyrido[3,4-d]pyrimidin-4-ol | B |
| 94 | 2-[4-(4-chloro-N-methylanilino)phenoxy]pyrido[3,4-d]pyrimidin-4-ol | B |
| 95 | 2-[4-(3-chloro-N-methylanilino)phenoxy]pyrido[3,4-d]pyrimidin-4-ol | C |
| 96 | 2-[4-(3-fluoro-N-methylanilino)phenoxy]pyrido[3,4-d]pyrimidin-4-ol | B |
| 97 | 2-[4-[(5-ethylpyridin-2-yl)-methylamino]phenoxy]pyrido[3,4-d]pyrimidin-4-ol | B |
| 98 | 2-[4-[4-(3,6-dihydro-2H-pyran-4-yl)-N-methylanilino]phenoxy]pyrido[3,4-d]pyrimidin-4-ol | C |
| 99 | 2-[4-[N-methyl-4-(oxan-4-yl)anilino]phenoxy]pyrido[3,4-d]pyrimidin-4-ol | B |
| 100 | 2-[4-[4-[1-(2-methoxyethylamino)propan-2-yl]-N-methylanilino]phenoxy]pyrido[3,4-d]pyrimidin-4-ol | A |
| 101 | 2-[4-[4-(cyclopropylmethoxy)-N-methylanilino]phenoxy]pyrido[3,4-d]pyrimidin-4-ol | C |
| 102 | 2-[4-[N-(2-methoxyethyl)-4-propan-2-ylanilino]phenoxy]pyrido[3,4-d]pyrimidin-4-ol | B |
| 103 | 2-(1-phenylindol-5-yl)oxypyrido[3,4-d]pyrimidin-4-ol | C |
| 104 | 2-(1-piperidin-4-ylindol-5-yl)oxypyrido[3,4-d]pyrimidin-4-ol | A |
| 105 | 2-[4-[N,4-dimethyl-3-(4-methylpiperazin-1-yl)anilino]phenoxy]pyrido[3,4-d]pyrimidin-4-ol | A |
| 106 | 2-[4-[N-methyl-4-(2,2,2-trifluoroethyl)anilino]phenoxy]pyrido[3,4-d]pyrimidin-4-ol | C |
| 107 | 2-[4-[N-methyl-4-[1-(trifluoromethyl)cyclopropyl]anilino]phenoxy]pyrido[3,4-d]pyrimidin-4-ol | C |
| 108 | 2-[4-[N-methyl-4-(1,1,1-trifluoropropan-2-yl)anilino]phenoxy]pyrido[3,4-d]pyrimidin-4-ol | B |
| 109 | 2-[4-[methyl-(6-propan-2-ylpyridin-3-yl)amino]phenoxy]pyrido[3,4-d]pyrimidin-4-ol | B |
| 110 | 2-[4-[N-methyl-4-(trifluoromethoxy)anilino]phenoxy]pyrido[3,4-d]pyrimidin-4-ol | C |
| 111 | 2-[4-(N-methyl-4-propan-2-yloxyanilino)phenoxy]pyrido[3,4-d]pyrimidin-4-ol | B |
| 114 | 2-{4-[(4-isopropyl-phenyl)-(2,2,2-trifluoro-ethyl)-amino]-phenoxy}-pyrido[3,4-d]pyrimidin-4-ol | B |
| 115 | 2-(4-{[4-(3-dimethylamino-1-methyl-propyl)-phenyl]-methyl-amino}-phenoxy)-pyrido[3,4-d]pyrimidin-4-ol | A |
| 116 | (3,3-dimethyl-2,3-dihydro-benzofuran-6-yl)-methyl-[4-(4-methyl-pyrido[3,4-d]pyrimidin-2-yloxy)-phenyl]-amine | B |
| 117 | 2-(4-(ethyl(4-isopropylphenyl)amino)phenoxy)pyrido[3,4-d]pyrimidin-4-ol | C |
| 118 | 2-(4-((4-isopropylphenyl)(tetrahydro-2H-pyran-4-yl)amino)phenoxy)pyrido[3,4-d]pyrimidin-4-ol | B |

Note:
Biochemical assay IC$_{50}$ data are designated within the following ranges:
A: ≤0.10 μM
B: >0.10 μM to ≤1.0 μM
C: >1.0 μM to ≤10 μM
D: >10 μM Example 2: In Vitro Cell-Based Assay The primary cellular assay for JMJD2C inhibition is an assay which measures cellular proliferation via Bromodeoxyuridine (BrdU) incorporation after 168 hours of compound incubation. Cell lines tested include the JMJD2C gene amplified cell line KYSE-150. This is a quantitative ELISA assay measuring DNA incorporation of BrdU during S-phase as a direct readout of cellular proliferation.

Assay Principle: This is a colorimetric immunoassay for the quantification of cell proliferation. Cells treated for 168 hours with test compounds are assayed for their ability to go through S-phase as a measure of their proliferative potential.

Assay Method: The human KYSE-150 (SMAD4 mut, TP53 mut) esophageal carcinoma cell line was seeded at 2,000 cells/well on a 96-well tissue culture treated plate. After an overnight incubation, cells were treated with compound in an 11-point dilution series with final concentrations ranging from 100 μM to 2 nM. Cells were then incubated in the presence of compound for 168 hours. After compound incubation the cells were assayed using a BrdU Cell Proliferation ELISA (Roche). The cells were first incubated with BrdU labeling reagent for 2 hours. After 2 hours, the BrdU incorporated cells were fixed and denatured, probed with an anti-BrdU-Peroxidase antibody for 1.5 hours and washed. Finally, a tetramethylbenzidine peroxidase substrate was added to each well for 15 minutes followed by a $H_2SO_4$ stop solution. The plate was read at 450 nm, and the raw optical density data was transferred into XLFit (IDBS) for $IC_{50}$ calculation using the formula: fit=(D+((Vmax*(x^n))/((x^n)+(Km^n))))

Table 4 provides the cellular $IC_{50}$ values of various compounds disclosed herein.

TABLE 4

| Ex. | Cellular $IC_{50}$ |
|---|---|
| 1 | C |
| 2 | A |
| 3 | B |
| 4 | B |
| 5 | B |
| 6 | A |
| 7 | C |
| 12 | C |
| 13 | C |
| 15 | C |
| 19 | B |
| 23 | C |
| 24 | D |
| 26 | D |
| 27 | D |
| 29 | B |
| 30 | A |
| 32 | C |
| 36 | B |
| 37 | D |
| 38 | A |
| 39 | A |
| 40 | D |
| 41 | C |
| 42 | B |
| 43 | B |
| 44 | D |
| 45 | D |
| 46 | D |
| 47 | B |
| 48 | D |
| 49 | B |
| 50 | D |
| 51 | C |
| 52 | C |
| 53 | B |
| 54 | D |
| 55 | C |
| 56 | D |
| 57 | D |
| 58 | D |
| 59 | D |
| 60 | D |
| 61 | D |
| 62 | C |
| 64 | B |
| 65 | D |
| 66 | C |
| 67 | A |
| 68 | B |
| 69 | A |
| 70 | D |
| 71 | C |
| 72 | D |
| 73 | A |
| 74 | A |
| 75 | A |
| 76 | A |
| 77 | A |
| 78 | A |
| 79 | A |
| 80 | B |
| 81 | D |
| 82 | D |
| 83 | B |
| 84 | A |
| 85 | A |
| 86 | B |
| 87 | B |
| 88 | D |
| 89 | C |
| 90 | D |
| 91 | D |
| 92 | A |
| 94 | B |
| 95 | C |
| 96 | C |
| 97 | B |
| 98 | D |
| 99 | A |
| 100 | D |
| 101 | B |
| 102 | B |
| 103 | D |
| 104 | D |
| 105 | C |
| 106 | A |
| 107 | A |
| 108 | A |
| 109 | C |
| 110 | B |
| 111 | B |
| 115 | D |
| 117 | A |

Note:
Cell assay $IC_{50}$ data are designated within the following ranges:
A: ≤0.10 μM
B: >0.10 μM to ≤1.0 μM
C: >1.0 μM to ≤10 μM
D: >10 μM Example 3: In Vivo Xenograph Study Time release pellets containing 0.72 mg 17-3 Estradiol are subcutaneously implanted into nu/nu mice. MCF-7 cells are grown in RPMI containing 10% FBS at 5% $CO_2$, 37° C. Cells are spun down and re-suspended in 50% RPMI (serum free) and 50% Matrigel at $1\times10^7$ cells/mL. MCF-7 cells are subcutaneously injected (100 μL/animal) on the right flank 2-3 days post pellet implantation and tumor volume (length× width²/2) is monitored bi-weekly. When tumors reach an average volume of ~200 mm³ animals are randomized and treatment is started. Animals are treated with vehicle or compound daily for 4 weeks. Tumor volume and body weight are monitored bi-weekly throughout the study. At the conclusion of the treatment period, plasma and tumor samples are taken for pharmacokinetic and pharmacodynamic analyses, respectively.

III. Preparation of Pharmaceutical Dosage Forms

Example 1: Oral Tablet

A tablet is prepared by mixing 48% by weight of a compound of Formula (I) or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

We claim:

1. A compound of Formula (II), or pharmaceutically acceptable salt thereof,

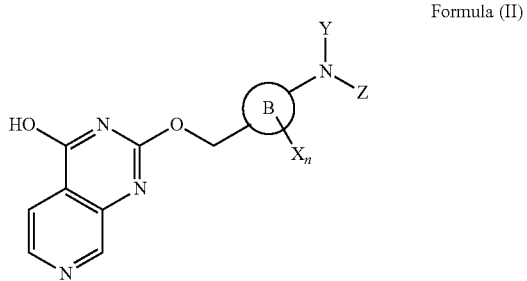

Formula (II)

wherein,
X is halogen and n is 0 or 1;
ring B is chosen from:

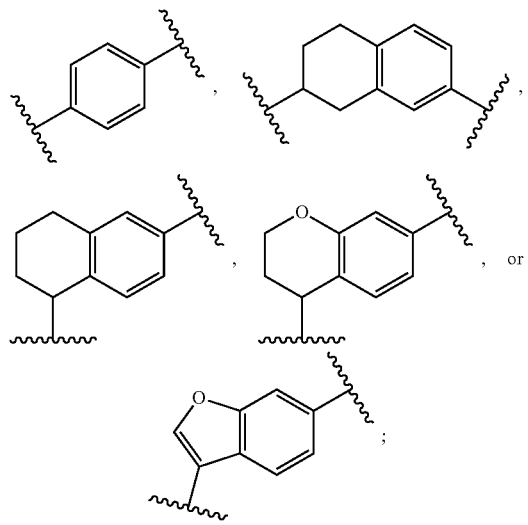

Y is $C_1$-$C_3$ alkyl; and
Z is aryl or heteroaryl.

2. The compound of claim 1, or pharmaceutically acceptable salt thereof, wherein n is 0.

3. The compound of claim 1, or pharmaceutically acceptable salt thereof, wherein n is 1 and X is fluoro.

4. The compound of claim 1, or pharmaceutically acceptable salt thereof, wherein Y is $C_1$ alkyl.

5. The compound of claim 1, or pharmaceutically acceptable salt thereof, wherein Y is $C_2$ alkyl.

6. The compound of claim 1, or pharmaceutically acceptable salt thereof, wherein ring B is

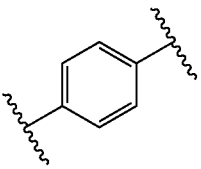

7. The compound of claim 1, or pharmaceutically acceptable salt thereof, wherein Z is aryl.

8. The compound of claim 7, or pharmaceutically acceptable salt thereof, wherein Z is phenyl optionally substituted with alkyl, —(C=O)N($R^a$)$_2$, heteroaryl, or heterocyclyl and wherein each $R^a$ is independently hydrogen or $C_1$-$C_3$ alkyl.

9. The compound of claim 1, or pharmaceutically acceptable salt thereof, wherein Z is heteroaryl.

10. The compound of claim 9, or pharmaceutically acceptable salt thereof, wherein Z is

11. A pharmaceutical composition comprising the compound of claim 1, or pharmaceutically acceptable salt thereof, and at least one pharmaceutically acceptable excipient.

12. A method of inhibiting a histone demethylase enzyme comprising contacting the histone demethylase enzyme with a compound of claim 1.

13. A method of treating a histone demethylase-associated esophageal and breast cancer in a subject comprising administering to said subject a therapeutically effective dose of a compound of claim 1 or a pharmaceutically acceptable salt thereof.

* * * * *